US011779768B2

(12) United States Patent
Rousso et al.

(10) Patent No.: US 11,779,768 B2
(45) Date of Patent: Oct. 10, 2023

(54) PROTEIN ACTIVITY MODIFICATION

(71) Applicant: Impulse Dynamics NV, Willemstad (CW)

(72) Inventors: Benny Rousso, Rishon-LeZion (IL); Yuval Mika, Closter, NJ (US); Shlomo Ben-Haim, Geneva (CH); Hani N. Sabbah, Waterford, MI (US)

(73) Assignee: Impulse Dynamics NV, Willemstad (CW)

( * ) Notice: Subject to any disclaimer, the term of this patent is extended or adjusted under 35 U.S.C. 154(b) by 22 days.

(21) Appl. No.: 17/524,015

(22) Filed: Nov. 11, 2021

(65) Prior Publication Data

US 2022/0062631 A1 Mar. 3, 2022

Related U.S. Application Data

(63) Continuation of application No. 16/232,088, filed on Dec. 26, 2018, now abandoned, which is a
(Continued)

(51) Int. Cl.
*A61N 1/362* (2006.01)
*A61N 1/32* (2006.01)
(Continued)

(52) U.S. Cl.
CPC ............ *A61N 1/3627* (2013.01); *A61N 1/32* (2013.01); *A61N 1/3628* (2013.01); *A61N 2/004* (2013.01);
(Continued)

(58) Field of Classification Search
CPC ...... A61N 1/205; A61N 1/3627; A61N 2/004; A61N 1/32; A61N 1/3629; A61N 1/3628;
(Continued)

(56) References Cited

U.S. PATENT DOCUMENTS 1,918,386 A 7/1933 Esau
3,211,154 A 10/1965 Becker et al.
(Continued)

FOREIGN PATENT DOCUMENTS

CA 2240943 A1 * 7/1997
EP 0148687 7/1985
(Continued)

OTHER PUBLICATIONS

Morita, Hideaki et al., Cardiac Contractility Modulation With Nonexcitatory Electric Signals Improves Left Ventricular Function in Dogs With Chronic Heart Failure, Feb. 2003, Journal of Cardiac Failure, vol. 1, No. 1, pp. 69-75 (Year: 2003).*
(Continued)

*Primary Examiner* — Catherine M Voorhees

(57) ABSTRACT

A method of modifying tissue behavior, comprising:
determining a desired modification of tissue behavior for at least one of treatment of a disease, short or long term modification of tissue behavior, assessing tissue state and assessing tissue response to stimulation;
selecting an electric field having an expected effect of modifying protein activity of at least one protein as an immediate response of a tissue to the field, said expected effect correlated with said desired modification; and
applying said field to said tissue.

17 Claims, 54 Drawing Sheets

Related U.S. Application Data continuation of application No. 15/249,506, filed on Aug. 29, 2016, now Pat. No. 10,352,948, which is a continuation of application No. 14/641,480, filed on Mar. 9, 2015, now Pat. No. 9,440,080, which is a continuation of application No. 13/970,647, filed on Aug. 20, 2013, now Pat. No. 8,977,353, which is a continuation of application No. 11/919,491, filed as application No. PCT/US2006/017281 on May 4, 2006, now Pat. No. 8,548,583, which is a continuation of application No. PCT/IL2006/000204, filed on Feb. 16, 2006, and a continuation-in-part of application No. PCT/US2005/044557, filed on Dec. 9, 2005, which is a continuation-in-part of application No. PCT/US2004/007589, filed on Mar. 10, 2004.

(60) Provisional application No. 60/719,517, filed on Sep. 22, 2005, provisional application No. 60/677,761, filed on May 4, 2005, provisional application No. 60/634,625, filed on Dec. 9, 2004.

(51) Int. Cl.
*C12N 13/00* (2006.01)
*A61N 2/00* (2006.01)
*A61N 1/20* (2006.01)
*C12Q 1/6883* (2018.01)
*G01N 33/68* (2006.01)

(52) U.S. Cl.
CPC .............. *C12N 13/00* (2013.01); *A61N 1/205* (2013.01); *A61N 1/3629* (2017.08); *C12Q 1/6883* (2013.01); *C12Q 2600/112* (2013.01); *C12Q 2600/158* (2013.01); *G01N 33/6893* (2013.01); *G01N 2800/325* (2013.01)

(58) Field of Classification Search
CPC ............ C12Q 1/6883; C12Q 2600/112; C12Q 2600/158; G01N 33/6893; G01N 2800/325; C12N 13/00
See application file for complete search history.

(56) References Cited

U.S. PATENT DOCUMENTS

| | | |
|---|---|---|
| 3,541,390 A | 11/1970 | Jahnke |
| 3,572,345 A | 3/1971 | Auphan |
| 3,587,567 A | 6/1971 | Schiff |
| 3,651,805 A | 3/1972 | Breiling |
| 3,651,806 A | 3/1972 | Hirshberg |
| 3,796,221 A | 3/1974 | Hagfors |
| 3,911,930 A | 10/1975 | Hagfors et al. |
| 3,933,147 A | 1/1976 | Du Vall et al. |
| 3,942,536 A | 3/1976 | Mirowski et al. |
| 3,944,740 A | 3/1976 | Murase et al. |
| 3,952,750 A | 4/1976 | Mirowski et al. |
| 4,030,509 A | 6/1977 | Heilman et al. |
| 4,106,494 A | 8/1978 | McEachern |
| 4,164,216 A | 8/1979 | Person |
| 4,168,711 A | 9/1979 | Cannon, III et al. |
| 4,184,493 A | 1/1980 | Langer et al. |
| 4,202,340 A | 5/1980 | Langer et al. |
| 4,223,678 A | 9/1980 | Langer et al. |
| 4,237,895 A | 12/1980 | Johnson |
| 4,273,114 A | 6/1981 | Barkalow et al. |
| 4,293,734 A | 10/1981 | Pepper, Jr. |
| 4,312,354 A | 1/1982 | Walters |
| 4,315,503 A | 2/1982 | Ryaby et al. |
| 4,316,472 A | 2/1982 | Mirowski et al. |
| 4,337,776 A | 7/1982 | Daly et al. |
| 4,369,791 A | 1/1983 | Friedman |
| 4,384,585 A | 5/1983 | Zipes |
| 4,387,717 A | 6/1983 | Brownlee et al. |
| 4,403,614 A | 9/1983 | Engle et al. |
| 4,406,288 A | 9/1983 | Horwinski et al. |
| 4,407,288 A | 10/1983 | Langer et al. |
| 4,411,268 A | 10/1983 | Cox |
| 4,428,366 A | 1/1984 | Findl et al. |
| 4,440,172 A | 4/1984 | Langer |
| 4,506,680 A | 3/1985 | Stokes |
| 4,537,195 A | 8/1985 | McDonnell |
| 4,537,203 A | 8/1985 | Machida |
| 4,543,738 A | 10/1985 | Mower |
| 4,543,956 A | 10/1985 | Herscovici |
| 4,550,221 A | 10/1985 | Mabusth |
| 4,554,922 A | 11/1985 | Prystowsky et al. |
| 4,554,992 A | 11/1985 | Kassai |
| 4,559,946 A | 12/1985 | Mower |
| 4,559,947 A | 12/1985 | Renger et al. |
| 4,566,456 A | 1/1986 | Koning et al. |
| 4,572,191 A | 2/1986 | Mirowski et al. |
| 4,628,934 A | 12/1986 | Pohndorf et al. |
| 4,637,397 A | 1/1987 | Jones et al. |
| 4,639,720 A | 1/1987 | Rympalski et al. |
| 4,651,716 A | 3/1987 | Forester et al. |
| 4,674,508 A | 6/1987 | DeCote |
| 4,679,572 A | 7/1987 | Baker, Jr. |
| 4,686,332 A | 8/1987 | Greanias et al. |
| 4,690,155 A | 9/1987 | Hess |
| 4,693,253 A | 9/1987 | Adams |
| 4,708,145 A | 11/1987 | Tacker et al. |
| 4,717,581 A | 1/1988 | Robblee |
| 4,726,279 A | 2/1988 | Kepler et al. |
| 4,726,379 A | 2/1988 | Altman et al. |
| 4,765,341 A | 8/1988 | Mower et al. |
| 4,807,632 A | 2/1989 | Liess et al. |
| 4,830,006 A | 5/1989 | Haluska et al. |
| 4,834,100 A | 5/1989 | Charms |
| 4,850,959 A | 7/1989 | Findl |
| 4,870,974 A | 10/1989 | Wang |
| 4,878,553 A | 11/1989 | Yamanami et al. |
| 4,884,576 A | 12/1989 | Alt |
| 4,914,624 A | 4/1990 | Dunthorn et al. |
| 4,928,688 A | 5/1990 | Mower |
| 4,967,749 A | 11/1990 | Cohen |
| 4,971,058 A | 11/1990 | Pless et al. |
| 4,979,507 A | 12/1990 | Heinz et al. |
| 4,988,837 A | 1/1991 | Murakami et al. |
| 4,996,984 A | 3/1991 | Sweeney |
| 4,998,531 A | 3/1991 | Bocchi et al. |
| 4,998,532 A | 3/1991 | Griffith |
| 5,002,052 A | 3/1991 | Haluska et al. |
| 5,003,976 A | 4/1991 | Alt |
| 5,018,522 A | 5/1991 | Mehra |
| 5,020,544 A | 6/1991 | Dahl et al. |
| 5,022,396 A | 6/1991 | Watanabe |
| 5,026,397 A | 6/1991 | Aoki et al. |
| 5,031,617 A | 7/1991 | Klettner |
| 5,041,107 A | 8/1991 | Heil, Jr. |
| 5,044,375 A | 9/1991 | Bach, Jr. et al. |
| 5,048,522 A | 9/1991 | Petrofsky |
| 5,063,929 A | 11/1991 | Bartelt et al. |
| 5,067,940 A | 11/1991 | Liboff et al. |
| 5,083,564 A | 1/1992 | Scherlag |
| 5,144,554 A | 1/1992 | Zhang et al. |
| 5,085,218 A | 2/1992 | Heil et al. |
| 5,087,243 A | 2/1992 | Avitall |
| 5,097,832 A | 3/1992 | Buchanan |
| 5,097,833 A | 3/1992 | Campos |
| 5,097,843 A | 3/1992 | Soukup et al. |
| 5,107,834 A | 4/1992 | Ideker et al. |
| 5,111,814 A | 5/1992 | Goldfarb |
| 5,111,815 A | 5/1992 | Mower |
| 5,101,814 A | 7/1992 | Palti |
| 5,129,394 A | 7/1992 | Mehra |
| 5,133,354 A | 7/1992 | Kallok |
| 5,137,021 A | 8/1992 | Wayne et al. |
| 5,154,501 A | 10/1992 | Svenson et al. |
| 5,156,147 A | 10/1992 | Warren et al. |
| 5,156,149 A | 10/1992 | Hudrlik |
| 5,161,527 A | 11/1992 | Nappholz et al. |
| 5,163,427 A | 11/1992 | Keimel |

(56) References Cited

U.S. PATENT DOCUMENTS

| | | |
|---|---|---|
| 5,163,428 A | 11/1992 | Pless |
| 5,172,690 A | 12/1992 | Nappholz et al. |
| 5,172,699 A | 12/1992 | Svenson et al. |
| 5,174,286 A | 12/1992 | Chirife |
| 5,184,616 A | 2/1993 | Weiss |
| 5,184,620 A | 2/1993 | Cudahy et al. |
| 5,185,620 A | 2/1993 | Cooper |
| 5,188,104 A | 2/1993 | Wernicke et al. |
| 5,188,106 A | 2/1993 | Nappholz et al. |
| 5,190,041 A | 2/1993 | Palti |
| 5,199,428 A | 4/1993 | Obel et al. |
| 5,205,284 A | 4/1993 | Freeman |
| 5,213,098 A | 5/1993 | Bennett et al. |
| 5,231,381 A | 7/1993 | Duwaer |
| 5,233,985 A | 8/1993 | Hudrlik |
| 5,236,413 A | 8/1993 | Feiring |
| 5,243,980 A | 9/1993 | Mehra et al. |
| 5,267,560 A | 12/1993 | Cohen |
| 5,281,219 A | 1/1994 | Kallok |
| 5,282,785 A | 2/1994 | Shapland et al. |
| 5,284,491 A | 2/1994 | Sutton et al. |
| 5,286,254 A | 2/1994 | Shapland et al. |
| 5,305,745 A | 4/1994 | Zacouto |
| 5,318,591 A | 6/1994 | Causey, III et al. |
| 5,320,543 A | 6/1994 | Barton et al. |
| 5,320,642 A | 6/1994 | Scherlag |
| 5,320,643 A | 6/1994 | Roline et al. |
| 5,324,327 A | 6/1994 | Cohen |
| 5,325,856 A | 7/1994 | Nitzsche et al. |
| 5,327,887 A | 7/1994 | Nowakowski |
| 5,292,344 A | 8/1994 | Douglas |
| 5,346,506 A | 9/1994 | Mower et al. |
| 5,350,403 A | 9/1994 | Stroetmann et al. |
| 5,353,800 A | 10/1994 | Pohndorf et al. |
| 5,336,485 A | 11/1994 | Kroll et al. |
| 5,365,461 A | 11/1994 | Stein et al. |
| 5,366,486 A | 11/1994 | Zipes et al. |
| 5,368,040 A | 11/1994 | Carney |
| 5,370,665 A | 12/1994 | Hudrlik |
| 5,374,787 A | 12/1994 | Miller et al. |
| 5,381,160 A | 1/1995 | Landmeier |
| 5,386,835 A | 2/1995 | Elphick et al. |
| 5,386,837 A | 2/1995 | Sterzer |
| 5,387,419 A | 2/1995 | Levy et al. |
| 5,391,192 A | 2/1995 | Lu et al. |
| 5,391,199 A | 2/1995 | Ben-Haim |
| 5,397,344 A | 3/1995 | Garfield et al. |
| 5,398,683 A | 3/1995 | Edwards et al. |
| 5,402,151 A | 3/1995 | Duwaer |
| 5,405,365 A | 4/1995 | Hoegnelid et al. |
| 5,411,531 A | 5/1995 | Hill et al. |
| 5,415,629 A | 5/1995 | Henley |
| 5,417,717 A | 5/1995 | Salo et al. |
| 5,419,763 A | 5/1995 | Hildebrand |
| 5,447,526 A | 5/1995 | Karsdon |
| 5,423,872 A | 6/1995 | Cigaina |
| 5,425,363 A | 6/1995 | Wang |
| 5,431,682 A | 7/1995 | Hedberg |
| 5,431,688 A | 7/1995 | Freeman |
| 5,431,693 A | 7/1995 | Schroeppel |
| 5,433,730 A | 7/1995 | Alt |
| 5,443,485 A | 8/1995 | Housworth et al. |
| 5,443,489 A | 8/1995 | Ben-Haim |
| 5,445,609 A | 8/1995 | Lattin et al. |
| 5,447,520 A | 9/1995 | Spano et al. |
| 5,447,525 A | 9/1995 | Powell et al. |
| 5,458,568 A | 10/1995 | Racchini et al. |
| 5,464,020 A | 11/1995 | Lerner |
| 5,464,429 A | 11/1995 | Hedberg et al. |
| 5,468,254 A | 11/1995 | Hahn et al. |
| 5,472,453 A | 12/1995 | Alt |
| 5,476,484 A | 12/1995 | Hedberg |
| 5,476,485 A | 12/1995 | Weinberg et al. |
| 5,476,487 A | 12/1995 | Sholder |
| 5,476,497 A | 12/1995 | Mower et al. |
| 5,480,422 A | 1/1996 | Ben-Haim |
| 5,482,052 A | 1/1996 | Lerner |
| 5,561,165 A | 1/1996 | Lautt et al. |
| 5,489,293 A | 2/1996 | Pless et al. |
| 5,495,077 A | 2/1996 | Miller et al. |
| 5,499,971 A | 3/1996 | Shapland et al. |
| 5,501,662 A | 3/1996 | Hofmann |
| 5,505,700 A | 4/1996 | Leone et al. |
| 5,510,813 A | 4/1996 | Makinwa et al. |
| 5,514,162 A | 5/1996 | Bornzin et al. |
| 5,520,642 A | 5/1996 | Bigagli et al. |
| 5,522,853 A | 6/1996 | Kroll |
| 5,527,345 A | 6/1996 | Infinger |
| 5,528,002 A | 6/1996 | Katabami |
| 5,531,764 A | 7/1996 | Adams et al. |
| 5,534,015 A | 7/1996 | Kroll et al. |
| 5,540,722 A | 7/1996 | Clare et al. |
| 5,540,730 A | 7/1996 | Terry, Jr. et al. |
| 5,540,734 A | 7/1996 | Zabara |
| 5,543,589 A | 8/1996 | Buchana et al. |
| 5,546,951 A | 8/1996 | Ben-Haim |
| 5,549,646 A | 8/1996 | Katz et al. |
| 5,556,421 A | 9/1996 | Prutchi et al. |
| 5,556,760 A | 9/1996 | Nakamura et al. |
| 5,558,640 A | 9/1996 | Pfeiler et al. |
| 5,562,708 A | 10/1996 | Combs et al. |
| 5,565,632 A | 10/1996 | Ogawa |
| 5,568,809 A | 10/1996 | Ben-Haim |
| 5,571,143 A | 11/1996 | Hoegnelid et al. |
| 5,571,997 A | 11/1996 | Gray et al. |
| 5,578,061 A | 11/1996 | Stroetmann et al. |
| 5,584,803 A | 12/1996 | Stevens et al. |
| 5,584,804 A | 12/1996 | Klatz et al. |
| 5,584,868 A | 12/1996 | Salo et al. |
| 5,587,200 A | 12/1996 | Lorenz et al. |
| 5,589,856 A | 12/1996 | Stein et al. |
| 5,601,609 A | 2/1997 | Duncan |
| 5,601,611 A | 2/1997 | Fayram et al. |
| 5,620,468 A | 4/1997 | Mongeon et al. |
| 5,622,687 A | 4/1997 | Krishnan et al. |
| 5,626,622 A | 5/1997 | Cooper |
| 5,632,267 A | 5/1997 | Hoegnelid et al. |
| 5,634,895 A | 6/1997 | Igo et al. |
| 5,634,899 A | 6/1997 | Shapland et al. |
| 5,649,966 A | 7/1997 | Noren et al. |
| 5,651,378 A | 7/1997 | Matheny et al. |
| 5,654,030 A | 8/1997 | Munshi et al. |
| 5,662,687 A | 9/1997 | Hedberg et al. |
| 5,670,755 A | 9/1997 | Kwon |
| 5,674,251 A | 10/1997 | Combs et al. |
| 5,674,259 A | 10/1997 | Gray |
| 5,683,429 A | 11/1997 | Mehra |
| 5,683,431 A | 11/1997 | Wang |
| 5,687,734 A | 11/1997 | Dempsey et al. |
| 5,690,691 A | 11/1997 | Chen et al. |
| 5,694,945 A | 12/1997 | Ben-Haim |
| 5,697,953 A | 12/1997 | Kroll et al. |
| 5,713,924 A | 2/1998 | Min et al. |
| 5,713,929 A | 2/1998 | Hess et al. |
| 5,713,935 A | 2/1998 | Prutchi et al. |
| 5,720,768 A | 2/1998 | Verboven-Nelissen |
| 5,735,876 A | 4/1998 | Kroll et al. |
| 5,738,096 A | 4/1998 | Ben-Haim |
| 5,738,105 A | 4/1998 | Kroll |
| 5,741,791 A | 4/1998 | Olsen |
| 5,749,906 A | 5/1998 | Kieval et al. |
| 5,755,740 A | 5/1998 | Nappholz |
| 5,777,607 A | 7/1998 | Koolen |
| 5,779,661 A | 7/1998 | Stephen et al. |
| 5,782,876 A | 7/1998 | Flammang |
| 5,782,881 A | 7/1998 | Lu et al. |
| 5,783,951 A | 7/1998 | Inoue et al. |
| 5,790,106 A | 8/1998 | Hirano et al. |
| 5,790,107 A | 8/1998 | Kasser et al. |
| 5,792,198 A | 8/1998 | Nappholz |
| 5,792,208 A | 8/1998 | Gray |
| 5,797,967 A | 8/1998 | KenKnight |
| 5,800,464 A | 9/1998 | Kieval |
| 5,807,234 A | 9/1998 | Bui et al. |

(56) References Cited

U.S. PATENT DOCUMENTS

| | | |
|---|---|---|
| 5,807,306 A | 9/1998 | Shapland et al. |
| 5,814,079 A | 9/1998 | Kieval |
| 5,825,352 A | 10/1998 | Bisset et al. |
| 5,841,078 A | 11/1998 | Miller et al. |
| 5,854,881 A | 12/1998 | Yoshida et al. |
| 5,861,014 A | 1/1999 | Familoni |
| 5,865,787 A | 2/1999 | Shapland et al. |
| 5,871,506 A | 2/1999 | Mower |
| 5,906,607 A | 5/1999 | Taylor et al. |
| 5,962,246 A | 5/1999 | Ladner et al. |
| 5,911,223 A | 6/1999 | Weaver et al. |
| 5,913,876 A | 6/1999 | Taylor et al. |
| 5,914,465 A | 6/1999 | Allen et al. |
| 5,919,216 A | 7/1999 | Houben et al. |
| 5,920,309 A | 7/1999 | Bisset et al. |
| 5,927,284 A | 7/1999 | Borst et al. |
| 5,954,761 A | 9/1999 | Machek et al. |
| 5,956,020 A | 9/1999 | D'Amico et al. |
| 5,991,649 A | 11/1999 | Garfield et al. |
| 5,995,872 A | 11/1999 | Bourgeois |
| 6,002,594 A | 12/1999 | Ledin et al. |
| 6,006,134 A | 12/1999 | Hill et al. |
| 6,026,326 A | 2/2000 | Bardy |
| 6,032,074 A | 2/2000 | Collins |
| 6,057,374 A | 2/2000 | Huntington et al. |
| 6,032,672 A | 3/2000 | Taylor |
| 6,037,882 A | 3/2000 | Levy |
| 6,041,252 A | 3/2000 | Walker et al. |
| 6,083,249 A | 4/2000 | Familoni |
| 6,066,163 A | 5/2000 | John |
| 6,067,470 A | 5/2000 | Mower |
| 6,071,305 A | 6/2000 | Brown et al. |
| 6,075,520 A | 6/2000 | Inoue et al. |
| 6,086,582 A | 7/2000 | Altman et al. |
| 6,093,167 A | 7/2000 | Houben et al. |
| 6,023,640 A | 8/2000 | Ross |
| 6,122,536 A | 9/2000 | Sun et al. |
| 6,128,007 A | 10/2000 | Seybold et al. |
| 6,133,906 A | 10/2000 | Geaghan |
| 6,135,978 A | 10/2000 | Houben et al. |
| 6,136,019 A | 10/2000 | Mower |
| 6,141,586 A | 10/2000 | Mower |
| 6,141,587 A | 10/2000 | Mower |
| 6,151,586 A | 11/2000 | Brown |
| 6,178,351 B1 | 1/2001 | Mower |
| 6,296,693 B1 | 2/2001 | McCarthy |
| 6,298,254 B2 | 2/2001 | Tamada |
| 6,298,268 B1 | 2/2001 | Ben-Haim et al. |
| 6,285,906 B1 | 4/2001 | Ben-Haim et al. |
| 6,233,484 B1 | 5/2001 | Ben-Haim et al. |
| 6,233,487 B1 | 5/2001 | Mika et al. |
| 6,236,887 B1 | 5/2001 | Ben-Haim et al. |
| 6,239,389 B1 | 5/2001 | Allen et al. |
| 6,243,607 B1 | 5/2001 | Mintchev et al. |
| 6,261,280 B1 | 7/2001 | Houben et al. |
| 6,278,443 B1 | 8/2001 | Amro et al. |
| 6,292,693 B1 | 9/2001 | Darvish et al. |
| 6,292,704 B1 | 9/2001 | Malonek et al. |
| 6,295,470 B1 | 9/2001 | Mower |
| 6,317,631 B1 | 11/2001 | Ben-Haim et al. |
| 6,330,476 B1 | 12/2001 | Ben-Haim |
| 6,337,995 B1 | 1/2002 | Mower |
| 6,341,235 B1 | 1/2002 | Mower |
| 6,343,232 B1 | 1/2002 | Mower |
| 6,363,279 B1 | 3/2002 | Ben-Haim et al. |
| 6,381,495 B1 | 4/2002 | Jenkins |
| 6,392,636 B1 | 5/2002 | Ferrari et al. |
| 6,411,847 B1 | 6/2002 | Mower |
| 6,417,846 B1 | 7/2002 | Lee |
| 6,424,864 B1 | 7/2002 | Matsuura |
| 6,433,069 B1 | 8/2002 | Oeltjen et al. |
| 6,463,324 B1 | 8/2002 | Ben-Haim et al. |
| 6,449,511 B1 | 9/2002 | Mintchev et al. |
| 6,452,514 B1 | 9/2002 | Philipp |
| 6,463,323 B1 | 10/2002 | Conrad-Vlasak |
| 6,473,069 B1 | 10/2002 | Gerpheide |
| 6,480,737 B1 * | 11/2002 | Policker ............... A61N 1/3622 607/2 |
| 6,498,944 B1 | 12/2002 | Ben-Haim et al. |
| 6,504,530 B1 | 1/2003 | Wilson et al. |
| 6,505,745 B1 | 1/2003 | Anderson |
| 6,507,093 B2 | 1/2003 | Kaneda et al. |
| 6,587,721 B1 | 1/2003 | Prutchi et al. |
| 6,612,983 B1 | 2/2003 | Marchal |
| 6,658,297 B2 | 2/2003 | Loeb |
| 6,572,542 B1 | 3/2003 | Houben et al. |
| RE38,119 E | 5/2003 | Mower |
| 6,567,700 B1 | 5/2003 | Turcott et al. |
| 6,570,557 B1 | 5/2003 | Westerman et al. |
| 6,571,127 B1 | 5/2003 | Ben-Haim et al. |
| 6,583,676 B2 | 7/2003 | Krah et al. |
| 6,587,093 B1 | 7/2003 | Shaw et al. |
| 6,600,953 B2 | 7/2003 | Flesler et al. |
| 6,630,123 B1 | 7/2003 | Woltering et al. |
| 6,611,258 B1 | 8/2003 | Tanaka et al. |
| 6,633,280 B1 | 10/2003 | Matsumoto et al. |
| 6,634,895 B2 | 10/2003 | Agro |
| 6,640,135 B1 | 10/2003 | Salo et al. |
| 6,652,444 B1 | 11/2003 | Ross |
| 6,667,740 B2 | 12/2003 | Ely et al. |
| 6,684,104 B2 | 1/2004 | Gordon et al. |
| 6,690,156 B1 | 2/2004 | Weiner et al. |
| 6,690,963 B2 | 2/2004 | Ben-Haim et al. |
| 6,762,752 B2 | 7/2004 | Perski et al. |
| 6,781,577 B2 | 8/2004 | Shigetaka |
| 6,810,286 B2 | 10/2004 | Donovan et al. |
| 6,853,862 B1 | 2/2005 | Marchal et al. |
| 6,919,205 B2 | 7/2005 | Brighton |
| 6,949,081 B1 | 9/2005 | Chance |
| 7,006,871 B1 | 2/2006 | Darvish et al. |
| 7,027,863 B1 * | 4/2006 | Prutchi ............... A61N 1/3621 607/5 |
| 7,062,318 B2 | 6/2006 | Ben-Haim et al. |
| 7,092,753 B2 | 8/2006 | Darvish et al. |
| 7,167,748 B2 | 1/2007 | Ben-Haim et al. |
| 7,171,263 B2 | 1/2007 | Darvish et al. |
| 7,190,997 B1 | 3/2007 | Darvish et al. |
| 7,218,963 B2 | 5/2007 | Ben-Haim et al. |
| 7,412,289 B2 | 8/2008 | Malonek et al. |
| 7,460,907 B1 | 12/2008 | Darvish et al. |
| 7,840,262 B2 | 11/2010 | Mika et al. |
| 7,840,263 B2 | 11/2010 | Girouard et al. |
| 8,326,416 B2 | 12/2012 | Mika et al. |
| 8,958,872 B2 | 2/2015 | Ben-Haim et al. |
| 2002/0010492 A1 | 1/2002 | Donovan et al. |
| 2002/0026141 A1 | 2/2002 | Houben et al. |
| 2002/0052632 A1 | 5/2002 | Ben-Haim et al. |
| 2002/0065455 A1 | 5/2002 | Ben-Haim et al. |
| 2002/0183682 A1 | 5/2002 | Darvish et al. |
| 2002/0183686 A1 | 5/2002 | Darvish et al. |
| 2002/0081732 A1 | 6/2002 | Bowlin et al. |
| 2002/0123771 A1 | 9/2002 | Ideker et al. |
| 2002/0161414 A1 | 10/2002 | Flesler et al. |
| 2003/0018367 A1 | 1/2003 | DiLorenzo |
| 2003/0028221 A1 | 2/2003 | Zhu et al. |
| 2003/0040777 A1 | 2/2003 | Shemer et al. |
| 2003/0055464 A1 | 3/2003 | Darvish et al. |
| 2003/0100889 A1 | 5/2003 | Duverger et al. |
| 2003/0208242 A1 | 6/2003 | Harel et al. |
| 2003/0167476 A1 | 9/2003 | Conklin |
| 2003/0181958 A1 | 9/2003 | Doubak, III |
| 2003/0188899 A1 | 10/2003 | Chao et al. |
| 2003/0211475 A1 | 11/2003 | Roberts |
| 2004/0059393 A1 | 3/2004 | Policker et al. |
| 2004/0106954 A1 | 3/2004 | Whitehurst et al. |
| 2004/0095333 A1 | 5/2004 | Morag et al. |
| 2004/0105040 A1 | 6/2004 | Oh et al. |
| 2004/0138710 A1 | 7/2004 | Shemer et al. |
| 2004/0155871 A1 | 8/2004 | Perski et al. |
| 2004/0158289 A1 | 8/2004 | Girouard et al. |
| 2004/0172079 A1 | 9/2004 | Chinchoy |
| 2004/0193231 A1 | 9/2004 | David et al. |
| 2004/0230273 A1 | 11/2004 | Cates et al. |
| 2004/0243190 A1 | 12/2004 | Ben-Haim et al. |

(56) References Cited

U.S. PATENT DOCUMENTS

| | | |
|---|---|---|
| 2004/0249421 A1 | 12/2004 | Harel et al. |
| 2005/0192542 A1 | 1/2005 | Dev et al. |
| 2005/0033396 A1 | 2/2005 | Ospyka |
| 2005/0095227 A1 | 5/2005 | Rosenzweig et al. |
| 2005/0267542 A1 | 12/2005 | David et al. |
| 2005/0277993 A1 | 12/2005 | Mower |
| 2006/0036126 A1 | 2/2006 | Ross et al. |
| 2006/0079475 A1 | 4/2006 | Zhang et al. |
| 2006/0085045 A1 | 4/2006 | Harel et al. |
| 2006/0097991 A1 | 5/2006 | Hotelling et al. |
| 2006/0184207 A1 | 8/2006 | Darvish et al. |
| 2007/0027487 A1 | 2/2007 | Mika et al. |
| 2007/0027490 A1 | 2/2007 | Ben-Haim et al. |
| 2007/0088393 A1 | 4/2007 | Ben-Haim et al. |
| 2007/0156177 A1 | 7/2007 | Harel et al. |
| 2007/0162079 A1 | 7/2007 | Shemer et al. |
| 2007/0171211 A1 | 7/2007 | Perski et al. |
| 2007/0293901 A1 | 12/2007 | Rousso et al. |
| 2008/0058879 A1 | 3/2008 | Ben-Haim et al. |
| 2008/0065159 A1 | 3/2008 | Ben-Haim et al. |
| 2008/0065163 A1 | 3/2008 | Ben-Haim et al. |
| 2008/0065164 A1 | 3/2008 | Ben-Haim et al. |
| 2008/0140142 A1 | 6/2008 | Darvish et al. |
| 2009/0062893 A1 | 3/2009 | Spehr et al. |
| 2009/0280103 A1 | 11/2009 | Flueck |
| 2009/0292324 A1 | 11/2009 | Rousso et al. |
| 2010/0016923 A1 | 1/2010 | Rousso et al. |
| 2010/0035963 A1 | 2/2010 | Chajut et al. |
| 2010/0269180 A1 | 10/2010 | Ranscht et al. |
| 2013/0096639 A1 | 4/2013 | Ben-Haim et al. |
| 2013/0338425 A1 | 12/2013 | Rousso et al. |
| 2014/0236250 A1 | 8/2014 | Ben-Haim et al. |
| 2015/0157857 A1 | 6/2015 | Ben-Haim et al. |
| 2015/0174404 A1 | 6/2015 | Rousso et al. |
| 2016/0136418 A1 | 5/2016 | Ben Haim et al. |
| 2016/0370384 A1 | 12/2016 | Rousso et al. |
| 2018/0221655 A1 | 8/2018 | Rousso et al. |
| 2019/0137513 A1 | 5/2019 | Rousso et al. |

FOREIGN PATENT DOCUMENTS

| | | |
|---|---|---|
| EP | 0156593 | 10/1985 |
| EP | 0250931 | 1/1988 |
| EP | 0314078 | 5/1989 |
| EP | 0481684 | 4/1992 |
| EP | 0503839 | 9/1992 |
| EP | 0528751 | 2/1993 |
| EP | 0220916 | 4/1994 |
| EP | 0727241 | 8/1996 |
| EP | 1263498 | 12/2002 |
| EP | 0910429 | 3/2005 |
| GB | 1394171 | 5/1975 |
| GB | 2280377 | 2/1995 |
| JP | 62-112530 | 5/1987 |
| JP | 62-275471 | 11/1987 |
| JP | 04-117967 | 4/1992 |
| JP | 04-282168 | 10/1992 |
| JP | 04-365493 | 12/1992 |
| JP | 06-169998 | 6/1994 |
| JP | 06-506619 | 7/1994 |
| JP | 07-126600 | 5/1995 |
| JP | 07-144024 | 6/1995 |
| JP | 08-243176 | 9/1996 |
| JP | 2003-512884 | 4/2003 |
| JP | 2010-194334 | 9/2010 |
| RU | 386634 | 6/1973 |
| RU | 553977 | 5/1977 |
| RU | 831131 | 5/1981 |
| RU | 2014844 | 6/1994 |
| RU | 2055606 | 3/1996 |
| RU | 2075980 | 3/1997 |
| RU | 2077273 | 4/1997 |
| RU | 2078547 | 5/1997 |
| WO | WO 91/19534 | 12/1991 |
| WO | WO 92/00716 | 1/1992 |
| WO | WO 92/13592 | 8/1992 |
| WO | WO 93/02743 | 2/1993 |
| WO | WO 93/02745 | 2/1993 |
| WO | WO 93/08874 | 5/1993 |
| WO | WO 93/18820 | 9/1993 |
| WO | WO 94/17855 | 8/1994 |
| WO | WO 95/08316 | 3/1995 |
| WO | WO 96/05768 | 2/1996 |
| WO | WO 96/10358 | 4/1996 |
| WO | WO 96/16696 | 6/1996 |
| WO | WO 97/15227 | 1/1997 |
| WO | WO 97/06849 | 2/1997 |
| WO | WO 97/24983 | 7/1997 |
| WO | WO 97/25098 | 7/1997 |
| WO | WO 97/25101 | 7/1997 |
| WO | WO 97/26042 | 7/1997 |
| WO | WO 97/27900 | 7/1997 |
| WO | WO 97/29682 | 8/1997 |
| WO | WO 97/29684 | 8/1997 |
| WO | WO 97/29700 | 8/1997 |
| WO | WO 97/29701 | 8/1997 |
| WO | WO 97/29709 | 8/1997 |
| WO | WO 98/10828 | 3/1998 |
| WO | WO 98/10829 | 3/1998 |
| WO | WO 98/10830 | 3/1998 |
| WO | WO 98/10831 | 3/1998 |
| WO | WO 98/10832 | 3/1998 |
| WO | WO 98/11840 | 3/1998 |
| WO | WO 98/15317 | 4/1998 |
| WO | WO 98/19719 | 5/1998 |
| WO | WO 98/56378 | 12/1998 |
| WO | WO 98/57701 | 12/1998 |
| WO | WO 99/06105 | 2/1999 |
| WO | WO 99/09971 | 3/1999 |
| WO | WO 99/55360 | 4/1999 |
| WO | WO 99/24110 | 5/1999 |
| WO | WO 99/29307 | 6/1999 |
| WO | WO 99/59548 | 11/1999 |
| WO | WO 00/01443 | 1/2000 |
| WO | WO 00/04947 | 2/2000 |
| WO | WO 00/16741 | 3/2000 |
| WO | WO 00/27475 | 5/2000 |
| WO | WO 00/27476 | 5/2000 |
| WO | WO 00/42914 | 7/2000 |
| WO | WO 00/12525 | 9/2000 |
| WO | WO 00/53257 | 9/2000 |
| WO | WO 00/74773 | 12/2000 |
| WO | WO 01/24871 | 4/2001 |
| WO | WO 01/30139 | 5/2001 |
| WO | WO 01/30445 | 5/2001 |
| WO | WO 01/49367 | 7/2001 |
| WO | WO 01/52931 | 7/2001 |
| WO | WO 01/66183 | 9/2001 |
| WO | WO 01/82771 | 11/2001 |
| WO | WO 01/91854 | 12/2001 |
| WO | WO 01/93950 | 12/2001 |
| WO | WO 01/93951 | 12/2001 |
| WO | WO 02/10791 | 2/2002 |
| WO | WO 02/053093 | 7/2002 |
| WO | WO 02/082968 | 10/2002 |
| WO | WO 03/045493 | 5/2003 |
| WO | WO 2004/059393 | 7/2004 |
| WO | WO 2004/070396 | 8/2004 |
| WO | WO 2004/080533 | 9/2004 |
| WO | WO 2005/023081 | 3/2005 |
| WO | WO 2005/087310 | 9/2005 |
| WO | WO 2005/114369 | 12/2005 |
| WO | WO 2006/073671 | 7/2006 |
| WO | WO 2006/087717 | 8/2006 |
| WO | WO 2006/097934 | 9/2006 |
| WO | WO 2006/097935 | 9/2006 |
| WO | WO 2006/119467 | 9/2006 |

OTHER PUBLICATIONS

Notice of Allowance dated Jun. 14, 2022 From the US Patent and Trademark Office Re. U.S. Appl. No. 15/942,637. (8 Pages).
Pokrovsky et al. "Physiology of Man", 1: 82-83, 94, 2: 42, 54.

(56) References Cited

OTHER PUBLICATIONS

Porksen et al. "Section 6: Pulsatile and Phasic Insulin Release in Normal and Diabetic Man. Pulsatile Insulin Secretion: Detection, Regulation, and Role in Diabetes", Diabetes, 51(Suppl.l): S245-S254, Feb. 2002.
Pumir et al. "Control of Rotating Waves in Cardiac Muscle: Analysis of the Effect of Electric Fields", Proceedings of the Royal Society B: Biological Sciences, 257(1349): 129-134, 1994. Abstract.
Ranjan et al. "Electrical Stimulation of Cardiac Myocytes", Annals of Biomedical Engineering, 23(6): 812-821, 1995, Abstract.
Rivera et al. "Regulation of Protein Secretion Through Controlled Aggregation in the Endoplasmic Reticulum", Science, 287(5454): 826-830, Feb. 4, 2000. Abstract.
Sabbah et al. "Treating Heart Failure With Cardiac Contractility Modulation Electrical Signals", Current Heart Failure Reports, 3(21): 21-24, 2006.
Saksena et al. "Prevention of Recurrent Atrial Fibrillation With Chronic Dual-Site Right Atrial Pacing", Journal of the American College of Cardiology, 28(3): 687-694, 1996, Abstract.
Sakuma et al. "A Model Analysis of Aftereffects of High-Intensity DC Stimulation on Action Potential of Ventricular Muscle", IEEE Transactions on Biomedical Engineering, 45(2): 258-267, 1998.
San Mauro et al. "Nerves of the Heart: A Comprehensive Review With A Clinical Point of View", Neuroanatomy, 8: 28-31, 2009.
Schirra et al. "Exendin(9-39) Amide Is An Antagonist of Glucagon-Like Peptide-1(7-36) Amide in Humans", Journal of Clinical Investigation, 101(7): 1421-1430, Apr. 1998.
Schirra et al. "Mechanisms of the Antidiabetic Action of Subcutaneous Glucagon-Like Peptide-1 (17-36) Amide In Non-Insulin Dependent Diabetes Mellitus", Journal of Endocrinology Ltd., 156(1): 177-186, Jan. 1998. Abstract.
Schwartz et al. "Exposure of Frog Hearts to CW or Amplitude-Modified VHF Fields: Selective Efflux of Calcium Ions at 16 Hz", Bioelectromagnetics, 11(4): 349-358, 1990, Abstract.
Serre et al. "Exendin-(9-39) Is An Inverse Agonist of the Murine Glucagon-Like Peptide-1 Receptor: Implications for Basal Intracellular Cyclic Adenosine 3',5'-Monophosphate Levels and ?-Cells Glucose Competence", Endocrinology, 139(11): 4448-4454, 1998.
Shah et al. "Impact of Lack of Suppression of Glucagon on Glucose Tolerance in Humans", American Journal of Physiology, AJP—Endocrinology and Metabolism, 277(2 Pt. 1): E283-E290, 1999.
Shmit et al. "Physiology of Man", Moscow Medicine, Mir, 1: 78, 1996.
Shuba et al. "Physiology of Vessel Smooth Muscles", Kiev Naukova Dumka, 142: 11-15, 142, 1988.
Shumaik et al. "Oleander Poisoning: Treatment With Digoxin-Specific Fab Antibody Fragments", Annals of Emergency Medicine, 17(7): 732-735, 1988.
Singh et al. "Effects of Islet Hormones on Nerve-Mediated and Acetylcholine-Evoked Secretory Responses in the Isolated Pancreas of Normal and Diabetic Rats", International Journal of Molecular Medicine, 1(3): 627-634, Mar. 1998. Abstract.
Skale et al. "Inhibition of Premature Ventricular Extrastimuli by Subthreshold Conditioning Stimuli", Journal of the American College of Cardiology, 6: 133-140, 1985. Abstract.
Solomonow et al. "Control of Muscle Contractile Force Through Indirect High-Frequency Stimulation", American Journal of Physical Medicine, 62(2): 71-82, Apr. 1983. Abstract.
Soria et al. "Cytosolic Calcium Oscillations and Insulin Release in Pancreatic Islets of Langerhans", Diabetes & Metabolism, 24: 37-40, 1998.
Stevenson et al. "Electrophysiologic Characteristics of Ventricular Tachycardia or Fibrillation in Relation to Age of Myocardial Infarction", The American Journal of Cardiology, 57(6): 387-391, Feb. 15, 1986. Abstract.
Stix et al. "FT Chronic Electrical Stimulation During the Absolute Refractory Period of the Myocardium Improves Severe Heart Failure", European Heart Journal, 3: 1-6, Feb. 2004.
Sukhorukov et al. "The Effect of Electrical Deformation Forces on the Electropermeabilization of Erythrocyte Membranes in Low-and High-Conductivity Media", The Journal of Membrane Biology, 163(3): 235-245, 1998. Abstract.
Supino "The System", Implantable Cardioverter Defibrillator Therapy: The Engineering-Clinical Interface, Kluwer Academic Publishers, Chap.8: 163-172, 1997.
Sutton et al. "The Foundation of Cardiac Pacing, Part I: An Illustrated Practical Guide to Basic Pacing", The Bakken Research Center Series, Chap.4: 50-59, 1991.
Sutton et al. "What Is A Pacemaker?", The Foundations of Cardiac Pacing, Part I: An Illustrated Practical Guide to Basic Pacing, Chap.4.5: 73-74, 1991.
Sweeny et al. "Countershock Strength-Duration Relatlonship for Myocardial Refractory Period Extension", Academic Emergency Medicine, 2(1): 57-62, 1995, Abstract.
Sweeny et al. "Refractory Interval After Transcardiac Shocks During Ventricular Fibrillation", Circulation, 94(11): 2947-2952, 1996.
Sweeny et al. "Ventricular Refractory Period Extension Caused by Defibrillation Shocks", Circulation, 82(3): 965-972, 1990.
Swerdlow et al. "Cardiovascular Collapse Caused by Electrocardiographically Silent 60-Hz Intracardiac Leakage Current: Implications for Electrical Safety", Circulation, 99: 2559-2564, 1999.
Talit et al. "The Effect of External Cardiac Pacing on Stroke Volume", PACE, 13(5): 598-602, May 1990. Abstract.
Taniguchi et al. "Inhomogeneity of Cellular Activation Time and Vmax in Normal Myocardial Tissue Under Electrical Field Stimulation", American Journal of Physiology—Heart and Circulatory Physiology, 267: H694-H705, 1994, Abstract.
Thakor et al. "Effect of Varying Pacing Waveform Shapes on Propagation and Hemodynamics in the Rabbit Heart", The Americal Journal of Cardiology, 79(6A): 36-43, 1997. Abstract.
Todd et al. "Subcutaneous Glucagon-Like Peptide I Improves Postprandial Glycaemic Control Over A 3-Week Period in Patients With Early Type 2 Diabetes", Clinical Science, 95: 325-329, 1998.
Tsong "Electroporation of Cell Membranes", Biophysical Journal, 60: 297-306, 1991.
Valdeolmillos et al. "In Vivo Synchronous Membrane Potential Oscillations in Mouse Pancreatic Beta-Cells: Lack of Co-Ordination Between Islets", Journal of Physiology, 493(1): 9-18, 1996.
Van Riper et al. "Electrical Field Stimulation-Mediated Relaxation of A Rabbit Middle Cerebral Artery. Evidence of A Cholinergic Endothelium-Dependent Component", Circulation Research, 70(6): 1104-1112, Jun. 1992.
Verrier et al. "Electrophysiologic Basis for T Wave Alternans as An Index of Vulnerability to Ventricular Fibrillation", Journal of Cardiovascular Electrophysiology, 5(5): 445-461, 1994. Abstract.
Wang et al. "Islet Amyloid Polypeptide Tonally Inhibits Beta-, Alpha-, and Delta-Cell Secretion in Isolated Rat Pancreatic Islets", American Journal of Physiology, AJP—Endocrinology and Metabolism, 276(1 Pt. 1): E19-E24, 1999.
Webster "Design of Cardiac Pacemakers", IEEE Press, p. xi-xiii, 1995.
Webster "Electrodes, Leads, and Biocompatibility", Design of Cardiac Pacemakers, IEEE Press, p. 141-144, 1995.
Wessale et al. "Stroke Volume and the Three Phase Cardiac Output Rate Relationship With Ventricular Pacing", PACE, 13: 673-680, 1990.
Windle et al. "Subthreshold Conditioning Stimuli Prolong Human Ventricular Refractoriness", American Journal of Cardiology, 57(6): 381-386, 1986. Abstract.
Wirtzfeld et al. "Physiological Pacing: Present Status and Future Developments", PACE, 10(Part I): 41-57, Jan. 1987. Abstract.
Wright et al. "Structure of Fab hGR-2 F6, A Competitive Antagonist of the Glucagon Receptor", Acta Crystallographica, Section D, Biological Crystallography, 56(Pt.5): 573-580, May 2000. Abstract.
Xue et al. "Neural-Network-Based Adaptive Matched Filtering for QRS Detection", IEEE Transactions on Biomedical Engineering, 39(4): 317-329, 1992. Abstract.
Yokoyama "The Phase of Supernormal Excitation in Relation to the Strength of Subthreshold Stimuli", Japanese Heart Journal, 17(3): 315-325, May 1976.

(56) References Cited

OTHER PUBLICATIONS

Yonemura et al. "Amelioration of Diabetes Mellitus in Partially Depancreatized Rats by Poly(ADP-Ribose) Synthetase Inhibitors. Evidence of Islet B-Cell Regeneration", Diabetes, 33(4): 401-404, Apr. 1984. Abstract.
Zhou et al. "Prevention of Action Potentials During Extracellular Electrical Stimulation of Long Duration", Journal of Cardiovascular & Electrophysiology, 8(7): 779-789, 1997. Abstract.
Zipes et al. "Cardiac Electrophysiology—From Cell to Bedside", Saunders Co., 4th Ed., 2004. Book Description.
Gussoni et al. "Dystrophin Expression in the MDX Mouse Restored by Stem Cell Transplantation", Nature, 401(6751): 390-394, 1999.
Ham et al. "Classification of Cardiac Arrhythmias Using Fuzzy Artmap", IEEE Transactions on Biomedical Engineering, 43(4): 425-429, 1996, Abstract.
Hammond et al. "Motor Innervation of the Cricopharyngeus Muscle by the Recurrent Lanryngeal Nerve", Journal of Applied Physiology, JAP, 83: 89-94, 1997.
Hardage et al. "Anti-Tachycardla Pacing and Cardioversion", Developments in Cardiovascular Medicine, Kluwer Academic Publishers, 188: 325-342, 1997.
Highfill et al. "Large-Scale Production of Murine Bone Marrow Cells in An Airlift Packed Bed Bioreactor", Biotechnology and Bioengineering, 50(5): 514-520, 1996.
Hinke et al. "Dipeptidyl Peptidase IV (DPIV/CD26) Degradation of Glucagon. Characterization of Glucagon Degradation Products and DPIV-Resistant Analogs", The Journal of Biological Chemistry, 275(6): 3827-3834, Feb. 11, 2000.
Hoffman et al. "Effects of Postextrasystolic Potentiation on Normal and Failing Hearts", Bulletin of the New York Academy of Medicine, 41(5): 498-534, 1965.
Holst et al. "Nervous Control of Pancreatic Endocrine Secretion in Pigs. I. Insulin and Glucagon Responses to Electrical Stimulation of the Vagus Nerves", Acta Physiologica Scandinavica, 111(1): 1-7, Jan. 1981. Abstract.
Holst et al. "Nervous Control of Pancreatic Endocrine Secretion in Pigs. II. The Effect of Pharmacological Blocking Agents on the Response to Vagal Stimulation", Acta Physiologica Scandinavica, 111(1): 9-14, 1981. Abstract.
Horner et al. "Electrode for Recording Direction of Activation, Conduction Velocity and Monophasic Action Potential of Myocardium", American Journal of Physiology, 272(4): H1917-H1927, 1997. Abstract.
Jaremko et al. "Advances Towards the Implantable Artifical Pancreas for Treatment of Diabetes", Diabetes Care, 21(3): 444-450,1998.
Josephson "Clinical Cardiac Electrophysiology: Techniques and Interpertations", Lea & Febiger, 2nd Ed., 2 P., 1991.
Kanno et al. "Establishment of A Simple and Practical Procedure Applicable to Therapeutic Angiogenesis", Circulation, 99: 2682-2687, 1999.
King et al. "Tire Inotropic Action of Paired Pulse Stimulation in the Normal and Failing Heart: An Experimental Study", Cardiovascular Research, 2: 122-129, 1968.
Knisley et al. "Effect of Field Stimulation on Cellular Repolarization in Rabbit Myocardium. Implications for Reentry Induction", Circulation Research, 70(4): 707-715, Apr. 1992.
Knisley et al. "Prolongation and Shortening of Action Potentials by Electrical Shocks in Frog Ventricular Muscle", American Journal of Physiology, 266(6): H2348-H2358, 1994.
Koller et al. "Relation Between Repolarization and Refractoriness During Programmed Electrical Stimulation in the Human Right Ventricle", Circulation, 91(9): 2378-2384, 1995.
Kurose et al. "Glucagon, Insulin and Somatostatin Secretion in Response to Sympathetic Neural Activation in Streptozotocin-Induced Diabetic Rats. A Study With the Isolated Perfused Rat Pancreas In Vitro", Diabetologia, 35(11): 1035-1041, Nov. 1992. Abstract.

Langberg et al. "Identification of Ventricular Tachycardia With Use of the Morphology of the Endocardial Electrogram", Circulation, 77(6): 1363-1369, 1988.
Lawo et al. "Electrical Signals Applied During the Absolute Refractory Period. An Investigational Treatment for Advanced Heart Failure in Patients With Normal QRS Duration", Journal of the American College of Cardiology, 46(12): 2229-2236, 2005.
Lindstroem et al. "Intracellular Calcium Oscillations in A T-Cell Line After Exposure to Extremely-Low-Frequency Magnetic Fields With Variable Frequencies and Flux Densities", Bioelectromagnetics, 16(1): 41-47, 1995. Abstract.
Loginov "[Accumulation of Calcium Ions in Myocardial Sarcoplasmic Reticulum of Restrained Rats Exposed to the Pulsed Electromagnetic Field]", Aviakosmicheskaia i Ekologicheskaia Meditsina (Aerospace and Environmental Medicine), 26(2): 49-51, Mar.-Apr. 1992. Abstract.
Loginov et al. "Effects of an Impulse Electromagnetic Field on Calcium Ion Accumulation in the Sarcoplasmic . . . ", Kosm. Biol. Aviakosm. Med., 15: 51-53, 1991. Abstract.
Lubart et al. "Effect of Light on Calcium Transport in Bull Sperm Cells", Journal of Photochemistry and Photobiology B, Biology, 15(4): 337-341, Sep. 15, 1992. Abstract.
Luiken et al. "Contraction-Induced Fatty Acid Translocase/CD36 Translocation in Rat Cardiac Myocytes Is Mediated Through AMP-Activated Protein Kinase Signaling", Diabetes, 52: 1627-1634, 2003.
Magnus et al. "Model of Beta-Cell Mitochondrial Calcium Handling and Electrical Activity. II. Mitochondrial Variables", American Journal of Physiology, Cell Physiology, 274(43): C1174-C1184, 1998.
Matheny et al. "Vagus Nerve Stimulation as A Method to Temporarily Slow or Arrest the Heart", Annals of Thoracic Surgery, 63(6 Suppl.): S28-29, 1997. Abstract.
McVeigh et al. "Noninvasive Measurement of Transmural Gradients in Myocardial Strain With MR Imaging", Radiology, 180(3): 677-684, 1991.
Mercando et al. "Automated Detection of Tachycardias by Antitachycardia Devices", Cardiac Electrophysiology: From Cell to Bedside, Chap. 100: 943-948, 2004.
Meurer et al. "Properties of Native and in Vitro Glycosylated Forms of the Glucogan-Like Peptide-1 Receptor Antagonist Exendin(9-39)", Metabolism: Clinical and Experimental, 48(6): 716-724, Jun. 1999. Abstract.
Miledi et al. "Effects of Membrane Polarization on Sarcoplasmic Calcium Release in Skeletal Muscle", Proceedings of the Royal Society of London, Series B, Containing Papers of A Biological Character, 213(1190): 1-13, Sep. 17, 1981. Abstract.
Misler et al. "Electrophysiology of Stimulus-Secretion Coupling in Human Beta-Cells", Diabetes, 41(10): 1221-1228, Oct. 1992. Abstract.
Moran et al. "Digoxin-Specific Fab Fragments Impair Renal Function in the Rat", Journal of Pharmacy and Pharmacology, 46(10): 854-856, 1994, Abstract.
Morse et al. "A Guide to Cardiac Pacemakers, Defibrillators and Related Products", Droege Computing Services, Inc., vol. I, Nov. 19, 1996.
Nadal et al. "Homologous and Heterologous Asynchronicity Between Identified Alpha-, Beta- and Delta-Cells Within Intact Islets of Langerhans in the Mouse", Journal of Physiology, 517(Pt.1): 85-93, 1999.
Nannini et al. "Muscle Recruitment With Intrafascicular Electrodes", IEEE Transactions on Biomedical Engineering, 38: 769-776, 1991. Abstract.
Neelagaru et al. "Nonexcilatory, Cardiac Contractility Modulation Electrical Impulses: Feasibility Study for Advanced Heart Failure in Patients With Normal QRS Duration", Heart Rythm, 3(10): 1140-1147, 2006.
Ohinata et al. "Proadrenomedullin N-Terminal 20 Peptide (PAMP) Elevates Blood Glucose Levels Via Bombesin Receptor in Mice", FEBS Letters, 473(2): 207-211, May 2000. Abstract.
Palti et al. "Islets of Langerhans Generate Wavelike Electric Activity Modulated by Glucose Concentration", Diabetes, 45(5): 595-601, May 1996. Abstract.

(56) References Cited

OTHER PUBLICATIONS

Pappone et al. "Cardiac Contractility Modulation by Electric Currents Applied During the Refractory Period in Patients With Heart Failure Secondary to Ischemic or Idiopathic Dilated Cardiomyopathy", The American Journal of Cardiology, 90(12): 1307-1313, Dec. 15, 2002.
Pappone et al. "Electrical Modulation of Cardiac Contractility: Clinical Aspects in Congestive Heart Failure", Heart Failure Reviews, 6(1): 55-60, Jan. 2001.
Pappone et al. "First Human Chronic Experience With Cardiac Contractility Modulation by Nonexcitatory Electrical Currents for Treating Systolic Heart Failure: Mid-Term Safety and Efficacy Results From A Multicenter Study", Journal of Cardiovadcular Electrophysiology, 15(4): 418-427, Apr. 2004.
Park et al. "Significant Cholinergic Role in Secretin-Stimulated Exocrine Secretion in Isolated Rat Pancreas", American Journal of Physiology, AJP—Gastrointestinal and Liver Physiology, 274(2): G413-G418, Feb. 1998.
Patterson et al. "Therapeutic Angiogenesis: The New Electrophysiology?", Circulation, 99(20): 2614-2616, 1999.
Paul et al. "Automatic Recognition of Ventricular Arrhythmias Using Temporal Electrogram Analysis", PACE, 14: 1265-1273, 1991.
U.S. Appl. No. 90/008,688, filed Jun. 15, 2007, Ben Haim.
U.S. Appl. No. 90/008,689, filed Jun. 23, 2009, Ben Haim.
U.S. Appl. No. 90/008,707, filed Jun. 7, 2007, Ben Haim.
U.S. Appl. No. 95/000,032, filed Sep. 8, 2009, Ben Haim.
Advisory Action Before the Filing of An Appeal Brief dated May 9, 2013 From the US Patent and Trademark Office Re. U.S. Appl. No. 11/673,812.
Advisory Action Before the Filing of An Appeal Brief dated Mar. 22, 2012 From the US Patent and Trademark Office Re. U.S. Appl. No. 11/886,154.
Amended Request for Ex Parte Reexamination of U.S. Pat. No. 6,317,631 Dated Aug. 20, 2007 From the US Patent and Trademark Office Re.: U.S. Appl. No. 90/008,689.
Applicant-Initiated Interview Summary dated Dec. 9, 2019 From the US Patent and Trademark Office Re. U.S. Appl. No. 15/942,637. (3 pages).
Applicant-Initiated Interview Summary dated Apr. 11, 2013 From the US Patent and Trademark Office Re. U.S. Appl. No. 11/673,812.
Applicant-Initiated Interview Summary dated Dec. 11, 2013 From the US Patent and Trademark Office Re. U.S. Appl. No. 13/970,647.
Applicant-Initiated Interview Summary dated Dec. 13, 2013 From the US Patent and Trademark Office Re. U.S. Appl. No. 10/116,201.
Applicant-Initiated Interview Summary dated Jul. 14, 2017 From the US Patent and Trademark Office Re. U.S. Appl. No. 11/792,811. (3 Pages).
Applicant-Initiated Interview Summary dated Sep. 15, 2017 From the US Patent and Trademark Office Re. U.S. Appl. No. 15/249,506. (3 pages).
Applicant-Initiated Interview Summary dated Apr. 23, 2015 From the US Patent and Trademark Office Re. U.S. Appl. No. 11/673,812.
Applicant-Initiated Interview Summary dated Nov. 28, 2012 From the US Patent and Trademark Office Re. U.S. Appl. No. 11/919,491.
Brief Communication: Oral Proceedings on Jan. 12, 2016 Dated Dec. 17, 2015 From the European Search Report Re. Application No. 06759102.4.
Communication Pursuant to Article 71(3) EPC dated Mar. 1, 2016 From the European Patent Office Re. Application No. 05853465.2.
Communication Pursuant to Article 94(3) EPC dated Mar. 2, 2009 From the European Patent Office Re. Application No. 05853465.2.
Communication Pursuant to Article 94(3) EPC dated Jun. 5, 2014 From the European Patent Office Re. Application No. 04719312.3.
Communication Pursuant to Article 94(3) EPC dated Nov. 10, 2015 From the European Patent Office Re. Application No. 01928181.5.
Communication Pursuant to Article 94(3) EPC dated Aug. 11, 2010 From the European Patent Office Re. Application No. 99931435.4.
Communication Pursuant to Article 94(3) EPC dated Nov. 11, 2015 From the European Patent Office Re. Application No. 04106247.2.
Communication Pursuant to Article 94(3) EPC dated Sep. 12, 2014 From the European Patent Office Re. Application No. 05853465.2.
Communication Pursuant to Article 94(3) EPC dated Jun. 17, 2008 From the European Patent Office Re. Application No. 01928181.5.
Communication Pursuant to Article 94(3) EPC dated Aug. 26, 2011 From the European Patent Office Re. Application No. 05853465.2.
Communication Pursuant to Article 94(3) EPC dated Aug. 26, 2011 From the European Patent Office Re. Application No. 06759102.4.
Communication Pursuant to Article 94(3) EPC dated Jan. 29, 2009 From the European Patent Office Re. Application No. 04106247.2.
Communication Pursuant to Article 96(2) EPC dated Mar. 2, 2007 From the European Patent Office Re. Application No. 97929478.2.
Communication to Pursuant to Article 94(3) EPC dated Mar. 4, 2009 From the European Search Report Re. Application No. 06759102.4.
Communication to Pursuant to Article 94(3) EPC dated Sep. 12, 2014 From the European Search Report Re. Application No. 06759102.4.
Communication Under Rule 71(3) EPC dated Mar. 4, 2015 From the European Patent Office Re. Application No. 04719312.3.
Communication Under Rule 71(3) EPC dated Feb. 5, 2016 From the European Search Report Re. Application No. 06759102.4.
Communication Under Rule 71(3) EPC dated May 24, 2017 From the European Patent Office Re. Application No. 01928181.5. (10 Pages).
Corrected Notice Of Allowability dated Nov. 3, 2015 From the US Patent and Trademark Office Re. U.S. Appl. No. 10/039,845.
Corrected Notice of Allowability dated Jul. 13, 2012 From the US Patent and Trademark Office Re. U.S. Appl. No. 11/933,168.
Corrected Notice of Allowability dated Aug. 17, 2012 From the US Patent and Trademark Office Re. U.S. Appl. No. 11/931,724.
Examination Report dated Jan. 9, 2014 From the Government of India, Patent Office, Intellectual Property Building Re. Application No. 5571/CHENP/2007.
Examination Report dated Sep. 17, 2013 From the Government of India, Patent Office, Intellectual Property Building Re. Application No. 5571/CHENP/2007.
Examination Report dated Feb. 20, 2013 From the Government of India, Patent Office, Intellectual Property Building Re. Application No. 5571/CHENP/2007.
Examination Report dated Feb. 27, 2013 From the Government of India, Patent Office, Intellectual Property Building Re. Application No. 2014/CHENP/2008.
Examination Report dated Dec. 30, 2013 From the Government of India. Patent Office, Intellectual Property Building Re. Application No. 5571/CHENP/2007.
Final Official Action dated Nov. 23, 2021 from US Patent and Trademark Office Re. U.S. Appl. No. 15/942,637. (16 pages).
Final Official Action dated Jun. 11, 2021 from the US Patent and Trademark Office Re. U.S. Appl. No. 16/232,088. (20 pages).
Final Official Action dated Apr. 17, 2020 from the US Patent and Trademark Office Re. U.S. Appl. No. 15/942,637. (8 pages).
Final Official Action dated Aug. 19, 2020 from the US Patent and Trademark Office Re. U.S. Appl. No. 15/942,637. (9 pages).
Hearing Notice Dated Aug. 3, 2017 From the Government of India, Patent Office, Intellectual Property Building Re. Application No. 2014/CHENP/2008. (2 Pages).
Hearing Notice in Reference of Application 5571/CHENP/2007 Dated Nov. 25, 2014 From the Government of India, Patent Office, Intellectual Property Building Re. Application No. 5571/CHENP/2007.
Hearing Notice in Reference of Application No. 5571/CHENP/2007 Dated Mar. 6, 2014 From the Government of India, Patent Office, Intellectual Property Building Re. Application No. 5571/CHENP/2007.
Inter Partes Reexamination Communication of Patent U.S. Pat. No. 6,330,476 Dated Sep. 4, 2007 From the US Patent and Trademark Office Re.: U.S. Appl. No. 95/000,032.
International Preliminary Report on Patentability dated Nov. 15, 2007 From the International Bureau of WIPO Re. Application No. PCT/US2006/017281.
International Preliminary Report on Patentability dated Jun. 21, 2007 From the International Bureau of WIPO Re. Application No. PCT/US2005/044557.

(56) References Cited

OTHER PUBLICATIONS

International Preliminary Report on Patentability dated Sep. 27, 2007 From the International Bureau of WIPO Re. Application No. PCT/IL2006/000345.
International Search Report and the Written Opinion dated May 12, 2006 From the International Searching Authority Re. Application No. PCT/US05/44557.
International Search Report and the Written Opinion dated Oct. 16, 2006 From the International Searching Authority Re. Application No. PCT/US06/17281.
Interview Summary dated Aug. 13, 2021 from the US Patent and Trademark Office Re. U.S. Appl. No. 16/232,088. (3 pages).
Invitation Pursuant to Rule 62a(1) EPC and Rule 63(1) EPC dated May 5, 2010 From the European Patent Office Re. Application No. 04719312.3.
Notice of Allowability dated Jul. 13, 2012 From the US Patent and Trademark Office Re. U.S. Appl. No. 11/933,168.
Notice Of Allowance dated May 6, 2016 From the US Patent and Trademark Office Re. U.S. Appl. No. 14/641,480.
Notice of Allowance dated Oct. 8, 2014 From the US Patent and Trademark Office Re. U.S. Appl. No. 14/181,900.
Notice of Allowance dated Jul. 10, 2015 From the US Patent and Trademark Office Re. U.S. Appl. No. 14/621,988.
Notice of Allowance dated Oct. 10, 2012 From the US Patent and Trademark Office Re. U.S. Appl. No. 11/802,685.
Notice of Allowance dated Jul. 11, 2012 From the US Patent and Trademark Office Re. U.S. Appl. No. 11/550,560.
Notice of Allowance dated Sep. 13, 2013 From the US Patent and Trademark Office Re. U.S. Appl. No. 13/662,775.
Notice Of Allowance dated Dec. 14, 2016 From the US Patent and Trademark Office Re. U.S. Appl. No. 11/673,812. (14 pages).
Notice of Allowance dated Jan. 14, 2011 From the US Patent and Trademark Office Re. U.S. Appl. No. 11/550,560.
Notice of Allowance dated May 15, 2012 From the US Patent and Trademark Office Re. U.S. Appl. No. 11/932,149.
Notice of Allowance dated Jul. 16, 2012 From the US Patent and Trademark Office Re. U.S. Appl. No. 11/931,889.
Notice of Allowance dated May 16, 2012 From the US Patent and Trademark Office Re. U.S. Appl. No. 11/886,154.
Notice of Allowance dated May 16, 2013 From the US Patent and Trademark Office Re. U.S. Appl. No. 11/919,491.
Notice Of Allowance dated Nov. 17, 2017 From the US Patent and Trademark Office Re. U.S. Appl. No. 11/792,811. (5 pages).
Notice of Allowance dated Jul. 18, 2012 From the US Patent and Trademark Office Re. U.S. Appl. No. 11/931,724.
Notice of Allowance dated Sep. 18, 2015 From the US Patent and Trademark Office Re. U.S. Appl. No. 10/039,845.
Notice of Allowance dated Jun. 20, 2012 From the US Patent and Trademark Office Re. U.S. Appl. No. 11/933,168.
Notice of Allowance dated May 20, 2014 From the US Patent and Trademark Office Re. U.S. Appl. No. 10/116,201.
Notice Of Allowance dated May 22, 2019 From the US Patent and Trademark Office Re. U.S. Appl. No. 15/249,506. (5 pages).
Notice of Allowance dated May 23, 2018 From the US Patent and Trademark Office Re. U.S. Appl. No. 15/249,506. (9 Pages).
Notice of Allowance dated Jan. 25, 2013 From the US Patent and Trademark Office Re. U.S. Appl. No. 11/919,491.
Notice of Allowance dated Jun. 27, 2012 From the US Patent and Trademark Office Re. U.S. Appl. No. 11/932,064.
Notice of Allowance dated May 27, 2010 From the US Patent and Trademark Office Re. U.S. Appl. No. 10/549,216.
Notice of Allowance dated Oct. 27, 2014 From the US Patent and Trademark Office Re. U.S. Appl. No. 13/970,647.
Notice of Allowance dated Dec. 28, 2010 From the US Patent and Trademark Office Re. U.S. Appl. No. 11/932,064.
Notice of Allowance dated Aug. 31, 2012 From the US Patent and Trademark Office Re. U.S. Appl. No. 12/910,943.
Notice of Non-Compliant Amendment dated Jun. 1, 2011 From US Patent and Trademark Office Re. U.S. Appl. No. 11/886,154.
Notice of Non-Compliant Amendment dated Dec. 12, 2011 From the US Patent and Trademark Office Re. U.S. Appl. No. 11/792,811.
Notice of Non-Compliant Amendment dated Jul. 15, 2011 From the US Patent and Trademark Office Re. U.S. Appl. No. 11/886,154.
Notice of Non-Compliant Amendment dated Jun. 17, 2013 From the US Patent and Trademark Office Re. U.S. Appl. No. 10/039,845.
Notice of Non-Compliant Amendment dated Mar. 23, 2017 From the US Patent and Trademark Office Re. U.S. Appl. No. 11/792,811. (3 pages).
Notification of Non-Compliant Appeal Brief (37 CFR 41.37) Dated Sep. 23, 2014 From the US Patent and Trademark Office Re. U.S. Appl. No. 10/039,845.
Notification of Reexamination dated Apr. 4, 2014 From the State Intellectual Property Office of the People's Republic of China Re. Application No. 200480012687.5 and Its Translation Into English.
Office Action dated Jan. 8, 2010 From the State Intellectual Property Office (SIPO) of the People's Republic of China Re.: Application No. 200480012687.5 and Its Translation Into English.
Office Action dated Oct. 12, 2004 From the Israeli Patent Office Re. Application No. 128955.
Office Action dated Jul. 13, 2009 From the State Intellectual Property Office of the People's Republic of China Re. Application No. 200480027283.3 and Its Translation Into English.
Office Action dated Dec. 15, 2008 From the State Intellectual Property Office (SIPO) of the People's Republic of China Re. Application No. 200480012687.5 and Its Translation Into English.
Office Action dated Jan. 18, 2012 From the State Intellectual Property Office (SIPO) of the People's Republic of China Re. Application No. 200480012687.5 and Its Translation Into English.
Office Action dated Oct. 21, 2014 From the State Intellectual Property Office (SIPO) of the People's Republic of China Re. Application No. 200480012687.5 and Its Translation Into English.
Office Action dated Nov. 25, 2010 From the State Intellectual Property Office (SIPO) of the People's Republic of China Re. Application No. 200480012687.5 and Its Translation Into English.
Office Action dated Apr. 30, 2015 From the State Intellectual Property Office (SIPO) of the People's Republic of China Re. Application No. 200480012687.5 and Its Translation Into English.
Official Action dated Apr. 1, 2021 From the US Patent and Trademark Office Re. U.S. Appl. No. 15/942,637. (16 Pages).
Official Action dated Aug. 1, 2007 From the US Patent and Trademark Office Re. U.S. Appl. No. 90/008,312.
Official Action dated Jul. 1, 2014 From the US Patent and Trademark Office Re. U.S. Appl. No. 10/116,201.
Official Action dated Jun. 1, 2009 From the US Patent and Trademark Office Re. U.S. Appl. No. 10/039,845.
Official Action dated Dec. 2, 2009 From the US Patent and Trademark Office Re. U.S. Appl. No. 11/932,149.
Official Action dated Jun. 2, 2016 From the US Patent and Trademark Office Re. U.S. Appl. No. 11/673,812.
Official Action dated Jan. 3, 2011 From the US Patent and Trademark Office Re. U.S. Appl. No. 11/932,149.
Official Action dated Jul. 3, 2012 From the US Patent and Trademark Office Re. U.S. Appl. No. 12/910,943.
Official Action dated Nov. 3, 2009 From the US Patent and Trademark Office Re. U.S. Appl. No. 11/931,724.
Official Action dated Feb. 4, 2010 From the US Patent and Trademark Office Re. U.S. Appl. No. 10/039,845.
Official Action dated Jan. 4, 2012 From the US Patent and Trademark Office Re. U.S. Appl. No. 11/673,812.
Official Action dated Dec. 5, 2008 From the US Patent and Trademark Office Re. U.S. Appl. No. 11/550,560.
Official Action dated Jan. 5, 2010 From the US Patent and Trademark Office Re. U.S. Appl. No. 11/802,685.
Official Action dated Nov. 5, 2009 From the US Patent and Trademark Office Re. U.S. Appl. No. 10/549,216.
Official Action dated Oct. 5, 2010 From the US Patent and Trademark Office Re. U.S. Appl. No. 10/039,845.
Official Action dated Jan. 6, 2010 From the US Patent and Trademark Office Re. U.S. Appl. No. 11/933,168.
Official Action dated Jan. 6, 2011 From the US Patent and Trademark Office Re. U.S. Appl. No. 11/931,724.

(56) References Cited

OTHER PUBLICATIONS

Official Action dated Jan. 6, 2012 From the US Patent and Trademark Office Re. U.S. Appl. No. 11/933,168.
Official Action dated Mar. 6, 2009 From the US Patent and Trademark Office Re. U.S. Appl. No. 11/931,889.
Official Action dated Mar. 6, 2009 From the US Patent and Trademark Office Re. U.S. Appl. No. 11/932,064.
Official Action dated Oct. 6, 2009 From the US Patent and Trademark Office Re. U.S. Appl. No. 11/550,560.
Official Action dated Feb. 8, 2021 From the US Patent and Trademark Office Re. U.S. Appl. No. 16/232,088. (28 Pages).
Official Action dated Jun. 8, 2017 From the US Patent and Trademark Office Re. U.S. Appl. No. 11/792,811. (15 pages).
Official Action dated Nov. 8, 2011 From the US Patent and Trademark Office Re. U.S. Appl. No. 11/931,889.
Official Action dated Oct. 8, 2009 From the US Patent and Trademark Office Re. U.S. Appl. No. 10/116,201.
Official Action dated Aug. 9, 2011 From the US Patent and Trademark Office Re. U.S. Appl. No. 11/932,149.
Official Action dated Oct. 10, 2008 From the US Patent and Trademark Office Re. U.S. Appl. No. 09/980,748.
Official Action dated Sep. 10, 2013 From the US Patent and Trademark Office Re. U.S. Appl. No. 10/039,845.
Official Action dated Jun. 11, 2010 From the US Patent and Trademark Office Re. U.S. Appl. No. 11/550,560.
Official Action dated Jun. 11, 2010 From the US Patent and Trademark Office Re. U.S. Appl. No. 11/932,064.
Official Action dated Oct. 11, 2011 From the US Patent and Trademark Office Re. U.S. Appl. No. 11/919,491.
Official Action dated Sep. 11, 2009 From the US Patent and Trademark Office Re. U.S. Appl. No. 09/980,748.
Official Action dated May 12, 2011 From the US Patent and Trademark Office Re. U.S. Appl. No. 10/039,845.
Official Action dated Sep. 12, 2008 From the US Patent and Trademark Office Re. U.S. Appl. No. 10/039,845.
Official Action dated Aug. 13, 2020 from the US Patent and Trademark Office Re. U.S. Appl. No. 16/232,088. (66 pages).
Official Action dated Jan. 13, 2011 From the US Patent and Trademark Office Re. U.S. Appl. No. 11/931,889.
Official Action dated May 13, 2011 From the US Patent and Trademark Office Re. U.S. Appl. No. 11/933,168.
Official Action dated Oct. 13, 2010 From the US Patent and Trademark Office Re. U.S. Appl. No. 11/919,491.
Official Action dated Apr. 14, 2011 From the US Patent and Trademark Office Re. U.S. Appl. No. 11/932,149.
Official Action dated Jan. 14, 2014 From the US Patent and Trademark Office Re. U.S. Appl. No. 10/039,845.
Official Action dated Jul. 14, 2017 From the US Patent and Trademark Office Re. U.S. Appl. No. 15/249,506. (330 Pages).
Official Action dated Sep. 14, 2009 From the US Patent and Trademark Office Re. U.S. Appl. No. 11/931,889.
Official Action dated Sep. 14, 2011 From the US Patent and Trademark Office Re. U.S. Appl. No. 11/886,154.
Official Action dated Apr. 15, 2014 From the US Patent and Trademark Office Re. U.S. Appl. No. 13/970,647.
Official Action dated Dec. 15, 2011 From the US Patent and Trademark Office Re. U.S. Appl. No. 12/910,943.
Official Action dated Feb. 15, 2012 From the US Patent and Trademark Office Re. U.S. Appl. No. 11/802,685.
Official Action dated Jan. 15, 2015 From the US Patent and Trademark Office Re. U.S. Appl. No. 11/673,812.
Official Action dated Jul. 15, 2008 From the US Patent and Trademark Office Re. U.S. Appl. No. 10/116,201.
Official Action dated Sep. 15, 2016 From the US Patent and Trademark Office Re. U.S. Appl. No. 14/941,790.
Official Action dated Oct. 16, 2013 From the US Patent and Trademark Office Re. U.S. Appl. No. 13/970,647.
Official Action dated Feb. 17, 2012 From the US Patent and Trademark Office Re. U.S. Appl. No. 11/932,149.
Official Action dated Jun. 17, 2010 From the US Patent and Trademark Office Re. U.S. Appl. No. 10/549,216.
Official Action dated Jan. 18, 2012 From the US Patent and Trademark Office Re. U.S. Appl. No. 11/886,154.
Official Action dated Jul. 18, 2007 From the US Patent and Trademark Office Re. U.S. Appl. No. 10/039,845.
Official Action dated Sep. 19, 2016 From the US Patent and Trademark Office Re. U.S. Appl. No. 11/792,811.
Official Action dated Dec. 20, 2011 From the US Patent and Trademark Office Re. U.S. Appl. No. 10/039,845.
Official Action dated Dec. 21, 2012 From the US Patent and Trademark Office Re. U.S. Appl. No. 11/673,812.
Official Action dated Feb. 21, 2012 From the US Patent and Trademark Office Re. U.S. Appl. No. 10/116,201.
Official Action dated Jul. 21, 2010 From the US Patent and Trademark Office Re. U.S. Appl. No. 11/802,685.
Official Action dated May 21, 2007 From the US Patent and Trademark Office Re. U.S. Appl. No. 09/980,748.
Official Action dated May 21, 2010 From the US Patent and Trademark Office Re. U.S. Appl. No. 10/116,201.
Official Action dated Oct. 21, 2019 From the US Patent and Trademark Office Re. U.S. Appl. No. 15/942,637. (311 pages).
Official Action dated Mar. 22, 2011 From the US Patent and Trademark Office Re. U.S. Appl. No. 11/886,154.
Official Action dated Dec. 23, 2010 From the US Patent and Trademark Office Re. U.S. Appl. No. 09/980,748.
Official Action dated Jun. 23, 2009 From the US Patent and Trademark Office Re. U.S. Appl. No. 10/549,216.
Official Action dated Jan. 24, 2011 From the US Patent and Trademark Office Re. U.S. Appl. No. 11/919,491.
Official Action dated Jun. 26, 2008 From the US Patent and Trademark Office Re. U.S. Appl. No. 11/536,794.
Official Action dated Oct. 26, 2017 From the US Patent and Trademark Office Re. U.S. Appl. No. 15/249,506. (12 pages).
Official Action dated Aug. 27, 2012 From the US Patent and Trademark Office Re. U.S. Appl. No. 11/919,491.
Official Action dated Aug. 27, 2015 From the US Patent and Trademark Office Re. U.S. Appl. No. 11/673,812.
Official Action dated Apr. 28, 2011 From the US Patent and Trademark Office Re. U.S. Appl. No. 11/931,889.
Official Action dated Apr. 28, 2015 From the US Patent and Trademark Office Re. U.S. Appl. No. 14/621,988.
Official Action dated Aug. 28, 2009 From the US Patent and Trademark Office Re. U.S. Appl. No. 11/802,685.
Official Action dated Aug. 28, 2009 From the US Patent and Trademark Office Re. U.S. Appl. No. 11/932,064.
Official Action dated Feb. 28, 2008 From the US Patent and Trademark Office Re. U.S. Appl. No. 09/980,748.
Official Action dated Jun. 28, 2010 From the US Patent and Trademark Office Re. U.S. Appl. No. 11/931,889.
Official Action dated Apr. 29, 2009 From the US Patent and Trademark Office Re. U.S. Appl. No. 09/980,748.
Official Action dated Jul. 29, 2013 From the US Patent and Trademark Office Re. U.S. Appl. No. 10/116,201.
Official Action dated May 29, 2013 From the US Patent and Trademark Office Re. U.S. Appl. No. 13/662,775.
Official Action dated Sep. 29, 2010 From the US Patent and Trademark Office Re. U.S. Appl. No. 11/933,168.
Official Action dated Apr. 30, 2010 From the US Patent and Trademark Office Re. U.S. Appl. No. 11/931,724.
Official Action dated Apr. 30, 2010 From the US Patent and Trademark Office Re. U.S. Appl. No. 11/932,149.
Official Action dated Aug. 30, 2006 From the US Patent and Trademark Office Re. U.S. Appl. No. 09/980,748.
Official Action dated Aug. 31, 2007 From the US Patent and Trademark Office Re. U.S. Appl. No. 11/536,794.
Official Action dated Aug. 31, 2010 From the US Patent and Trademark Office Re. U.S. Appl. No. 11/550,560.
Official Action dated Mar. 31, 2011 From the US Patent and Trademark Office Re. U.S. Appl. No. 11/673,812.
Pre-Appeal Brief Request for Review Dated Aug. 9, 2011 From the US Patent and Trademark Office Re. U.S. Appl. No. 11/933,168.

(56) References Cited

OTHER PUBLICATIONS

Provision of the Minutes in Accordance With Rule 124(4) EPC dated May 23, 2017 From the European Patent Office Re. Application No. 01928181.5. (7 Pages).
Request for Ex Parte Reexamination of U.S. Pat. No. 6,363,279—IDS Submitted Dec. 31, 2007 From the US Patent and Trademark Office Re.: U.S. Appl. No. 90/008,688.
Request for Ex Parte Reexamination of U.S. Pat. No. 6,363,279—Notice of Intent to Issue Reexamination Certificate Dated Mar. 18, 2009 From the US Patent and Trademark Office Re.: U.S. Appl. No. 90/008,688.
Request for Ex Parte Reexamination of U.S. Pat. No. 6,363,279—Official Action Dated Jun. 20, 2008 From the US Patent and Trademark Office Re.: U.S. Appl. No. 90/008,688.
Request for Ex Parte Reexamination of U.S. Pat. No. 6,363,279—Order Granting Request Dated Nov. 5, 2007 From the US Patent and Trademark Office Re.: U.S. Appl. No. 90/008,688.
Request for Ex Parte Reexamination of U.S. Pat. No. 6,363,279 Dated Jun. 8, 2007 From the US Patent and Trademark Office Re.: U.S. Appl. No. 90/008,688.
Request for Ex Parte Reexamination of U.S. Pat. No. 6,363,279, Response to Official Action Dated Jun. 20, 2008 Submitted Aug. 20, 2008 From the US Patent and Trademark Office Re.: U.S. Appl. No. 90/008,688.
Request for Ex Parte Reexamination of U.S. Pat. No. 6,236,887—IDS Submitted Oct. 17, 2007 From the US Patent and Trademark Office Re.: U.S. Appl. No. 90/008,707.
Request for Ex Parte Reexamination of U.S. Pat. No. 6,236,887—IDS Submitted Sep. 29, 2008 From the US Patent and Trademark Office Re.: U.S. Appl. No. 90/008,707.
Request for Ex Parte Reexamination of U.S. Pat. No. 6,236,887—Notice of Intent to Issue Ex Parte Examination Certificate Dated Mar. 19, 2009 From the US Patent and Trademark Office Re.: U.S. Appl. No. 90/008,707.
Request for Ex Parte Reexamination of U.S. Pat. No. 6,236,887—Official Action and IDS Considered Dated Jun. 20, 2008 From the US Patent and Trademark Office Re.: U.S. Appl. No. 90/008,707.
Request for Ex Parte Reexamination of U.S. Pat. No. 6,236,887—Official Action Granting Request for Ex Parte Examination Dated Aug. 17, 2007 From the US Patent and Trademark Office Re.: U.S. Appl. No. 90/008,707.
Request for Ex Parte Reexamination of U.S. Pat. No. 6,236,887 Dated Jun. 13, 2007 From the US Patent and Trademark Office Re.: U.S. Appl. No. 90/008,707.
Request for Ex Parte Reexamination of U.S. Pat. No. 6,298,268—Certificate of Reexamination Issued Mar. 7, 2006, U.S. Appl. No. 90/006,788.
Request for Ex Parte Reexamination of U.S. Pat. No. 6,298,268—IDS Considered Feb. 22, 2005, U.S. Appl. No. 90/006,788.
Request for Ex Parte Reexamination of U.S. Pat. No. 6,298,268—Notice of Intent to Issue Certificate of Reexamination Dated Mar. 29, 2005, U.S. Appl. No. 90/006,788.
Request for Ex Parte Reexamination of U.S. Pat. No. 6,298,268 Dated Oct. 10, 2003, U.S. Appl. No. 90/006,788.
Request for Ex Parte Reexamination of U.S. Pat. No. 6,298,268 Order Granting Request for Ex Parte Reexamination Dated Dec. 19, 2003, U.S. Appl. No. 90/006,788.
Request for Ex Parte Reexamination of U.S. Pat. No. 6,317,631—Amendment in Response to Official Action Dated Jun. 20, 2008, Filed Aug. 20, 2008 From the US Patent and Trademark Office Re.: U.S. Appl. No. 90/008,689.
Request for Ex Parte Reexamination of U.S. Pat. No. 6,317,631—IDS Dated Sep. 26, 2008 From the US Patent and Trademark Office Re.: U.S. Appl. No. 90/008,689.
Request for Ex Parte Reexamination of U.S. Pat. No. 6,317,631—IDS Dated Dec. 31, 2007 From the US Patent and Trademark Office Re.: U.S. Appl. No. 90/008,689.
Request for Ex Parte Reexamination of U.S. Pat. No. 6,317,631—Notice of Intent to Issue Certificate of Reexamination Dated Mar. 18, 2009 From the US Patent and Trademark Office Re.: U.S. Appl. No. 90/008,689.
Request for Ex Parte Reexamination of U.S. Pat. No. 6,317,631—Official Action Dated Jun. 20, 2008, U.S. Appl. No. 90/008,689.
Request for Ex Parte Reexamination of U.S. Pat. No. 6,317,631—Order Granting Reexamination Dated Nov. 5, 2007, U.S. Appl. No. 90/008,689.
Request for Ex Parte Reexamination of U.S. Pat. No. 6,317,631—IDS Dated Jun. 8, 2007, U.S. Appl. No. 90/008,689.
Request for Ex Parte Reexamination of U.S. Pat. No. 6,330,476—IDS Dated May 31, 2006.
Request for Ex Parte Reexamination of U.S. Pat. No. 6,330,476—Comments by 3rd Party Requestor, Response Thereto and Official Action Issued Jul. 16, 2008, U.S. Appl. No. 95/000,032.
Request for Ex Parte Reexamination of U.S. Pat. No. 6,330,476—Communication of Right to Appeal Dated Jul. 16, 2008, Re. U.S. Appl. No. 95/000,032.
Request for Ex Parte Reexamination of U.S. Pat. No. 6,330,476—IDS Filed May 4, 2007 Re. U.S. Appl. No. 95/000,032.
Request for Ex Parte Reexamination of U.S. Pat. No. 6,330,476—Official Action by USPTO Issued Mar. 23, 2004, U.S. Appl. No. 95/000,032.
Request for Ex Parte Reexamination of U.S. Pat. No. 6,330,476—Order Granting Request for Reexamination Dated Mar. 23, 2004 From the US Patent and Trademark Office Re.: U.S. Appl. No. 95/000,032.
Request for Ex Parte Reexamination of U.S. Pat. No. 6,330,476 Dated Dec. 31, 2003 From the US Patent and Trademark Office Re.: U.S. Appl. No. 95/000,032.
Request for Ex Parte Reexamination of U.S. Pat. No. 6,463,324—Amendment in Response to Official Action Dated Aug. 1, 2007 Filed Oct. 1, 2007 From the US Patent and Trademark Office Re.: U.S. Appl. No. 90/008,312.
Request for Ex Parte Reexamination of U.S. Pat. No. 6,463,324—Certificate of Reexamination Dated Apr. 29, 2008 From the US Patent and Trademark Office Re.: U.S. Appl. No. 90/008,312.
Request for Ex Parte Reexamination of U.S. Pat. No. 6,463,324—Official Action—Notice of Intent to Reexamine Dated Jan. 24, 2008 From the US Patent and Trademark Office Re.: U.S. Appl. No. 90/008,312.
Request for Ex Parte Reexamination of U.S. Pat. No. 6,463,324—Official Action Dated Aug. 1, 2007 From the US Patent and Trademark Office Re.: U.S. Appl. No. 90/008,312.
Request for Ex Parte Reexamination of U.S. Pat. No. 6,463,324—Official Action, Interview Summary and References Considered Dated Nov. 6, 2007 From the US Patent and Trademark Office Re.: U.S. Appl. No. 90/008,312.
Request for Ex Parte Reexamination of U.S. Pat. No. 6,463,324 Dated Nov. 1, 2006 From the US Patent and Trademark Office Re.: U.S. Appl. No. 90/008,312.
Response dated Aug. 1, 2011 to Notice of Non-Compliant Amendment of Jul. 15, 2011 From the US Patent and Trademark Office Re. U.S. Appl. No. 11/886,154.
Response dated Jul. 1, 2010 to Invitation Pursuant to Rule 62a(1) EPC and Rule 63(1) EPC of May 5, 2010 From the European Patent Office Re.: Application No. 04719312.3.
Response dated Mar. 1, 2010 to Official Action of Aug. 28, 2009 From the US Patent and Trademark Office Re. U.S. Appl. No. 11/932,064.
Response dated Oct. 1, 2007 to Official Action of Aug. 1, 2007 From the US Patent and Trademark Office Re. U.S. Appl. No. 90/008,312.
Response dated Sep. 1, 2004 to Communication Pursuant to Article 96(2) EPC of Mar. 2, 2004 From the European Patent Office Re.: Application No. 97929478.2.
Response dated Feb. 2, 2010 to Official Action of Dec. 2, 2009 From the US Patent and Trademark Office Re. U.S. Appl. No. 11/932,149.
Response dated Feb. 3, 2011 to Official Action of Jan. 3, 2011 From the US Patent and Trademark Office Re. U.S. Appl. No. 11/932,149.
Response dated Mar. 4, 2010 to Official Action of Nov. 5, 2010 From the US Patent and Trademark Office Re. U.S. Appl. No. 10/549,216.

(56) References Cited

OTHER PUBLICATIONS

Response dated May 4, 2009 to Official Action of Nov. 3, 2008 From the US Patent and Trademark Office Re. U.S. Appl. No. 10/116,201.
Response dated May 4, 2010 to Official Action of Jan. 5, 2010 From the US Patent and Trademark Office Re. U.S. Appl. No. 11/802,685.
Response dated Oct. 4, 2007 to Official Action of Sep. 4, 2007 From the US Patent and Trademark Office Re. U.S. Appl. No. 95/000,032.
Response dated Apr. 6, 2010 to Official Action of Oct. 6, 2009 From the US Patent and Trademark Office Re. U.S. Appl. No. 11/550,560.
Response dated May 6, 2010 to Office Action dated Jan. 8, 2010 From the State Intellectual Property Office (SIPO) of the People's Republic of China Re.: Application No. 200480012687.5.
Response dated Feb. 7, 2010 to Official Action dated Dec. 2, 2009 From the US Patent and Trademark Office Re. U.S. Appl. No. 11/932,149.
Response dated Feb. 7, 2010 to Official Action dated Nov. 3, 2009 From the US Patent and Trademark Office Re. U.S. Appl. No. 11/931,724.
Response dated Feb. 7, 2011 to Official Action dated Oct. 5, 2010 From the US Patent and Trademark Office Re. U.S. Appl. No. 10/039,845.
Response dated Jun. 7, 2010 to Official Action dated Jan. 6, 2010 From the US Patent and Trademark Office Re. U.S. Appl. No. 11/933,168.
Response dated Dec. 8, 2011 to Office Action dated Aug. 3, 2011 From the State Intellectual Property Office (SIPO) of the People's Republic of China Re.: Application No. 200480012687.5.
Response dated Dec. 8, 2011 to Official Action dated Aug. 9, 2011 From the US Patent and Trademark Office Re. U.S. Appl. No. 11/932,149.
Response dated Feb. 9, 2010 to Official Action dated Oct. 8, 2009 From the US Patent and Trademark Office Re. U.S. Appl. No. 10/116,201.
Response dated Apr. 10, 2011 to Official Action dated Jan. 6, 2011 From the US Patent and Trademark Office Re. U.S. Appl. No. 11/931,724.
Response dated Aug. 10, 2011 to Official Action dated May 13, 2011 From the US Patent and Trademark Office Re. U.S. Appl. No. 11/933,168.
Response dated Oct. 11, 2011 to Official Action dated May 12, 2011 From the US Patent and Trademark Office Re. U.S. Appl. No. 10/039,845.
Response dated Oct. 12, 2010 to Official Action dated Jun. 11, 2010 From the US Patent and Trademark Office Re. U.S. Appl. No. 11/932,064.
Response dated Dec. 13, 2010 to Official Action dated Jun. 11, 2010 From the US Patent and Trademark Office Re. U.S. Appl. No. 11/550,560.
Response dated Dec. 13, 2010 to Official Action dated Oct. 13, 2010 From the US Patent and Trademark Office Re. U.S. Appl. No. 11/919,491.
Response dated Jul. 13, 2010 to Notice of Reasons for Rejection dated Apr. 27, 2010 From the Japanese Patent Office Re. Application No. 2007-206282.
Response dated Oct. 13, 2010 to Official Action dated Apr. 30, 2010 From the US Patent and Trademark Office Re. U.S. Appl. No. 11/932,149.
Response dated Dec. 14, 2011 to Official Action dated Sep. 14, 2011 From the US Patent and Trademark Office Re. U.S. Appl. No. 11/886,154.
Response dated Feb. 14, 2011 to Official Action dated Jan. 13, 2011 From the US Patent and Trademark Office Re. U.S. Appl. No. 11/931,889.
Response dated Mar. 15, 2010 to Official Action dated Sep. 14, 2009 From the US Patent and Trademark Office Re. U.S. Appl. No. 11/931,889.
Response dated May 15, 2011 to Office Action dated Nov. 25, 2010 From the State Intellectual Property Office (SIPO) of the People's Republic of China Re.: Application No. 200480012687.5. & Claims in English.
Response dated Jan. 17, 2008 to Official Action dated Jul. 18, 2007 From the US Patent and Trademark Office Re. U.S. Appl. No. 10/039,845.
Response dated Apr. 20, 2006 to Communication Pursuant ot Article 96(2) EPC dated Nov. 2, 2005 From the European Patent Office Re.: Application No. 97929478.2.
Response dated Apr. 20, 2011 to Official Action dated Mar. 22, 2011 From the US Patent and Trademark Office Re. U.S. Appl. No. 11/886,154.
Response dated Aug. 20, 2008 to Official Action dated Jun. 20, 2008 From the US Patent and Trademark Office Re. U.S. Appl. No. 90/008,689.
Response dated Sep. 20, 2010 to Official Action dated May 21, 2010 From the US Patent and Trademark Office Re. U.S. Appl. No. 10/116,201.
Response dated May 21, 2008 to Office Action dated Dec. 11, 2007 From the Japanese Patent Office Re. Application No. 09-525055.
Response dated Nov. 22, 2009 to Official Action dated Jun. 1, 2009 From the US Patent and Trademark Office Re. U.S. Appl. No. 10/039,845.
Response dated Nov. 22, 2010 to Official Action dated Jul. 21, 2010 From the US Patent and Trademark Office Re. U.S. Appl. No. 11/802,685.
Response dated Dec. 24, 2006 to Office Action dated Jul. 18, 2006 From the Japanese Patent Office Re. Application No. 10-513446.
Response dated Jan. 24, 2011 to Supplementary Partial European Search Report dated Nov. 4, 2010 From the European Patent Office Re. Application No. 04719312.3.
Response dated Dec. 25, 2006 to Notice of Reasons for Rejection dated Jul. 18, 2006 From the Japanese Patent Office Re. Application No. 09-529637.
Response dated Jul. 25, 2011 to Official Action dated Jan. 24, 2011 From the US Patent and Trademark Office Re. U.S. Appl. No. 11/919,491.
Response dated Dec. 27, 2011 to Communication Pursuant to Article 94(3) EPC dated Aug. 26, 2011 From the European Patent Office Re. Application No. 06759102.4.
Response dated Dec. 27, 2011 to Communication Pursuant to Article 94(3) EPC dated Aug. 26, 2011 From the European Patent Office Re.: Application No. 05853465.2.
Response dated Jul. 27, 2011 to Official Action dated Apr. 28, 2011 From the US Patent and Trademark Office Re. U.S. Appl. No. 11/931,889.
Response dated Oct. 28, 2010 to Official Action dated Jun. 28, 2010 From the US Patent and Trademark Office Re. U.S. Appl. No. 11/931,889.
Response dated Jun. 29, 2011 to Notice of Non-Compliant Amendment dated Jun. 1, 2011 From the US Patent and Trademark Office Re. U.S. Appl. No. 11/886,154.
Response dated Sep. 30, 2010 to Official Action dated Apr. 30, 2010 From the US Patent and Trademark Office Re. U.S. Appl. No. 11/931,724.
Response dated Aug. 31, 2011 to Official Action dated Mar. 31, 2011 From the US Patent and Trademark Office Re. U.S. Appl. No. 11/673,812.
Response dated Jan. 31, 2011 to Official Action dated Sep. 29, 2010 From the US Patent and Trademark Office Re. U.S. Appl. No. 11/933,168.
Response dated Jul. 31, 2011 to Official Action dated Apr. 14, 2011 From the US Patent and Trademark Office Re. U.S. Appl. No. 11/932,149.
Response in Conjunction With An RCE dated May 4, 2010 to Official Action dated Feb. 4, 2010 From the US Patent and Trademark Office Re.: U.S. Appl. No. 10/039,845.
Restriction Official Action dated Mar. 17, 2016 From the US Patent and Trademark Office Re. U.S. Appl. No. 11/792,811.
Second Notice Of Allowance dated Sep. 28, 2018 From the US Patent and Trademark Office Re. U.S. Appl. No. 15/249,506. (5 pages).

(56) References Cited

OTHER PUBLICATIONS

Summons to Attend Oral Proceedings Pursuant to Rule 115(1) EPC Dated May 8, 2015 From the European Search Report Re. Application No. 06759102.4.
Summons to Attend Oral Proceedings Pursuant to Rule 115(1) EPC Dated Dec. 22, 2008 From the European Patent Office Re.: Application No. 97929480.8.
Summons to Attend Oral Proceedings Pursuant to Rule 115(1) EPC Dated Jun. 22, 2015 From the European Patent Office Re. Application No. 05853465.2.
Summons to Attend Oral Proceedings Pursuant to Rule 115(1) EPC Dated Dec. 23, 2016 From the European Patent Office Re. Application No. 01928181.5. (2 Pages).
Summons to Attend Oral Proceedings Pursuant to Rule 115(1) EPC Dated Sep. 26, 2016 From the European Patent Office Re. Application No. 01928181.5.
Supplemental Notice of Allowability dated Aug. 9, 2013 From the US Patent and Trademark Office Re. U.S. Appl. No. 11/919,491.
Supplemental Notice of Allowability dated Dec. 17, 2014 From the US Patent and Trademark Office Re. U.S. Appl. No. 13/970,647.
Supplemental Notice of Allowability dated Aug. 27, 2013 From the US Patent and Trademark Office Re. U.S. Appl. No. 11/919,491.
Supplemental Response dated Apr. 18, 2011 to Response of Apr. 10, 2011 to Official Action dated Jan. 6, 2011 From the US Patent and Trademark Office Re.: U.S. Appl. No. 11/931,724.
Supplementary European Search Report and the European Search Opinion dated Nov. 28, 2008 From the European Patent Office Re. Application No. 05853465.2.
Supplementary European Search Report and the European Search Opinion dated Nov. 28, 2008 From the European Patent Office Re.: Application No. 006759102.4.
Supplementary Partial European Search Report dated Nov. 4, 2010 From the European Patent Office Re. Application No. 04719312.3.
Supplementary Partial European Search Report dated Sep. 6, 2006 From the European Patent Office Re. Application No. 01928181.5.
Translation of Notice of Reasons for Rejection dated Jul. 18, 2006 From the Japanese Patent Office Re. Application No. 09-529637.
Translation of Notice of Reasons for Rejection dated Apr. 27, 2010 From the Japanese Patent Office Re. Application No. 2007-206282.
Translation of Office Action dated Aug. 3, 2011 From the State Intellectual Property Office (SIPO) of the People's Republic of China Re.: Application .No. 200480012687.5.
Translation of Office Action dated Apr. 20, 2011 From the State Intellectual Property Office (SIPO) of the People's Republic of China Re.: Application No. 200480012687.5.
USPTO Public Print Out of Interference File Content of Interference dated Apr. 4, 2011 From the US Patent and Trademark Office Re. Interference No. 105,765.
USPTO Public Print Out of Interference File Content of Interference dated Apr. 4, 2011 From the US Patent and Trademark Office Re. Interference No. 105,768.
Adeghate et al. "Effect of Electrical Field Stimulation on Insulin and Glucagon Secretion From the Pancreas of Normal and Diabetic Rats", Hormone and Metabolic Research, 33(5): 281-289, May 2001. Abstract.
Antman et al. "Treatment of 150 Cases of Life-Threatening Digitalis Intoxication With Digoxin-Specific Fab Antibody Fragments", Circulation, 81(6): 1744-1752, Jun. 1990.
Antoni et al. "Polarization Effects of Sinusoidal 50-Cycle Alternating Current on Membrane Potential of Mammalian Cardiac Fibres", Pfl?gers Archiv European Journal of Physiology, 314(4): 274-291, 1970. Abstract.
Augello et al. "Cardiac Contractility Modulation by Non-Excitatory Electrical Currents. The New Frontier for Electrical Therapy of Heart Failure", Italian Heart Journal, 5(Suppl.6): 68S-75S, 2004.
Babsky et al. Translation of Physiology of Man, Moscow Medicine, p. 115, 348-351, 376, Extracts, 1972.
Bach "Tach Arrhythmia Detection", Implantable Cardioverter Defibrilator Therapy: The Engineering—Clinical Interface, Kluwer Academic Publishers, Chap. 15: 303-323, 1997.

Bakker et al. "Beneficial Effects of Biventricular Pacing of Congestive Heart Failure", Pace, 17(PartII): 318, 1994.
Bakker et al. "Biventricular Pacing in End-Stage Heart Failure Improves Functional Capacity and Left Ventricular Function", Journal of Interventional Cardiac Electrophysiology 4: 395-404, 2000.
Bargheer et al. "Prolongation of Monophasic Action Potential Duration and the Refractory Period in the Human Heart by Tedisamil, A New Potassium-Blocking Agent", Journal European Heart, 15(10): 1409-1414, 1994.
Bergsten et al. "Synchronous Oscillations of Cytoplasmic Ca2+ and Insulin Release in Glucose-Stimulated Pancreatic Islets", The Journal of Biological Chemistry, 269(12): 8749-8753, Mar. 25, 1994.
Bers "Excitation-Contracting Coupling", Excitation-Contraction Coupling and Cardiac Contractile Force, 2nd Ed., Chap.8: 203-407, 2001. (Part 1).
Bers "Excitation-Contracting Coupling", Excitation-Contraction Coupling and Cardiac Contractile Force, 2nd Ed., Chap.8: 203-407, 2001. (Part 2).
Blank et al. "Initial Interactions in Electromagnetic Field-Induced Biosynthesis", Journal of Cellular Physiology, 199: 359-363, 2004.
Borst et al. "Coronary Artery Bypass Gratting Without Cardiopulomonary Bypass and Without Interuption of Native Coronary Flow Using A Novel Anastomosis Site Restraining Device (Octupus)", Journal of the American College of Cardiology, 27(6): 1356-1364, 1996.
Bronzino "Biomedical Engineering Handbook", IEEE Press/CRC Press, Chap. 82.5: 1288, 1995.
Brumwell et al. "The Amplifier Sensing the Depolarization", Implantable Cardioverter Defibrillator Therapy: The Engineering-Clinical Interface, Kluwer Academic Publishers, Chap. 14: 275-302, 1997.
Burfeind et al "The Effects of Mechanical Cardiac Stabilization on Left Ventricular Performance", European Journal of Cardio-Thoracic Surgery, 14: 285-289, 1998.
Burkhoff et al. "Nonexcitatory Electrical Signals for Enhancing Ventricular Contractility: Rationale and Initial Investigations of An Experimental Treatment for Heart Failure", American Journal of Physiology—Heart and Circulatory Physiology, 288(6): H2550-H2556, Jun. 2005.
Butter et al. "Enhanced Inotropic State of the Failing Left Ventricle by Cardiac Contractility Modulation Electrical Signals Is Not Associated With Increased Myocardial Oxvgen Consumption", Journal of Cardiac Failure, 13(2): 137-142, 2007.
Cano et al. "Dose-Dependent Reversal of Dixogin-Inhibited Activity of An In-Vitro Na+K+ATPase Model by Digoxin-Specific Antibody", Toxicology Letters, 85(2): 107-1011, 1996.
Cazeau et al. "Multisite Pacing for End-Stage Heart Failure: Early Experience", Pacing and Clinical Electrophysiology, 19(11): 1748-1757, 1996. Abstract.
Cheng et al. "Calcium Sparks: Elementary Events Underlying Excitation-Contraction Coupling in Heart Muscle", Science, 262(5134): 740-744, 1993. Abstract.
Cooper "Postextrasystolic Potention. Do We Really Know What It Means and How to Use It?", Circulation, 88: 2962-2971, 1993.
Coulton et al. "Magnetic Fields and Intracellular Calcium; Effects on Lymphocytes Exposed to Conditions for 'Cyclotron Resonance'", Phys. Med. Biol., 38: 347-360, 1993, Abstract.
Devedeux et al. "Uterine Electromyography: A Critical Review", American Journal of Obstetric Gynecology, 169(6): 1636-1653, 1993.
Dillon "Optial Recordings in the Rabbit Heart Show That Defibrillation Strength Shocks Prolong the Duration of Depolarization and the Refractory Period", Circulation Research, 69: 842-856, 1991.
Dillon "Synchronized Repolarization After Defibrillation Shocks. A Possible Component of the Defibrillation Process Demonstration by Optical Recordings in Rabbit Heart", Circulation, 85(5): 1865-1878, 1992.
Erol-Yilmaz et al. "Reversed Remodelling of Dilated Left Sided Cardiomyopathy After Upgrading from VVIR to VVIR Biventricular Pacing", Europace, 4: 445-449, 2002.
Fain et al. "Improved Internal Defibrillation Efficacy With A Biphasic Waveform", American Heart Journal, 117(2): 358-364, 1989. Abstract.

(56) References Cited

OTHER PUBLICATIONS

Fleg et al. "Impact of Age on the Cardiovasvular Response to Dynamic Upright Exercise in Healthy Men and Women", Journal of Applied Physiology, 78: 890-900, 1995. Abstract.

Fleischhauer et al. "Electrical Resistances of Interstitial and Microvascular Space as Determinants of the Extracellular Electrical Field and Velocity of Propagation in Ventricular Myocardium", Circulation, 92: 587-594, 1995.

Foster et al. "Acute Hemodynamic Effects of Atrio—Biventricular Padng in Humans", The Society of Thoracic Surgeons, 59: 294-300, 1995.

Franz "Bridging the Gap Between Basic Clinical Electrophysiology: What Can Be Learned From Monophasic Action Potential Recordings?", Journal Cardiovasc Electrophysiology, 5(8): 699-710, 1994, Abstract.

Franz "Method and Theory of Monophasic Action Potential Recording", Progress in Cardiovascular Diseases, 33(6): 347-368, 1991. Abstract.

Franz "Monophasic Action Potential Symposium, I. Introduction", Progress in Cardiovascular Diseases, 33(6): 345-346, 1991.

Fromer et al. "Ultrarapid Subthreshold Stimulation for Termination of Atriventricular Node Reentrant Tachycardia", Journal of the American College Cardiology, 20: 879-883, 1992.

Fu et al. "System Identification of Electrically Coupled Smooth Music Cells: The Passive Electrically Coupled Smooth Muscle Cells: The Passive Electrical Properties", IEEE Transactions on Biomedical Engineering, 38(11): 1130-1140, 1991. Abstract.

Gardner "Natriuretic Peptides: Markers or Modulators of Cardiac Hypertrophy?", Trends in Endocrinology and Metabolism, 14(9): 411-416, Nov. 2003.

Gill et al. "Refractory Period Extension During Ventricular Pacing at Fibrillatory Pacing Rates", Pacing and Clinical Elctrophysiology, 20(3): 647-653, 1997. Abstract.

Gilmour Jr. et al. "Dynamics of Circus Movement Re-Entry Across Canine Purkinje Fibre-Muscle Junctions", The Journal of Physiology, 476(3): 473-485, 1994.

Gilmour Jr. et al. "Overdrive Suppression of Conduction at the Canine Purkinje-Muscle Junction", Circulation, 76(6): 1388-1396, 1987.

Gold et al. "Evidence That Glucose 'Marks' Beta Cells Resulting in Preferential Release of Newly Synthesized Insulin", Science, 218(4567): 56-58, Oct. 1, 1982. Abstract.

Gomis et al. "Oscillatory Patterns of Electrical Activity in Mouse PancreaticIslets of Langerhans Recorded in Vivo", Pflueger's Archiv European Journal of Physiology, 432(3): 510-515, 1996.

\* cited by examiner

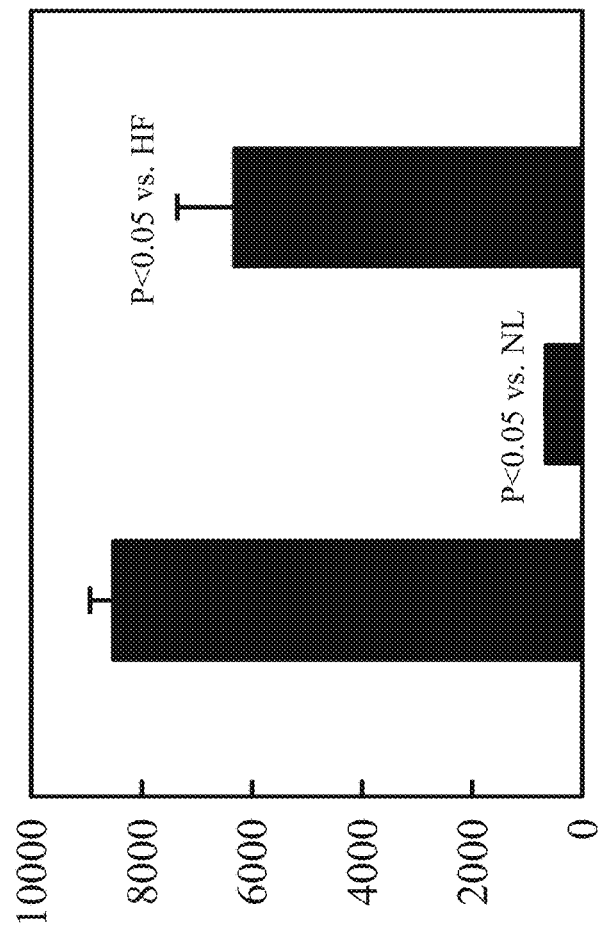 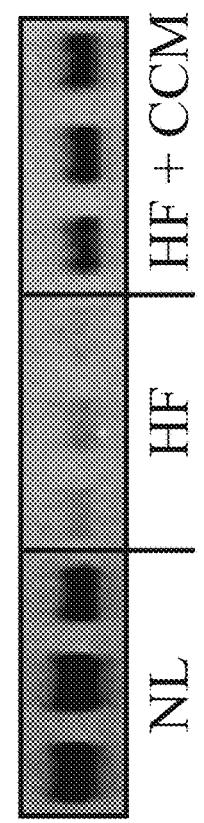
Fig. 2G

Fetal Program Genes
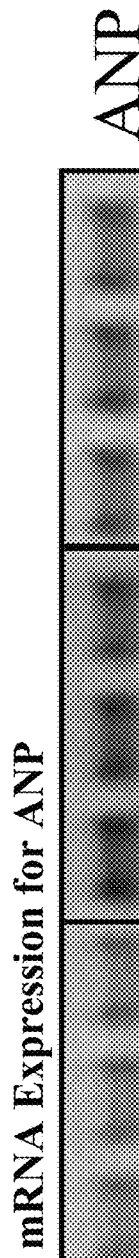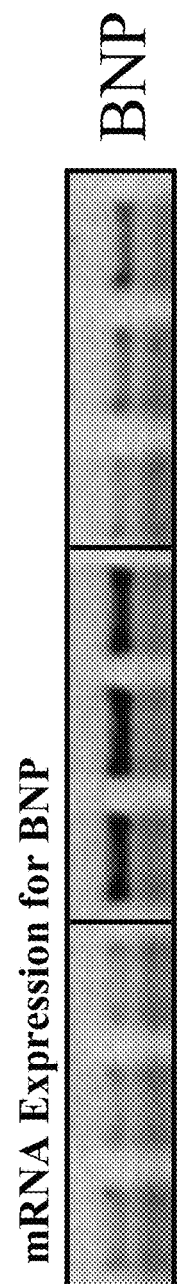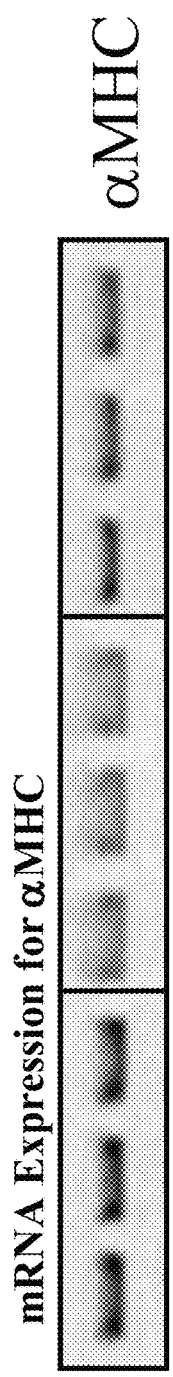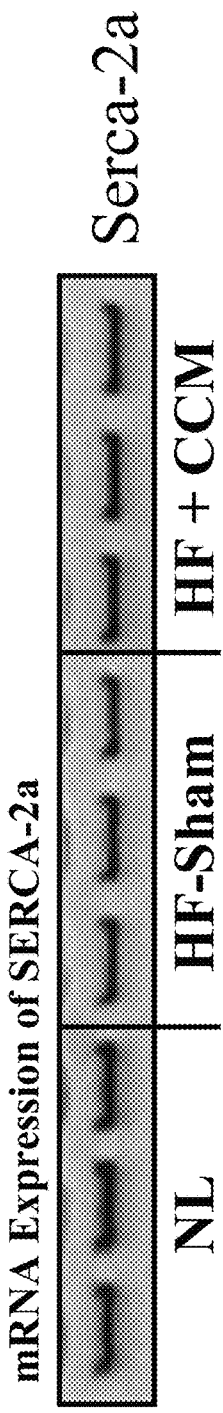
FIG 2N

Phosphorylation of Phospholamban, GATA-4 and Ryanodine Receptors In Isolated Failing Cardiomyocytes after Application of a Pacing Signal (3V, 0.75 msec) for 10, 20, 30, 40 and 60 Seconds

| seconds | 0 | 10 | 20 | 30 | 40 | 60 | |
|---|---|---|---|---|---|---|---|
| P-PLB @ Serine-16 | | | | | | | |
| | 46 | 38 | 42 | 43 | 38 | 38 | densitometric units |
| P-PLB @ Threonine-17 (monomeric) | | | | | | | |
| | 22 | 23 | 22 | 27 | 23 | 23 | densitometric units |
| P-PLB @ Threonine-17 (pentameric) | | | | | | | |
| | 29 | 28 | 26 | 25 | 23 | 23 | densitometric units |
| Phosphorylation of GATA-4 | | | | | | | |
| | 22 | 24 | 24 | 24 | 24 | 23 | densitometric units |
| Phosphorylation Ryanodine Receptor | | | | | | | |
| | 86 | 92 | 90 | 85 | 86 | 86 | densitometric units |

P-PLB = Phosphorylation of phospholamban

Fig. 3E

LV Tissue Levels of Cardiac Sarcoplasmic Reticulum Proteins in Dogs with Heart Failure Treated Long-Term (3 months) with CCM Therapy Protein Expression of Calsequestrin (CSQ)

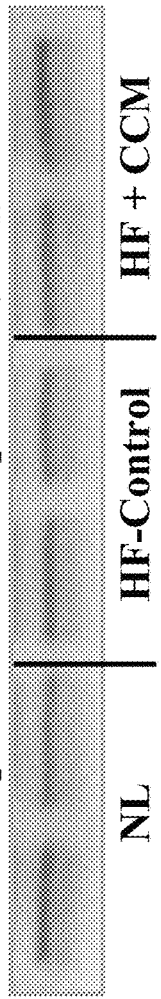

NL | HF-Control | HF + CCM

Protein Expression of SERCA-2a

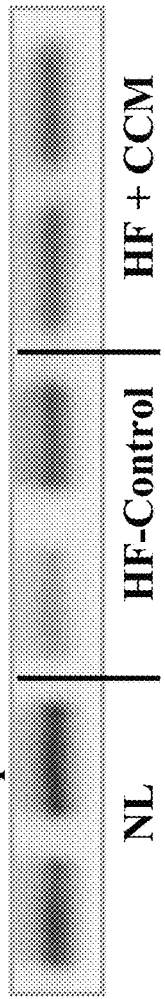

NL | HF-Control | HF + CCM

Protein Expression of Phospholamban (PLB)

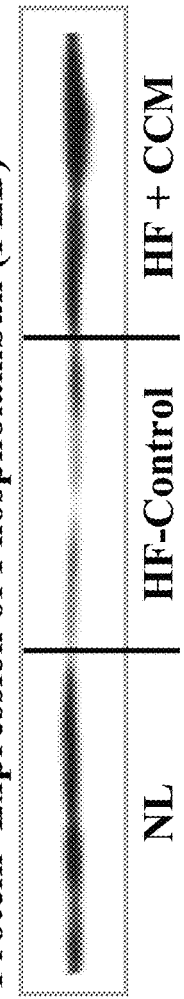

NL | HF-Control | HF + CCM

Protein Expression of Ryanodine Receptors (RyR)

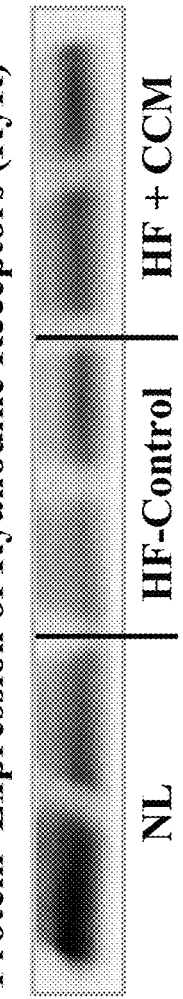

NL | HF-Control | HF + CCM

Fig. 5A

LV Tissue Protein Levels of the Transcription Factors GATA-4 And GATA-1 in Dogs with Heart Failure Treated Long-Term (3 months) with CCM Therapy
Protein Expression of GATA-4
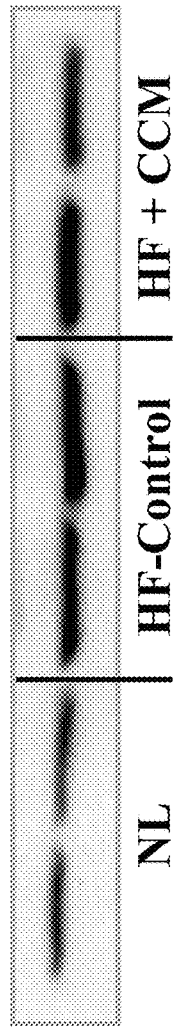
NL | HF-Control | HF + CCM
Protein Expression of GATA-1
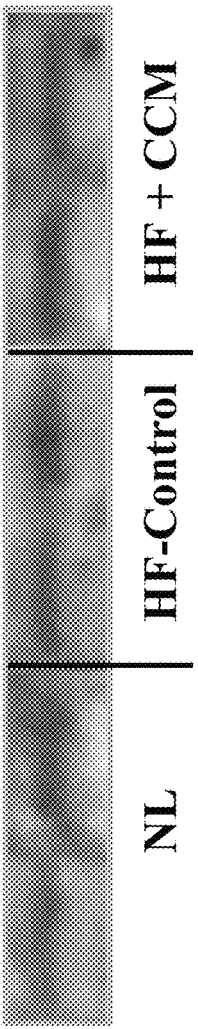
NL | HF-Control | HF + CCM
Fig. 5H LV Tissue Protein Levels of the Matrix Metalloproteinases (MMP-1 and MMP-9) in Dogs with Heart Failure Treated Long-Term (3 months) with CCM Therapy
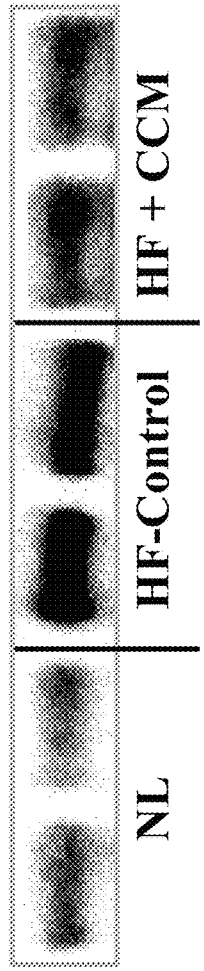
Protein Expression of MMP-1
NL | HF-Control | HF + CCM
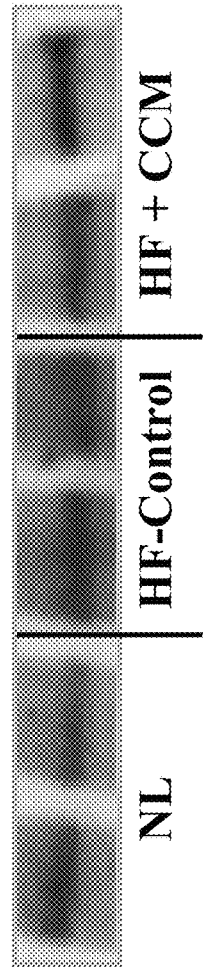
Protein Expression of MMP-9
NL | HF-Control | HF + CCM
Fig. 51

LV Tissue Levels of the Cytoskeletal Proteins Tubulin-Alpha and Beta and Titin in Dogs with Heart Failure Treated Long-Term (3 months) with CCM Therapy
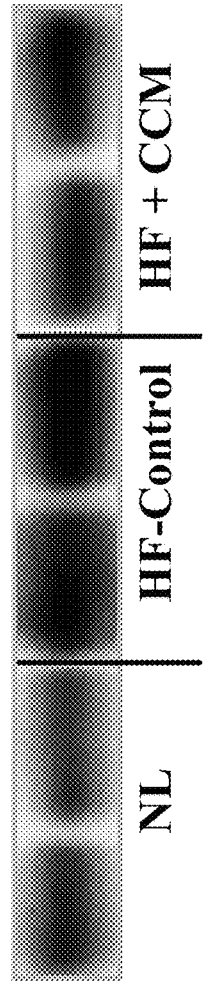
Protein Expression of Tubulin-Alpha
NL | HF-Control | HF + CCM
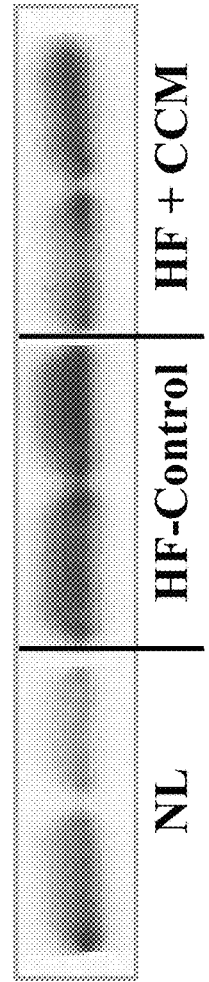
Protein Expression of Tubulin-Beta
NL | HF-Control | HF + CCM
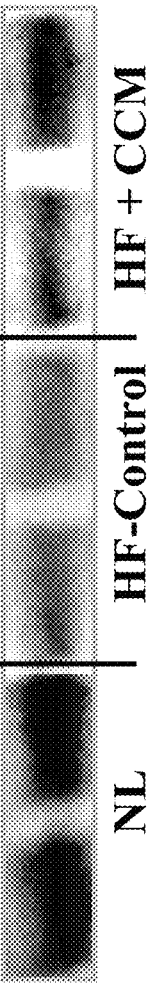
Protein Expression of Titin
NL | HF-Control | HF + CCM
Fig. 5J LV Tissue Protein Levels of the pro-Inflammatory Cytokine Interleukin-6 (IL-6) and Tissue Necrosis Factor-alpha (TNFa) in Dogs with Heart Failure Treated Long-Term (3 months) with CCM Therapy
Protein Expression of IL-6
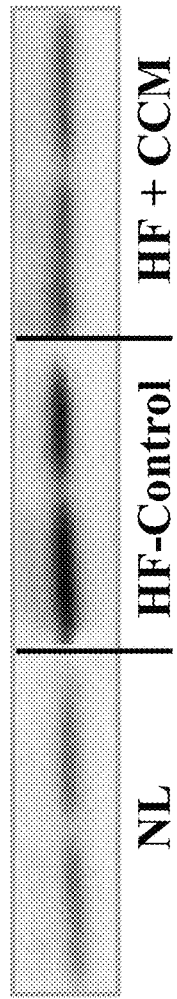
NL | HF-Control | HF + CCM
Protein Expression of TNF-α
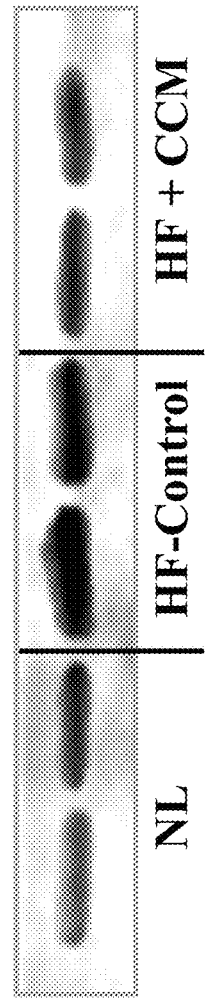
NL | HF-Control | HF + CCM
Fig. 5M LV Tissue Protein Levels of Tissue Inhibitors of Matrix Metalloproteinase-1 and 2 (TIMP-1 and TIMP-2) in Dogs with Heart Failure Treated Long-Term (3 months) with CCM Therapy
Protein Expression of TIMP-1
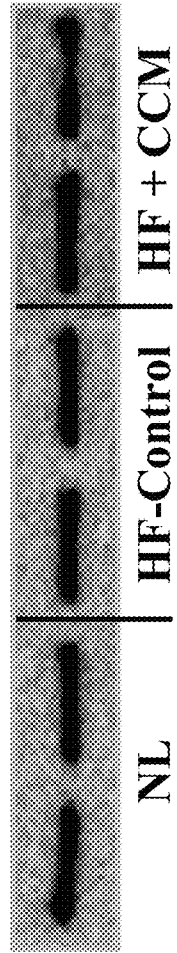
NL | HF-Control | HF + CCM
Protein Expression of TIMP-2
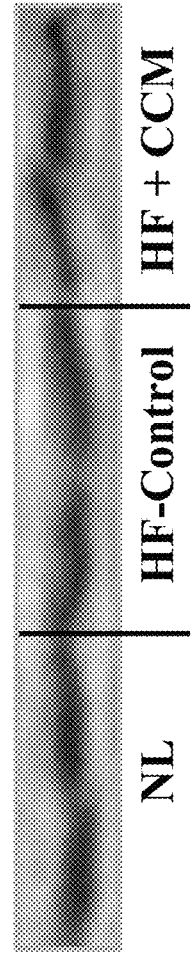
NL | HF-Control | HF + CCM
Fig. 50

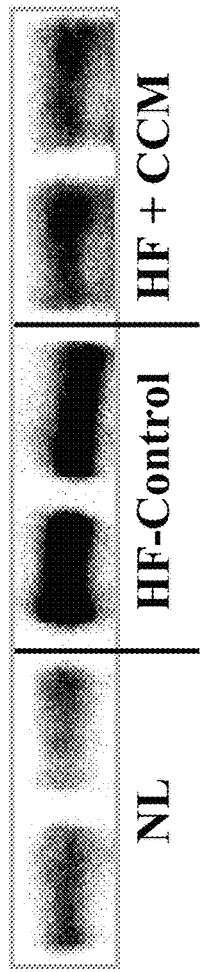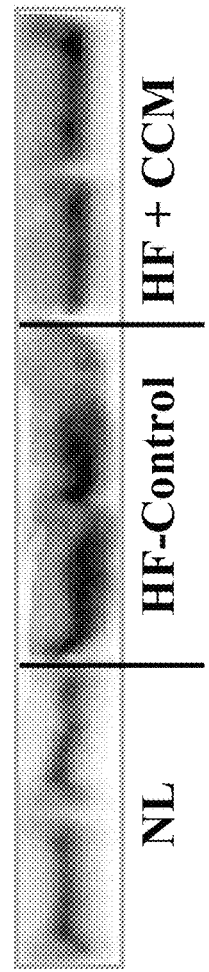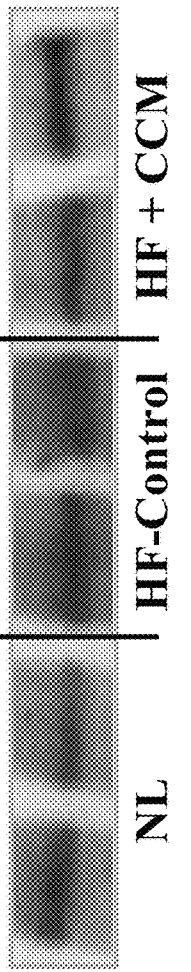
Fig. 5Q
LV Tissue Protein Levels of the Matrix Metalloproteinases (MMP-1, -2 and -9) in Dogs with Heart Failure Treated Long-Term (3 months) with CCM Therapy
Protein Expression of MMP-1 — NL | HF-Control | HF + CCM
Protein Expression of MMP-2 — NL | HF-Control | HF + CCM
Protein Expression of MMP-9 — NL | HF-Control | HF + CCM

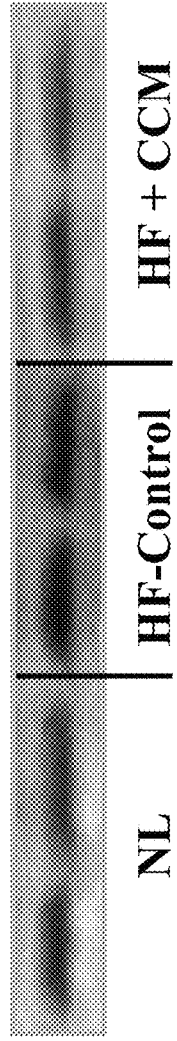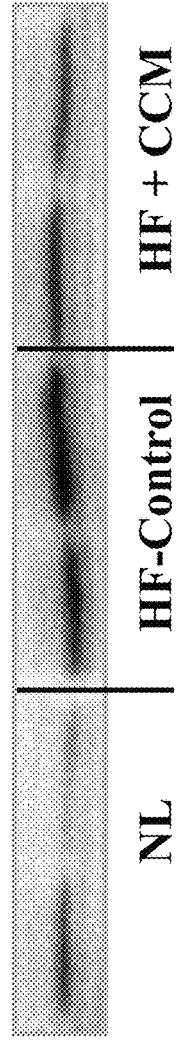
LV Tissue Protein Levels of Atrial (ANP) and Brain (BNP) Natriuretic Peptides in Dogs with Heart Failure Treated Long-Term (3 months) with CCM Therapy
Fig. 5R LV Tissue Protein Levels of Phosphorylated Phospholamban in Dogs with Heart Failure Treated Long-Term (3 months) with CCM Therapy
Phosphorylated Phospholamban at Serine-16
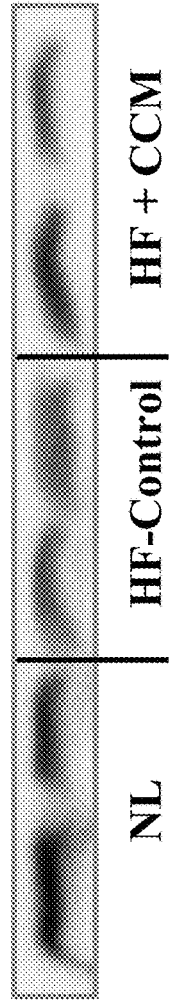
NL | HF-Control | HF + CCM
Phosphorylated Phospholamban at Threonine-17
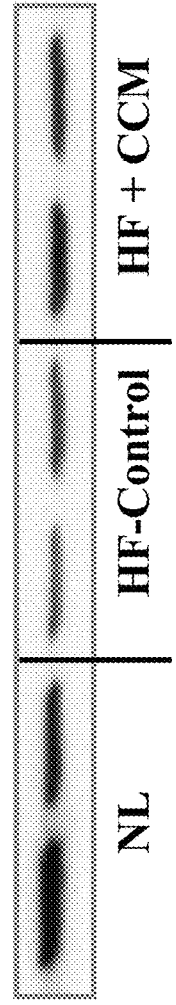
NL | HF-Control | HF + CCM
Fig. 8

FIGURE 11
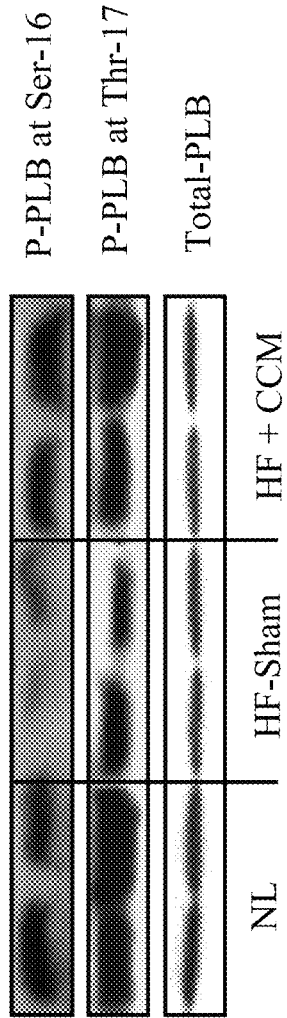
Inter-Ventricular Septum
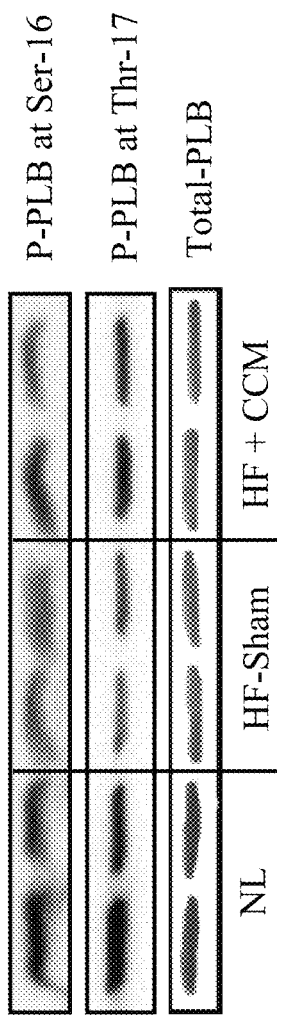
LV Free Wall mRNA and Protein Expression of the Calcium Binding Protein Sorcin in LV Tissue of Dogs with Heart Failure Treated Long-Term (3 months) with CCM Therapy mRNA Expression of Sorcin NL    HF-Control    HF + CCM Protein Expression of Sorcin NL    HF-Control    HF + CCM mRNA and Protein Expression of the Presenilin-1 and 2 in LV Tissue of Dogs with Heart Failure Treated Long-Term (3 months) with CCM Therapy mRNA and Protein Expression of the Calstabin in LV Tissue of Dogs with Heart Failure Treated Long-Term (3 months) with CCM Therapy mRNA Expression of Calstabin-2

NL | HF-Control | HF + CCM

Protein Expression of Calstabin-2

NL | HF-Control | HF + CCM

PROTEIN ACTIVITY MODIFICATION

RELATED APPLICATIONS

This application is a continuation of U.S. patent application Ser. No. 16/232,088 filed on Dec. 26, 2018, which is a continuation of U.S. patent application Ser. No. 15/249,506 filed on Aug. 29, 2016, now U.S. Pat. No. 10,352,948, which is a continuation of U.S. patent application Ser. No. 14/641,480 filed on Mar. 9, 2015, now U.S. Pat. No. 9,440,080, which is a continuation of U.S. patent application Ser. No. 13/970,647 filed on Aug. 20, 2013, now U.S. Pat. No. 8,977,353, which is a continuation of U.S. patent application Ser. No. 11/919,491 filed on Mar. 8, 2009, now U.S. Pat. No. 8,548,583, which is a National Phase of PCT Patent Application No. PCT/US2006/017281 filed on May 4, 2006, which is a Continuation-in-Part (CIP) of PCT Patent Application No. PCT/US2005/044557 filed on Dec. 9, 2005, which claims the benefit of priority of U.S. Provisional Patent Application Nos. 60/634,625 filed on Dec. 9, 2004, 60/677,761 filed on May 4, 2005 and 60/719,517 filed on Sep. 22, 2005. PCT Patent Application No. PCT/US2005/044557 is also a Continuation-in-Part (CIP) of PCT Patent Application No. PCT/US2004/007589 filed on Mar. 10, 2004.

PCT Patent Application No. PCT/US2006/017281 is also a continuation of PCT Patent Application No. PCT/IL2006/000204 filed on Feb. 16, 2006. This application is also related to PCT Patent Application Nos. PCT/IL97/00012 filed on Jan. 8, 1997, and PCT/IB00/01523 filed on Oct. 4, 2000.

The contents of the above applications are all incorporated by reference as if fully set forth herein in their entirety.

FIELD AND BACKGROUND OF THE INVENTION

The present invention relates to modification of tissue behavior, for example using electric fields and for example using biochemical markers as feedback.

While some proteins have a mainly structural role in cellular life, many proteins are biologically active. Living cells include many mechanisms by which the biological activity of a protein is modulated, including: modification of concentration of the protein or its substrates, modification of the concentration of materials that catalyzes protein activity, indirect modification of protein structure, such as by changing of pH or concentrations of materials that modify protein structure, and direct modification of protein spatial structure and/or charge distribution by attachment of cofactors such as a phosphate moiety (phosphorylation), glucose, ions, metal ions, heme groups or iron-sulfur complexes and coenzymes for example.

The symptoms of many diseases include changes in protein activity, as indicated, for example, by phosphorylation (hyper- or hypo-). One example is cardiac heart failure, where, as the disease progresses the phosphorylation of some proteins goes down and others go up. Levels of various proteins also change.

As described, for example in N Engl J Med 346:1357, 2002, the disclosure of which is incorporated herein by reference, patients with CHF who respond to therapy with beta blockers manifest reversal that is normalization of the maladaptive fetal gene program.

In a paper entitled "Voltage-dependent potentiation of the activity of cardiac L-type calcium channel a1 subunits due to phosphorylation by cAMP-dependent protein kinese", by Adrian SCULPTOREANU, Eric ROTMAN, Masami TAKAHASHI, Todd SCHEUER, and William A. CATTERALL, in Proc. Natl. Acad. Sci. USA Vol. 90, pp. 10135-10139, November 1993 (Physiology), the disclosure of which is incorporated herein by reference, fast phosphorylation of trans-membrane calcium channels and a possible mechanism therefore, are described.

U.S. Pat. No. 6,919,205, the disclosure of which is incorporated herein by reference, describes regulation of type II cartilage genes and proteins using electromagnetic and electric fields.

PCT publication WO 2005/056111, the disclosure of which is incorporated herein by reference describes using a PMF signal on calcium dependent myosin phosphorylation in a cell free reaction mixture.

PCT publication WO 2005/102188, the disclosure of which is incorporated herein by reference, describes PMF stimulation applied to Jurkat cells reduces DNA synthesis and makes them behave like normal T-lymphocytes stimulated by antigens at the T-cell receptor such as anti-CD3, possibly by interacting with the T-cell receptor.

PCT publication WO 2005/105013, the disclosure of which is incorporated herein by reference, describes applying a PMF to a heart in order to achieve angiogenesis and neovascularization.

SUMMARY OF THE INVENTION

A broad aspect of some embodiments of the invention relates to modifying the activity of proteins or other biochemicals optionally in situ and/or in vivo, for example, by modifying protein phosphorylation, using electro-magnetic or electrostatic fields. In an exemplary embodiment of the invention, the activity of the protein that is modified is one or more of signaling, catalysis, material transport and/or charge transport. While the term phosphorylation is used in the specific sense, the embodiments described herein are intended to cover other attachment/detachment of protein cofactors. In an exemplary embodiment of the invention, the electric field is applied directly or induced, for example, using induction coils, magnetic fields or by methods of charge transport in the tissue, such as changing of ionic concentration.

Some embodiments of the invention are based on the surprising discovery by the inventors that an electric field can have an immediate effect on phosphorylation of proteins.

In some embodiments of the invention, modification of protein expression and/or mRNA expression are practiced, in addition to or instead of phosphorylation changes. In an exemplary embodiment of the invention, protein levels of at least two proteins are normalized by application of an electric field.

In an exemplary embodiment of the invention, the modification method is used as a therapy and/or in diagnosis, for example for a diseased heart and/or for other organs in the body.

In an exemplary embodiment of the invention, the modification of the protein activity is a relatively direct result of the method, rather than a side effect. This directness can be noticed, for example in the time scale of some embodiments of the invention, where a change in phosphorylation is noticeable within a few seconds or minutes. Alternatively or additionally, the directness can be noticed in a lack of intermediates, for example as indicated by the change in phosphorylation taking place even in cell homogenate, or even in the presence of protein inhibitors.

In an exemplary embodiment of the invention, protein activity modification comprises changing the actual work done by proteins in the cell. Optionally, as noted herein, this work is modified without synthesis of new proteins, for example, by modification of phosphorylation and/or activation of pathways.

In an exemplary embodiment of the invention, the modification is evident without requiring the synthesis of new protein. For example, phosphorylation of existing proteins may be provided.

In an exemplary embodiment of the invention, modification of protein activity and/or phosphorylation comprises modifying a steady state average level of such phosphorylation. Optionally, this modification comprises periodically increasing the percentage of phosphorylated proteins. Alternatively or additionally, the modification is achieved by shifting a balance between phosphorylation and dephosphorylation. In some embodiments, the modification relates to a single heart beat.

In an exemplary embodiment of the invention, the modification is on the time scale of a single or small number of heart beats, or faster (e.g., 1 second or faster). Optionally, an effect of the modification is noticeable on a same time scale.

In an exemplary embodiment of the invention, the affected proteins are proteins that act on a non-protein substrate, for example calcium channel proteins. Alternatively or additionally, the proteins are signaling proteins and/or act on other proteins and/or are acted on by other proteins. For example, the affected protein enhances the activity of various enzymes, which, in turn, regulate essential ion channels and pumps. One example is that phospholamban, when phosphorylated, can increase the activity of calcium ATPase also known as SERCA-2a.

An aspect of some embodiments of the invention relates to using phosphorylation as a target for therapy, especially a therapy where the therapy method can be controlled at a relatively fast rate. For example, phosphorylation of phospholamban leads to increased activity of calcium ATPase and/or increase of the affinity of calcium ATPase pump for calcium. This, in turn, leads to increased or enhanced uptake of calcium from the cell cytosol to the sarcoplasmic reticulum (SR).

In an exemplary embodiment of the invention, changing phosphorylation will stabilize the cell biochemistry and prevent or undo decline in cell functionality. This may allow a general improvement in the patient to occur, for example, as natural feedback and healing processes can kick into action.

In an exemplary embodiment of the invention, an indication of protein activity other than phosphorylation is used for example, either as feedback or to determine efficacy, for example, microbiological parameters such as SR calcium level or macro parameters such as cardiac output as a function of $MVO_2$.

In an exemplary embodiment of the invention, the target of therapy is achieving a relative phosphorylation level. Alternatively or additionally, the target is achieving an absolute phosphorylation level. Such a target may be a window, with the values of the window optionally being variable. In one example, the values are dependent on one or more of 1) the state of phosphorylation of the protein, 2) the availability of the protein itself, 3) the condition and viability of the organ, 4) stressful conditions imposed upon the organ as a result of daily activity and/or 5) resulting from variation in circadian rhythm.

In an exemplary embodiment of the invention, the target of therapy is achieving an effect of change in phosphorylation, for example, a change of cellular function, caused for example, by rebalancing a previously upset balance between the activity of various proteins or setting a new set point of a new, less hazardous balance (e.g., for therapy of a condition where the balance is hazardous).

In an exemplary embodiment of the invention, the target is achieving a certain value or profile of protein activity, for example, a certain calcium pumping rate or pumping profile (as dependent on concentration and/or cell stress), which value or profile is determined by the phosphorylated protein, alone or in conjunction with other associated proteins or cellular mechanisms.

In an exemplary embodiment of the invention, when the phosphorylation is used as a target, the therapy is increased, decreased and/or otherwise modified based on its actual or expected effect on phosphorylation. In an exemplary embodiment of the invention, feedback is provided for the method by measuring phosphorylation directly or indirectly.

In an exemplary embodiment of the invention, phosphorylation is used as a negative or minimum target. For example, when it is not possible to achieve a desired effect on an entire heart, for example, due to power limits or side effect limits, a minimum phosphorylation target is set for various parts of the heart and the therapy is configured so that this minimum achievable target is achieved. In another example, it may be desirable to minimize the amount of phosphorylation, for example in the event that hyperphosphorylation leads to progressive worsening of disease. In this case, the pulse sequences applied may be optimized to minimize the global and/or regional expected or measured phosphorylation of a particular protein. In an exemplary embodiment of the invention, phosphorylation modification in ischemic and non-ischemic regions is different or otherwise dependent on the condition of underlying tissue. For example, ischemic regions being controlled to improve phosphorylation and non-ischemic regions are controlled to also increase contractility.

In an exemplary embodiment of the invention, phosphorylation is used as a single or as one of several parameters in optimization or selection of a pulse sequence.

In an exemplary embodiment of the invention, phosphorylation is used as a guide for electrification sequence parameters settings. In some cases it may not be practical to use phosphorylation as an indicator for feedback, however, general experiments (such as those described herein) may show that certain sequences have a certain effect on phosphorylation. In an exemplary embodiment of the invention, sequences that are defined for another effect, for example, contractility modulation, are modified to take into account the results of these experiments. In another example, a sequence that is shown to have a certain phosphorylation effect is used in an open or semi-open loop, rather than a closed loop. The phrase "semi-open loop" is used to mean that feedback and modification of the sequence is at a much slower rate than the application of the sequence, for example, once a week or once a month for a sequence applied once an hour or more often.

An aspect of some embodiments of the invention relates to kits and methods of use thereof. In an exemplary embodiment of the invention, a kit includes a means to analyze a tissue sample to determine some indication of its phosphorylation levels, protein expression levels, mRNA levels and/or other biochemical markers. Optionally, the kit includes 1, 4, 10, 20, 25 or more or intermediate numbers of biochemical marker detectors for markers as described herein and/or additional markers.

In an exemplary embodiment of the invention, the type and/or severity of the disease is classified using the expression results and/or response to treatment results for a plurality of genes/proteins, for example, 3, 5, 10, 20 or more. In an exemplary embodiment of the invention, a database is built up by storing typical results for different patients and detecting relationships between levels/responses that are associated with certain outcomes and/or pathologies. It is expected that with increase in the number of biochemical markers and/or treatments that such classifications can be detected.

In an exemplary embodiment of the invention, the kit includes instructions for use, optionally including thresholds of expected values and/or changes in values expected over time. Optionally, the kit is useful for one or more of diagnosis, detecting treatment progress and/or classifying patients according to expected responsiveness.

In an exemplary embodiment of the invention, the kit is included with suitable software which tracks values and/or provides results.

In an exemplary embodiment of the invention, the kit is used while device implanting, to assess a suitable implantation area of electrodes in the heart for example, according to the response to acute stimulation indicated by the kit.

Optionally, the kit is used by taking a tissue biopsy, for example, using a needle or a catheter and testing the levels of bio-chemicals in a biopsy sample.

In an exemplary embodiment of the invention, the kit is used for active testing of a tissue sample. A tissue sample is extracted and optionally homogenized (e.g., using a separate device) and then an electric field or other treatment is applied to the sample. Depending on the response of the sample, a diagnosis, progress and/or classification is determined. Optionally, the kit is provided with a set of electrodes which can be selectively attached to an implantable device, to assess its effect on homogenate. Alternatively or additionally, a stand-alone electrification system is used. Optionally, this stand-alone system includes a controller adapted to apply multiple electrification schemes and optionally store the effect of each scheme. Optionally, the stand-alone device includes a sampling chamber for selecting a part of the tested sample and applying a test thereto, for example, determining instantaneous or near instantaneous phosphorylation.

In another example, the kit is used to test pre-treatment levels of biochemicals, including, for example, phosphorylation level.

In an exemplary embodiment of the invention, the kit is packaged as a separate entity, while in some cases, multiple kits may be used, which may be packaged as a set. Optionally, different kits for different sets of biochemical markers are provided. Alternatively or additionally, the kits are provided, for example, as single or multiple one-time kits, with a cardiac controller, to be used as part of the implantation and/or electrode location searching process.

Optionally, the kit is used during implantation, before implantation is finalized, to help decide if the device should be left in the body or not, depending on its acute efficacy, for example, on phosphorylation.

Optionally, a kit is used to test treatment other than electrical treatments, for example, drug treatments or exercise treatments. Optionally, the kit is used by sampling a sample before and after the treatment or by applying a proposed treatment to the sample itself and seeing if the sample exhibits a positive effect.

An aspect of some embodiments of the invention relates to controlling tissue, for example soft tissue and/or non-cartilagous tissue and/or non-supporting tissue such as the heart, by directly affecting a balance point of phosphorylation or other biochemical activities therein.

In an exemplary embodiment of the invention, the electrical activity of a cell is considered as having a resetting effect on the cell. Applying a field at the time of activation of the cell may miss this reset period. In an exemplary embodiment of the invention, a field which modifies the cell balance is applied before/after resetting time, then, when the resetting is applied by cellular activation, the cell is at a new balance point. In some cases, multiple {set balance; reset} cycles are applied to achieve a desired change in a cell or population of cells. In some cases, rest periods between applications are required, for example, to allow a cell to stabilize and/or find a new balance state absent external effects.

In an exemplary embodiment of the invention, an electric field is applied which skews a balance between phosphorylation and dephosphorylation of a protein. This skewing optionally includes a long term increase in phosphorylation, for example if the time constants of dephosphorylation are higher than those of dephosphorylation. In an exemplary embodiment of the invention, the protein affected is phospholamban or an ion channel, for example a trans-membrane calcium channel.

In an exemplary embodiment of the invention, the effect is a short term effect, for example, by applying the field in a manner which allows long term phosphorylation levels to recover and thus prevent a long term change in cellular behavior, while providing an acute effect. In a particular example, the field is applied for a short time and then stopped until (e.g., according to measurement or estimation) the phosphorylation levels received. Optionally, the field is applied for a short enough time that the total acute change is small, for example a few percent (e.g., <10 percent). Optionally, a mix or intermediate situation between short and long term effect is provided. Optionally, both large acute changes and gradual long term changes are provided, for example with long term changes being on the range of hours and acute changes seconds or minutes.

Optionally, the field is applied often enough to cause a long term effect. Optionally, the frequency of application causes only a slow change in acute values, optionally causing no acute effects to be seen.

In an exemplary embodiment of the invention, the applied field is modified to take into account the change in cellular behavior and/or change in phosphorylation.

It is noted that a test field applied for testing tissue response may not be the same as the treatment field. In one example, the test field is stronger. In another example, the treatment field is modified based on the results of the test field.

In an exemplary embodiment of the invention, the balance between phosphorylation and dephosphorylation is tipped to restore a correct balance. Alternatively or additionally, the balance is skewed to be abnormal, for example to drive a cellular homeostasis mechanism in a direction to correct a defect in cellular behavior and/or compensate for such behavior.

Optionally, the applied electric field is a dual function field, for example, being used for pacing or preventing arrhythmia. Optionally, the applied field does not acutely (e.g., within 10 heart beats or fewer) increase contractility by more than 3%, or less.

A broad aspect of some embodiments of the invention relates to non-immediate effects of therapy. A first type of non-immediate effect is an effect that lasts a considerable amount of time after the application of the therapy. This type of effect may allow relatively long non-therapy periods between therapy application times, while still providing useful treatment of a patient. A second type of non-immediate effect is an effect that lasts after therapy is stopped, for example, physical and/or biochemical remodeling of the heart or cells thereof. A third type of non-immediate effect is an effect that only becomes noticeable after a time, for example, protein expression changes which are not associated with immediate (acute) hemodynamic changes.

An aspect of some embodiments of the invention relate to new therapeutic non-excitatory sequences for the heart. Optionally, these sequences have as an aim to improve phosphorylation, rather than only contractility and in some cases, without immediate improvement in contractility. Optionally, a phosphorylation improving sequence, while generally capable of contractility enhancement, is applied at too low a repetition rate and/or power to achieve a meaningful change in contractility. An example is calsequestrin that, when phosphorylated, increases the sequestration of calcium into the sarcoplasmic reticulum but does not increase contractility.

In an exemplary embodiment of the invention, the sequences are optimized to one or more of acute or longer term effects of one or more of phosphorylation, protein and/or mRNA levels.

Acute effects have some potential benefits for use as feedback, including one or more of faster feedback so faster optimization and/or per patient optimization can more easily be achieved, relative steadiness of physiological condition during optimization and/or ability to control an ongoing process, such as titrating of therapeutic drugs particularly in i.v. type drugs or delivery of any drug and dose.

In an exemplary embodiment of the invention, the optimization (including a semi-optimization) is on a per patient, per tissue (e.g., location in heart), per diagnosis and/or per patient classification group.

In an exemplary embodiment of the invention, as compared to contractility modifying signals, the sequences have a lower duty cycle and/or more quiet periods between sequences, designed such that a desired phosphorylation effect is achieved, even if a sufficient charge is not delivered each beat (or any beat) to cause significant increase in contractility. In an exemplary embodiment of the invention, the sequence is based on a delivery of minimum signals that increase phosphorylation, at time intervals timed so that decay of phosphorylation between applications is smaller than or the same as the increase achieved by an application. Optionally, the delay between signals and/or signal length and/or other parameters vary over time to track a possibly varying effect of the signal on phosphorylation as phosphorylation changes.

In some cases, a field which would otherwise reduce contractility (e.g., a hyperpolarizing field) is used.

In an exemplary embodiment of the invention, a power saving sequence is defined, which, for example, is designed to maintain phosphorylation levels, even if a desired contractility enhancement is not directly achieved, by reducing pulse amplitude, frequency of application and/or other power-related parameters. In some cases, contractility is not a consequence of the phosphorylation normalization.

In an exemplary embodiment of the invention, a minimum dosage sequence is defined, which achieves a desired phosphorylation effect, without necessarily achieving other immediate beneficial effects such as contractility enhancement effects. Long-term, the improvement in phosphorylation may also improve contractility. In an exemplary embodiment of the invention, a therapeutically effective sequence comprises applying a field to the heart less often than once in 5 minutes, once in 10 minutes, once in 30 minutes, once an hour, once a day and/or once a week. For some uses, a set of signals, for example, 10, 20 or 30 signals (each signal corresponding to one heart beat), may be applied at such intervals, with an optional inter-signal spacing.

In an exemplary embodiment of the invention, a phosphorylation-effecting signal comprises applying signals at different times in the cardiac cycle, such as absolute or relative refractory periods and excitatory period. The signal may be synchronized to the heart as a whole or to local activity, for example. Optionally, the signal is excitatory in some times of application. Optionally, the signal, at some embodiments thereof, may be applied at any point in the cycle, or at least during 60%, 80% or more of the cycle.

In an exemplary embodiment of the invention, the optimizing of the pulse sequence is based on selecting a pulse or pulse parameters which will have a desired effect on the patient, for example, phosphorylation, e.g., above 10% increase, 20%, 40%, 100%, 200%, 500%, 1000% or intermediate or larger percentage increases. In some cases, a decrease is desired, for example, a decrease of 20%, 40%, 70%, 90% or intermediate or greater percentage reductions. Not all such increases and/or decreases are available for all biochemicals.

In an exemplary embodiment of the invention, a method of manufacturing is provided in which a pacemaker or another electrical field applying device is programmed to have a pulse known to have a desired biochemical effect, such as phosphorylation, optionally even if such pulse has a reduction in other effect.

An aspect of some embodiments of the invention relates to applying therapy, for example, electro-biochemical control therapy as described herein, by selecting a long term therapy effect (e.g., as described herein) and modifying the therapy to match the effect. In an exemplary embodiment of the invention, the modifying comprises changing the daily duration of signals, modifying rest periods between signals and/or changing the applied signals. Optionally, the modifications are between patients and/or within a patient, for example, as therapy progresses. Optionally, secondary targets for optimization when modifying a therapy are total applied charge and existence of side effects (positive or negative). Other parameters as described herein may be varied as well.

In an exemplary embodiment of the invention, one or more of the following targets is selected: ejection fraction elevation. Cardiac muscle dimensions (e.g., reduction), chamber volume (e.g., reduction), quality of life (e.g., as measured using various tests), peak O2 consumption (e.g., increase), anaerobic threshold (e.g., improve), 6 m walking distance, fluid retention, sleep apnea severity and/or episodes and/or exercise tolerance.

In an exemplary embodiment of the invention, the patients selected for therapy are those not indicated for cardiac resynchronization therapy.

In an exemplary embodiment of the invention, patients selected have a normal QRS (not wide, no conduction problems) and/or no desynchrony.

In an exemplary embodiment of the invention, patients have a narrow QRS.

Optionally, the patients are NYHFA class III-IV severity patients.

An aspect of some embodiments of the invention relates to controlling a heart taking into account differences between local and remote effects of a treatment such as electrical field application.

In an exemplary embodiment of the invention, a local area is an area which is directly affected by the treatment, for example a tissue area lying between two electrodes that are electrified or an areas to which a pharmaceutical is provided, for example using a path or using local injection or using other methods known in the art. In an exemplary embodiment of the invention, the tissue in this area is used to detect immediate effects of the field, for example, change in phosphorylation and changes in contractility. Optionally, a sensor is provided at the local area for example, a sensor that measures local muscle function and/or biochemical behavior, which sensor generates an indication of the effect of the sequence. Optionally, a one time use sensor is used, for example an anti-body covered optical fiber. Optionally, several such sensors are provided.

Alternatively or additionally to acute measurements within minutes or seconds, measurements on a scale of hours are made.

In an exemplary embodiment of the invention, the remote area is in the same heart chamber or in a different heart chamber and serves to indicate general progress in the cardiac condition. Optionally, such general progress is detected by measuring changes in biochemical markers in such remote tissue.

Optionally, a treatment aims to improve one or both of local and remote effects.

In an exemplary embodiment of the invention, areas to treat are selected based on a desired local and/or remote effect. In one example, local (e.g., electrode application) areas are selected such that a general improvement in cardiac function and a subsequent remote effect may be expected. In another example, multiple local areas are selected so as to positively control the cellular behavior in those areas, for example simultaneously or in series. In an exemplary embodiment of the invention, progress is measured by detecting a wave-like propagation of tissue improvement, starting at the sites of electrode application. Such sites may be selected to provide a desired such propagation of improvement over the heart. Alternatively or additionally, progress is detected by measuring gradual improvement in multiple locations simultaneously. Optionally, if improvement is measured using biopsies, different locations are sampled each time.

In an exemplary embodiment of the invention, electrode location are selected so as to best utilize exciting tissue resources, for example, enhance weak tissue rather than strong tissue or optimize use of blood flow resources. Optionally, the treatment areas are selected to increase blood demand and drive angiogenesis. Optionally, treatment is applied at areas where blood flow is reduced, as some treatments do not increase oxygen demand.

In an exemplary embodiment of the invention, electrode placement is selected to provide a desired stretching behavior to nearby tissue. Alternatively or additionally, electrode placement is selected to minimize diffusion or travel distances for biochemicals between treated areas and other areas.

In an exemplary embodiment of the invention, a local area is 20 cm$^2$ 10 cm$^2$, 5 cm$^2$, 3 cm$^2$, 2 cm$^2$, 1 cm$^2$ or greater or smaller or intermediate sizes.

An aspect of some embodiments of the invention relates to applying a phosphorylation affecting signal on generally non-contracting tissue, such as plugs, transplants and/or scar tissue (especially at boundaries thereof). In an exemplary embodiment of the invention, this application is used to stabilize and/or improve phosphorylation levels in such tissue. In an exemplary embodiment of the invention, tissue plugs are removed and treated and then reinserted back into the heart (autograft). Optionally, the grafts are inserted into scar tissue.

In an exemplary embodiment of the invention, plugs are extracted whole from tissue. Alternatively, plugs are built up and treated before, during and/or after build-up. In one example, plugs are formed by settling tissue on a matrix.

In an exemplary embodiment of the invention, apparatus is provided for holding a plurality of tissue plugs (e.g., 3, 5, 10, 20 or more) while an electric field is applied thereto, for example, the apparatus including a chamber with physiological fluid, the chamber optionally including supports for the plugs. Optionally, one or more plugs are sampled or tested to see an effect of eth field. Optionally, one or more electrodes are provide din or adjacent the walls of said chamber.

In an exemplary embodiment of the invention, stimulation of scar tissue can cause it to regain mechanical activity, for example by stimulation and/or healing of dormant tissue therein.

In an exemplary embodiment of the invention, stimulation of a transplant is used to enhance its activity and/or prevent degradation due to removal and implant. Optionally, the stimulation used does not cause significant mechanical activity, for example, being applied at long time intervals. Optionally, the signal is applied to cooled, non-contracting tissue. Possibly, phosphorylation of a particular protein can lead to activity that stimulates the release, for example of specific neurohormones and activation of essential proteins. Optionally, the application of the signal to a cooled or cardioplegic heart is used during cardiac and/or brain surgery to facilitate restarting of the heart after such surgery.

An aspect of some embodiments of the invention relates to detecting of changes in biochemical behavior in the heart.

In an exemplary embodiment of the invention, changes in ECG morphology which indicate changes in protein levels and/or phosphorylation, are detected. Optionally, the morphology is a single cell clamp measurement.

In an exemplary embodiment of the invention, a catheter biopsy is used to extract tissue.

In an exemplary embodiment of the invention, a tissue sample is extracted and tested by stimulation/treatment thereof outside the body. Optionally, the tissue is homogenized and/or separated into individual cells.

In an exemplary embodiment of the invention, biochemical state is determined by measuring reactivity to other biochemicals. For example, the responsiveness to beta blockers may be detected to change when certain proteins are phosphorylated.

Optionally, antibody based tracers are used, for example, in conjunction with florescent dyes and/or radioactive materials.

In an exemplary embodiment of the invention, biochemical changes are detected by identifying macroscopic properties of the heart. In one example, changed protein expression is expected to increase conduction velocity or maximum contraction velocity. Optionally, these parameters are measured and used to detect and/or estimate a change due to protein expression. Optionally, a database calibrating changes in macroscopic parameters with biochemical parameters, is provided. In an exemplary embodiment of the invention, conduction velocity is measured or estimated from measured ECG signals, for example, measured using the device. Optionally, these changes are measured at a time that a field application device is not active, for example, not active for a period of a few minutes, hours or days.

A broad aspect of some embodiments of the invention relates to complex therapy utilizing modification of tissue behavior. In one exemplary embodiment, electrical tissue biochemical behavior modification is used together with pharmaceutical provision to achieve a synergistic effect, for example, one therapy compensating for failing of the other therapy or two therapies acting to achieve a common goal. One example is beta-blocker therapy in which an initial reduction in cardiac output may be offset using an electrical therapy. After beta blocker therapy has a positive effect, electrical therapy may be used to provide a further increase in cardiac improvement. Optionally, a same pathway or mechanism is targeted using multiple therapies. In another exemplary embodiment, multiple pathways are treated, some with biochemical behavior modification using electrical means and some, optionally, with other means, such as pharmaceuticals. In another example, another therapy or application is used to modify the effect of electrical therapy, for example, applying or reducing stress before or during electrical therapy application. It should be noted that in some cases contractility change is minimal, absent or in the form of reduction.

An aspect of some embodiments of the invention relates to targeted therapy delivery and/or modulation of therapy. In an exemplary embodiment of the invention, a signal that modulates phosphorylation is applied, while the availability of a substrate relevant for phosphorylation is modified. In one example, a pharmaceutical which reduces or increases the phosphorylated protein is provided. In another example, the electric field is used to activate proteins generated using gene therapy, such as DNA plasmid injection coding for SERCA-2a, whereby phosphorylation of phospholamban would enhance the activity of the SERCA-2a. In an exemplary embodiment of the invention, targeting is achieved by therapy requiring the temporal and spatial intersection of the substrate/precursor and the signal which has the phosphorylation effect. Optionally, an area is drained of or filled with substrate, for example, by previous application of suitable signals, exercises and/or pharmaceuticals. For example, a cardiac region may be stressed to increase or reduce its susceptibility to the phosphorylation modifying signal.

In an exemplary embodiment of the invention, it is noted that the need of a substrate to be available for a protein to be phosphorylated allows selective achievement of the contractility modulation effect and the phosphorylation effect, for example by selectively applying the signal when there is no substrate and/or by selectively applying the signals often enough to achieve phosphorylation but not often enough for significant contractility enhancement.

In an exemplary embodiment of the invention, particular proteins are selectively affected by timing the lengths of signals applied so that they differentially affect one protein or another. Optionally, the signals are repeated in order to have a sufficient effect on a desired protein. Optionally, the signals are delayed from one another in order to allow changes in activity levels of a protein to decay. Optionally, selective mRNA expression is provided by selectively affecting proteins which cause mRNA changes.

In an exemplary embodiment of the invention, selective inhibitors are provided, for example, anti-sense DNA or protein inhibitors, to inhibit certain biochemical pathways. Alternatively or additionally, substrates or exciting materials are provided to enhance certain pathways.

An aspect of some embodiments of the invention relates to selective control of different proteins, for example selective phosphorylation rates thereof. In an exemplary embodiment of the invention, an electric field is used to differentially affect more that one of phospholamban and calcium channels. Such differentiability is to be expected due to the difference in location in the cell of the two proteins (transmembrane and intracellular) and due to the different mechanism for dephosphorylation, each of which generally has a different time rate. Thus, applying pulses of electricity at a certain amplitude and/or a certain rate may be expected to affect one protein more than the other. Phosphorylation and dephosphorylation rates are optionally controlled by controlling availability of substrates and/or catalytic enzyme, for example, using suitable bio-chemicals applied to the cell or patient.

It should be noted that multiple mechanisms for improving contractility generally exist in a cell. Each of the calcium channels and the phospholamban, affect contractility in a different manner and this may allow selecting what manner of affect is desired.

In an exemplary embodiment of the invention, contractility increase of a cell is blocked using one biochemical, while using phosphorylation control to improve cellular homeostasis. Optionally, such blocking is applied locally, for example to small parts of the heart where the overall cardiac output will not be too damaged. Optionally, antiarrhythmic treatment (e.g., electrical or drug) is applied at a same time.

In an exemplary embodiment of the invention, a local effect is applied to enhance local function of the heart, for example in viable regions of a ventricle after massive myocardial infarction. Alternatively or additionally, a local effect is applied to suppress the over contraction of a region of the heart as in patients with hyperdynamic septum as in asymmetrical septal hypertrophy.

In an exemplary embodiment of the invention, tissue viability (e.g., after infarct, donor organ) is tested using methods as described herein for examining activity.

In an exemplary embodiment of the invention, one or more of the following mechanism are addressed using electrical therapy as described herein: affecting calcium availability (intra- or inter-beat time scale), affecting phosphorylation (intra- or inter-beat time scale, affecting mRNA expression directly or indirectly (e.g., by calcium availability and/or phosphorylation) and protein synthesis (days) which affects the cellular steady state. By suitable mixing of therapies or giving therapies with opposite effects at suitable timing, various results can be achieved, for example, long term improvement due to protein synthesis may be offset by momentary blocking of protein activity (e.g., with a pharmaceutical). Similarly, once protein synthesis is underway, a delay of a few days will not completely undo the effects of therapy. In a particular example, prior to starting with beta blockers, electrical therapy may be applied for a while and then, once synthesis has started, e.g., after a few days or a week or based on measurements, electrical therapy may be stopped or applied only every few days, while beta-blockers (or other pharmaceuticals) are applied.

There is therefore provided in accordance with an exemplary embodiment of the invention, a method of modifying tissue behavior, comprising:

determining a desired modification of tissue behavior for at least one of treatment of a disease, short or long term modification of tissue behavior, assessing tissue state and assessing tissue response to stimulation;

selecting an electric field having an expected effect of modifying protein activity of at least one protein as an immediate response of a tissue to the field, said expected effect correlated with said desired modification; and applying said field to said tissue.

In an exemplary embodiment of the invention, said applying has a local effect only on said tissue.

In an exemplary embodiment of the invention, said tissue comprises cardiac tissue.

In an exemplary embodiment of the invention, at least one of said at least one protein is an SR protein.

In an exemplary embodiment of the invention, at least one of said at least one protein is not sensitive to physiologically occurring inter-cellular electric fields.

In an exemplary embodiment of the invention, at least one of said at least one protein is not an ion transport protein.

In an exemplary embodiment of the invention, at least one of said at least one protein controls another protein.

In an exemplary embodiment of the invention, said at least one protein comprises phospholamban.

In an exemplary embodiment of the invention, said at least one protein comprises a trans-membrane calcium channel.

In an exemplary embodiment of the invention, said at least one protein comprises a plurality of proteins. Optionally, said plurality of proteins belongs to at least 2 separate biochemical control pathways. Alternatively or additionally, said plurality of proteins belong to at least 3 separate biochemical control pathways. Alternatively or additionally, said plurality of proteins belong to at least 4 separate biochemical control pathways. Alternatively or additionally, said separate pathways are protein interaction pathways. Alternatively or additionally, said separate pathways include genomic control.

In an exemplary embodiment of the invention, modifying protein activity comprises attaching or detaching a cofactor to at least on of said at least one protein.

In an exemplary embodiment of the invention, modifying comprises phosphorylation.

In an exemplary embodiment of the invention, modifying comprises dephosphorylation.

In an exemplary embodiment of the invention, modifying protein activity comprises modifying the activities of existing proteins, without synthesizing new proteins.

In an exemplary embodiment of the invention, said immediate response comprises a response within less than 10 minutes. Alternatively or additionally, said immediate response comprises a response within less than 2 minutes. Alternatively or additionally, said immediate response comprises a response within less than 20 seconds. Alternatively or additionally, said immediate response comprises a response within less than 2 seconds. Alternatively or additionally, said immediate response comprises a response within less than 0.5 seconds.

In an exemplary embodiment of the invention, said modifying is a transient modification temporally correlated with said applying.

In an exemplary embodiment of the invention, said modifying is a persistent modification lasting at least 10 times the length of said applying. Optionally, said modifying is a persistent modification lasting at least 100 times the length of said applying.

In an exemplary embodiment of the invention, said modifying comprises modifying a ratio between protein configurations of different activation levels of at least one of said at least one protein by a factor of at least 1.2. Optionally, said factor is at least 2. Alternatively or additionally, said factor is at least 5.

In an exemplary embodiment of the invention, determining a desired modification comprises determining a desired modification of tissue behavior. Optionally, said modification is a short term modification significant within 3 hours. Alternatively or additionally, said modification is a long term modification significant within 3 weeks. Alternatively or additionally, said modification is a long term modification which comprises changes in protein expression levels. Alternatively or additionally, said change is a change in at least 5 proteins associated with said behavior. Alternatively or additionally, said change does not include a change in expression of at least two housekeeping genes.

In an exemplary embodiment of the invention, determining a desired modification of tissue behavior comprises determining said modification for treating a disease. Optionally, treating comprises increasing contractility. Alternatively or additionally, treating comprises reversing a heart failure state in said tissue. Alternatively or additionally, said reversing comprises reversing on a cellular level. Alternatively or additionally, treating comprises normalizing protein expression levels. Alternatively or additionally, treating comprises normalizing protein activity levels. Alternatively or additionally, treating comprises skewing protein activity levels to compensate for said disease. Alternatively or additionally, treating comprises changing cellular homeostasis to a different set point. Alternatively or additionally, treating comprises modifying said treatment using a modification of protein activation levels as a target of said treating.

In an exemplary embodiment of the invention, modifying comprises changing a balance between activation and deactivation of a protein in said tissue.

In an exemplary embodiment of the invention, determining a desired modification of tissue behavior comprises determining said modification for assessing of tissue state. Optionally, said assessing comprises assessing based on said tissue response to said applying. Alternatively or additionally, said assessing comprises assessing based on a response of said tissue to said applying. Alternatively or additionally, said assessing comprises assessing based on tissue biochemical markers. Alternatively or additionally, assessing comprises classifying at least one of a disease state and disease severity. Alternatively or additionally, assessing comprises selecting a treatment according to said tissue response. Alternatively or additionally, assessing comprises assessing during an implantation procedure for a therapeutic device. Alternatively or additionally, assessing comprises assessing during a set-up stage for a therapeutic device. Alternatively or additionally, assessing comprises assessing as part of an on-going therapy using a therapeutic device. Alternatively or additionally, assessing comprises sampling said tissue for analysis thereof. Alternatively or additionally, assessing comprises selecting a placement for at least one electrode based on said assessing.

In an exemplary embodiment of the invention, said tissue comprises a tissue sample.

In an exemplary embodiment of the invention, said tissue comprises in-vivo tissue.

In an exemplary embodiment of the invention, said tissue comprises separated cells.

In an exemplary embodiment of the invention, said tissue comprises broken down tissue in which cells are broken down.

In an exemplary embodiment of the invention, said tissue comprises tissue homogenate.

In an exemplary embodiment of the invention, said determining a desired modification of tissue behavior comprises determining a modification for assessing a tissue response to stimulation.

In an exemplary embodiment of the invention, the method comprises modifying a selected field according to a response of said tissue to said applying. Optionally, said modifying a selected field comprises improving said field with respect to a desired effect of said field on said tissue.

In an exemplary embodiment of the invention, the method comprises programming a therapeutic device with said improved field.

In an exemplary embodiment of the invention, the method comprises measuring an immediate response of said tissue to said field.

In an exemplary embodiment of the invention, the method comprises measuring a non-immediate response of said tissue to said field.

In an exemplary embodiment of the invention, the method comprises measuring a non-local effect on remote tissue physiologically associated with said tissue in response to said field.

In an exemplary embodiment of the invention, said field is non-excitatory for said tissue.

In an exemplary embodiment of the invention, said tissue is contractile tissue and wherein said field reduces contraction of said tissue.

In an exemplary embodiment of the invention, applying comprises applying said field in conjunction with a pharmaceutical, which has an interaction with an effect of said field on said tissue.

In an exemplary embodiment of the invention, modifying protein activity comprises modifying protein activation levels.

In an exemplary embodiment of the invention, applying said field is by induction.

There is also provided in accordance with an exemplary embodiment of the invention, apparatus for treating tissue, comprising:

at least one electrode adapted to apply an electric field to in-vivo tissue;

a controller including a memory having stored therein at least one electric field sequence which modifies protein activity levels in said tissue, said controller being configured to determine that a modification of said protein activity is desired and apply said sequence in response said determination. Optionally, said controller memory has stored therein a plurality of sequences or sequence parameters and wherein said controller is configured to select between the sequences or parameters. Alternatively or additionally, the apparatus comprises an input and wherein said controller makes said determination according to a signal received on said input.

There is also provided in accordance with an exemplary embodiment of the invention, a method of manufacturing a therapeutic device comprising:

selecting a pulse sequence according to its effect on protein activity modification; and programming a controller of said therapeutic device to apply said sequence.

In an exemplary embodiment of the invention, said sequence is electrical.

In an exemplary embodiment of the invention, said sequence is selected to treat heart failure.

There is also provided in accordance with an exemplary embodiment of the invention, a therapeutic device manufactured by the methods described herein.

There is also provided in accordance with an exemplary embodiment of the invention, a method of tissue treatment, comprising:

providing a plurality of tissue plugs;

applying an electric field to said plugs to modify biochemical behavior thereof; and implanting said plugs. Optionally, said plugs are cardiac tissue plugs.

In an exemplary embodiment of the invention, the method comprises excising tissue of said plugs from a same heart into which the plugs are later implanted.

In an exemplary embodiment of the invention, the method comprises genetically modifying said plugs prior to said implantation.

There is also provided in accordance with an exemplary embodiment of the invention, a method of therapy, comprising:

selectively applying a therapy material to a tissue; and selectively modifying protein activation in said tissue utilizing a second therapy. Optionally, said therapy material is gene therapy material and wherein selectively modifying comprises selectively modifying protein activity of a protein generated as a result of said therapy.

In an exemplary embodiment of the invention, said therapy material is a substrate for a protein and wherein selectively modifying comprises selectively modifying protein activity of said protein.

In an exemplary embodiment of the invention, selectively applying comprises making said substrate inaccessible to said protein.

In an exemplary embodiment of the invention, said therapy material increases the availability of a protein and wherein selectively modifying comprises selectively modifying protein activity of said protein.

In an exemplary embodiment of the invention, said second therapy comprises applying an electric field.

There is also provided in accordance with an exemplary embodiment of the invention, a method of modifying tissue behavior, comprising:

determining a desired modification of tissue behavior for at least one of treatment of a disease, short or long term modification of tissue behavior, assessing tissue state and assessing tissue response to stimulation;

selecting a tissue modifying activity having an expected effect of modifying protein activation levels of at least one protein as an immediate response of a tissue to the activity, said expected effect correlated with said desired modification; and applying said activity to said tissue.

In an exemplary embodiment of the invention, said activity comprises a pharmaceutical.

There is also provided in accordance with an exemplary embodiment of the invention, a method of modifying tissue behavior, comprising:

selecting a desired balance between a pair of agonist and antagonist reactions in a cell; and applying an electric field to said cell such that said field modifies an existing balance towards said desired balance. Optionally, said balance is a balance between phosphorylation and dephosphorylation.

There is also provided in accordance with an exemplary embodiment of the invention, a biochemical assaying kit, comprising:

an indicator of protein phosphorylation; and instructions for using said phosphorylation as an indicator of tissue state. Optionally, said instructions comprise software.

In an exemplary embodiment of the invention, said kit includes at least one electrode adapted to apply an electric field to a sample being tested with said kit.

In an exemplary embodiment of the invention, the kit includes a chamber and including a sampler adapted to remove a sample for assaying.

In an exemplary embodiment of the invention, the kit is adapted for use with a controller adapted to affect tissue in the body using an electric field.

In an exemplary embodiment of the invention, the kit comprises a plurality of indicators for a plurality of protein or mRNA expression levels.

There is also provided in accordance with an exemplary embodiment of the invention, apparatus for treating cardiac dysfunction, comprising:

at least one electrode adapted to apply an electric field to tissue of a patient; and a controller configured to apply an electrical sequence in spurts of applications with delays between the spurts, said field being configured to have an affirmative modifying effect which modifies a behavior of said tissue in a positive manner, such that a lasting effect from a spurt continues for a significant time after the spurt. Optionally, said lasting effect has a wash-out period.

In an exemplary embodiment of the invention, a total effect of said controller is to modify protein expression levels in a heart of said patient.

In an exemplary embodiment of the invention, said lasting effect comprises enhanced tissue function of tissue to which said field is applied.

In an exemplary embodiment of the invention, said lasting effect comprises enhanced tissue function of tissue to which said field is not applied.

In an exemplary embodiment of the invention, said field is a non-excitatory field.

In an exemplary embodiment of the invention, said delay is at least 1 minute.

In an exemplary embodiment of the invention, said delay is at least 5 minutes.

In an exemplary embodiment of the invention, said delay is at least 10 minutes.

In an exemplary embodiment of the invention, said spurt is applied for less than a single heartbeat.

In an exemplary embodiment of the invention, said spurt is applied for less than 3 seconds.

In an exemplary embodiment of the invention, said spurt is applied for less than 10 seconds.

In an exemplary embodiment of the invention, said spurt is applied for less than 100 seconds.

In an exemplary embodiment of the invention, said field increases contractility.

In an exemplary embodiment of the invention, said controller is adapted to measure washout response to a spurt for said patient.

In an exemplary embodiment of the invention, said delay is at least 3 times a length of said spurt.

In an exemplary embodiment of the invention, said delay is at least 10 times a length of said spurt.

In an exemplary embodiment of the invention, said delay is at least 50 times a length of said spurt.

There is also provided in accordance with an exemplary embodiment of the invention, a method of treating a patient with an electrical therapy, comprising:

applying an electrical field to an organ of the patient;

stopping said application for a length of time which is a function of an expected washout time of an effect of said field.

In an exemplary embodiment of the invention, said organ is a heart and wherein said electric field enhances cardiac function.

In an exemplary embodiment of the invention, said organ is a heart and wherein said electric field enhances cardiac output on a level of a single heartbeat.

In an exemplary embodiment of the invention, said effect is an immediate effect. Alternatively or additionally, said effect is a short-term effect. Alternatively or additionally, said effect is a long-term effect.

In an exemplary embodiment of the invention, the method comprises repeating said applying and said stopping at least 20 times. Optionally, said stopping time varies between repetitions. Alternatively or additionally, said stopping time is varied as the number of hours of application during a day.

In an exemplary embodiment of the invention, said effect is selected to be a change in one or more of ejection fraction, cardiac muscle dimension, cardiac chamber dimension, quality of life as measured by a questionnaire, peak oxygen consumption, anaerobic tolerance, 6 meter walk distance, fluid retention, sleep apnea severity, and exercise tolerance.

In an exemplary embodiment of the invention, the method comprises selecting a patient for therapy responsive to the patient not having an increased QRS length or desynchrony.

In an exemplary embodiment of the invention, said therapy is non-excitatory.

There is also provided in accordance with an exemplary embodiment of the invention, a method of therapy location placement for therapy of tissue, comprising:

applying a test therapy to the tissue; and deciding on suitability of the placement based on an effect of protein activity levels of said test therapy. Optionally, said test therapy is applied outside the body.

In an exemplary embodiment of the invention, said therapy is electrical therapy for the heart.

There is also provided in accordance with an exemplary embodiment of the invention, a method of therapy location placement for therapy of tissue, comprising:

providing an organ to be treated; and selecting at least one location of treatment, according to a desired propagation of biochemical effect of said treatment in said organ. Optionally, said propagation is a mechanical propagation. Alternatively or additionally, said propagation is a biochemical propagation.

In an exemplary embodiment of the invention, said at least one location comprises a plurality of locations.

There is also provided in accordance with an exemplary embodiment of the invention, a method of therapy location placement for therapy of tissue, comprising:

applying a test therapy to the tissue; and deciding on suitability of the placement based on an effect of protein activity levels of said test therapy, even if an improvement in organ function is not detected.

In an exemplary embodiment of the invention, said test is applied to a part of an organ separate from the organ.

In an exemplary embodiment of the invention, said therapy is electrical therapy.

There is also provided in accordance with an exemplary embodiment of the invention, a method of therapy, comprising:

applying a therapy at a first location;

determining if the therapy is having a first effect by measuring a short term response at said first location; and determining if the therapy is having a second effect by measuring a long-term response at a second, untreated, location. Optionally, the method comprises tracking progression of said therapy based on improvement of said second location.

In an exemplary embodiment of the invention, said therapy is electrical therapy.

There is also provided in accordance with an exemplary embodiment of the invention, a method of treating cardiac tissue, comprising:

selecting a tissue with reduced oxygen transport thereto; and applying an electric field to said tissue, which field does not reduce activity thereof. Optionally, said field increases contractility of said tissue. Alternatively or additionally, said field reduces oxygen consumption of said tissue.

There is also provided in accordance with an exemplary embodiment of the invention, a method of assessing tissue state, comprising determining biochemical activity, concurrently in relation to biochemical markers associated with at least two genes associated with heart failure.

There is also provided in accordance with an exemplary embodiment of the invention, a method of assessing cardiac tissue state, comprising determining biochemical activity, concurrently in relation to biochemical markers associated with at least two genes.

In an exemplary embodiment of the invention, the method comprises assessing tissue state in response to a therapy applied thereto.

In an exemplary embodiment of the invention, said assessing is in response to at least 5 markers concurrently. Alternatively or additionally, said assessing is in response to at least 10 markers concurrently. Alternatively or additionally, said assessing is in response to at least 20 markers concurrently. Alternatively or additionally, said markers include mRNA expression levels. Alternatively or additionally, said markers include protein expression levels. Alternatively or additionally, said markers include protein activity levels.

In an exemplary embodiment of the invention, the method comprises improving a therapy using said biochemical markers as a target.

In an exemplary embodiment of the invention, said biochemical markers include GATA-4.

In an exemplary embodiment of the invention, said biochemical markers include phosphorylation of phospholamban.

In an exemplary embodiment of the invention, said determining comprises determining an immediate effect.

In an exemplary embodiment of the invention, said determining comprises determining a short term effect.

In an exemplary embodiment of the invention, said biochemical markers include markers from at least two pathways in the tissue.

There is also provided in accordance with an exemplary embodiment of the invention, a kit adapted to perform the determining as described herein.

There is also provided in accordance with an exemplary embodiment of the invention, a method of treating cardiac dysfunction, comprising:

determining a desired effect on protein activity; and applying a field to cardiac tissue to cause such desired change.

In an exemplary embodiment of the invention, said desired effect comprises a selective effect on fewer than 5 proteins.

In an exemplary embodiment of the invention, said desired effect comprises a selective effect on fewer than 10 proteins.

In an exemplary embodiment of the invention, said desired effect comprises a selective effect on fewer than 40 proteins.

There is also provided in accordance with an exemplary embodiment of the invention, a method of treating cardiac dysfunction, comprising applying an electric field to said heart which is sufficient to have a significant normalization effect on protein phosphorylation levels without significant effect on contractility.

There is also provided in accordance with an exemplary embodiment of the invention, apparatus for delivering an electric field to cardiac tissue, being programmed to use a minimum amount of power sufficient to affect positively the phosphorylation of HF-related proteins.

There is also provided in accordance with an exemplary embodiment of the invention, a method of treating tissue, comprising:

determining a desired effect on levels of at least one of phospholamban and phosphorylation thereof; and applying a field to tissue to cause such desired change.

There is also provided in accordance with an exemplary embodiment of the invention, a method of treating cardiac tissue, comprising:

selecting a signal according to its not being expected to increase mean oxygen consumption; and applying an electric field with said signal to cardiac tissue, which field does not reduce activity thereof.

There is also provided in accordance with an exemplary embodiment of the invention, a method of manufacturing a cardiac device, comprising:

selecting a signal which is expected not to increase mean oxygen consumption while not reducing tissue activity; and programming a cardiac device with said signal.

There is also provided in accordance with an exemplary embodiment of the invention, a cardiac controller, comprising:

a signal application circuit adapted to apply a first signal which increases mean oxygen consumption and second signal which does not increase said oxygen consumption; and a control circuit adapted to control said signal application circuit to selectively apply one of said two signals, based on oxygen availability.

BRIEF DESCRIPTION OF THE SEVERAL VIEWS OF THE DRAWINGS

Non-limiting embodiments of the invention will be described with reference to the following description of exemplary embodiments, in conjunction with the figures. The figures are generally not shown to scale and any sizes are only meant to be exemplary and not necessarily limiting. In the figures, identical structures, elements or parts that appear in more than one figure are preferably labeled with a same or similar number in all the figures in which they appear, in which:

FIGS. 3A-3E show the immediate effect of CCM signals on proteins in accordance with exemplary embodiments of the invention;

FIG. 8 shows levels of phosphorylated phospholamban in dog septum with heart failure with chronic treatment, in accordance with an exemplary embodiment of the invention;

FIG. 11 presents western blot data illustrating effect of 3 months of CCM according to an exemplary embodiment of the invention on levels of P-PLB at serine-16 and threonine-17 in the LV free wall and inter-ventricular septum relative to sham-operated HF dogs and normal dogs;

DESCRIPTION OF SPECIFIC EMBODIMENTS OF THE INVENTION

Overview

Figure 1:
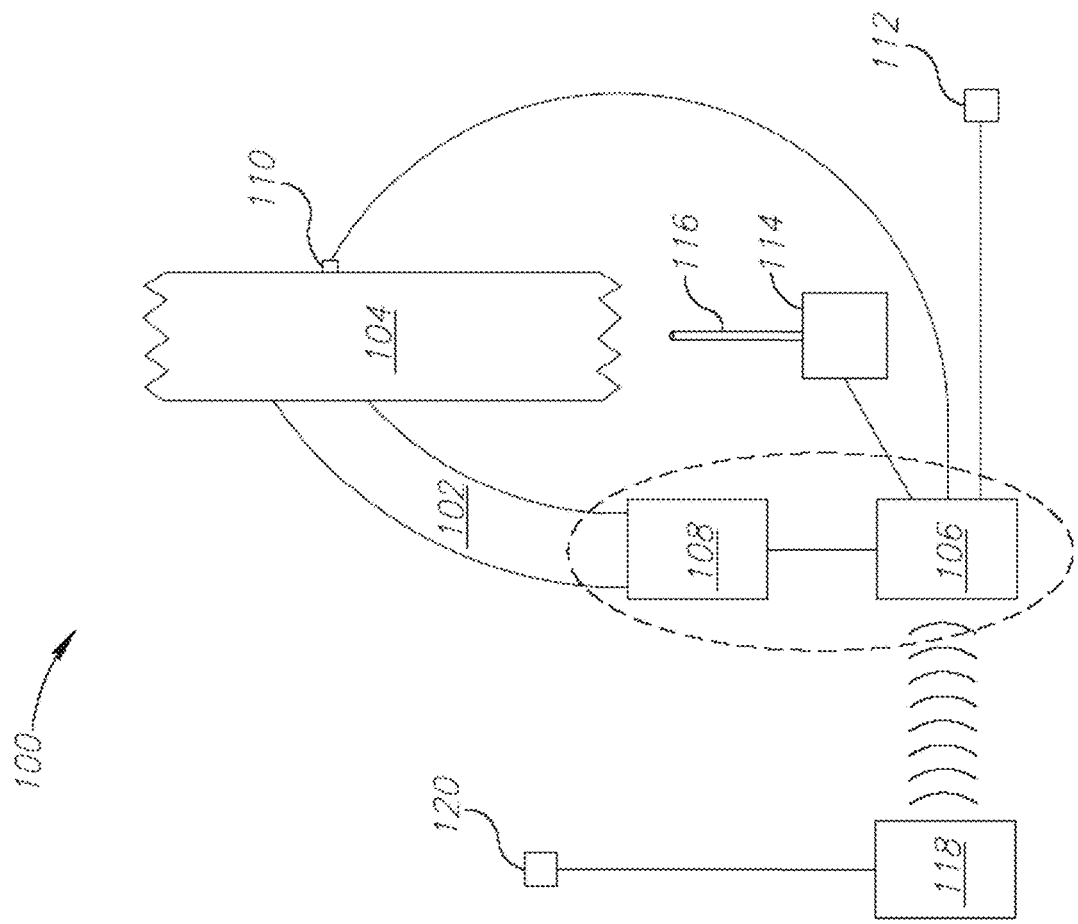
FIG. 1 is a schematic diagram of a tissue controller utilizing an electrical field to achieve a phosphorylation effect, in accordance with an exemplary embodiment of the invention.

Exemplary embodiments of the present invention are based on the discovery that certain electrical signals have an immediate effect on the phosphorylation of certain cardiac proteins, for example, at least one, at least 2, at least 3 or at least 5 proteins. Optionally, a set of proteins is affected, for example proteins that relate to calcium availability. In particular, an effect on proteins that control calcium pumping and others (all of which are known to change in heart failure), has been discovered. Selectively in which proteins were affected is also shown. Proteins not related to heart failure are apparently not affected. The effect has been found to work in a range of tissue organization levels starting from tissue homogenate, through isolated cells and even in in-vivo dog hearts. The effect remains (in dog hearts) for 15 minutes at least, and an initial effect is noticeable after as little as 1 minute or even a few seconds, such as 3-10 seconds, for tissue samples from a foci of signal application. Some proteins were phosphorylated and some were unphosphorylated by the signal. Generally, the results show a change in the phosphorylation values in a direction of "normal" levels, or their being maintained at normal values. Experiments using pacing signals have not shown this effect.

This phosphorylation effect is optionally in addition to or instead of effects on mRNA expression and protein expression levels, which, in some embodiments of the invention are normalized, changed to more normal values and/or changed in a manner which overcompensates for a deficit.

In accordance with exemplary embodiments of the invention, this discovery is used in the design of methods and apparatus for treating tissue, especially cardiac tissue.

For purposes of this specification and the accompanying claims, the terms "expression" and "regulation" should be construed in their broadest possible sense so that they include any factor which influences a biological activity. Thus expression and/or regulation include, but are not limited to factors such as control exercised at the genomic DNA level, the RNA level, the protein level and secretion level.

With regard to genomic DNA, control may be exercised, for example, by altering a phosphorylation and/or a methylation state at one or more sites in a relevant genomic sequence.

With regard to RNA, control may be exercised, for example, by regulating a rate of transcription of an mRNA transcript, and/or by altering a stability of an mRNA transcript, and/or by altering a relative amount of splice variants from a single mRNA transcript.

With regard to protein, control may be exercised, for example, by regulating one or more cleavage events and/or addition of one or more side chains and/or protein stability. In some cases cleavage of a protein may increase a biological activity of the protein and/or facilitate secretion from a cell. In other cases, cleavage of a protein may reduce or eliminate activity of the protein. The term side chains, as used herein, denotes any molecular moiety which can be attached to an amino acid of the protein. In some cases, side chains are attached after translation. In other cases a tRNA molecule may attach an amino acid bearing a side chain during translation.

With regard to secretion, control may be exercised, for example, by allowing or preventing of secretion of compounds, such as connective tissue dissolving enzymes and biochemical signaling molecules.

Schematic Device

FIG. 1 is a schematic diagram of a tissue controller 100 utilizing an electrical field to achieve a phosphorylation effect, in accordance with an exemplary embodiment of the invention. In an exemplary embodiment of the invention, controller 100 comprises at least one electrode 102 adapted to apply an electric field to a tissue 104, for example a heart. A control circuitry 106 optionally controls the output of a power drive 108 which electrifies the at least one electrode 102. One or more optional physiological sensors 110 optionally provide feedback to be used by circuitry 106 in controlling the electrification of the at least one electrode 102, for example, general feedback about the heart (e.g., ECG) and/or a micro-biological sensor, for example for mRNA expression profiles or protein activity level. Optionally, such sensors include fiber-optic anti-body based sensors, DNA or protein chips and/or lab-on-chip type sensors. General body sensors, such as a sensor 112 may be used as well, for example, to estimate fluid retention or motion of the patient (e.g., rest/exercise as estimated using an accelerator).

In an exemplary embodiment of the invention, controller 100 is in the form of a pacemaker or non-excitatory controller, for example as described in one or more of the following applications and publications.

Exemplary protocols for the actual delivery of signals to the heart and/or implantation of wires to deliver CCM signals is set forth in PCT publication No. WO 97/25098 and U.S. Pat. No. 6,317,631, both of which are incorporated herein by reference in their entirety. Following is a list of patents and publications which describe apparatus and methods which may be useful in conjunction with the present invention, the disclosures of all of which are incorporated herein by reference, as are the disclosures of all publications mentioned in this application:

Cardiac output enhanced pacemaker, U.S. Pat. No. 6,463, 324, Apparatus And Method For Controlling The Contractility Of Muscles, U.S. Pat. No. 6,233,484, Controlling Heart Performance Using A Non-Excitatory Electric Field, U.S. Pat. No. 6,317,631, Muscle Contraction Assist Device, U.S. Pat. No. 6,285,906, Modulation Of Intracellular Calcium Concentration Using Non-Excitatory Electrical Signals Applied To The Tissue, PCT WO01/24871 and PCT WO00/12525, Electrical Muscle Controller, U.S. Pat. No. 6,363, 279, Electrical Muscle Controller using a Non-Excitatory Field, U.S. Pat. No. 6,330,476, Cardiac Output Controller, U.S. Pat. No. 6,298,268, Cardiac Output Enhanced Pacemaker, U.S. Pat. No. 6,463,324, Sensor Based Regulation of Excitable Tissue Control of the Heart, WO00/27475, Regulation of Excitable Tissue Control of the Heart based on Physiological Input, WO00/27476, Trigger Based Regulation of Excitable Tissue Control of the Heart, U.S. Pat. No. 6,587,721, Pacing with Hemodynamic Enhancement, PCT WO/1998/023211A1, ETC Delivery via RV Septum, PCT WO0182771A3, Anti-Arrhythmia Device having Cardiac Contractility Modulation Capabilities, PCT WO01/30445, and Anti-Arrhythmic Device & a Method for Delivering Anti-Arrhythmic Cardiac Therapy, PCT WO01/30139.

In some embodiments of the invention, the devices described in PCT publications WO 2005/056111, WO 2005/102188 and/or WO 2005/105013, with suitable changes in programming, are used.

In an exemplary embodiment of the invention, controller 100 includes a memory in which various measured and/or expected values and behaviors of tissue and bio-chemicals are stored. Controller 100 may be implanted, only the electrodes implanted or be wholly outside the body, optionally only with a sensor implanted, optionally with a sensor inserted as needed.

In an exemplary embodiment of the invention, controller 100 includes a molecule source 114 or controls an external molecule source (not shown), for example, using a data line or a wireless communication. Optionally, the molecule source sends a signal to controller 100 that a molecule was provided. Alternatively, an external trigger is used for both controller 100 and molecule source 114. Optionally, the source is provided using a tube or other delivery system 116. Such a source may be used, for example, as described below with reference to FIG. 4.

In an exemplary embodiment of the invention, controller 100 uses one or more external sensors 120 (e.g., body ECG) and/or an external control 118 to guide its behavior. Optionally, an external programmer/monitor is used for communication from a patient to a caregiver, for example, a hospital or monitoring agency. Optionally, such a programmer/monitor is used to send programs and/or setting to controller 100 and/or send queries regarding the effects of certain treatment sequences. Optionally, controller 100 maintains a log of physiological measures and/or applied sequences and/or synchronization thereof. The log may be limited to times before and after the treatment and/or include random times or times triggered by various physiological measurements.

Controller 100 optionally provides one or more of the therapeutic effects listed following this paragraph. Optionally, when two or more effects are provided, the effects are provided simultaneously or alternately (e.g., alternating or otherwise intermixed electrification signals to have the multiple desired effects). In some cases, the behavior of the controller is modified to provide a tradeoff between multiple effects. Some of the effects may be enhanced and/or caused by modification of protein activity and/or mRNA expression. In some cases, the sequences used for "standard" effects are modified so that desired biochemical effects as described herein are achieved. Such modification may be by per patient optimization or by off-line general quasi-optimization independent of any particular target patient. Optionally, the controller is programmable, for example, using outside programming to perform one or more of the following therapies, as described elsewhere:

a) pacing;
b) contractility enhancement;
c) cardiac resynchronization;
d) conduction velocity modification;
e) remodeling;
f) arrhythmia treatment and/or prevention;
g) healing of diseased cardiac tissue; and
h) stabilizing cardiac condition.

Phosphorylation Modification

As noted above and as will be described below, it has been discovered that pulses originally designed for cardiac contractility modification (CCM) have an immediate and/or a long range effect on genomic expression (e.g., as evidenced by mRNA expression) and/or on protein activity. However, it is believed that other pulses also have such effects. In particular, CCM pulses often require a certain timing, which may not be required for some phosphorylation effects. In particular also, CCM pulses may need to be applied more often for significant CCM effects than for significant phosphorylation effects. In particular also, phosphorylation effects may be achieved even when CCM or at least contractility increase is reversed or null or fluctuates. In particular also, phosphorylation effects may also be achieved using excitatory signals or a combination of excitatory and non-excitatory signals and not only with pure non-excitatory signals.

In an exemplary embodiment of the invention, within seconds of applying the electric field to the tissue in-vivo or in-vitro, existing phospholamban protein is phosphorylated, without the need to synthesize more protein, but rather making use of what is already there in a "dephosphorylated state". In some embodiments, while the phosphorylation provides an "immediate response", the treatment and/or phosphorylation act as a trigger for later synthesis or change in synthesis of proteins.

In an exemplary embodiment of the invention, one or both of between beat and within beat phosphorylation levels are controlled. For example, to reduce inter-beat effects, phosphorylation increase is kept at a level which cellular homeostasis mechanism can counteract by the next time a field is applied. In some cases, this requires one or both of control of field amplitude and frequency of application.

Optionally, different proteins are differently controlled, for example intra-cellular and trans-membrane proteins.

Figure 4:
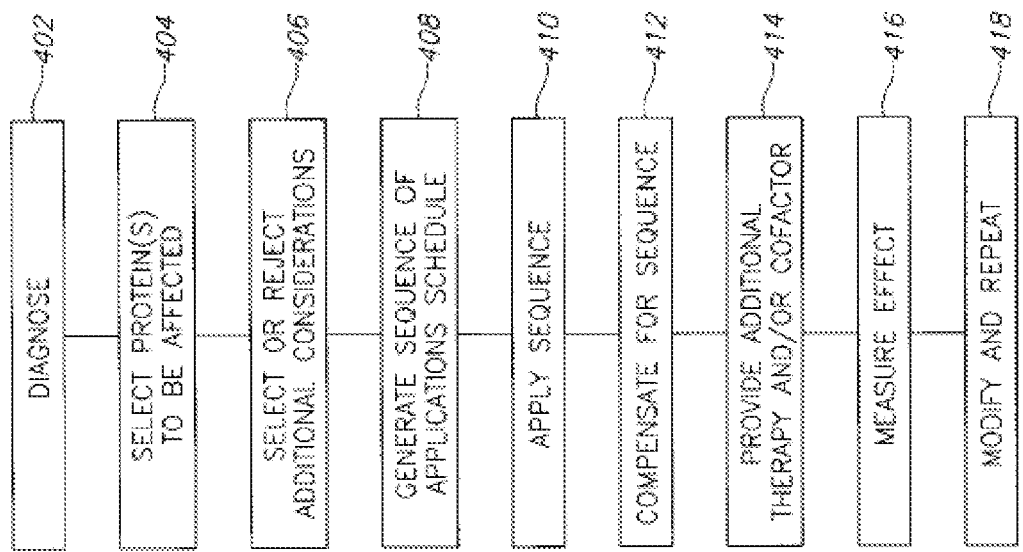
FIG. 4 is a flowchart of a method of therapy taking phosphorylation into account, in accordance with an exemplary embodiment of the invention.

FIG. 4 is a flowchart of a method of therapy taking phosphorylation (or other biochemical change) into account, in accordance with an exemplary embodiment of the invention.

At 402 a diagnosis of a patient is optionally made. Optionally, the patient is re-diagnosed as his therapy advances.

At 404, one or more proteins to be affected by the electrical signals are selected. Optionally, the proteins are selected based on the diagnosis. Optionally, a set of related proteins, for example, calcium availability proteins, are selected. Optionally, one or more locations in the heart to be affected are selected. Optionally, target protein, mRNA and/or phosphorylation levels and/or other tissue or organ effects are selected.

At 406, additional considerations are selected and/or rejected. In one example, the additional consideration is that the heart be paced and/or its LVEF (left ventricular ejection fraction) be increased. In a different example, considering that the pulses may be applied less often than pacing pulses, more painful treatments, such as external pulses, are used. Optionally, pro-arrhythmic pulses are used, for example, if the treatment is under a hospital setting or if the treatment is infrequent enough so that the total danger of arrhythmia over a time period is within acceptable parameters. Controller 100 optionally includes a defibrillation and/or fencing function applied through the same or other electrodes. In an exemplary embodiment of the invention, immediate reduction in cardiac efficiency is acceptable, as this is under controlled conditions and increased cardiac health will follow shortly (e.g., within minutes, hours, days or weeks).

In another example, a protein modifying signal is applied as an exciting signal. In another example, a protein modifying signal is applied in parts of the cardiac cycle where it reduces contractility (or dP/dt) and/or prevents normal signal propagation in the heart. Optionally, the part of the heart to which the signal is applied is decoupled or deactivated, for example, by cold, by fencing or by various cardioplegia drugs.

In an exemplary embodiment of the invention, it is assumed that the protein modification signal has an effect that is at least partly independent of the point in the cardiac cycle at which it is applied, at least for some proteins, such as proteins that are not electrically sensitive to the electrical cycle in the cell. For example, the effect depends on the availability of ATP for phosphorylation and not on the particular charge conditions in the cell. For some applied signals, the ion concentrations may have an effect on the efficacy of the signal and these may be dependent on the phase in cell depolarization/repolarization cycle. In an exemplary embodiment of the invention, the effect of a particular sequence and/or for a particular patient is taken into account when deciding on the strength and/or other parameter of a signal.

In an exemplary embodiment of the invention, it is assumed that a CMM-type signal has multiple effects on cardiac tissue which may be targeted separately, at least to some extent. Some effects are causative, but may be at least partially decoupled or require multiple inputs to generate a particular desired result. Some of the effects are:

a) Effect on tissue polarization. This may include, for example, hyper-polarization, pacing and depolarization.

b) Effect on repolarization/depolarization cycle. This may include, for example, extending a plateau duration.

c) Effect on tissue function (external), for example, increased contraction strength and inhibition of mechanical and/or electrical activity.

d) Effect on protein phosphorylation.

e) Effect on genomic expression.

f) Short vs. long term effects (e.g., remodeling).

At 408 a pulse sequence and/or application schedule (e.g., once a week) are optionally generated or selected, for example, using a look-up table or by searching for a solution. Many optimization and search methods are known in the art and may be used to help determine a treatment protocol; for example, linear programming, hill climbing and trial and error experimentation (e.g., manual or automatic experiments). The particular characteristics of the tissue and/or patient may also be determined, for example, by experimentation or by a table linking disease type to an expected (and/or desired) effect of a change in the protocol. The generation is optionally performed on controller 100. Optionally, the generation is at a treatment center, for example, if the patient comes in periodically for treatment or, if treatment is by remote means, by using a telephone link to control an implanted or external field source.

At 410, the sequence is applied to the tissue.

At 412, compensation for the effects of the sequence may be provided, if necessary, for example, anti-arrhythmia treatment or oxygen provision. Optionally, the compensation is provided before and/or during the sequence application, or intermingled therewith.

At 414 an additional therapy and/or cofactor are optionally provided, which optionally interact synergistically with the sequence, for example, on a cellular level or by one assisting the other to have an effect. In one example, the additional therapy is pharmaceutical. In another example, the additional therapy provides a cofactor or substrate which the proteins need to change their activity level. In another example, DNA therapy is made more specific by the proteins being generated and/or being activated by the field. In another example, exercise or rest is enforced so as to build-up a supply of substrate (e.g., protein or phosphor) on which the field can have an effect.

In an exemplary embodiment of the invention, the additional therapy is applied systemically. Alternatively or additionally, at least one additional therapy is applied locally, for example, using targeting methods and/or local delivery methods as known in the art. Optionally, the methods of PCT publications WO 01/93951, WO 00/74773 and/or WO 01/93950, the disclosures of which are incorporated by reference, are used. Optionally, in accordance with some of these methods, a same electrical field source applies both a therapeutic-effect field and a targeting/transport field.

At 416, the effect of the field is optionally measured. Optionally, the measurement is in substantial real-time. In an exemplary embodiment of the invention, a gene or protein chip are used to detect protein, phosphorylation and/or mRNA levels. Alternatively or additionally, an optical sensor is used, for example an anti-body carrying optical detector. Optionally, the sensor is consumable and lasts, for example, for 5, 10, 20 or 100 uses (e.g., a multiplicity of single use sensors may be supplied). Optionally, spectroscopy methods are used, for example, Raman spectroscopy.

While phosphorylation may be measured directly, optionally, cellular and/or organ behavior characteristics are measured instead, for example, stroke volume and effect on ECG.

In an exemplary embodiment of the invention, evaluation methods as described in U.S. provisional application Ser. No. 60/765,974, filed Feb. 7, 2006, by inventors Benny ROUSSO et al., the disclosure of which is incorporated herein by reference, are used.

In an exemplary embodiment of the invention, evaluation is used to evaluate one or more of patients state, disease state and/or disease progression. Evaluation means may be included in controller 100 or be external to patient. Evaluation may be applied relatively continuously, for example more often than once a day, or less often for example, weekly or monthly or less often. In an exemplary embodiment of the invention, evaluation is used to identify events where changes in therapy are desirable, for example, where therapy was insufficient, where patient reached his bounds or where adverse effects are found.

In an exemplary embodiment of the invention, evaluation comprises detecting changes in cardiac activation due to change sin conduction velocity. Optionally, the changes are detected by detecting a change in relative timing of events on an impedance measurement of the heart.

At 418, the sequence is optionally repeated, optionally being modified according to the obtained results.

Optionally, multiple feedback loops are maintained, for example, some parameters being measured on a second by second or minute by minute basis and others being measured on an hourly, daily, weekly and/or monthly schedule.

Optionally, the measurements are off-line, for example, by biopsy taking. Optionally, the sample is frozen, for example in liquid nitrogen, to prevent changes. The results are optionally transmitted to controller 100.

In an exemplary embodiment of the invention, the intended effect of the electrical therapy is to tip a balance between phosphorylation and dephosphorylation mechanisms in the cell. For example, the electric field can be applied so that a protein (such as calcium channel) is more easily phosphorylated, while dephosphorylation mechanisms stay the same (or vice-versa). This can cause both an immediate (intra-beat) effect on phosphorylation levels and, possibly depending on the ratio between the immediate effect and the dephosphorylation mechanism, can cause a longer term increase.

In some cases, the long term increase is carried past normal levels, for example, to force a certain operation state of the controlled tissue.

In an exemplary embodiment of the invention, the electrical modification of proteins is used to achieve an effect that does not directly translate into long term changes in protein levels.

In an exemplary embodiment of the invention, the electrical modification is used to trigger a change in cellular state. For example, once certain cellular balances are upset, cellular mechanism will then change the operational mode of the cell in a desired manner.

In an exemplary embodiment of the invention, the electrical modification is used to support a failing cellular mechanism so that the cell can recover.

In an exemplary embodiment of the invention, electrical modification of biochemical behavior works together with existing control mechanism of the body, in addition to or instead of over-expression or under-expression of body biochemicals. In an exemplary embodiment of the invention, existing control mechanism are not disrupted, but rather utilized, for example, using existing control mechanism to control functionality provided by the therapy, causing existing control mechanism to act when they are inhibited from acting for some reason and/or inhibiting over-reactive control mechanism.

In an exemplary embodiment of the invention, the electrical modification is used to damp or overcome an over-protective or run-away protection/control mechanism. One example, in cardiac cells, is a mechanism that when the cell feels over stressed, reduces contractility so that the cell can funnel its resources to viability. The electrical modification can be used to suppress this mechanism, so that contractility can resume, especially if the cell is actually capable of contraction and such contraction is suppressed or reduced by a run-away mechanism. Optionally, if there is a degradation in function, for example as detected by reduction in cardiac output or degraded ECG signals, the protein modification is stopped and is used as an indication that the cellular protection mechanism was not actually being over protective.

In an exemplary embodiment of the invention, the electrical modification increases calcium availability, thereby allowing existing control mechanism to "decide" if this increased availability should be utilized at any given instant to increase cardiac output. It is noted that the available increase and ability to work with existing mechanism can prevent degradation of heart tissue.

In an exemplary embodiment of the invention, the therapy does not require any particular ligand or effector to tie to, but acts directly on bio-molecules.

In an exemplary embodiment of the invention, the electrical modification is not treated as a systemic therapy, but as a local therapy, for example, limited in effect to tissue directly or indirectly affected.

Exemplary Considerations for Pulse and/or Schedule Design

Further to the examples above, following are exemplary considerations to be taken into account during sequence and/or schedule design. In particular, pulse length, power, shape, intra-pulse delay, repetition rate and/or delay between sequences may be modified and/or optimized to have a desired effect (or mainly such a desired effect).

a) Pulse rate and length. Protein specificity is optionally achieved based on one or both of length of each pulse and delay between pulses. As noted, some proteins are significantly affected by short pulses. Such a protein can be selectively affected by using shorter pulses than needed for other purposes, and repeating the pulses at inter-pulse delays shorter than a relaxation time for the affected protein. Optionally, proteins are targeted based on their location in the cell and the type (e.g., amplitude, frequency and/or waveform) of pulse that is expected to penetrate sufficiently into the cell and/or affect the particular protein. Optionally, pulse rate and/or delays and/or length are modified as needed to achieve a target. This allows for targeting the effect to a limited number of proteins.

b) mRNA vs. protein effects. In an exemplary embodiment of the invention, mRNA and/or protein effects are selected by applying pulses which have a short term effect on proteins but the effect is not long enough to trigger significant mRNA expression effects. For example, if a protein phosphorylation level is not elevated for long enough, it may be that mRNA effects will be absent. However, phosphorylation may be increased multiple discrete times (with delays between them). In accordance with some embodiments of the invention, some mRNA effects are directly determined by proteins, so that protein levels may be controlled in order to achieve selective mRNA effects.

c) Counter effects. In an exemplary embodiment of the invention, the control is selected so that mRNA effects and phosphorylation effects are not synchronized. For example, long plateaus of increased phosphorylation may be used to increase mRNA effect, but total phosphorylation modification may be selected to be insignificant over a time period. One reason for this may be lack of sufficient blood flow to the heart, so that acute changes are less desirable than gradual changes. In another example, pharmaceuticals which counteract an effect may be provided to effectively select certain effect(s). It is noted however, that phosphorylation changes associated with increased contractility did not show increased oxygen demand, in some experiments at least and in at least one experiment, even reduction in oxygen demands.

d) Stability. Optionally, the long term effect of treatment is a new balanced set point between the various proteins. However, in the short term, such a balancing need not be achieved. Optionally, the heart is controlled so that the various proteins are not at a balance with regard to their respective activities.

e) Physiological time scales. In an exemplary embodiment of the invention, the rate of application and/or duration relates to the time scales of physiological behavior, for example, sleep/wake cycles, eating times, time scale for formation of protein and/or mRNA transcription (e.g., 1-3 days and 1-4 hours, respectively).

f) Triggering. In an exemplary embodiment of the invention, a pulse sequence is applied and/or modified in response to a trigger event. In an exemplary embodiment of the invention, controller 100 has stored thereon (or on an external controller) a table of situations and response (e.g., different sequence application parameters). Alternatively or additionally, to a table, other programming means may be used, for example, logic and neural networks. Exemplary trigger events include, stress, arrhythmia, ischemia, eating, resting, changes in concentration of biochemicals (e.g., intra-cellular, extra-cellular and/or blood) and/or changes in electrical signals (e.g., ECG, EMG and/or EEG). Possibly, this allows the sequences to be applied only where there is a need and/or when they will have a significant effect.

g) Treatment of areas and combination of therapies. In an exemplary embodiment of the invention, treatment is applied to multiple areas. Optionally, sequences are not applied in parallel to different areas, but in series. For example, one area being treated and then a second area is treated. Optionally, the duration of each treatment and/or cycle time depend on one or more of stabilization times, relaxation times and/or length of effect times. In one example, each area is treated one hour on and several hours off, with other areas (e.g., 2, 3, 4) being treated in the "off" time. In an example of therapy combination, if the allowed delay between applications of one therapy are longer than the application times of another therapy, the two therapies can be applied in a mixed manner to tissue. In some cases, two therapies can be applied simultaneously, for example, signals with different electrical frequencies, each of which has a selective effect on different biochemical pathways, for example, one signal which affects nerves (e.g., high frequency) and a second signal which affects phosphorylation.

One example is found in skeletal muscles, where their biochemical state (aerobic or anaerobic) can depend on nerve stimulation. Optionally, nerve stimulation is used to prompt cells to be more (or less) sensitive to phosphorylation control of phospholamban.

h) Noticeability of effects. In some cases, it may be desirable to prevent any immediate effects (e.g., contractility changes), while still providing therapy. For example, if only 10% of beats are treated, this may not be noticeable on a daily basis, but the cumulative effects of protein synthesis will be noticeable after a while. Optionally, the sequence is provided in a manner which will not be noticeable over time scales of minutes (e.g. 1-20), hours (e.g., 1-10) and/or days (e.g., 1-7). In an exemplary embodiment of the invention, the lack of noticeability is used to prevent interfering with the patient's lifestyle.

i) Compliance. In an exemplary embodiment of the invention, electrical field application does not require compliance from the patient and this can be a benefit. Optionally, applying the signal at a time when the patient is asleep, can prevent the patient from causing (intentionally or unintentionally) physiological states where the therapy is not applied for various reasons (e.g., safety, suitability). Optionally, however, compliance is required, for example, for taking of a medication that works together with the therapy. Optionally, if a patient does not indicate to the system that the medication was taken (e.g., using a wireless communication device), or if this lack is sensed by the system, the applied sequence is changed, initiated and/or inhibited, to compensate for this lack.

j) Adaptation. In general, electrical signals are expected to be less susceptible to adaptation than pharmaceuticals, because the duration of electrical therapy and its onset can be controlled better than for pharmaceuticals. In an exemplary embodiment of the invention, providing the therapy in a manner which is specific in time, prevent adaptation mechanism that relate to the mere existence of the therapy. Optionally, the therapy is changed over time, to prevent and/or counteract adaptation. Optionally, the therapy is changed when an adaptation is suggested by lack of or reduced reaction of the patient.

In general, short term effects/goals and long term effects/goals may be at odds.

Exemplary Pulse Properties

While CCM pulses as described herein may be used, optionally, the pulses used are modified, for example, to save power and/or reduce the need for synchronization.

In an exemplary embodiment of the invention, the applied pulses and/or sequences require considerably less power than CCM signals (e.g., 7.73 volts for 33 ms each 45 seconds), for example, only 20%, only 10%, only 5%, only 1%, or intermediate or smaller power usage. Optionally, the power per pulse is maintained, but the number of pulses in a time period is reduced, so that a cumulative power level is reduced (e.g., as compared to CCM signals).

In an exemplary embodiment of the invention, the amplitude and/or duration used is insufficient for contractility, for example, being under the amount (if any) which causes a 20%, 10%, 3%, 2%, 1% or intermediate or smaller increase in contractility over a period of 5 minutes from initial application. For example, the application rate, power and/or duration are smaller.

In an exemplary embodiment of the invention, the voltage used is lower than for CCM, for example, being 0.1, 0.5-1 volts, or less, or values such as 2V or 3V or other values smaller than 8 Volts. It should be noted that in the results shown below, the CCM signal was clearly more than required to achieve a meaningful phosphorylation, and thus a signal less powerful may be suitable. Larger voltages such as 10, 20 or 30 volts may be used in some embodiments.

In an exemplary embodiment of the invention, the duration of the pulses is as short as 1 ms (with an optional associated increase in power), or longer, such as 10 ms, 20 ms or more. Alternatively, the signal may be lengthened, for example, being 50, 100, 150, 200, 300, 400 ms or more. Optionally, medication which increases a refractory period is used in conjunction with long pulses. Optionally, fast and short term acting medication is used during pulse application.

In an exemplary embodiment of the invention, a total charge carried by a phosphorylation pulse is at least 5, 10, 30, 50 or 100 times the charge carried by a pacing pulse, such as a 3V 0.75 ms pulse.

High power pulses are optionally applied as sub-threshold (for excitation) pulses.

In an exemplary embodiment of the invention, the current for the pulse is between 0.2 ma and 20 mA, or intermediate or higher values. Other exemplary values for current (maximum current) are 0.4, 0.8, 1, 3, 7 or 10 mA (or intermediate values).

In an exemplary embodiment of the invention, the applied signal comprises a series of pulses, for example, each pulse being bi-phasic, with each phase being 5.5 msec (~100 Hz), applied in synchronization with a local pacing activity (e.g., at a delay thereto). Optionally, the series is of 2-3 pulses, or a larger number, for example, 5, 10, 20 or more or intermediate numbers.

Other waveforms can be used, for example, sinus waves or triangular waves. Optionally, a delay is provided between pulses of a series. Optionally, a pulse includes both excitatory and non-excitatory components.

In an exemplary embodiment of the invention, signals applied outside the absolute refractory period are applied at lower amplitudes. The relevant thresholds are optionally determined by experimentation or using standard values (noting that diseased tissue may have a lower threshold and/or abnormal refractory periods. Optionally, medication is provided to extend the refractory period and allow a greater charge and/or longer pulse sequence to be delivered during a single beat.

In an exemplary embodiment of the invention, a tune-up of the pulse parameter is carried out, for example, to enable power to be reduced to a minimum which has an effect and/or as the patient response changes.

In an exemplary embodiment of the invention, the application schedule includes reducing the number of applied sequences and/or increasing the delay between them. For example, as shown below, a 1 min application has an effect even after 15 minutes. Thus, it is expected that a short application, for example, 20-60 seconds can be used to maintain more normalized phosphorylation levels for many minutes, for example, 15, 20, 40, 60 minutes or more. Optionally, a small number of spurts can thus be used to maintain relatively "normalized" levels for many hours, such as 1, 2, 4, 6, 10, 12, 24 or more per hour (e.g., one spurt for each beat or small number of beats such as 2, 5, 10, 20 or intermediate numbers). It should be noted that reduced frequency of application reduces total power needs.

In an exemplary embodiment of the invention, the delays between spurts are not electric field free. For example, a continuous low level filed may be applied, for example for causing hyper polarization of the tissue, reducing contractility and/or modifying immediate conduction velocity. Similarly, a pulse sequence may maintain a baseline signal (constant or varying) even between pulses of the sequence. Optionally, the base line signal is selected to be non-excitatory, for example, by virtue of its frequency (e.g., too high or too low) and/or power level. As noted herein, such a baseline signal may generate enough charge to positively affect phosphorylation.

In an exemplary embodiment of the invention, different stages in treatment are identified: immediate, mRNA, protein and physical remodeling. Each state has its own time constants for initiation and for decline. In an exemplary embodiment of the invention, a therapy is applied long enough to have a noticeable effect on the stage where effect is required. Times of no therapy application may be selected to match the stage. For example, at remodeling stage, delays (no application times) of days or weeks may be acceptable. Optionally, even at such a remodeling stage, applications to continue a lower level stage (e.g., immediate) may be applied, at least part of the time. In an exemplary embodiment of the invention, a complete therapy plan may include desired effects on the different stages and an overlap of sequences and sequence application times is generated to address the stages required at the point in the process required. Optionally, a model is created linking the different stages and therapy application. This model is used to decide when therapy may be applied and when it must be applied. Further, additional therapies may be evaluated for application depending on how they impact the overall strategy. In some cases, it is expected that computer modeling and/or such mechanisms will be required to find a useful solution for a give case.

In some embodiments, power is lower to reduce battery requirement, to prevent noticeable effects by a patient and/or prevent immediate tissue effects. Optionally, power is reduced for safety or comfort reasons, for example, by selecting a power level that does not affect other tissue or parts of tissue than the tissue for which therapy is desired.

In an exemplary embodiment of the invention, the comfort factor considered is pain caused by inadvertent stimulation of nerves. In an exemplary embodiment of the invention, pain is reduced and/or avoided, by selecting a subset of a plurality of leads, electrodes and/or power settings which minimizes pain and/or discomfort, while still providing useful therapy (e.g., increase phosphorylation). Alternatively or additionally, what is minimized is stimulation of the autonomous nervous system. Optionally, stimulation parameters are changed, as the patient habituates. In an exemplary embodiment of the invention, the effect of a signal is estimated by calculating the field which will reach target tissue and base don tables which link the field strength on effects. Optionally, the tables are generated using tissue homogenate and/or extracted cardiomyocytes. Optionally, the testing is on the patient's own tissue.

In an exemplary embodiment of the invention, pulse duration is in the range of 5-150 msec, for example, 10-40 msec. Alternatively pulse duration may be of one or combined groups in ranges such as 1 nsec-0.5 usec, 0.1-10 usec, 1-100 usec, 10-500 usec, 100-1000 usec, 500 usec-10 msec, 1-100 msec, 10-1000 msec, 100-10000 msec.

Additional exemplary pulse properties are now described.

Applied signals optionally are composed of such pulses, and their combinations. Signals may also be applied to excitatory tissue within the refractory period of such tissue, or outside such refractory period, or during a relative refractory period extending after the end of such period. Signals may be composed of pulses, square, saw-tooth, smooth or continuous waveforms, whether applied in stand alone pulses, in series, continuously, or superimposed.

Signals may be applied on every tissue activation cycle, e.g. every heart beat, or other physiological cycle (breathing, sympathetic and parasympathetic systems cycle, other muscle contraction, etc). Alternatively, the application may be intermittently in only some of the cycles. Alternatively, signals may be applied at random timing or at a predetermined timing.

Treatment period may last, for example seconds, minutes, hours, days, weeks, months, or years.

Treatment may be alternating such as to be applied for some time period, and some rest period intermittently. For example, such treatment schedule may be activated for several hours (e.g. about 1-5 hours) every several hours (e.g. every 3-24 hours), or activated 12 hours out of every 24 hours (12 continuous hours every day or 12 intermittent hours: 1 hour on followed by 1 hour off).

Treatment schedule may be configured for alternating among days or weeks, such as 3 days of treatment followed by 2 days of rest, repeatedly, or 4 weeks of treatment followed by 1 week of rest.

Alternatively, signals may be applied to provide treatment in a manner that changes according to changes in physiological condition. Such change in physiological may be sensed by the device, or may be communicated to the device.

Signals may be selected from a group of signals, each with properties selected for a desired effect, and the device may alternate among the signals, superimpose two or more of the signals, automatically adjust one or more of the signals, and/or change the ratio among the delivery time and magnitude of those signals.

Genes and Related Proteins

Following is a partial list of genes (and corresponding proteins) whose expression is correlated with some types of heart failure (termed "heart failure" in short below). In an exemplary embodiment of the invention, treatment is configured so that a particular gene/protein will be affected in a desirable manner. It is noted that in accordance with some embodiments of the invention, different heart failure states are identified based on the protein expression, mRNA expression and/or protein activity profiles; or based on changes in such profiles in response to treatment, for example, immediate response or longer term response (e.g., hours, weeks or months). The treatment may target particular proteins, pathways or groups of proteins, for example, SR proteins. Optionally, the treatment aims to undo the negative effects described below, for example, by modifying the protein level and/or activity. Optionally, analysis and/or treatment relates simultaneously to several genes, for example a set of two, a set of three, a set of five or sets of other numbers of genes, for example genes selected form the list below. Optionally, the set includes genes from at least two or from at least three different gene type classifications. A profile used for assessment can include, for example, 1, 2, 3, 4, 5 or more markers from each of the types of mRNA, protein and protein activity.

Various Genes a) ANP=atrial natriuretic peptide or A-type natriuretic peptide, is increased in heart failure. The increase in ANP is related to increased atrial enlargement and stretch which is bad. Increased ANP correlates with increased mortality and morbidity in heart failure.

b) BNP=Brain natriuretic peptide or B-type natriuretic peptide is increased in heart failure. BNP is elaborated from ventricular tissue. The increase in BNP is due largely to increased LV size and stretch which is bad in heart failure. Increased BNP in heart failure correlates with increased mortality and/or morbidity. BNP is also a member of the so-called "fetal gene program" which also negatively impacts heart failure.

c) GAPDH. This is a gene whose expression does not change in heart failure and is used as "a housekeeping gene" to ensure good quality RNA extraction. If the expression of this gene changes during RT-PCR this may indicate poor RNA quality and the results of all other gene expression measurements may become questionable.

SR Genes d) RYR2=ryanodine receptors also referred to as sarcoplasmic reticulum calcium release channels. These channels control the release of calcium from the sarcoplasmic reticulum. This is the calcium signal that is needed to activate the contractile apparatus (actin myosin cross bridging). These channels are hyperphosphorylated in heart failure and turn very active and, therefore, are "leaky," leading to possible calcium overload which is bad for the heart muscle cell. Reducing or normalizing phosphorylation may be desirable for these proteins.

e) NCX=sodium calcium exchanger. Under normal conditions, the NCX takes calcium out of the cell in return for Na. This maintains calcium homeostasis and prevents calcium overload which is bad for muscle cell function and survival. In heart failure the NCX is increased and is hyperphosphorylated and may begin to work in what is called "reverse mode", to compensate for reduced SERCA-2A activity, and may cause calcium overload (=diastolic dysfunction). Too much activity in forward mode depletes SR calcium (=systolic dysfunction).

f) PLB=Phospholamban. This is an essential sarcoplasmic reticulum protein. Under normal conditions PLB is phosphorylated (PLB-P). When that happens it activates SERCA-2a (calcium ATPase) which then pumps calcium from the cytosol into the SR and thus prevents calcium overload. PLB is decreased in heart failure and is dephosphorylated. Because of that, SERCA-2a activity is reduced and it is less able to pump calcium back into the sarcoplasmic reticulum. This leads to calcium overload. When the SR has reduced calcium, there is less calcium release through the calcium release channels and contractility decreases.

g) SERCA-2a=calcium ATPase. This sarcoplasmic reticulum (SR) pump, under normal conditions, pumps calcium from the cytosol into the SR. In heart failure SERCA-2a decreases dramatically and its activity also decreases leading to calcium overload and poor intracellular calcium cycling. This decreases contraction strength.

h) Calsequestrin (CSQ). Clasequestrin is an SR protein involved in calcium sequestration and does not change in heart failure. Because it does not change in heart failure, it is frequently used as a housekeeping gene. It may also be used to normalize when samples are inconsistent in the loading process.

Matrix Metalloproteinases (MMPs)

i) MMP1. This gene is involved in the degradation of connective tissue at all levels and, for this reason, its elevation in heart failure is not desirable and counteracted in some embodiments of the invention.

j) MMP2 and MMP9. These are referred to as to as "gelatinases". Inhibiting gelatinases in the setting of heart failure appears to be helpful particularly with respect to reducing "interstitial fibrosis" or the accumulation of connective tissue or collagen in the cardiac interstitium. Reducing interstitial fibrosis leads to improved LV diastolic compliance and, hence, improved diastolic filling and function.

Stretch Response Genes

Stretch response genes are up-regulated in the presence of progressive LV dilation and myocytes stretch as occurs in heart failure. The importance of these genes is they trigger maladaptive cardiomyocytes hypertrophy which then leads to abnormal calcium cycling.

k) p38=p38 alpha-beta mitogen activated protein kinese. This is a stretch response gene. Its expression increases in heart failure and that can lead to many abnormalities including the development of hypertrophy and activation of multiple transcription factors that lead to activation of the fetal gene program. An increase in P38 correlates with maladaptive hypertrophy and ventricular enlargement. This indicates a bad prognosis for heart failure.

l) p21 ras=This is also a stretch response gene. Its expression increases in heart failure due to ventricular enlargement and stretch. When stretch and wall stress increases in heart failure, these mechanical factors increase a family of cell surface proteins known as integrins. Integrins, when activated, lead to increase in p21 ras and p38 and both lead to maladaptive hypertrophy.

m) Integrin-a5. This is a cell surface receptor gene whose protein acts as a mechanical transducer. It is activated in response to mechanical stretch or stress mediated by LV dilation. When activated, it promotes regulation of stretch response protein. Down regulation of this gene in heart failure is a desirable feature of some embodiments of the invention.

Fetal Program Genes n) Alpha-MHC=alpha myosin heavy chain is reduced in heart failure. Because the alpha isoform of MHC is the isoform responsible for increased velocity of shortening of cardiac muscle cells, a reduction in alpha MHC impacts negatively on function/contraction of the failing ventricle. Alpha MHC restoration is associated (and optionally provided by some embodiments of the invention) with LV contraction improvements.

o) Beta1-Adrenergic Receptor. This gene is down-regulated in heart failure. Drugs such as metoprolol which are selective beta-1 receptor blockers which up-regulate the beta-1 receptor improve mortality and morbidity in heart failure and appear to also improve, albeit in a limited way, exercise tolerance. Up-regulation of this gene is viewed as a positive development in some embodiments of the invention which enhances the sensitivity of the contractile element of catecholamines.

SERCA-2a, mentioned above, is also a member of the so-called fetal program gene.

Calcium Binding Proteins

Enhanced expression of calcium binding proteins such as S100A1 and sorcin improve contractility by increasing calcium uptake into the sarcoplasmic reticulum. Expression of these proteins can also modify the behaviors of ryanodine calcium release channels. Alternatively down-regulation (or avoiding upregulation) of these calcium binding proteins can diminish contractility. This may be applicable to hypercontractile states of the heart associated with certain diseases such as hypertrophic obstructive cardiomyopathy. Contractility may also be reduced using hyperpolarizing fields.

Experimental Results—Long Term ("Chronic") and Short Term (Several Hours)

Before describing experiments in which an immediate effect was discovered on phosphorylation, experiments on relatively long term effects will be described, including effects that occur (at least to a significant degree) after a few hours of continuous CCM application and after 3 months. These experiments generally show that LV function in dogs with HF improves without an associated increase in $MVO_2$.

In this experimental preparation, chronic HF is produced by multiple sequential intracoronary embolizations with polystyrene Latex microspheres (70-102 µm in diameter) which result in loss of viable myocardium, LV enlargement and a decrease in LV ejection fraction. 14 healthy mongrel dogs weighing between 20 and 30 kg underwent coronary microembolizations to produce HF. Embolizations were performed one week apart and were discontinued when LV ejection fraction, determined angiographically, was <30%. Microembolizations were performed during cardiac catheterization under general anesthesia and sterile conditions. Animals were induced with intravenous oxymorphone hydrochloride (0.22 mg/kg) and diazepam (0.17 mg/kg) and a plane of anesthesia was maintained with 1-2% isoflurane. Some of the results shown herein use fewer than all dogs.

Two weeks after the target LV ejection fraction was reached, dogs were anesthetized as described above, intubated and ventilated with room air. The right external jugular vein was surgically exposed and used to position the CCM leads. Two standard active fixation leads were advanced into the right ventricle and positioned on the anterior and posterior septal grooves and were used to sense ventricular activity and deliver CCM electrical signals. A third active fixation lead was positioned in the right atrium for p-wave sensing. The leads were connected to a CCM signal generator (OPTIMIZER™ II, Impulse Dynamics NV, Curacao NV). The generator was implanted in a subcutaneous pocket created on the right side of the neck. All 14 animals were implanted and all were allowed to recover. Studies were performed 2 weeks after OPTIMIZER™ System implantation. This period of time was allowed to ensure that the leads stabilized in place.

Two weeks after OPTIMIZER™ System implantation, dogs were anesthetized and underwent a pre-treatment left and right heart catheterization to assess hemodynamics and measure $MVO_2$. Dogs were then randomized to an active treatment group (n=7) or to a sham-operated control group (n=7). In the active treatment group, the OPTIMIZER™ system was activated to deliver CCM therapy. CCM therapy was administered for 5 hours/day based on a duty cycle of one hour ON (CCM signal ±7.73 volts) and 3 hours and 48 minutes OFF for 3 months. Sham-operated control dogs did not receive any therapy whatsoever and were also followed for 3 months. At the end of 3 months of therapy or follow-up, all hemodynamic measures were repeated including $MVO_2$. After completion of all hemodynamic measurements and while under general anesthesia, the dogs' chest was opened and the heart rapidly harvested and tissue from the interventricular septum and LV free wall was obtained and prepared for histological and biochemical evaluation. Tissue from 6 normal dogs was obtained and prepared in the same manner and used for comparisons. All tissue was stored at −70° C. until needed.

To address certain aspects of the mechanisms of action of CCM therapy, a series of 6 additional dogs underwent intracoronary microembolizations to produce HF as described earlier. In these dogs, under general anesthesia, a mid-sternotomy was performed, the pericardium was opened and epicardial CCM leads were placed on the anterior wall between the 2nd and 3rd diagonal branches. Hemodynamic measurements including measurements of $MVO_2$ were made before and 2 hours after continuous CCM signal delivery at 7.73 volts. At the end of 2 hours of therapy, myocardial samples were obtained from the LV anterior wall in the region of the CCM leads and from the LV posterior wall remote from the CCM leads. Left ventricular tissue from 6 normal dogs and 6 HF dogs that were untreated was obtained and prepared in the same manner and used for comparisons. All tissue was rapidly frozen in liquid nitrogen and stored at −70° C. until needed.

Aortic and LV pressures were measured with catheter-tip micromanometers (Millar Instruments, Houston, Tex.) during cardiac catheterization. LV end-diastolic pressure was measured from the LV waveform. Single-plane left ventriculograms were obtained during each catheterization after completion of the hemodynamic measurements with the dog placed on its right side. Ventriculograms (approximately 60 right anterior oblique projection) were recorded on 35 mm cine film at 30 frames per second during the injection of 20 ml of contrast material (Reno-M-60, Squibb, Princeton, N.J.). Correction for image magnification was made with a radiopaque calibrated grid placed at the level of the LV. LV end-diastolic volume and end-systolic volume were calculated from ventricular silhouettes using the area-length method, such as described in Dodge H T, Sandler H, Baxley W A, Hawley R R. Usefulness and limitations of radiographic methods for determining left ventricular volume. *Am J Cardiol.* 1966; 18:10-24, the disclosure of which is incorporated herein by reference. Stroke volume was calculated as the difference between LV end-diastolic volume and end-systolic volume. Total coronary blood flow (CBF), and $MVO_2$, were measured and calculated as described, for example, in Chandler M P, Stanley W C, Morita H, Suzuki G, Roth B A, Blackburn B, Wolff A, Sabbah H N. Acute treatment with ranolazine improves mechanical efficiency in dogs with chronic heart failure. *Circ Res.* 2002; 91:278-280, the disclosure of which is incorporated herein by reference. LV mechanical efficiency was calculated as the ratio of LV power to $MVO_2$ following the same paper.

Calsequestrin (CSQ), atrial natriuretic peptide (ANP), brain natriuretic peptide (BNP), ryanodine receptor (RyR), total phospholamban (PLB), phosphorylated PLB (P-PLB), sarcoplasmic reticulum (SR) calcium ATPase (SERCA-2a), and $β_1$-adrenergic receptor ($β_1$-AR) were measured by Western Blots. Briefly, LV homogenate was prepared from ~100 mg LV powder as described, for example, in Gupta R C, Mishra S., Mishima T, Goldstein S, Sabbah H N. Reduced sarcoplasmic Reticulum $Ca^{2+}$-uptake and Phospholamban Expression in Ventricular Myocardium of Dogs with Heart Failure. *J Moll Cell Cardiol.* 1999; 31:1381-1389, the disclosure of which is incorporated herein by reference and protein determined using the Lowry method, for example as described in Lowry Ohio, Rosebrough N.J., Farr A L, Randall R J. Cleavage of structural proteins during the assembly of the head of bacteriophage T4. *Nature.* 1951; 27:680-685, the disclosure of which is incorporated herein by reference. CSQ, a calcium-binding protein located in the SR and is unchanged in HF was used to normalize protein loading on the gel. Approximately 20-100 µg protein of each sample was separated on 4-20% SDS-polyacrylamide gel and the separated proteins were electrophoretically transferred to a nitrocellulose membrane. The accuracy of the electrotransfer was confirmed by staining the membrane with 0.1% amido black. For identification of the desired protein, the nitrocellulose blot was incubated with the appropriately diluted primary monoclonal or polyclonal antibody specific to each protein based on the supplier's instructions. Antibody-binding proteins were visualized by autoradiography after treating the blots with horseradish peroxidase-conjugated secondary antibody (anti-rabbit) and ECL color developing reagents. ANP, BNP, $β_1$-AR, SERCA-2a, PLB, or RyR-specific antibody recognized 20, 14, 65, 110, 5.5, and 250 kDa protein bands respectively. Total P-PLB was quantified in SDS-phosphoprotein-enriched fraction (PPE)

prepared from LV homogenate using PLB specific monoclonal antibody. P-PLB at serine-16 or threonine-17 was quantified in SDS-LV homogenate using primary antibodies specific to the P-PLB at serine-16 or at threonine-17. PPE was prepared from LV tissue using a BD Bioscience phosphoprotein enrichment kit, for example as described in Gupta R C, Mishra S, Yang X P, Sabbah H N. Reduced inhibitor 1 and 2 activity is associated with increased protein phosphatase type 1 activity in left ventricular myocardium of one-kidney, one-clip hypertensive rats. *Mol Cell Biochem.* 2005; 269:49-57, the disclosure of which is incorporated herein by reference. Band intensity was quantified using a Bio-Rad GS-670 imaging densitometer and expressed as densitometric units×mm². In all instances, the antibody was present in excess over the antigen and the density of each protein band was in the linear scale.

mRNA expression of glyseraldehyde-3-phosphate dehydrogenase (GAPDH), α-myosin heavy chain (MHC), $\beta_1$-AR, ANP, BNP, SERCA-2a, total PLB, RyR and CSQ was measured. Total RNA with an absorbance ratio (260 nm/280 nm) above 1.7 was isolated from frozen LV tissue as described in *Mol Cell Biochem.* 2005; 269:49-57. Approximately 4-10 µg RNA was reverse-transcribed into cDNA in an assay volume of 80 microliter. For each polymerase chain reaction (PCR), 2-5 µl first-strand cDNA was added to 50 µl of a reaction mixture containing pmol of each forward and reverse primer of each gene, 200 µM of each dNTP, 10 mM Tris-HCl (pH 8.8), 50 mM KCl, 0.1% Triton-X100 and 3.0 mM $MgCl_2$ and 1 unit platinum Taq DNA polymerase (Invitrogen, Carlsbad, Calif.) and PCR allowed to proceed for 20 to 40 cycles. For each gene, PCR cycle was determined to ensure that the gene product is forming in linear range. PCR products were analyzed by subjecting 20 µl of each reaction mixture to electrophoresis on 1%-1.5% ethidium-bromide-agarose gels. Band size of the products was compared with standard DNA size markers and confirmed by sequencing of the forward (F) and reverse (R) primers for each gene and gene product. mRNA expression of α-MHC was measured by amplification of cDNA by reverse transcriptase-PCR followed by digestion with Pst1 restriction enzyme as described, for example, in Feldman A M, Ray P E, Silan C M, Mercer J A, Minobe W, Bristow M R. Selective gene expression in failing human heart: quantification of steady-state levels of messenger RNA in endomyocardial biopsies using the polymerase chain reaction. *Circulation.* 1991; 83: 1866-1872, the disclosure of which is incorporated herein by reference. Fluorescent band intensity was quantified using a Bio-Rad GS-670 imaging densitometer and expressed as optical density×mm².

From each heart, 3 transverse slices (approximately 3 mm thick) one each from basal, middle and apical thirds of the LV, were obtained. For comparison, tissue samples obtained from 7 normal dogs were prepared in an identical manner. From each slice, transmural tissue blocks were obtained and embedded in paraffin blocks. From each block, 6 µm thick sections were prepared and stained with Gomori trichrome to identify fibrous tissue. The volume fraction of replacement fibrosis, namely, the proportion of scar tissue to viable tissue in all three transverse LV slices, was calculated as the percent total surface area occupied by fibrous tissue using computer-based video densitometry (MOCHA, Jandel Scientific, Corte Madera, Calif.). Transmural tissue blocks were obtained from the free wall segment of the slice, mounted on cork using Tissue-Tek embedding medium (Sakura, Torrance, Calif.), and rapidly frozen in isopentane pre-cooled in liquid nitrogen and stored at −70° C. until used. Cryostat sections were prepared and stained with fluorescein-labeled peanut agglutinin (Vector Laboratories Inc., Burlingame, Calif.) after pretreatment with 3.3 U/ml neuraminidase type V (Sigma Chemical Co., St. Louis, Mo.) to delineate the myocyte border and the interstitial space, including capillaries, for example as described in Liu Y H, Yang X P, Sharov V G, Nass O, Sabbah H N, Peterson E, Carretero O A. Effects of angiotensin-converting enzyme inhibitors and angiotensin II type 1 receptor antagonists in rats with heart failure. Role of kinins and angiotensin II type 2 receptors. *J Clin Invest.* 1997; 99:1926-1935, the disclosure of which is incorporated herein by reference. Sections were double stained with rhodamine-labeled Griffonia simplicifolia lectin I (GSL I) to identify capillaries. Ten radially oriented microscopic fields (magnification ×100, objective ×40, and ocular 2.5), were selected at random from each section and photographed using 35 mm color film. Fields containing scar tissue (infarcts) were excluded. Average cross-sectional area of each myocyte was measured using computer-based planimetry. The volume fraction of interstitial collagen (reactive interstitial fibrosis) was calculated as the percent total surface area occupied by interstitial space, minus the percent total area occupied by capillaries (following *J Clin Invest.* 1997; 99:1926-1935). Capillary density was calculated as the number of capillaries per square millimeter and as the index capillary per fiber ratio. The oxygen diffusion distance was measured as half the distance between two adjoining capillaries.

To ensure that all hemodynamic measures were similar at baseline, comparisons were made between the two study groups before any embolization and at the time of randomization before initiating active therapy. To assess treatment effect, the change in each measure from pre-treatment to post-treatment was calculated for each of the study groups and then compared between groups. For these comparisons a t-statistic for two means was used with a probability value ≤0.05 considered significant. Within group comparisons between pre-treatment and post-treatment hemodynamic measures were made using a Student's paired t-test with p≤0.05 considered significant. Histomorphometric, biochemical and molecular differences between normal dogs, sham-operated untreated HF dogs and CCM-treated HF dogs were examined using one-way analysis of variance (ANOVA) with α set at 0.05. If significance was achieved, pairwise comparisons were performed among groups using the Student-Newman-Kuels test with a probability value of ≤0.05 considered significant. All hemodynamic, ventriculographic and histomorphometric assessments were made by investigators blinded to treatment group.

The results of these experiments are presented in summary below and in greater detail after.

At baseline, all dogs entered into the study had hemodynamic measures that were within normal limits for conditioned mongrel dogs. The hemodynamic and ventriculographic results obtained before initiating therapy or follow-up (pre-treatment) and 3 months after initiating therapy or follow-up (post-treatment) are shown in Table 1 for dogs randomized into the CCM-active treatment group and Table 2 for dogs randomized into the sham-operated untreated HF group. In sham-operated dogs, comparison of pre-treatment to post-treatment showed no differences in heart rate, systolic aortic pressure, LV end-diastolic pressure or stroke volume (Table 1). In this group, LV end-diastolic and end-systolic volume increased significantly while LV ejection fraction decreased significantly. This was associated with an increase in total CBF and an increase in $MVO_2$. LV mechanical efficiency tended to decrease but the reduction was not statistically significant (Table 1).

TABLE 1

Chronic Hemodynamic and Angiographic Findings in Sham-Operated Dogs with Heart Failure Before (Pre-Treatment) and After 3 Months of Follow-up (Post-Treatment) (n = 7)

|  | Pre-Treatment | Post-Treatment | P-Value |
| --- | --- | --- | --- |
| Heart Rate (beats/min) | 89 ± 4 | 101 ± 7 | NS |
| Systolic Aortic Pressure (mmHg) | 97 ± 6 | 104 ± 6 | NS |
| LV EDP (mmHg) | 13 ± 1 | 14 ± 1 | NS |
| LV EDV (ml) | 67 ± 2 | 77 ± 2 | 0.0001 |
| LV ESV (ml) | 49 ± 2 | 60 ± 2 | 0.0001 |
| LV EF (%) | 27 ± 1 | 23 ± 1 | 0.001 |
| Stroke Volume (ml) | 18 ± 1 | 17 ± 1 | NS |
| Total LV CBF (ml/min), n = 6 | 42 ± 4 | 59 ± 6 | 0.015 |
| $MVO_2$ (μmols/min), n = 6 | 193 ± 25 | 286 ± 36 | 0.026 |
| LV Efficiency (%), n = 6 | 28 ± 4 | 21 ± 3 | NS |

LV=left ventricular; EDP=end-diastolic pressure; EDV=end-diastolic volume; ESV=end-systolic volume; EF=ejection fraction; CBF=coronary blood flow; $MVO_2$=myocardial oxygen consumption. P-Value=Probability value based on comparison between Pre- and Post-Treatment. NS=Not significant.

In CCM-treated dogs, comparison of pre-treatment to post-treatment also showed no differences in heart rate and systolic aortic pressure. LV end-diastolic pressure decreased as did LV end-diastolic volume and end-systolic volume while stroke volume and LV ejection fraction increased (Table 2). This functional improvement was associated with a decrease in total CBF and a decrease in $MVO_2$ along with a significant increase in LV mechanical efficiency (Table 2).

TABLE 2

Chronic Hemodynamic and Angiographic Findings in CCM-Treated Dogs with Heart Failure Before (Pre-Treatment) and 3 Months After Initiating Treatment (n = 7)

|  | Pre-Treatment | Post-Treatment | P-Value |
| --- | --- | --- | --- |
| Heart Rate (beats/min) | 78 ± 3 | 87 ± 3 | NS |
| Systolic Aortic Pressure (mmHg) | 101 ± 4 | 102 ± 5 | NS |
| LV EDP (mmHg) | 14 ± 1 | 8 ± 1 | 0.01 |
| LV EDV (ml) | 70 ± 6 | 66 ± 5 | 0.08 |
| LV ESV (ml) | 52 ± 6 | 45 ± 4 | 0.008 |
| LV EF (%) | 27 ± 1 | 33 ± 1 | 0.0001 |
| Stroke Volume (ml) | 18 ± 1 | 21 ± 1 | 0.0001 |
| Total LV CBF (ml/min) | 73 ± 7 | 43 ± 3 | 0.005 |
| $MVO_2$ (μmols/min) | 275 ± 39 | 168 ± 19 | 0.01 |
| LV Efficiency (%) | 19 ± 4 | 36 ± 5 | 0.0001 |

The change (Δ) in hemodynamic and ventriculographic measures from pre-treatment to post-treatment was compared between the two study groups (Table 3). Heart rate and systolic aortic pressure were unchanged. Compared to sham-operated controls, CCM-treated dogs had a significantly lower LV end-diastolic pressure, end-diastolic volume and end-systolic volume along with significantly higher LV ejection fraction and stroke volume (Table 3). This improvement in LV function in CCM-treated dogs was accompanied by a significant reduction of CBF and $MVO_2$ and a significant increase in LV mechanical efficiency (Table 3).

TABLE 3

TREATMENT EFFECT
Comparison of the Change (Δ) from Pre-treatment to Post-Treatment between Sham-Operated Untreated Heart Failure Dogs and CCM-Treated Heart Failure Dogs

|  | Sham-Operated Untreated HF Dogs | CCM-Treated HF Dogs | P-Value |
| --- | --- | --- | --- |
| Heart Rate (beats/min) | 12 ± 8 | 8 ± 4 | NS |
| Systolic Aortic Pressure (mmHg) | 6 ± 6 | 1 ± 7 | NS |
| LV EDP (mmHg) | 1 ± 2 | −6 ± 2 | 0.029 |
| LV EDV (ml) | 10 ± 1 | −4 ± 2 | 0.0001 |
| LV ESV (ml) | 11 ± 1 | −7 ± 2 | 0.0001 |
| LV EF (%) | −4 ± 1 | 6 ± 1 | 0.0001 |
| Stroke Volume (ml) | −1 ± 0.5 | 3 ± 0.4 | 0.0001 |

TABLE 3-continued

TREATMENT EFFECT
Comparison of the Change (Δ) from Pre-treatment to Post-Treatment between Sham-Operated
Untreated Heart Failure Dogs and CCM-Treated Heart Failure Dogs

|  | Sham-Operated Untreated HF Dogs | CCM-Treated HF Dogs | P-Value |
| --- | --- | --- | --- |
| Total LV CBF (ml/min), n = 6 | 18 ± 5 | −30 ± 7 | 0.0001 |
| MVO$_2$ (μmols/min), n = 6 | 93 ± 30 | −96 ± 27 | 0.001 |
| LV Efficiency (%), n = 6 | −7 ± 4 | 16 ± 2 | 0.0001 |

P-Value=Probability value based on comparison between sham-operated and CCM-treated dogs. Other abbreviations are the same as in table 1.

Histomorphometric results are shown in Table 4. Volume fraction of replacement fibrosis, volume fraction of interstitial fibrosis and cardiomyocyte cross-sectional area were significantly higher in sham-operated dogs compared with normal dogs. Volume fraction of replacement fibrosis was reduced by 23%, volume fraction of interstitial fibrosis was reduced by 16% and average cardiomyocyte cross-sectional area was reduced by 19% compared to sham-operated HF dogs. Capillary density decreased in sham-operated HF dogs while oxygen diffusion distance increased when compared to normal dogs (Table 4). CCM therapy restored capillary density and oxygen diffusion distance to near normal levels (Table 4).

TABLE 4

Chronic Histomorhometric Findings in Left Ventricular Myocardium of Normal Dogs, Sham-Operated Untreated Heart Failure Dogs and CCM-Treated Heart Failure Dogs

|  | Normal Dogs | Sham-Operated Untreated HF Dogs | CCM-Treated HF Dogs |
| --- | --- | --- | --- |
| VFRF (%) | 0.0 | 14.3 ± 1.5* | 11.0 ± 0.8*† |
| VFIF (%) | 3.7 ± 0.1 | 11.2 ± 0.3* | 9.4 ± 0.7*† |
| MCSA (μm$^2$) | 409 ± 10 | 719 ± 36* | 581 ± 28*† |
| CD (# capillaries/mm$^2$) | 2607 ± 80 | 1882 ± 67* | 2192 ± 117*† |
| CD (# capillaries/fiber) | 1.00 ± 0.0 | 0.92 ± 0.02* | 1.03 ± 0.02*† |
| ODD (μm) | 8.9 ± 0.2 | 11.7 ± 0.3* | 10.2 ± 0.2*† |

VFRF=Volume fraction of replacement fibrosis; VFIF=Volume Fraction of Interstitial Fibrosis; MCSA=Cardiomyocyte cross-sectional area; CD=Capillary density; ODD=Oxygen diffusion distance. *=p<0.05 vs. normal dogs; †=p<0.05 vs. Sham-operated dogs.

In a set of short term experiments, 6 dogs that had micro-embolization induced HF were used. The CCM signal was a 7.73 volt, epicardial LV anterior wall signal. The definitions for the various variables follow Circulation Research 91:278, 2002, the disclosure of which is incorporated herein by reference. The signal is applied to the epicardial surface of the heart.

Where not otherwise specified, CCM is a pulse at 80 applications per minute (synchronized to a heart beat, if any), at 7.73 Volts, with between 4 and 6 phases, each phase being 5.56 ms long and being continuous and of opposite polarity of a previous phase. The number of phases was not changed within an experiment. The signal was generally applied to a septum, from a right chamber, with a distance of 1-2 cm between an electrode pair used to apply the signal.

The marking "NL" indicates normal tissue levels.

Figure 2A:
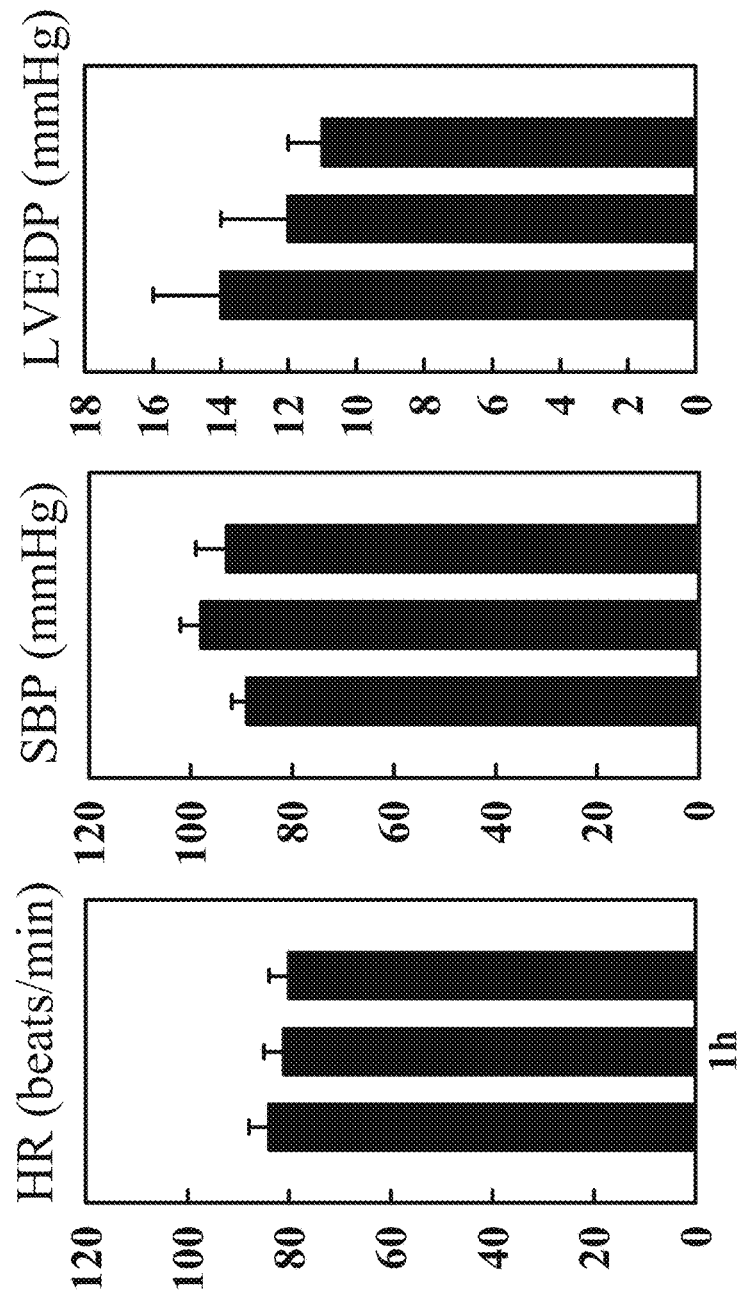
FIGS. 2A-2O show the effect of a short term or chronic (multi-month application period) CCM signal on proteins and mRNA in the heart, in accordance with an exemplary embodiment of the invention.
Figure 2B:
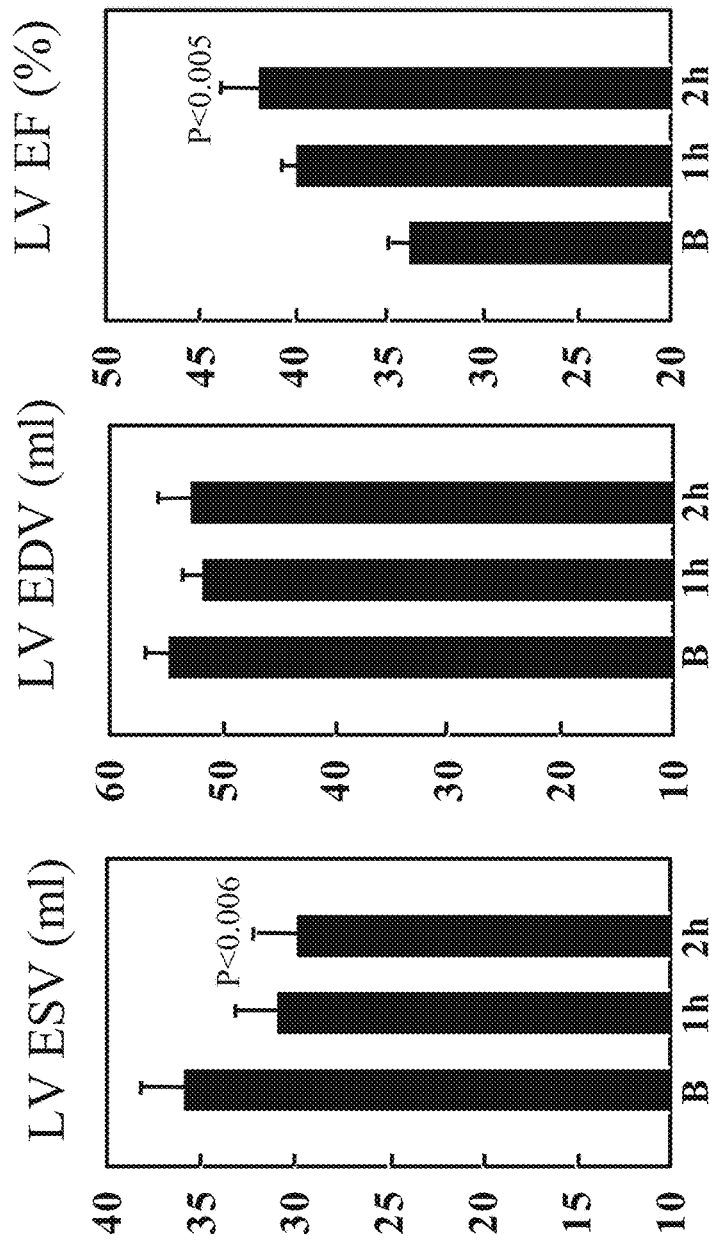
Figure 2C:
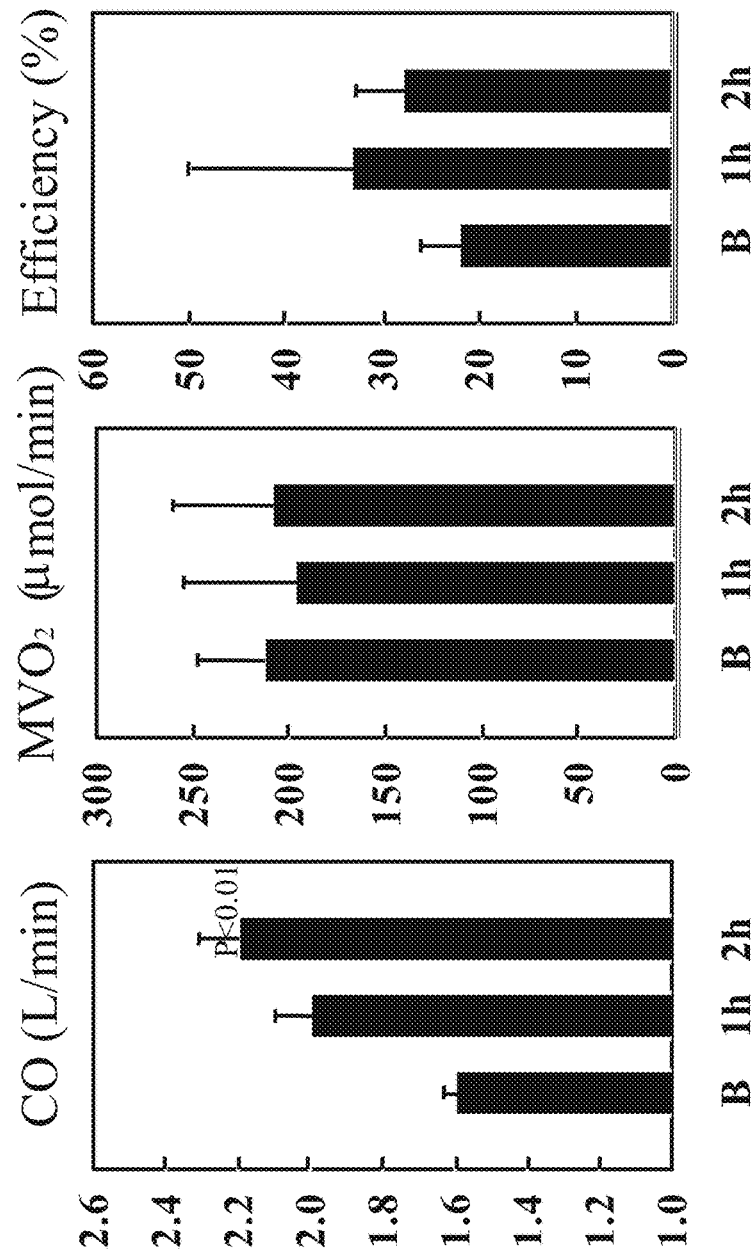
Figure 2D:
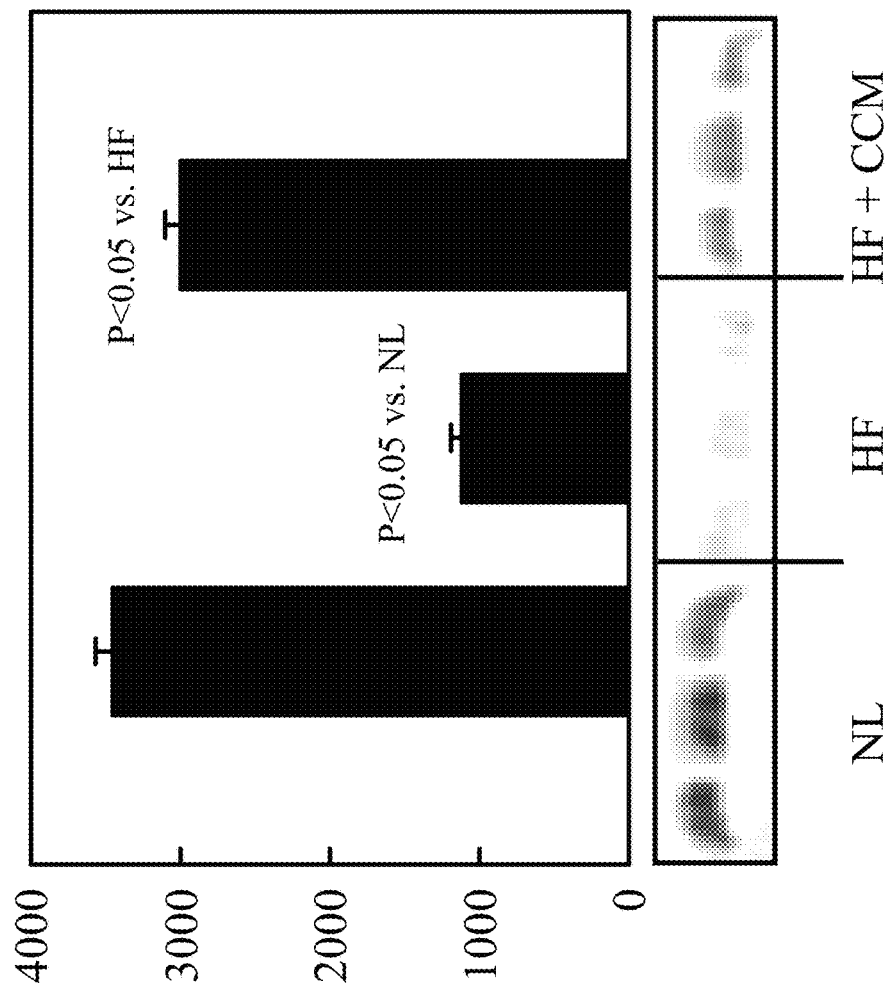
Figure 2E:
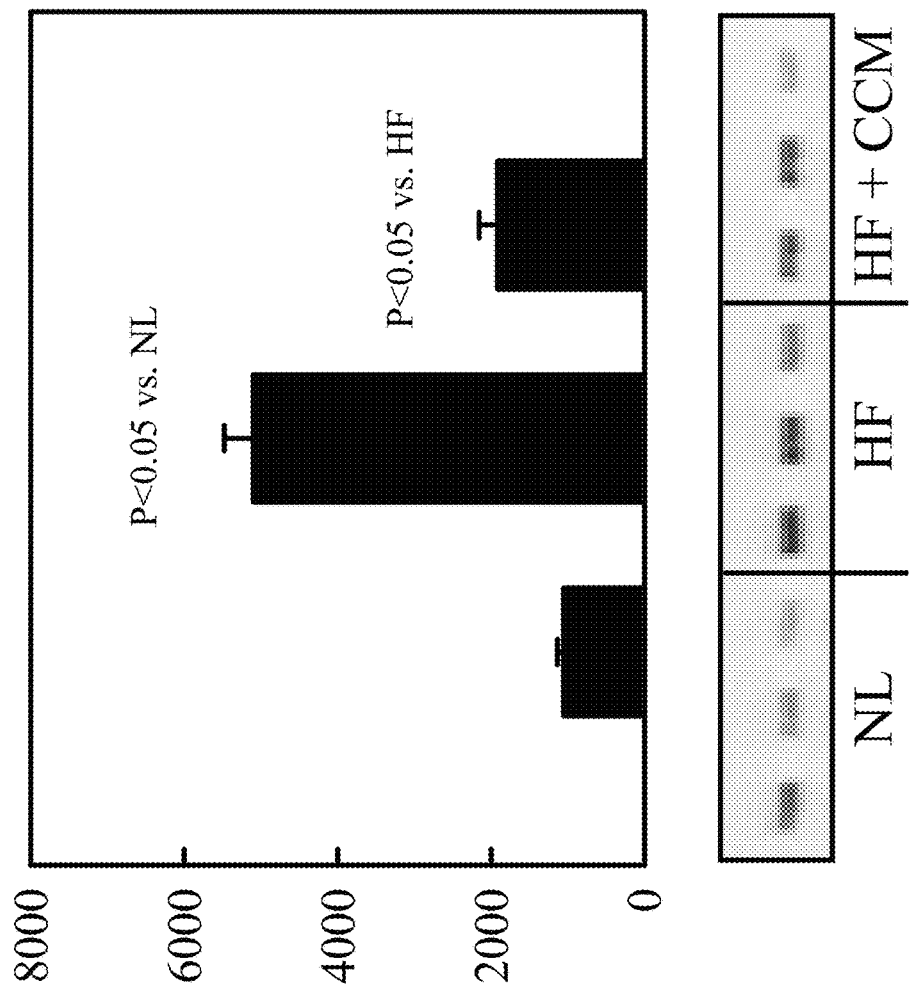
Figure 2F:
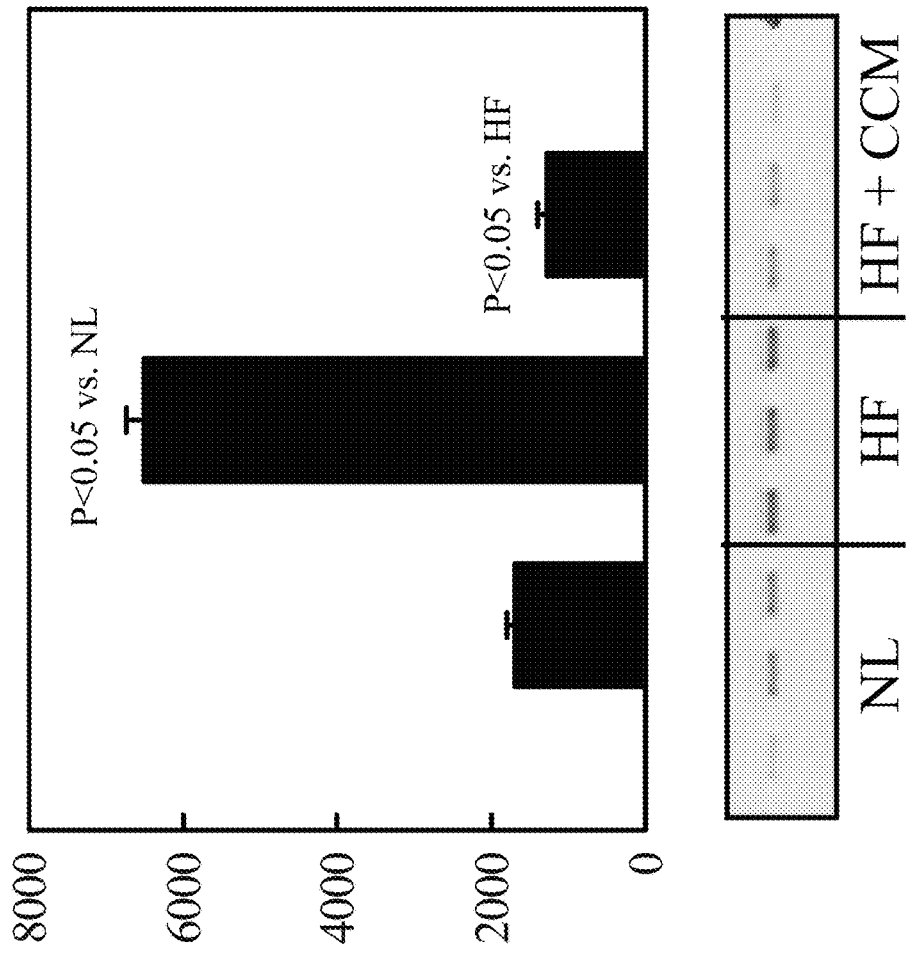

FIGS. 2A-2C show the improvement of LV function without MVO$_2$ increase, in CCM treated dogs as a function of time and compared to baseline values.

FIGS. 2D-2G show changes in mRNA expression of alpha-MHC, ANP, BNP and SERCA-2a in normal, HF and HF dogs with CCM treatment respectively, after several hours of treatment.

As will be shown below, effects on protein phosphorylation (at least) can be shown after a short time.

Figure 2H:
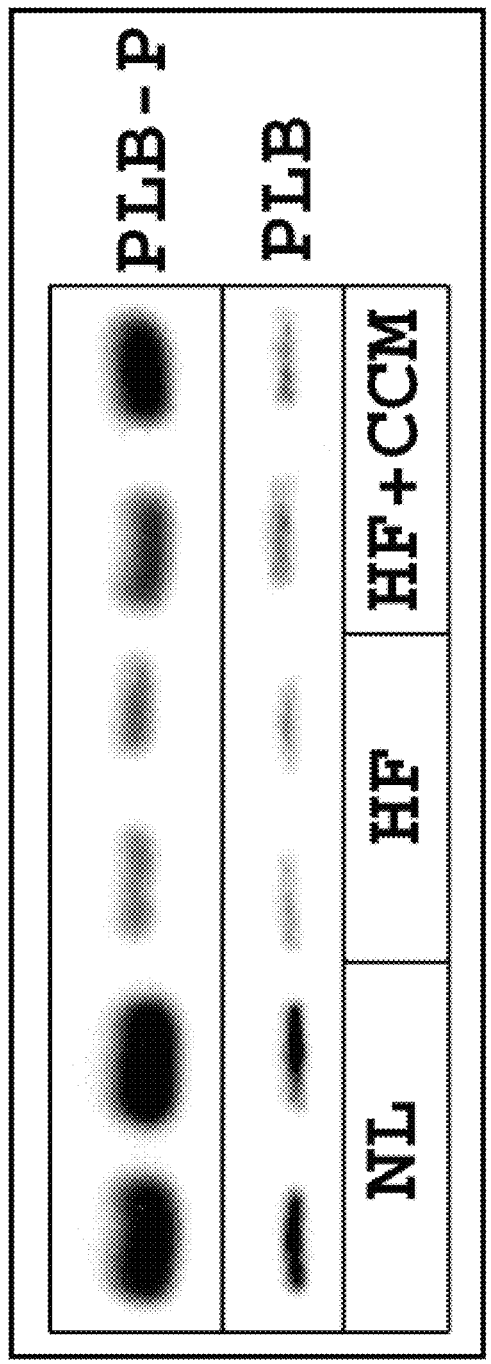
Figure 2I:
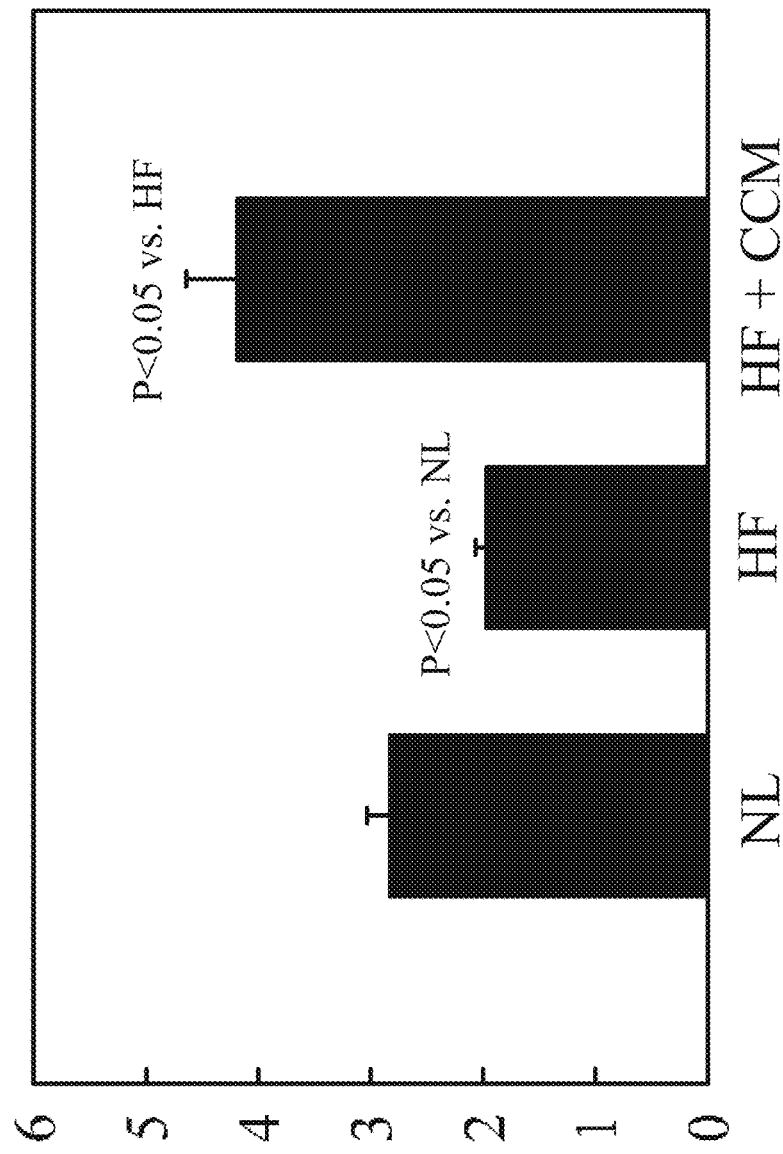

FIG. 2H shows phosphorylated phospholamban normalized to total phospholamban following therapy of several hours (indicated herein as "short-term"). FIG. 2I shows corresponding blots using a Western Blotting method. It should be noted that both phospholamban levels and phosphorylation levels thereof improve with therapy.

Figure 2J:
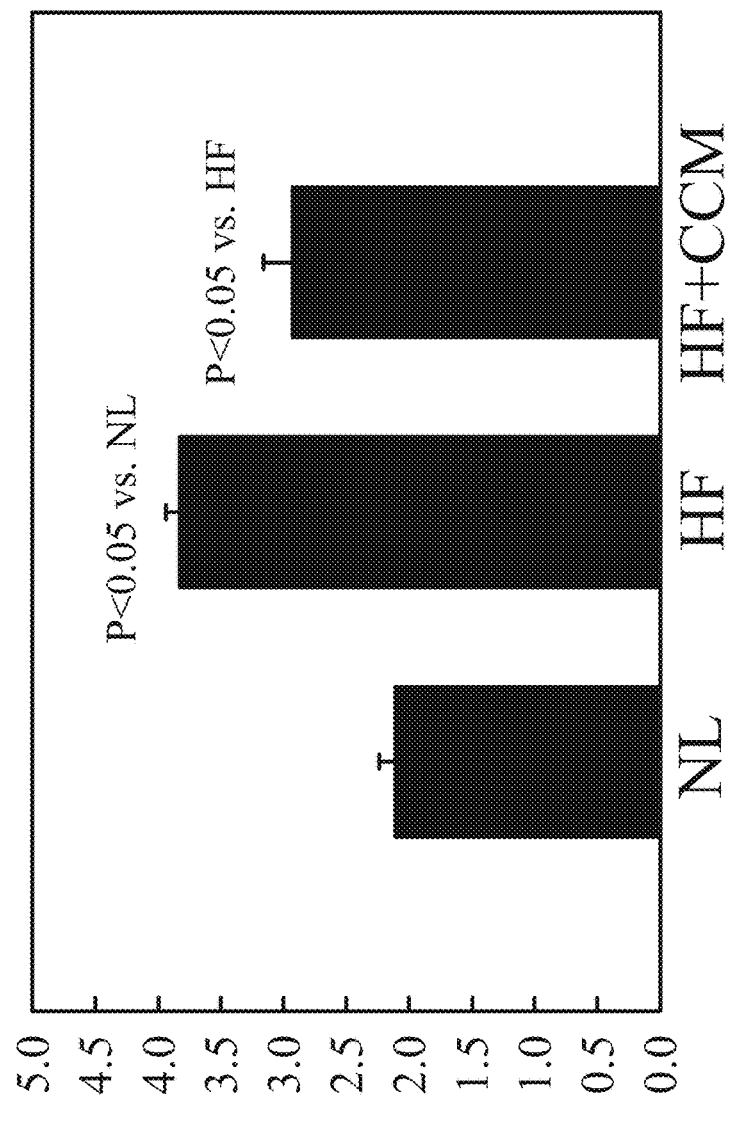
Figure 2K:
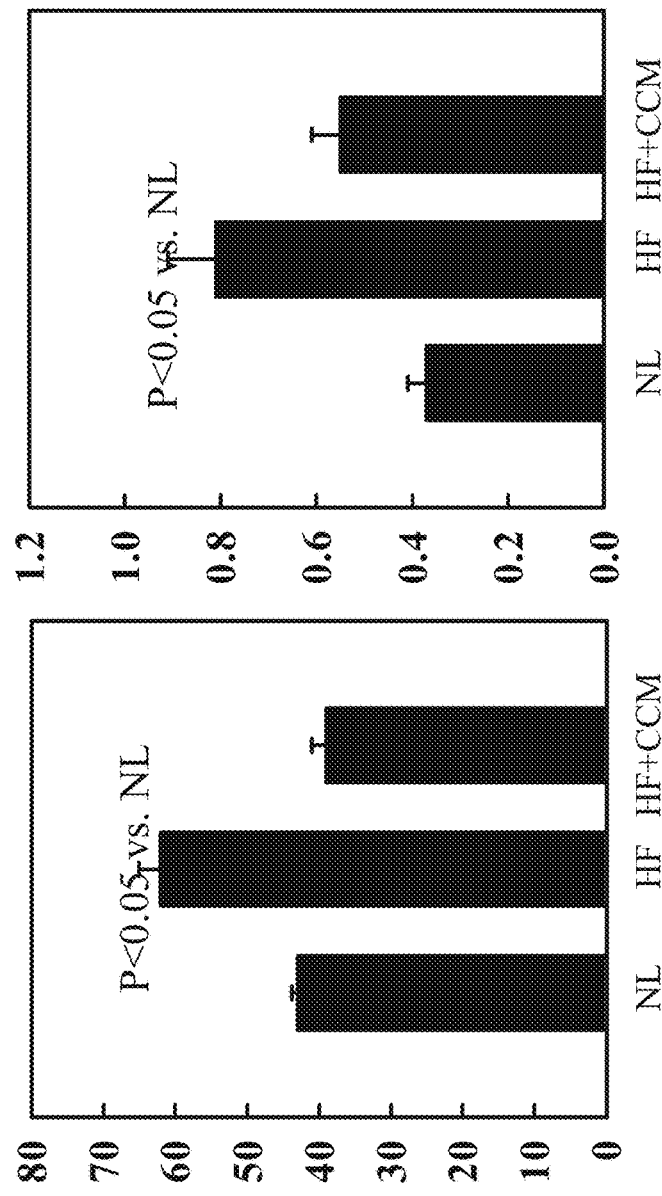

FIG. 2J shows reduction in mRNA expression of NCX following CCM treatment. FIG. 2K shows a general (or slight reduction) normalization of NCX protein values while still maintaining increased relative phosphorylation. This may allow some compensation for disturbed cardiac function.

Figure 2L:
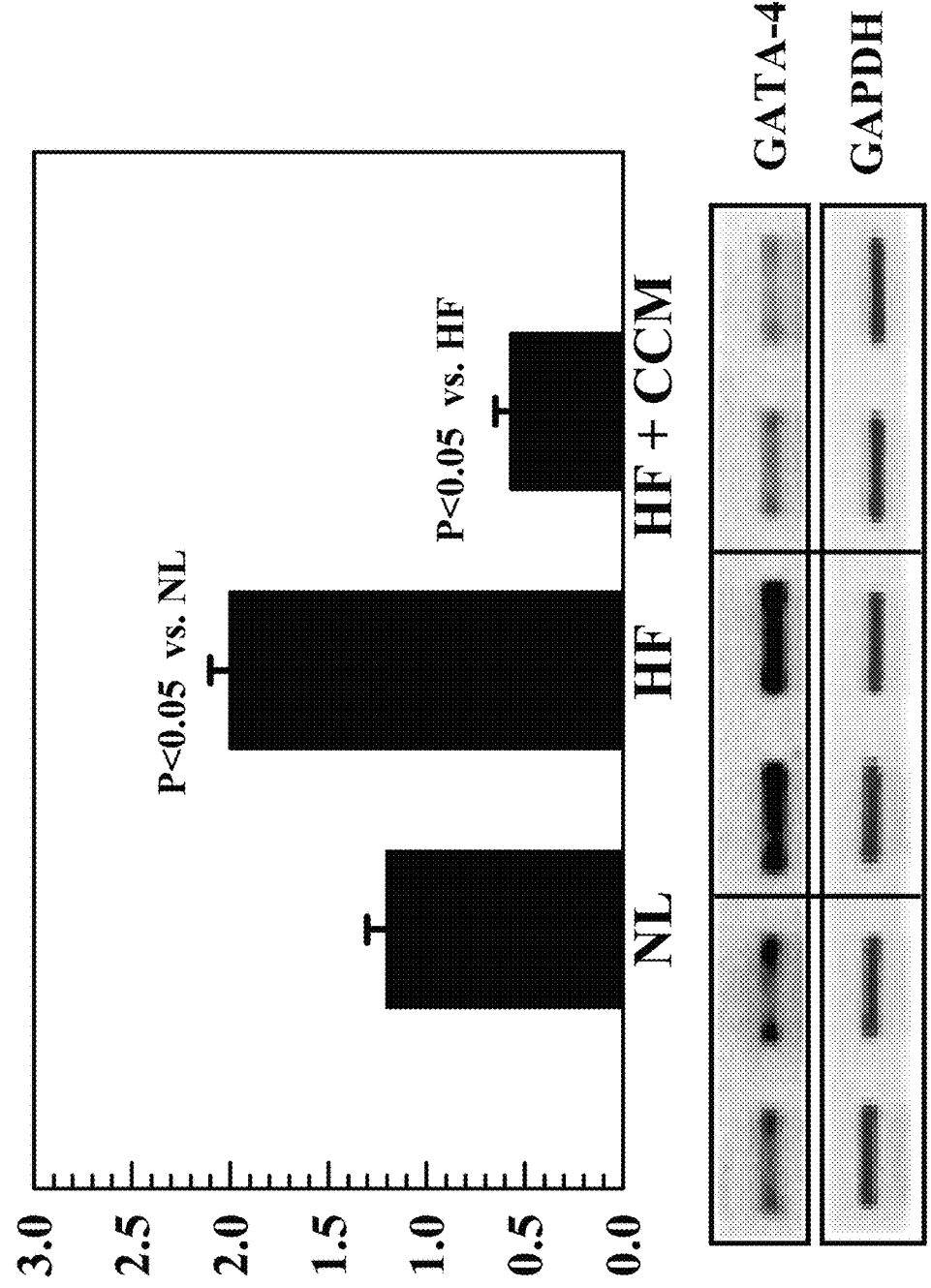
Figure 2M:
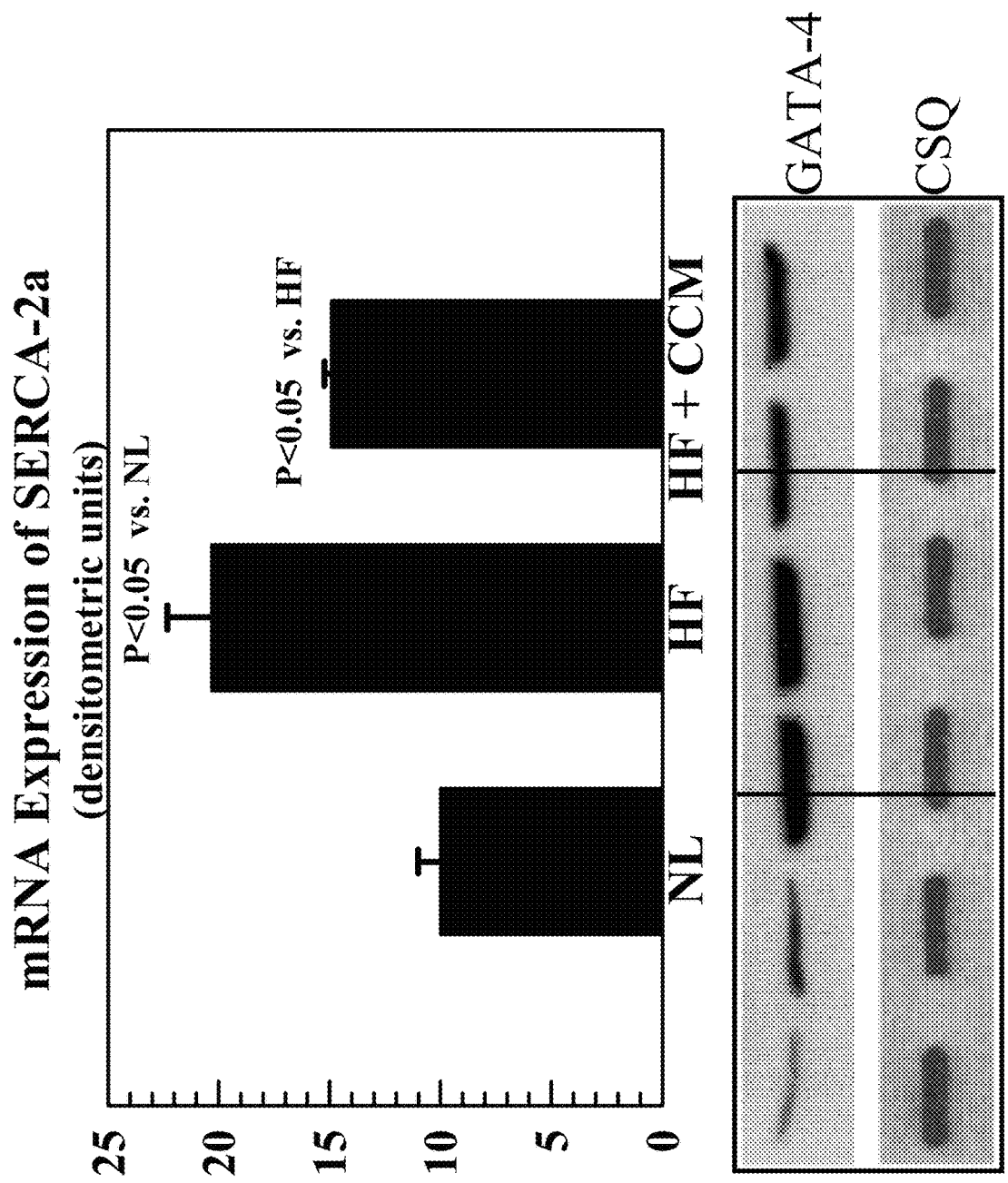
Figure 20:
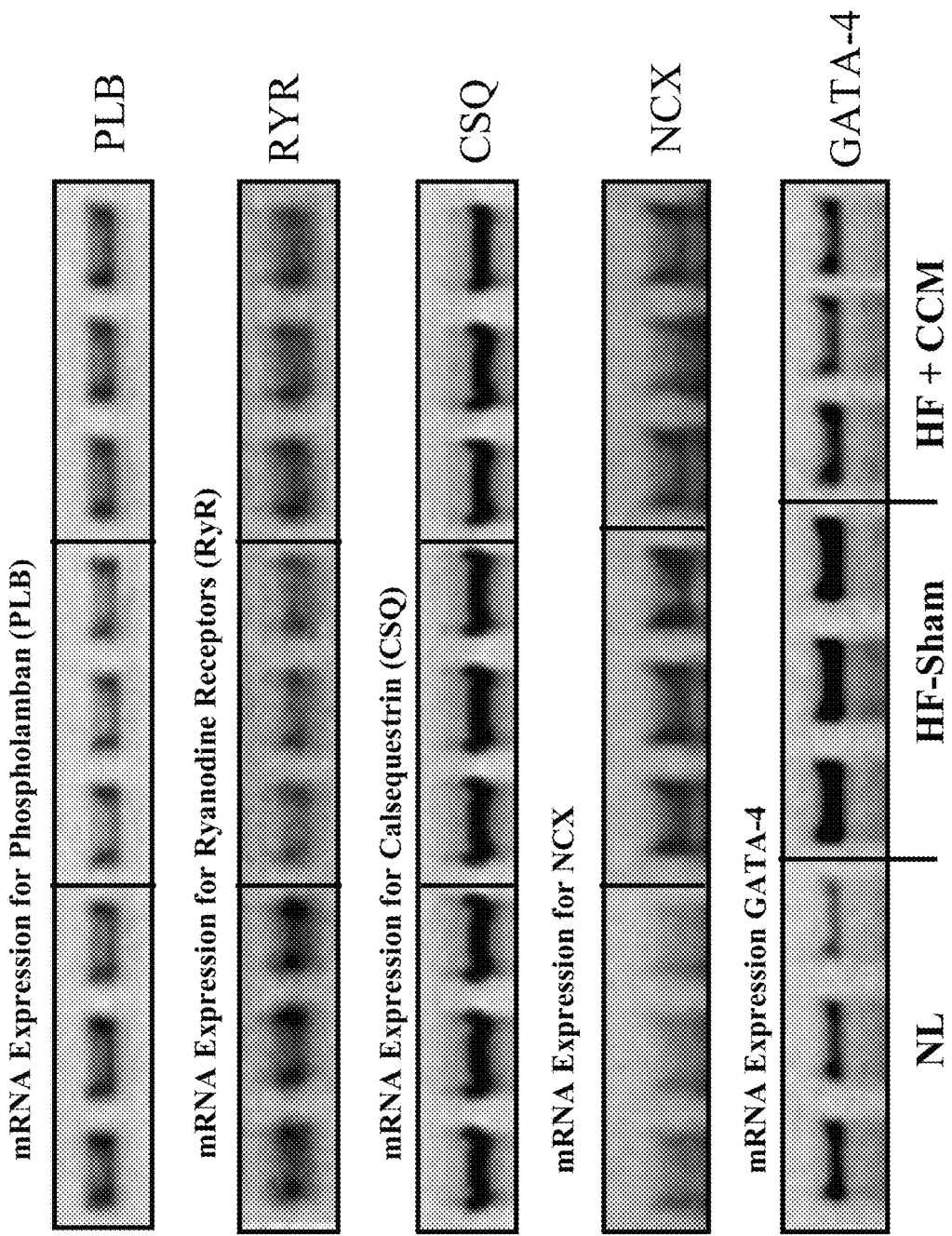

FIG. 2L shows decreased mRNA expression of GATA-4, to even below normal levels. FIG. 2M shows that protein expression of GATA-4, is however, still increased relative to normal. This may be useful for control of NCX and/or other proteins. This result also indicates that merely controlling mRNA may not sufficiently determine the cellular behavior, as protein levels and/or phosphorylation levels may compensate or over compensate. In general, however, the levels are normalized as compared to HF.

FIGS. 2N and 2O show the effect of chronic (e.g., 3 months) treatment with CCM on mRNA expression profiles. Normalization of these important proteins can be seen.

It should be noted that the electric field can operate differently on different proteins, for example, directly affecting some proteins and these proteins indirectly affecting the behavior and/or levels of other proteins. It should also be noted that there are multiple pathways in the cells and the electrical treatment may affect multiple (e.g., 1, 2, 3, 4 or more) pathways in parallel. The resulting effects on proteins may be increasing or decreasing their expression and/or activity levels. Different such effects may be desirable for different proteins and/or different disease conditions. Different proteins may be predisposed (e.g., based on their structure, surrounding materials and/or existing pathways) to differently increase and/or decrease. A particular experiment with Phospholamban is described below.

The following tables summarize the results on mRNA expression for normal dogs (NL), dogs with HF and dogs with HF and chronic CCM treatment. Protein levels and phosphorylation levels are described later on. A summarizing table is also provided later on in the application.

| Dog Numbers | |
|---|---|
| HF-Control | HF + CCM |
| 02-097 | 02-106 |
| 02-098 | 02-107 |
| 02-103 | 02-108 |
| 02-130 | 02-012 |
| 03-045 | 03-023 |
| 04-004 | 03-050 |
| 04-018 | 04-005 |

| mRNA Expression for GAPDH | | | |
|---|---|---|---|
| | NL | HF-Control | HF + CCM |
| | 223 | 195 | 246 |
| | 227 | 195 | 223 |
| | 238 | 223 | 232 |
| | 215 | 241 | 250 |
| | 217 | 227 | 229 |
| | 192 | 237 | 237 |
| | | 240 | 232 |
| Mean | 219 | 223 | 236 |
| STD | 15 | 20 | 10 |
| SEM | 6 | 8 | 4 |
| ANOVA = 0.16 | | | |

| mRNA Expression for TNF-alpha | | | |
|---|---|---|---|
| | NL | HF-Control | HF + CCM |
| | 48 | 235 | 85 |
| | 53 | 223 | 117 |
| | 36 | 182 | 107 |
| | 28 | 194 | 98 |
| | 39 | 232 | 144 |
| | 31 | 234 | 81 |
| | | 240 | 92 |
| Mean | 39 | 220 | 103 |
| STD | 10 | 23 | 22 |
| SEM | 4 | 9 | 8 |
| ANOVA = 0.0001 | | | |
| p vs. NL | | <0.05 | <0.05 |
| p vs. HF-Control | | | <0.05 |

| mRNA Expression for Activin-A | | | |
|---|---|---|---|
| | NL | HF-Control | HF + CCM |
| | 101 | 302 | 174 |
| | 104 | 295 | 142 |
| | 109 | 282 | 150 |
| | 136 | 269 | 148 |
| | 153 | 263 | 100 |
| | 199 | 232 | 92 |
| | | 245 | 88 |
| Mean | 134 | 270 | 128 |
| STD | 38 | 26 | 34 |
| SEM | 15 | 10 | 13 |
| ANOVA = 0.0001 | | | |
| p vs. NL | | <0.05 | NS |
| p vs. HF-Control | | | <0.05 |

| mRNA Expression for Tubulin-alpha | | | |
|---|---|---|---|
| | NL | HF-Control | HF + CCM |
| | 140 | 164 | 82 |
| | 120 | 160 | 124 |
| | 125 | 162 | 144 |
| | 117 | 185 | 146 |
| | 124 | 165 | 160 |
| | 125 | 176 | 141 |
| | | 163 | 168 |
| Mean | 125 | 168 | 138 |
| STD | 8 | 9 | 28 |
| SEM | 3 | 3 | 11 |
| ANOVA = 0.002 | | | |
| p vs. NL | | <0.05 | NS |
| p vs. HF-Control | | | <0.05 |

| mRNA Expression for ANP | | | |
|---|---|---|---|
| | NL | HF-Control | HF + CCM |
| | 21 | 35 | 26 |
| | 19 | 29 | 27 |
| | 17 | 27 | 29 |
| | 12 | 28 | 27 |
| | 18 | 38 | 28 |
| | 23 | 35 | 26 |
| | | 43 | 24 |
| Mean | 18 | 34 | 27 |
| STD | 4 | 6 | 2 |
| SEM | 2 | 2 | 1 |
| ANOVA = 0.0001 | | | |
| p vs. NL | | <0.05 | <0.05 |
| p vs. HF-Control | | | <0.05 |

| mRNA Expression for TIMP-1 | | | |
|---|---|---|---|
| | NL | HF-Control | HF + CCM |
| | 160 | 164 | 131 |
| | 185 | 188 | 146 |
| | 184 | 243 | 136 |
| | 203 | 235 | 191 |
| | 248 | 185 | 151 |
| | 270 | 130 | 170 |
| | | 173 | 174 |
| Mean | 208 | 188 | 157 |
| STD | 42 | 40 | 22 |
| SEM | 17 | 15 | 8 |
| ANOVA = 0.052 | | | |

| mRNA Expression for IL-6 | | | |
|---|---|---|---|
| | NL | HF-Control | HF + CCM |
| | 277 | 556 | 430 |
| | 302 | 533 | 409 |
| | 349 | 524 | 433 |
| | 337 | 547 | 409 |
| | 350 | 558 | 421 |
| | 348 | 552 | 381 |
| | | 567 | 365 |
| Mean | 327 | 548 | 407 |
| STD | 31 | 15 | 25 |
| SEM | 12 | 6 | 10 |
| ANOVA = 0.0001 | | | |
| p vs. NL | | <0.05 | <0.05 |
| p vs. HF-Control | | | <0.05 |

| mRNA Expression for Titin | | | |
|---|---|---|---|
| | NL | HF-Control | HF + CCM |
| | 183 | 137 | 281 |
| | 172 | 222 | 278 |
| | 241 | 182 | 242 |
| | 285 | 197 | 224 |
| | 313 | 124 | 257 |
| | 294 | 135 | 205 |
| | | 196 | 231 |
| Mean | 248 | 170 | 245 |
| STD | 60 | 38 | 28 |
| SEM | 24 | 14 | 11 |
| ANOVA = 0.005 | | | |
| p vs. NL | | <0.05 | NS |
| p vs. HF-Control | | | <0.05 |

| mRNA Expression for Tubulin-beta | | | |
|---|---|---|---|
| | NL | HF-Control | HF + CCM |
| | 88 | 123 | 75 |
| | 77 | 127 | 79 |
| | 68 | 115 | 94 |
| | 65 | 146 | 91 |
| | 60 | 133 | 108 |
| | 62 | 116 | 98 |
| | | 133 | 105 |
| Mean | 70 | 128 | 93 |
| STD | 11 | 11 | 12 |
| SEM | 4 | 4 | 5 |
| ANOVA = 0.0001 | | | |
| p vs. NL | | <0.05 | <0.05 |
| p vs. HF-Control | | | <0.05 |

| mRNA Expression for BNP | | | |
|---|---|---|---|
| | NL | HF-Control | HF + CCM |
| | 32 | 173 | 30 |
| | 13 | 182 | 47 |
| | 21 | 166 | 59 |
| | 31 | 173 | 56 |
| | 22 | 194 | 35 |
| | 17 | 186 | 25 |
| | | 163 | 58 |
| Mean | 23 | 177 | 44 |
| STD | 8 | 11 | 14 |
| SEM | 3 | 4 | 5 |
| ANOVA = 0.0001 | | | |
| p vs. NL | | <0.05 | <0.05 |
| p vs. HF-Control | | | <0.05 |

| mRNA Expression for TIMP-2 | | | |
|---|---|---|---|
| | NL | HF-Control | HF + CCM |
| | 233 | 252 | 222 |
| | 200 | 247 | 239 |
| | 223 | 238 | 235 |
| | 230 | 239 | 229 |
| | 210 | 229 | 225 |
| | 246 | 240 | 219 |
| | | 224 | 198 |

| mRNA Expression for TIMP-2 | | | |
|---|---|---|---|
| | NL | HF-Control | HF + CCM |
| Mean | 224 | 238 | 224 |
| STD | 17 | 10 | 13 |
| SEM | 7 | 4 | 5 |
| ANOVA = 0.12 | | | |

| mRNA Expression for MMP-1 | | | |
|---|---|---|---|
| | NL | HF-Control | HF+ CCM |
| | 24 | 40 | 29 |
| | 20 | 38 | 26 |
| | 18 | 32 | 30 |
| | 24 | 31 | 24 |
| | 23 | 41 | 25 |
| | 33 | 54 | 34 |
| | | 32 | 37 |
| Mean | 24 | 38 | 29 |
| STD | 5 | 8 | 5 |
| SEM | 2 | 3 | 2 |
| ANOVA = 0.003 | | | |
| p vs. NL | | <0.05 | NS |
| p vs. HF-Control | | | <0.05 |

| mRNA Expression for MMP-9 | | | |
|---|---|---|---|
| | NL | HF-Control | HF + CCM |
| | 35 | 60 | 45 |
| | 25 | 69 | 49 |
| | 29 | 43 | 49 |
| | 26 | 71 | 29 |
| | 31 | 44 | 42 |
| | 27 | 41 | 64 |
| | | 39 | 42 |
| Mean | 29 | 52 | 46 |
| STD | 4 | 14 | 11 |
| SEM | 2 | 5 | 4 |
| ANOVA = 0.003 | | | |
| p vs. NL | | <0.05 | <0.05 |
| p vs. HF-Control | | | NS |

| mRNA Expression for p38 MAPK | | | |
|---|---|---|---|
| | NL | HF-Control | HF + CCM |
| | 48 | 41 | 40 |
| | 52 | 60 | 44 |
| | 25 | 46 | 28 |
| | 41 | 57 | 29 |
| | 27 | 59 | 33 |
| | 25 | 67 | 20 |
| | | 56 | 20 |
| Mean | 36 | 55 | 31 |
| STD | 12 | 9 | 9 |
| SEM | 5 | 3 | 3 |
| ANOVA = 0.0001 | | | |
| p vs. NL | | <0.05 | NS |
| p vs. HF-Control | | | <0.05 | mRNA Expression for NCX

|      | NL | HF-Control | HF + CCM |
|------|----|-----------|----------|
|      | 25 | 85  | 31 |
|      | 30 | 115 | 41 |
|      | 36 | 63  | 55 |
|      | 32 | 139 | 50 |
|      | 28 | 39  | 46 |
|      | 29 | 121 | 53 |
|      |    | 126 | 62 |
| Mean | 30 | 98  | 48 |
| STD  | 4  | 37  | 10 |
| SEM  | 2  | 14  | 4  |

ANOVA = 0.0001
p vs. NL         <0.05        NS
p vs. HF-Control              <0.05 mRNA Expression for Beta1-receptor

|      | NL | HF-Control | HF + CCM |
|------|----|-----------|----------|
|      | 22 | 11 | 18 |
|      | 21 | 10 | 17 |
|      | 20 | 6  | 17 |
|      | 19 | 8  | 18 |
|      | 24 | 12 | 19 |
|      | 25 | 11 | 22 |
|      |    | 13 | 17 |
| Mean | 22 | 10 | 18 |
| STD  | 2  | 2  | 2  |
| SEM  | 1  | 1  | 1  |

ANOVA = 0.0001
p vs. NL         <0.05        <0.05
p vs. HF-Control              <0.05 mRNA Expression for MMP-2

|      | NL | HF-Control | HF + CCM |
|------|----|-----------|----------|
|      | 25 | 56 | 42 |
|      | 22 | 42 | 29 |
|      | 24 | 40 | 30 |
|      | 22 | 39 | 28 |
|      | 23 | 41 | 30 |
|      | 24 | 48 | 27 |
|      |    | 41 | 33 |
| Mean | 23 | 44 | 31 |
| STD  | 1  | 6  | 5  |
| SEM  | 0  | 2  | 2  |

ANOVA = 0.0001
p vs. NL         <0.05        <0.05
p vs. HF-Control              <0.05 mRNA Expression for p21RAS

|      | NL  | HF-Control | HF + CCM |
|------|-----|-----------|----------|
|      | 85  | 284 | 297 |
|      | 88  | 295 | 270 |
|      | 162 | 305 | 259 |
|      | 167 | 277 | 248 |
|      | 202 | 299 | 228 |
|      | 213 | 295 | 202 |
|      |     | 284 | 201 | mRNA Expression for p21RAS

|      | NL  | HF-Control | HF + CCM |
|------|-----|-----------|----------|
| Mean | 153 | 291 | 244 |
| STD  | 55  | 10  | 36  |
| SEM  | 22  | 4   | 13  |

ANOVA = 0.0001
p vs. NL         <0.05        <0.05
p vs. HF-Control              <0.05 mRNA Expresion for Integrin-a5

|      | NL | HF-Control | HF + CCM |
|------|----|-----------|----------|
|      | 7  | 17 | 7  |
|      | 10 | 14 | 9  |
|      | 4  | 14 | 10 |
|      | 11 | 15 | 7  |
|      | 8  | 25 | 6  |
|      | 7  | 20 | 10 |
|      |    | 12 | 16 |
| Mean | 8  | 17 | 9  |
| STD  | 2  | 4  | 3  |
| SEM  | 1  | 2  | 1  |

ANOVA = 0.0001
p vs. NL         <0.05        NS
p vs. HF-Control              <0.05 mRNA Expression for GATA-4

|      | NL  | HF-Control | HF + CCM |
|------|-----|-----------|----------|
|      | 83  | 153 | 84  |
|      | 142 | 247 | 103 |
|      | 136 | 138 | 242 |
|      | 105 | 240 | 191 |
|      | 78  | 164 | 113 |
|      | 71  | 254 | 254 |
|      |     | 233 | 135 |
| Mean | 103 | 204 | 160 |
| STD  | 31  | 50  | 69  |
| SEM  | 12  | 19  | 26  |

ANOVA = 0.012
p vs. NL         <0.05        <0.05
p vs. HF-Control              <0.05 mRNA Expression for SERCA-2a

|      | NL  | HF-Control | HF + CCM |
|------|-----|-----------|----------|
|      | 218 | 167 | 172 |
|      | 235 | 189 | 200 |
|      | 242 | 159 | 194 |
|      | 238 | 178 | 192 |
|      | 250 | 178 | 195 |
|      | 232 | 179 | 198 |
|      |     | 171 | 193 |
| Mean | 236 | 174 | 192 |
| STD  | 11  | 10  | 9   |
| SEM  | 4   | 4   | 3   |

ANOVA = 0.0001
p vs. NL         <0.05        <0.05
p vs. HF-Control              <0.05

| mRNA Expression for PLB | | | |
|---|---|---|---|
| | NL | HF-Control | HF + CCM |
| | 221 | 170 | 217 |
| | 229 | 149 | 224 |
| | 255 | 155 | 237 |
| | 241 | 146 | 222 |
| | 248 | 167 | 210 |
| | 200 | 149 | 190 |
| | | 109 | 182 |
| Mean | 232 | 149 | 212 |
| STD | 20 | 20 | 19 |
| SEM | 8 | 8 | 7 |

ANOVA = 0.0001
p vs. NL         <0.05         NS
p vs. HF-Control               <0.05

| mRNA Expression for CSQ | | | |
|---|---|---|---|
| | NL | HF-Control | HF + CCM |
| | 261 | 274 | 192 |
| | 258 | 271 | 225 |
| | 247 | 281 | 262 |
| | 280 | 291 | 299 |
| | 268 | 250 | 276 |
| | 269 | 276 | 281 |
| | | 279 | 281 |
| Mean | 264 | 275 | 259 |
| STD | 11 | 13 | 38 |
| SEM | 5 | 5 | 14 |

ANOVA = 0.47
p vs. NL         NS         NS
p vs. HF-Control            NS

| mRNA Expression for RYR | | | |
|---|---|---|---|
| | NL | HF-Control | HF + CCM |
| | 40 | 25 | 39 |
| | 36 | 23 | 30 |
| | 31 | 29 | 15 |
| | 42 | 18 | 33 |
| | 34 | 21 | 34 |
| | 42 | 22 | 58 |
| | | 17 | 43 |
| Mean | 38 | 22 | 36 |
| STD | 5 | 4 | 13 |
| SEM | 2 | 2 | 5 |

ANOVA = 0.008
p vs. NL         <0.05         NS
p vs. HF-Control               <0.05

| mRNA Expression for α-MHC | | | |
|---|---|---|---|
| | NL | HF-Control | HF + CCM |
| | 176 | 133 | 192 |
| | 212 | 136 | 165 |
| | 219 | 115 | 158 |
| | 218 | 140 | 181 |
| | 221 | 179 | 176 |
| | 224 | 192 | 194 |
| | | 144 | 192 |

| mRNA Expression for α-MHC | | | |
|---|---|---|---|
| | NL | HF-Control | HF + CCM |
| Mean | 212 | 148 | 180 |
| STD | 18 | 27 | 14 |
| SEM | 7 | 10 | 5 |

ANOVA = 0.0001
p vs. NL         <0.05         <0.05
p vs. HF-Control               <0.05

Short Discussion of Some Results

Phospholamban is down regulated in heart failure and is nearly normalized with CCM therapy. This may explain the improvement in LV function by CCM treatment. CCM appears to normalize the RYR message which is consistent with proper therapy. The up-regulation of alpha-MHC with CCM may be contributing to the sustained long-term improvement in LV ejection fraction. Decrease in MMP1 following CCM therapy is in and of itself desirable. Inhibiting gelatinases, as shown, is beneficial, possibly reducing interstitial fibrosis and leading to improved LV diastolic compliance and, hence, improved diastolic filling and function. p21RAS and p38 mitogen activated protein kinese (MAPK) are emissions of stretch response genes which are down-regulated following CCM therapy and correlate with reduced cardiomyocytes hypertrophy. Integrin-a5 is clearly normalized following long-term CCM therapy. Up-regulation of Beta1-Adrenergic Receptor is viewed as a positive development which enhances the sensitivity of the contractile element of catecholamines. Beta-blockers are known to enhance the sensitivity of the myocardium to exogenous as well as endogenous catecholamines when used in heart failure patients over long periods of time in excess of 3 months. In the normal heart, beta blockers reduce the sensitivity of the heart to catecholamines. As will be described below, the therapies as described herein may be used together with beta-blockers, for both short and long term synergistic effects.

Possibly, some therapies according to the present invention will focus on general improvement of health, while other therapies will focus on increasing tissue responsiveness, for example, to certain drugs, and thus focus on improving fewer than all mRNA and/or protein and/or phosphorylation indicators.

Experimental Results—Immediate

The inventors of the present application have discovered that, surprisingly, phosphorylation effects for at least some proteins can be generated in immediate time frames, such as less than 1 minute and even less than 10 or 5 seconds in some cases. Further, an immediacy of effect is also characterized by a reduced number of intermediate stages, indicated by the fact that protein phosphorylation effects can be imposed even in tissue homogenate. Further, specificity of the phosphorylation effects to certain proteins that are relevant for HF is also shown. Further, a lack of effect of an exemplary pacing signal is also shown.

Tissue Homogenate

Figure 3A:
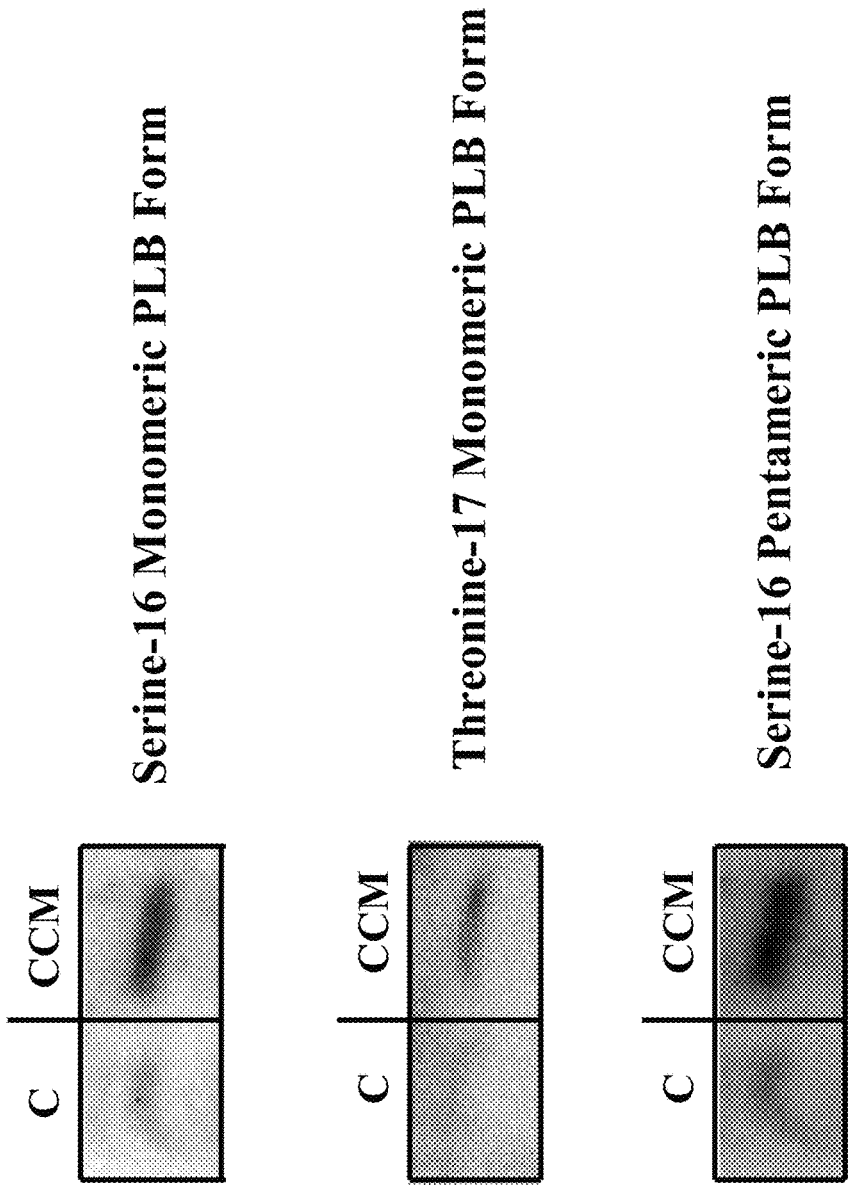
Figure 3B:
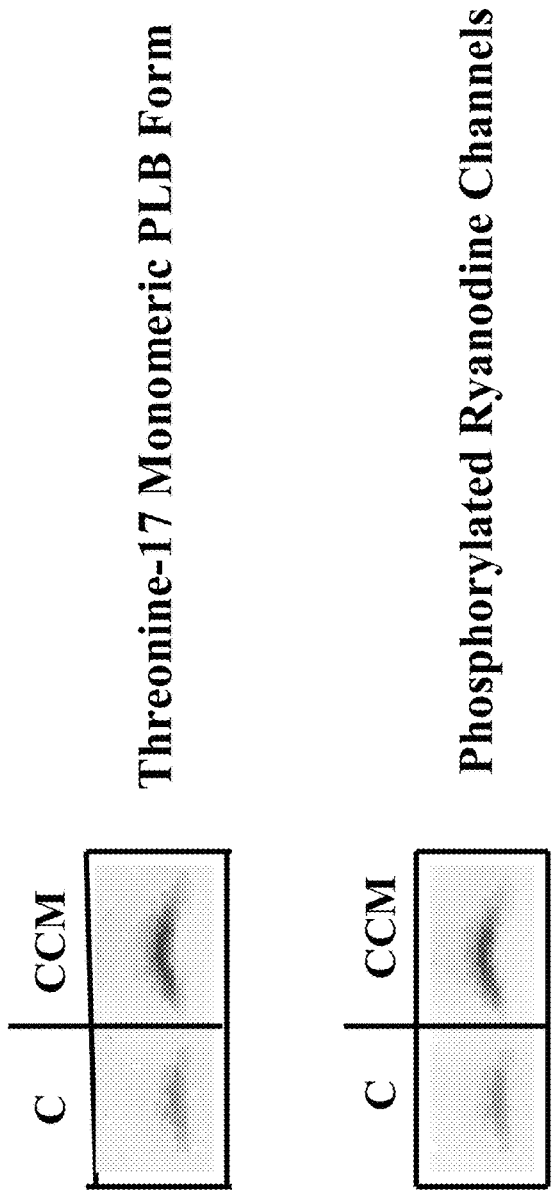

FIGS. 3A and 3B show the effect of a CMM signal applied to tissue homogenate from LV failed heart tissue. As can be seen, even a 10 second signal was sufficient to generate noticeable and significant changes in phosphorylation. Changes in phosphorylation are shown in Serine-16 Monometric PLB (Phospholamban) form, Threonin-17 mometric PLB form, Serine 16 Pentametric PLB form and Ryanodine channels.

The tissue homogenate was prepared in the following manner. Approximately 14 g frozen LV tissue from a dog with chronic HF in 42 ml 50 mM Tris-HCl, pH 7.5 was homogenized three times for 20 seconds each time using a 10-mm generator (Omni International, Waterbury, Conn.) at setting 10. The homogenate was then filtered through 4 layers of cheese cloth. The resulting homogenate was stored in ice and its protein concentration was determined by the Lowry method.

The CCM signals were delivered to the homogenate as follows. The homogenate was diluted 2 fold in homogenate buffer and subsequently aliquotted 3 ml each in assay tubes. Assay tubes were divided into 2 sets (Set A and Set B), each subset consisting of 7 assay tubes. CCM signals were delivered for 10", 30", 1', 5', 30', and 60' in one of the sets, while the other set served as time control. The reaction was stopped by adding concentrated SDS. Protein assay on all the samples were performed by Lowry method.

Phosphorylation of PLB at serine-16 (Ser-16) and threonine-17 (Thr-17) was determined by Western blotting using specific antibody as described in Mishra S, Sabbah H N, Jain J C, Gupta R C: "Reduced Ca2+-calmodulin-dependent protein kinase activity and expression in LV myocardium of dogs with heart failure", Am J Physiol Heart Circ Physiol 284:H876-H883, 2003, the disclosure of which is incorporated herein by reference. Briefly, approximately 100 microgram protein for Se-16 and 40 microgram for Thr-17 were elecrophoresed on 18% SDS-gel, protein was transferred from the gel to nitrocellulose membrane, the blot was probed with primary and secondary antibodies and finally bands were visualized by an ECL method.

It should be noted that tissue homogenate was generally activated at room temperature, below the normal operating temperature of a heart. This and other features of the results suggest a direct chemical or electrical effect on the proteins which is possibly divorced or semi divorced from cell function and/or complex biochemical mechanisms (e.g., more than two or three steps or with feedback). Such divorcing may help in the application of the effect under various conditions including various polarization conditions and tissue health states. In an exemplary embodiment of the invention, it is noted that the effect does not directly depend on the membrane polarization of the cell, therefore, this phosphorylation effect may be achieved at times other than a refractory period. Depending on the non-excitatory signal applied, therapy may be applied during a refractory period to avoid inadvertent pacing. However, if the tissue is desensitized, for example, using a suitable electrical signal, cold, or pharmaceutical, there is no need for specific timing. In another example, suitable charge provided during a pacing signal may be sufficient for a therapeutic effect.

For example, a typical pacing pulse is up to 1 ms and 5V, which at 500 Ohm lead impedance is 50 micro-joule. A CCM pulse as described herein is 2000 micro-joule per pulse and more if multiple pulses are provided in a single sequence (e.g., 4 pulses=8000 micro-joules).

In an exemplary embodiment of the invention, the provided charge per beat is at least 100, at least 300, at least 500, at least 1000, at least 2000, at least 5000 or more or intermediate values of micro-joules. It is hypothesized, that at least for some treatments, the applied field has to be above a minimum charge per heart beat, or the effect is lost, for example, due to electrical masking in the cell or due to biochemical interactions that occur within a heart beat.

In an exemplary embodiment of the invention, the applied energy is directed mostly at a tissue having a volume of less than 20 cm$^3$, less than 10 cm$^3$, less than 5 cm$^3$, less than 3 cm$^3$ or larger or intermediate volumes.

Phosphorylation Dependency on Protein Kinese (PK) Inhibitors

Additional experiments of tissue homogenate were carried out in the presence and absence of protein kinese inhibitors. The homogenate was the same as above, from dogs with heart failure. Two different phosphorylation locations (threonin-17 and serine-16) on phospholamban produced two different results in the presence of the kinese inhibitors (in its absence, the above results were reproduced). The kinese inhibitor is STAUROSPORIN, a Pale yellow solid. Advertised as a potent, cell-permeable, and broad spectrum inhibitor of protein kinases. Inhibits protein kinase A ($IC_{50}$=7 nM), CaM kinase ($IC_{50}$=20 nM), myosin light chain kinase ($IC_{50}$=1.3 nM), protein kinase C ($IC_{50}$=700 pM), and protein kinase G ($IC_{50}$=8.5 nM). Also inhibits platelet aggregation induced by collagen or ADP but has no effect on thrombin-induced platelet aggregation. Induces apoptosis in human malignant glioma cell lines. Arrests normal cells at the $G_1$ checkpoint. Purity: 97% by HPLC. CAS 62996-74-1. In the presence of the kinese inhibitors serine-16 responded close to usual, possibly with a somewhat delayed and/or reduced response (statistics are weak) and threonin-17 has a reduced and delayed response, in that no immediate effect was apparent, but some effect was apparent under longer stimulation times. This suggests two things. First, the pathways for phosphorylation are different for the two locations, when stimulated by an electric field. Second, there appears to be a synergistic effect between kinese and electric field application. These differential and synergist effects suggest the ability to select pathways in affecting tissue Without being limited to any particular hypothesis, it is hypothesized by the inventors that the synergistic effect is caused by the behavior of Akt (or similar proteins), which is described in a paper Gallo P, Santonastasi M, Ceci M, Scimia C, Di Sciascio G, Condorelli G. Akt overexpression improves cardiac function and ameliorates heart failure in pressure overload animal model phosphorylating key Ca2+ handling proteins. J Am Coll Cardiol 2006; 21:76A, the disclosure of which is incorporated herein by reference. In this paper, it is shown that Akt selectively phosphorylates phospholamban at the threonin-17 site. In this, non-limiting explanation, the different sites on phospholamban are physiologically set up to be phosphorylated under different mechanism and while an electric field has a direct effect on both locations, one location is more sensitive to electric fields and the other location is more sensitive to biochemical interaction (or at least such as mediated by kinese). It is further hypothesized that the effect of the electric field applied by the therapy mimics (possibly in an enhanced manner) a regulated effect provided naturally by electrical activity of the heart.

The following tables summarize the experimental results for serine-16:

| | Control | Control + CCM | Control + PK Inhibitor | PK Inhibitor + CCM |
|---|---|---|---|---|
| | \multicolumn{4}{c}{P-PLB with CCM Signals Delivered for 10 sec} | | | |
| | 5.9 | 19.9 | 8.0 | 22.9 |
| | 7.6 | 19.3 | 9.0 | 15.1 |
| | 13.5 | 21.2 | 13.7 | 11.0 |
| Av | 9.0 | 20.2 | 10.2 | 16.3 |

-continued

|    | Control | Control + CCM | Control + PK Inhibitor | PK Inhibitor + CCM |
|---|---|---|---|---|
| P-PLB with CCM Signals Delivered for 20 sec | | | | |
|    | 8.6  | 26.7 | 14.0 | 14.1 |
|    | 6.9  | 15.6 | 12.2 | 18.2 |
|    | 10.4 | 16.9 | 10.6 | 17.5 |
| Av | 8.6  | 19.7 | 12.3 | 16.6 |
| P-PLB with CCM Signals Delivered for 30 sec | | | | |
|    | 8.8  | 21.5 | 6.8  | 14.3 |
|    | 15.0 | 20.2 | 9.7  | 18.1 |
|    | 18.0 | 11.1 | 11.9 | 13.0 |
| Av | 13.9 | 17.6 | 9.4  | 15.1 |
| P-PLB with CCM Signals Delivered for 60 sec | | | | |
|    | 12.5 | 17.5 | 15.0 | 22.7 |
|    | 10.3 | 17.1 | 9.8  | 17.1 |
|    | 7.2  | 24.3 |      |      |
| Av | 10.0 | 19.6 | 12.4 | 19.9 |

The following tables summarize the experimental results for theronin-17:

|    | Control | Control + CCM | Control + PK Inhibitor | PK Inhibitor + CCM |
|---|---|---|---|---|
| P-PLB with CCM Signals Delivered for 10 sec | | | | |
|    | 7.8  | 10.2 | 8.9  | 14.6 |
|    | 10.2 | 11.4 | 12.2 | 9.9  |
|    | 10.7 | 7.3  | 9.5  | 8.7  |
| Av | 9.5  | 9.6  | 10.2 | 11.1 |
| P-PLB with CCM Signals Delivered for 20 sec | | | | |
|    | 8.5  | 26.4 | 13.2 | 15.0 |
|    | 9.1  | 41.1 | 6.2  | 12.5 |
|    | 16.0 | 42.3 | 7.6  | 8.3  |
| Av | 11.2 | 36.6 | 9.0  | 12.0 |
| P-PLB with CCM Signals Delivered for 30 sec | | | | |
|    | 7.4  | 16.1 | 8.2  | 24.0 |
|    | 5.4  | 13.4 | 12.8 | 11.5 |
|    | 7.7  | 9.5  | 16.0 | 14.9 |
| Av | 6.8  | 13.0 | 12.3 | 16.8 |
| P-PLB with CCM Signals Delivered for 60 sec | | | | |
|    | 8.7  | 28.0 | 18.3 | 17.1 |
|    | 13.2 | 20.5 | 12.1 | 12.9 |
|    | 15.2 | 17.8 | 11.2 |      |
| Av | 12.4 | 22.1 | 13.9 | 15.0 |

Failed Cardiomyocytes, Pacing and CCM

Figure 3C:
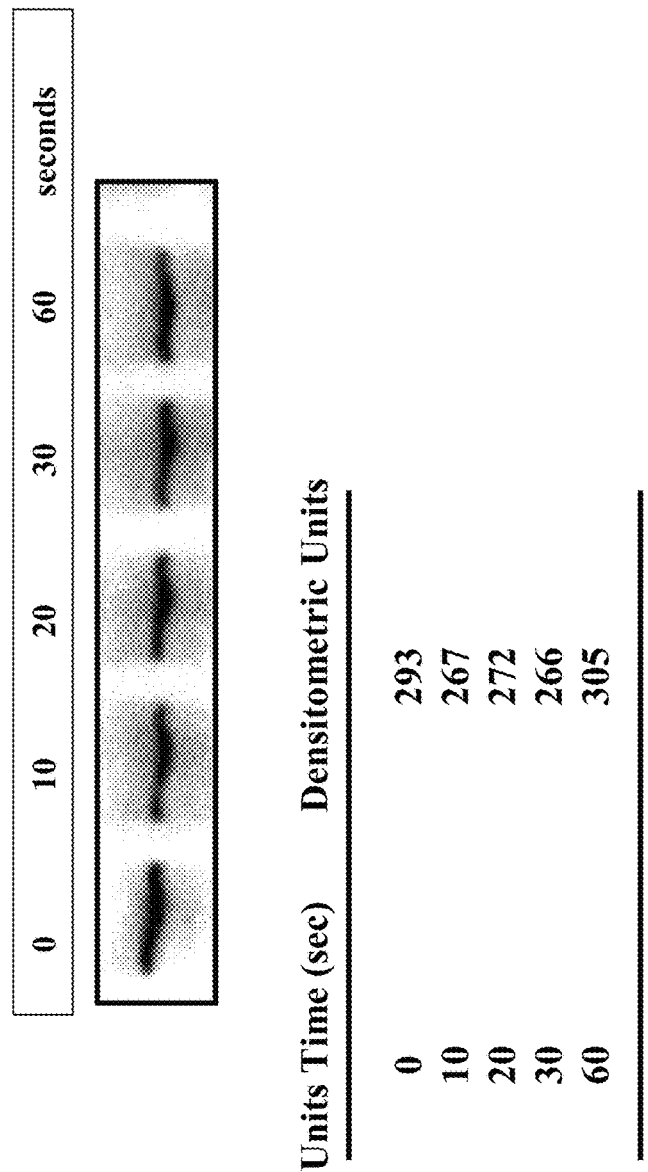

FIG. 3C shows phosphorylation of a Ryanodine receptor in isolated (in-vitro) failed cardiomyocytes, after application of CCM for 10, 20, 30 and 60 seconds. Lack of significant immediate effect is consistent with the lack of long-term effect shown above and serves to show that the effect of the CCM signal can be made specific to certain proteins.

Figure 3D:
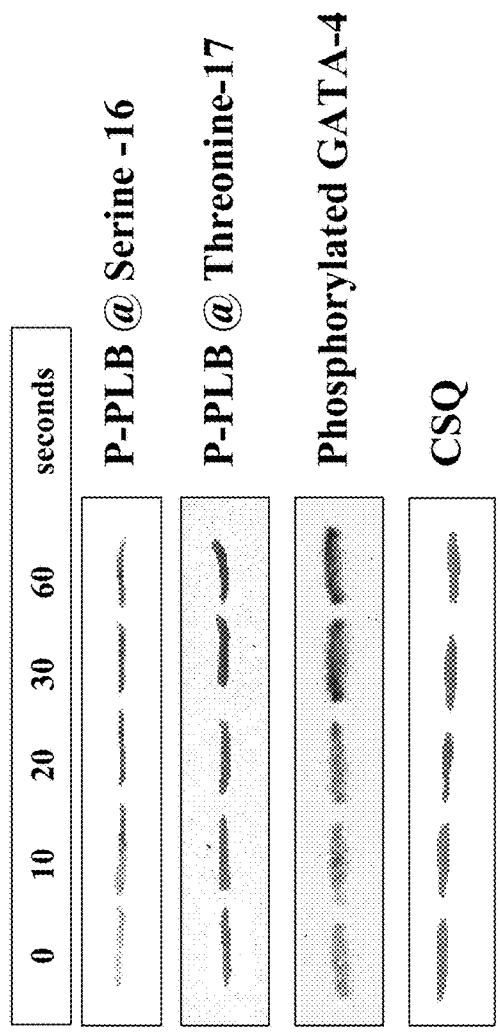

FIG. 3D shows phosphorylation of PLB and GATA, as compared to that of CSQ, in failed isolated myocytes. As can be seen a phosphorylation effect is shown for some of the proteins, which matches the general results for tissue homogenate. Also noteworthy is that the effect increases over time at different rates for different proteins. Relaxation times of phosphorylation levels for different proteins are also generally different. The change in GATA-4 is important because when GATA-4 is phosphorylated, this process decreases the activity of the sodium calcium exchanger and helps contractility improve quickly.

FIG. 3E shows that a pacing signal applied at 3V for pulses of 0.75 msec did not have any significant immediate effect on any of the proteins. Possibly, this is caused by the reduced current density of the pacing pulse and/or due to the substantially lower charge transport rate. Possibly, any minimal effect of the pacing signal is relaxed in the times between signals. Optionally, the pacing signal is not strong enough to pass a certain minimal threshold of effect.

In Vivo Heart

The following tables summarize the results from 2 heart failure dogs in which phosphorylation of phospholamban (PLB-P) after application of CCM signals was studied, while taking biopsies at 1, 5, 10, and 15 minutes. Normalization to CSQ was used to correct for any effect of blood in the biopsies. The increase in PLB-P matches a measured increase in dP/dt measured in these experiments. It is noted that PLB-P levels remained elevated for 15 minutes after application of CCM, suggesting a temporally sparse field application treatment. Optionally, such a prolonged elevation has a long term effect on mRNA expression. Various locations on the LV were tried, all with similar results, as shown below.

|  | CCM Time (min) | CSQ (du) | PLB-P @ Ser-16 (du) | PLB-P Thr-17 (du) | PLB-P Normalized to CSQ | |
|---|---|---|---|---|---|---|
|  |  |  |  |  | Ser-16 | Thr-17 |
| First dog First set | 0 | 146.09 | 34.80 | 28.98 | 0.24 | 0.20 |
|  | 1 | 145.94 | 60.61 | 34.72 | 0.42 | 0.24 |
|  | 5 | 125.88 | 60.67 | 50.51 | 0.48 | 0.40 |
|  | 10 | 103.76 | 92.46 | 33.09 | 0.89 | 0.32 |
| First dog Second set | 0 | 108.38 | 21.94 | 25.55 | 0.20 | 0.24 |
|  | 1 | 107.27 | 71.44 | 82.46 | 0.67 | 0.77 |
|  | 5 | 112.83 | 63.31 | 61.28 | 0.56 | 0.54 |
|  | 10 | 72.57 | 32.85 | 61.98 | 0.45 | 0.85 |
| First dog Third set | 0 | 103.06 | 26.76 | 20.16 | 0.26 | 0.20 |
|  | 1 | 116.54 | 65.60 | 96.83 | 0.56 | 0.83 |
|  | 5 | 139.30 | 79.67 | 144.88 | 0.57 | 1.04 |
|  | 10 | 112.53 | 61.41 | 62.99 | 0.55 | 0.56 |
|  | 15 | 121.23 | 55.86 | 68.86 | 0.46 | 0.57 |

-continued

| | | | | | | |
|---|---|---|---|---|---|---|
| Second | 0 | 117.25 | 20.93 | 16.76 | 0.18 | 0.14 |
| Dog | 1 | 119.63 | 36.03 | 33.77 | 0.30 | 0.28 |
| First set | 5 | 132.55 | 39.08 | 38.74 | 0.29 | 0.29 |
| | 10 | 80.44 | 22.24 | 16.80 | 0.28 | 0.21 |
| Second | 0 | 111.84 | 33.72 | 40.98 | 0.30 | 0.37 |
| Dog | 1 | 118.21 | 62.71 | 71.28 | 0.53 | 0.60 |
| Second | 5 | 68.39 | 31.31 | 32.52 | 0.46 | 0.48 |
| set | 10 | 38.79 | 26.91 | 29.31 | 0.69 | 0.76 |
| Second | 0 | 114.50 | 24.17 | 28.37 | 0.21 | 0.25 |
| Dog | 1 | 121.82 | 44.52 | 62.01 | 0.37 | 0.51 |
| Third set | 5 | 122.01 | 46.91 | 68.04 | 0.38 | 0.56 |
| | 10 | 134.98 | 69.64 | 94.13 | 0.52 | 0.70 |
| | 15 | 86.65 | 35.72 | 31.55 | 0.41 | 0.36 |

Average of all 6 sets obtained from 2 dogs

| | PLB-P Normalized to CSQ | |
|---|---|---|
| CCM Time (min) | Ser-16 | Thr-17 |
| 0 | 0.23 | 0.23 |
| 1 | 0.47 | 0.54 |
| 5 | 0.46 | 0.55 |
| 10 | 0.56 | 0.57 |
| 15 | 0.44 | 0.47 |

Two sets only (3rd set from each dog)

Without being limited to any particular hypothesis, it is hypothesized by the inventors that the applied electric field either has a direct effect on the proteins or has an effect on a cofactor or protein that enhance phosphorylation of proteins. The above "Voltage-dependent potentiation . . . " paper suggests that an electric field can directly modify the natural phosphorylation rate of a protein.

Human Results mRNA expression levels were measured for some genes in human subjects. Therapy with non-excitatory cardiac contractility modulation (CCM) electrical signals was delivered to LV muscle during the absolute refractory period improves LV function in patients with HF.

The effects of 3 months CCM therapy on mRNA expression of cardiac fetal and SR genes in 5 patients with advanced HF were examined. In the experiment, right sided endomyocardial biopsies were obtained at baseline, prior to activating CCM therapy, and at 3 and 6 months thereafter. CCM therapy was delivered in random order of ON for 3 months and OFF for 3 months. mRNA expression measurement was performed in a blinded fashion as to the ON/OFF order of therapy. Expression of the fetal genes A-type (ANP) and B-type (BNP) natriuretic peptides and α-myosin heavy chain (MHC), and the SR genes SERCA-2a, phospholamban (PLB) and ryanodine receptors (RYR) was measured using RT-PCR and bands quantified in densitometric units (du). The percent change in du between baseline and the ON and OFF 3 months phases was calculated.

The 3 months therapy OFF phase was associated with increased expression of ANP and BNP and decreased expression of α-MHC, SERCA-2a, PLB and RYR (Table). In contrast, the 3 months ON therapy phase resulted in decreased expression of ANP and BNP and increased expression of α-MHC, SERCA-2a, PLB and RYR (Table). This suggests that in patients with HF, CCM therapy reverses the cardiac maladaptive fetal gene program and normalizes expression of key SR Ca2+ cycling genes. These observations are consistent with the observed improvement in LV function in patients with HF following long-term CCM therapy.

| mRNA Expression (% Change from Baseline) | | | |
|---|---|---|---|
| | OFF Phase | ON Phase | P-Value |
| ANP | 82 ± 26 | −57 ± 9 | 0.009 |
| BNP | 81 ± 28 | −55 ± 9 | 0.007 |
| α-MHC | 29 ± 9 | 80 ± 16 | 0.004 |
| SERCA-2a | 21 ± 10 | 45 ± 14 | 0.039 |
| PLB | 4 ± 18 | 93 ± 45 | 0.084 |
| RYR | 20 ± 6 | 34 ± 6 | 0.002 |

Protein Results

FIGS. 5A-5R shows protein expression results for the following proteins in chronic dogs, in control, heart failure and treated heart failure conditions: CSQ, SERCA-2a, PLB, RyR, NCX, IL-6, GATA-4, GAPDH, MMP-9, Tubulin-Beta, GATA-1, MMP-1, Tubulin-Alpha, Titin, TIMP-1, Integrin-α5, TNF α, p21ras, p38 MAPK, TIMP-2, $\beta_1$-AR, MMP-2, ANP and BNP.

It should be noted that some blots are shown twice, in order to facilitate comparison between them.

Following is a tabular analysis of these results with a short discussion.

FIGS. 5A-5D show results for the following SR proteins: Calsequestrin, phospholamban, SERCA-2a (Calcium ATPase) and ryanodine receptors; the following Pump Proteins: Sodium-Calcium Exchanger; the following Transcription Factors: GATA-4; and the following Cytokines: Interleukin-6.

In general, these seven proteins moved directionally the same as their mRNA expression. Phospholamban showed complete normalization as did SERCA-2a.

These results are consistent with the concept that the CCM acute and chronic effect is mediated by favorable modification of calcium cycling within the sarcoplasmic reticulum. Also notable is that under chronic condition, the CCM signals appear to normalize the over-expression of the sodium-calcium exchanger.

Re FIG. 5A:

| Dog Numbers-same for all FIGS. 5A-5R | |
|---|---|
| HF-Control | HF + CCM |
| 02-097 | 02-106 |
| 02-098 | 02-107 |
| 02-103 | 02-108 |
| 02-130 | 02-012 |
| 03-045 | 03-023 |
| 04-004 | 03-050 |
| 04-018 | 04-005 |

| Protein Expression of CSQ | | | |
|---|---|---|---|
| | NL | HF-Control | HF + CCM |
| | 49 | 41 | 33 |
| | 41 | 44 | 40 |
| | 38 | 33 | 48 |
| | 45 | 42 | 38 |
| | 50 | 41 | 40 |
| | 34 | 37 | 47 |
| | | 44 | 61 |
| Mean | 43 | 40 | 44 |
| STD | 6 | 4 | 9 |
| SEM | 3 | 1 | 3 |

ANOVA = 0.49
p vs. NL
p vs. HF-Control

| Protein Expression of Phospholamban | | | |
|---|---|---|---|
| | NL | HF-Control | HF + CCM |
| | 64 | 30 | 75 |
| | 63 | 23 | 60 |
| | 74 | 27 | 97 |
| | 63 | 29 | 65 |
| | 75 | 18 | 80 |
| | 52 | 30 | 76 |
| | | 29 | 69 |
| Mean | 65 | 27 | 75 |
| STD | 8 | 5 | 12 |
| SEM | 3 | 2 | 5 |

ANOVA = 0.0001
p vs. NL           <0.05        NS
p vs. HF-Control                <0.05

| Protein Expression of SERCA-2a | | | |
|---|---|---|---|
| | NL | HF-Control | HF + CCM |
| | 77 | 37 | 94 |
| | 77 | 69 | 67 |
| | 89 | 54 | 68 |
| | 117 | 58 | 57 |
| | 95 | 39 | 59 |
| | 74 | 57 | 111 |
| | | 63 | 53 |

| Protein Expression of SERCA-2a (continued) | | | |
|---|---|---|---|
| | NL | HF-Control | HF + CCM |
| | 88 | 54 | 73 |
| | 16 | 12 | 21 |
| | 7 | 4 | 8 |

ANOVA = 0.007
p vs. NL           <0.05        NS
p vs. HF-Control                <0.05

| Protein Expression of RyR | | | |
|---|---|---|---|
| | NL | HF-Control | HF + CCM |
| | 129 | 75 | 115 |
| | 123 | 98 | 107 |
| | 153 | 102 | 119 |
| | 104 | 86 | 86 |
| | 140 | 100 | 78 |
| | 104 | 86 | 91 |
| | | 72 | 147 |
| | 126 | 88 | 106 |
| | 20 | 12 | 23 |
| | 8 | 5 | 9 |

Figure 5B:
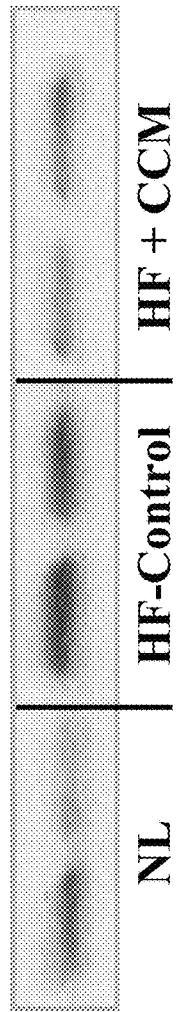
FIGS. 5A-5R are blots showing relative protein levels (in dogs) for control, heart failure and heart failure with chronic CCM application, in accordance with an exemplary embodiment of the invention.

ANOVA = 0.009
p vs. NL           <0.05        NS
p vs. HF-Control                NS Re FIG. 5B:

| Protein Expression of NCX | | | |
|---|---|---|---|
| | NL | HF-Control | HF + CCM |
| | 26 | 62 | 30 |
| | 43 | 50 | 39 |
| | 29 | 38 | 35 |
| | 36 | 45 | 29 |
| | 41 | 49 | 50 |
| | 44 | 76 | 25 |
| | | 58 | 51 |
| | 37 | 54 | 37 |
| | 8 | 12 | 10 |
| | 3 | 5 | 4 |

ANOVA = 0.013
p vs. NL           <0.05        NS
p vs. HF-Control                <0.05

Figure 5C:
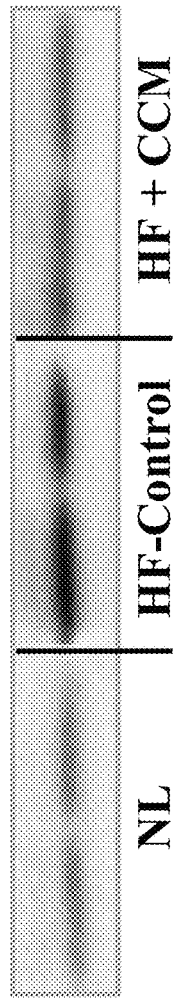

Re FIG. 5C:

| Protein Expression of IL-6 | | | |
|---|---|---|---|
| | NL | HF-Control | HF + CCM |
| | 56 | 74 | 31 |
| | 56 | 51 | 70 |
| | 43 | 87 | 51 |
| | 50 | 84 | 106 |
| | 47 | 107 | 65 |
| | 86 | 118 | 66 |
| | | 90 | 51 |
| | 56 | 87 | 63 |

Figure 5D:
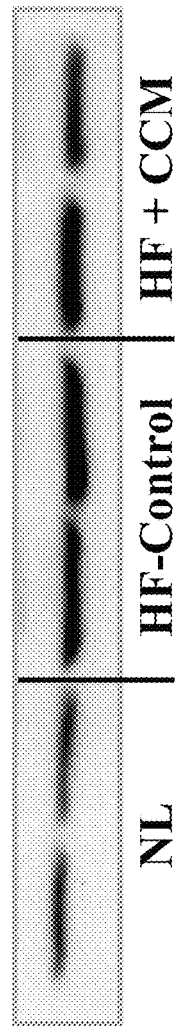

Re FIG. 5D:

| Protein Expression of IL-6 | | |
|---|---|---|
| NL | HF-Control | HF + CCM |
| 15 | 22 | 23 |
| 6 | 8 | 9 |

ANOVA = 0.033
p vs. NL       <0.05       NS
p vs. HF-Control            <0.05

Figure 5E:
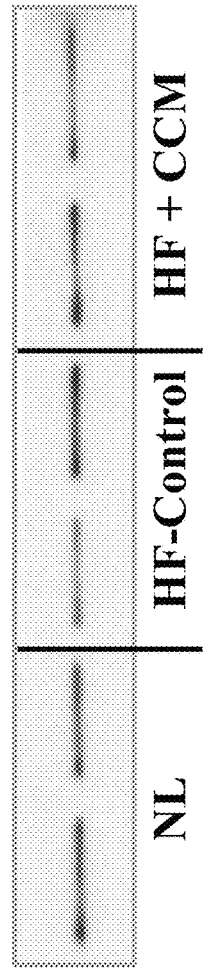

Re FIG. 5E

| Protein Expression of GATA-4 | | |
|---|---|---|
| NL | HF-Control | HF + CCM |
| 90 | 158 | 63 |
| 97 | 179 | 93 |
| 75 | 100 | 129 |
| 105 | 133 | 126 |
| 103 | 157 | 113 |
| 106 | 127 | 103 |
|  | 110 | 141 |
| 96 | 138 | 110 |
| 12 | 28 | 26 |
| 5 | 11 | 10 |

ANOVA = 0.018
p vs. NL       <0.05       NS
p vs. HF-Control            <0.05

FIGS. 5E-5H show results for GAPDH (Housekeeping), transcription factor GATA-1 which did not change, matrix metalloproteinase-9 which changes consistent with mRNA expression and cytoskeletal protein Tubulin-beta which also changes consistent with what is shown for mRNA expression. GATA-1 is shown in comparison with GATA-4.

Re FIG. 5E

| Protein Expression of GAPDH | | |
|---|---|---|
| NL | HF-Control | HF + CCM |
| 32 | 34 | 34 |
| 36 | 33 | 36 |
| 35 | 37 | 32 |
| 35 | 32 | 28 |
| 34 | 31 | 35 |
| 31 | 27 | 46 |
|  | 27 | 30 |
| 34 | 32 | 34 |
| 2 | 4 | 6 |
| 1 | 1 | 2 |

ANOVA = 0.54
p vs. NL       NS       NS
p vs. HF-Control            NS

Figure 5F:
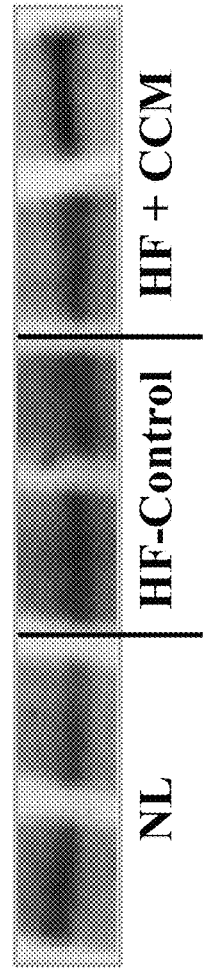

Re FIG. 5F:

| Protein Expression of MMP-9 | | |
|---|---|---|
| NL | HF-Control | HF + CCM |
| 394 | 637 | 668 |
| 448 | 779 | 569 |
| 452 | 821 | 611 |
| 455 | 733 | 551 |
| 488 | 687 | 504 |
| 426 | 643 | 572 |
|  | 742 | 486 |
| 444 | 720 | 566 |
| 32 | 69 | 62 |
| 13 | 26 | 23 |

ANOVA = 0.0001
p vs. NL       <0.05       <0.05
p vs. HF-Control            <0.05

Figure 5G:
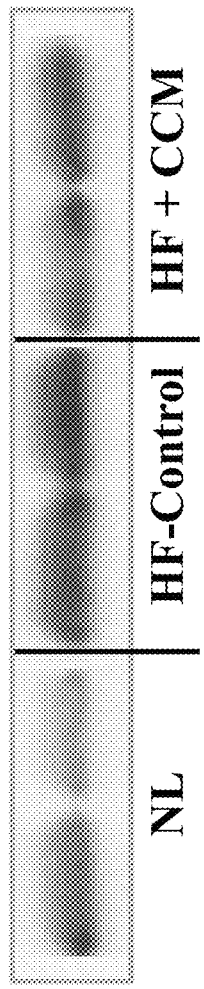

Re FIG. 5G:

| Tubulin-beta | | |
|---|---|---|
| NL | HF-Control | HF + CCM |
| 512 | 1008 | 656 |
| 644 | 810 | 693 |
| 584 | 973 | 647 |
| 450 | 725 | 543 |
| 390 | 693 | 654 |
| 301 | 778 | 675 |
|  | 1078 | 689 |
| 480 | 866 | 651 |
| 126 | 151 | 51 |
| 52 | 57 | 19 |

ANOVA = 0.0001
p vs. NL       <0.05       <0.05
p vs. HF-Control            <0.05

Re FIG. 5H

| Protein Expression of GATA-1 | | |
|---|---|---|
| NL | HF-Control | HF + CCM |
| 83 | 108 | 118 |
| 97 | 110 | 121 |
| 99 | 60 | 130 |
| 115 | 109 | 122 |
| 106 | 106 | 121 |
| 93 | 94 | 75 |
|  | 103 | 101 |
| 99 | 99 | 113 |
| 11 | 18 | 19 |
| 4 | 7 | 7 |

ANOVA = 0.22
p vs. NL       NS       NS
p vs. HF-Control            NS

FIGS. 5I-5L show results from the proteins matrix-metalloproteinase-1 (MMP-1), cytoskeletal proteins tubulin alpha and titin, tissue inhibitor of matrix-metalloproteinase-1 (TIMP-1) and cell surface protein integrin-alpha-5.

There were no apparent changes in TIMP-1. CCM therapy also had no significant effect on integrin-alpha-5. It should be noted that integrin-alpha-5 can be affected by other means, such as mechanically constraining the heart (e.g., thus directly affecting its transduction function).

CCM therapy, however, significantly down-regulated MMP-1, tubulin-alpha and titin which is consistent with the observation with respect to the effects of CCM on mRNA expression of these genes.

Re FIG. 5I

| Protein Expression of MMP-1 | | |
|---|---|---|
| NL | HF-Control | HF + CCM |
| 521 | 936 | 482 |
| 449 | 894 | 574 |
| 425 | 883 | 511 |
| 484 | 1066 | 538 |
| 437 | 985 | 527 |
| 525 | 997 | 539 |
|  | 971 | 476 |
| 474 | 962 | 521 |
| 43 | 63 | 34 |
| 18 | 24 | 13 |

ANOVA = 0.0001  
p vs. NL     <0.05      NS  
p vs. HF-Control      <0.05

Re FIG. 5J

| Tubulin-alpha | | |
|---|---|---|
| NL | HF-Control | HF + CCM |
| 196 | 298 | 217 |
| 161 | 322 | 233 |
| 129 | 359 | 187 |
| 136 | 283 | 214 |
| 142 | 307 | 239 |
| 158 | 260 | 257 |
|  | 274 | 250 |
| 154 | 300 | 228 |
| 24 | 33 | 24 |
| 10 | 13 | 9 |

ANOVA = 0.0001  
p vs. NL     <0.05      <0.05  
p vs. HF-Control      <0.05

| Protein Expression of Titin | | |
|---|---|---|
| NL | HF-Control | HF + CCM |
| 609 | 232 | 368 |
| 575 | 211 | 285 |
| 528 | 218 | 306 |
| 412 | 302 | 213 |
| 400 | 231 | 248 |
| 467 | 223 | 329 |
|  | 191 | 243 |
| 499 | 230 | 285 |
| 86 | 35 | 54 |
| 35 | 13 | 20 |

ANOVA = 0.0001  
p vs. NL     <0.05      <0.05  
p vs. HF-Control      NS

Figure 5K:
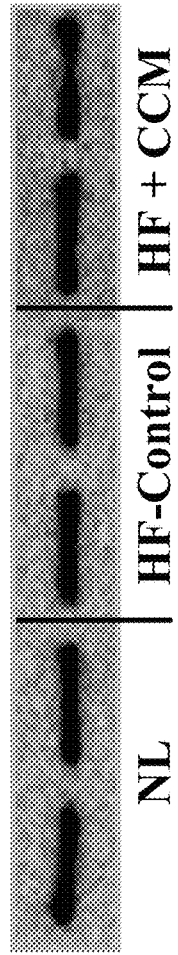

Re FIG. 5K:

| Protein Expression of TIMP-1 | | |
|---|---|---|
| NL | HF-Control | HF + CCM |
| 609 | 914 | 786 |
| 718 | 835 | 849 |
| 915 | 863 | 811 |
| 694 | 679 | 888 |
| 724 | 773 | 781 |
| 834 | 676 | 762 |
|  | 787 | 709 |
| 749 | 790 | 798 |
| 109 | 90 | 58 |
| 44 | 34 | 22 |

ANOVA = 0.57  
p vs. NL      NS      NS  
p vs. HF-Control      NS

Figure 5L:
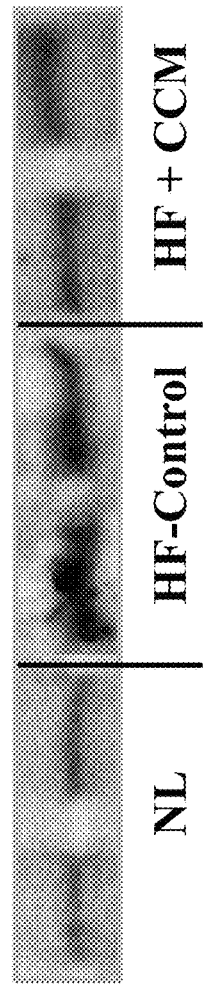

Re FIG. 5L:

| Integrin-alpha-5 | | |
|---|---|---|
| NL | HF-Control | HF + CCM |
| 228 | 340 | 254 |
| 153 | 455 | 239 |
| 160 | 437 | 212 |
| 223 | 358 | 193 |
| 185 | 332 | 168 |
| 201 | 356 | 253 |
|  | 324 | 249 |
| 192 | 372 | 224 |
| 31 | 52 | 34 |
| 13 | 20 | 13 |

ANOVA = 0.0001  
p vs. NL     <0.05      NS  
p vs. HF-Control      <0.05

FIGS. 5M-5P show results from the proteins TNF-α (showed in comparison to IL-6), p21ras, p38 MAPK, TIMP-2 (showed in comparison to TIMP-1 and β1-AR.

The lack of change in TIMP-2 is consistent with previous observations. Long-term CCM therapy significantly reduced protein expression of the cytokine TNF-α and significantly reduced the expression of the stretch proteins p21ras as well as p38 MAPK. This is consistent with the observation that CCM therapy attenuates cardiomyocyte hypertrophy. Also to be noted is up-regulation of the beta-1 adrenergic receptor, which is favorable.

Re FIG. 5M

| Protein Expression of IL-6 | | |
|---|---|---|
| NL | HF-Control | HF + CCM |
| 56 | 74 | 31 |
| 56 | 51 | 70 |
| 43 | 87 | 51 |
| 50 | 84 | 106 |
| 47 | 107 | 65 |
| 86 | 118 | 66 |
|  | 90 | 51 |
| 56 | 87 | 63 |
| 15 | 22 | 23 |
| 6 | 8 | 9 |

ANOVA = 0.033  
p vs. NL     <0.05      NS  
p vs. HF-Control      <0.05

| Protein Expression of TNFα | | |
|---|---|---|
| NL | HF-Control | HF + CCM |
| 44 | 155 | 63 |
| 44 | 161 | 89 |
| 31 | 149 | 53 |

| Protein Expression of TNFα | | |
|---|---|---|
| NL | HF-Control | HF + CCM |
| 47 | 125 | 87 |
| 51 | 168 | 75 |
| 39 | 180 | 96 |
|  | 176 | 80 |
| 43 | 159 | 78 |
| 7 | 19 | 15 |
| 3 | 7 | 6 |

ANOVA = 0.0001
p vs. NL      <0.05      <0.05
p vs. HF-Control           <0.05

Figure 5N:
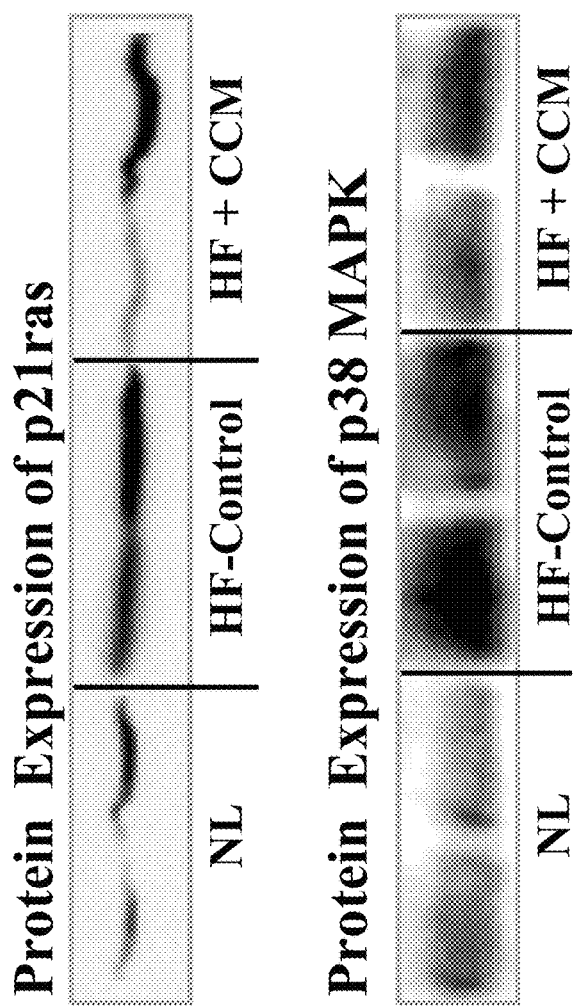

Re FIG. 5N:

| Protein Expression of p21ras | | |
|---|---|---|
| NL | HF-Control | HF + CCM |
| 44 | 112 | 92 |
| 57 | 142 | 89 |
| 38 | 138 | 83 |
| 30 | 123 | 110 |
| 34 | 66 | 61 |
| 36 | 73 | 53 |
|  | 90 | 72 |
| 40 | 106 | 80 |
| 10 | 31 | 20 |
| 4 | 12 | 7 |

ANOVA = 0.0001
p vs. NL      <0.05      <0.05
p vs. HF-Control           <0.05

| Protein Expression of p38 MAPK | | |
|---|---|---|
| NL | HF-Control | HF + CCM |
| 21 | 46 | 32 |
| 15 | 52 | 21 |
| 13 | 41 | 35 |
| 17 | 67 | 36 |
| 14 | 43 | 24 |
| 19 | 38 | 19 |
|  | 33 | 15 |
| 17 | 46 | 26 |
| 3 | 11 | 8 |
| 1 | 4 | 3 |

ANOVA = 0.0001
p vs. NL      <0.05      NS
p vs. HF-Control           <0.05

Re FIG. 5O:

| Protein Expression of TIMP-2 | | |
|---|---|---|
| NL | HF-Control | HF + CCM |
| 84 | 62 | 85 |
| 73 | 55 | 80 |
| 61 | 43 | 68 |
| 93 | 89 | 72 |
| 87 | 88 | 56 |
| 88 | 84 | 79 |
|  | 81 | 86 |
| 81 | 72 | 75 |
| 12 | 18 | 11 |
| 5 | 7 | 4 |

ANOVA = 0.53
p vs. NL      NS      NS
p vs. HF-Control           NS

Figure 5P:
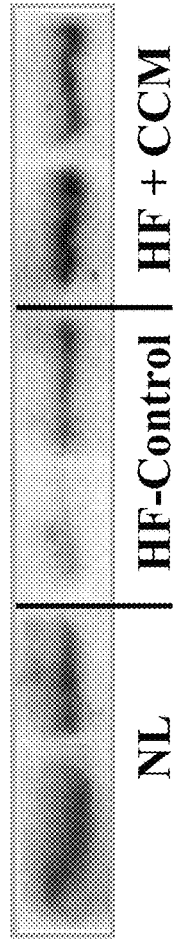

Re FIG. 5P:

| Protein Expression of β1-AR | | |
|---|---|---|
| NL | HF-Control | HF + CCM |
| 135 | 66 | 86 |
| 75 | 30 | 97 |
| 88 | 41 | 53 |
| 111 | 64 | 95 |
| 111 | 113 | 86 |
| 93 | 56 | 96 |
|  | 64 | 113 |
| 102 | 62 | 89 |
| 21 | 26 | 18 |
| 9 | 10 | 7 |

ANOVA = 0.015
p vs. NL      <0.05      NS
p vs. HF-Control           <0.05

FIGS. 5Q and 5R show results for MMP-2 (in comparison to MMP-1 and MMP-9) and ANP and BNP.

Re FIG. 5Q:

| Protein Expression of MMP-2 | | |
|---|---|---|
| NL | HF-Control | HF + CCM |
| 47 | 74 | 41 |
| 29 | 77 | 30 |
| 31 | 57 | 25 |
| 42 | 78 | 56 |
| 38 | 81 | 63 |
| 42 | 51 | 65 |
|  | 41 | 61 |
| 38 | 66 | 49 |
| 7 | 16 | 16 |
| 3 | 6 | 6 |

ANOVA = 0.0001
p vs. NL      <0.05      NS
p vs. HF-Control           <0.05

Re FIG. 5R:

| Protein Expression of ANP | | |
|---|---|---|
| NL | HF-Control | HF + CCM |
| 64 | 104 | 62 |
| 77 | 179 | 60 |
| 108 | 271 | 39 |
| 82 | 128 | 89 |
| 92 | 135 | 62 |
| 103 | 113 | 76 |
|  | 97 | 54 |
| 88 | 147 | 63 |
| 17 | 61 | 16 |
| 7 | 23 | 6 |

ANOVA = 0.002
p vs. NL      <0.05      NS
p vs. HF-Control           <0.05

| Protein Expression of BNP | | |
|---|---|---|
| NL | HF-Control | HF + CCM |
| 31 | 84 | 78 |
| 62 | 94 | 62 |
| 107 | 111 | 69 |
| 65 | 87 | 69 |
| 57 | 94 | 84 |
| 66 | 77 | 77 |
|  | 89 | 73 |
| 65 | 91 | 73 |
| 25 | 11 | 7 |
| 10 | 4 | 3 |

ANOVA = 0.002
p vs. NL        <0.05
p vs. HF-Control              <0.05        NS Comparison of mRNA Levels and Protein Levels in the LV Free Wall on Chronic Treated Dogs Referring back to the 14 dogs tested for chronic effects, mRNA expression in LV free wall of the housekeeping gene GAPDH and CSQ, the fetal program genes consisting of $\beta_1$-AR, αMHC, ANP, and BNP and the cardiac SR genes SERCA-2a, PLB, and RyR are shown in table 5 quantified in densitometric units. Expression of GAPDH and CSQ was unchanged among the 3 study groups namely, normal dogs, sham-operated HF dogs and HF CMM-treated dogs. mRNA expression of $\beta_1$-AR, αMHC, SERCA-2a, PLB and RyR decreased and expression of ANP and BNP increased significantly in sham-operated HF dogs compared to normal. Three months of CCM therapy restored the expression of all genes to near normal levels. Protein expression in the LV free wall of CSQ, $\beta_1$-AR, ANP, BNP SERCA-2a, PLB and RyR are also shown in Table 5 quantified in densitometric units. Protein levels of CSQ were unchanged among the 3 study groups. Protein levels of $\beta_1$-AR, SERCA-2a, PLB and RyR decreased and that of ANP and BNP increased significantly in sham-operated HF dogs compared to normal dogs. Long-term CCM therapy restored the expression of all measured proteins except PLB to near normal levels (Table 5). Possibly, phospholamban was not restored because of the differential phosphorylation thereof. In an exemplary embodiment of the invention, this mechanism is used to selectively increase synthesis of some proteins over others.

In an exemplary embodiment of the invention, this mechanism is used to test if a patient is getting better—by stopping a therapy which is directly causing phospohorylation and seeing if phospholamban levels normalize (or trend to) after a few days and/or if other protein levels trend towards disease state values.

In an exemplary embodiment of the invention, relaxation time between signal application is an integral part of therapy. In one example, relaxation time is used to allow the cell to find a new balance between the expressed proteins that are not on corresponding levels, such a balance may include protein levels (or mRNA levels or phosphorylation or structural remodeling) degrading and/or protein levels improving. Such relation times may be on order of seconds, minutes hours or days, depending on which mechanism are to be allowed to take part (e.g., protein based, etc.).

In an exemplary embodiment of the invention, when applying phosphorylation-modifying therapy as described herein, a process of weaning is applied. Possibly, if treatment is stopped suddenly, phospholamban levels will be too low to support suitable cardiac activity, possibly causing a downwards-spiral in patient health. In an exemplary embodiment of the invention, as protein levels normalize (for other proteins), therapy is reduced to allow phospholamban recovery. Optionally, the pauses are timed according to measured recovery in phospholamban levels.

In an exemplary embodiment of the invention, electrical therapy is applied selectively to tissue measured as having reduced phospholamban levels and/or phosphorylation levels, so as not to potentially damage healthy tissue. In some cases, changes to "healthy" tissue is desirable. For example, increasing phosphorylation and thus possibly reducing phospholamban may be desirable if long term reduction in contractility is desired. In another example, phosphorylation may be increased in normal tissue in order to cause over (or under) expression of some proteins, such as gap junction proteins or mechanical proteins. It should be appreciated that a therapy target of diseased tissue need not be a mirror of a healthy tissue state.

TABLE 5 mRNA and Protein Expression of Fetal Program and Sarcoplasmic Reticulum Genes/Proteins in Left Ventricular Free Wall of Normal Dogs (NL) (n = 6), Sham-Operated Untreated Heart Failure Dogs (Sham, n = 7) and CCM-Treated Heart Failure Dogs (CCM, n = 7)

|  | mRNA Expression (du) | | | Protein Expression (du) | | |
|---|---|---|---|---|---|---|
|  | NL | Sham | CCM | NL | Sham | CCM |
| B$_1$-AR | 22 ± 1 | 11 ± 1* | 18 ± 1*† | 102 ± 9 | 62 ± 10* | 89 ± 7† |
| A-MHC | 212 ± 7 | 148 ± 10* | 180 ± 5*† | — | — | — |
| ANP | 18 ± 2 | 34 ± 2* | 27 ± 1*† | 88 ± 7 | 147 ± 23* | 63 ± 6† |
| BNP | 23 ± 3 | 177 ± 4* | 44 ± 5*† | 65 ± 10 | 91 ± 4* | 73 ± 3† |
| SERCA-2a | 236 ± 4 | 154 ± 4* | 192 ± 3*† | 88 ± 7 | 54 ± 4* | 73 ± 8† |
| PLB | 232 ± 8 | 149 ± 8* | 212 ± 7† | 446 ± 19 | 277 ± 12* | 299 ± 9* |
| RyR | 38 ± 2 | 22 ± 2* | 36 ± 5† | 126 ± 8 | 88 ± 5* | 106 ± 9† |
| CSQ | 264 ± 5 | 275 ± 5 | 259 ± 14 | 43 ± 3 | 40 ± 1 | 44 ± 3 |
| GAPDH | 219 ± 6 | 223 ± 8 | 236 ± 4 | — | — | — | du = Densitometric units;
AR = Adrenergic receptor;
MHC = Myosin Heavy Chain;
ANP = A-type natriuretic peptide;
BNP = B-type natriuretic peptide;
SERCA-2A = Cardiac sarcoplasmic reticulum calcium ATPase;
PLB = Phospholamban;
RyR = Ryanodine receptor;
CSQ = Calsequestrin;
GAPDH = Glyseraldehyde-3-phosphate dehydrogenase.
*= p < 0.05 vs. NL;
†= p < 0.05 vs. Sham.

Local and Remote Effects

Figure 6:
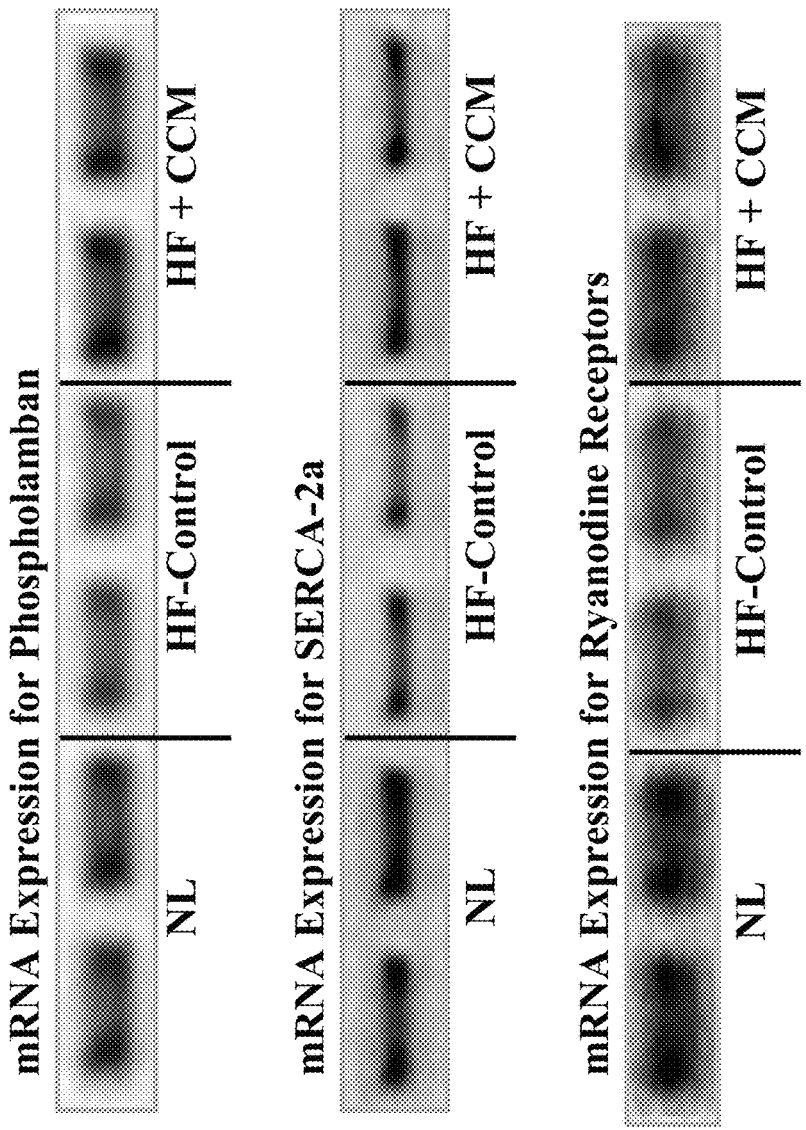
FIG. 6 shows mRNA expression levels in a cardiac septum (where signals are applied), in a chronic study, in accordance with an exemplary embodiment of the invention.

The above results showed analysis of tissue samples at the treated site. FIG. 6 shows mRNA expression levels for Phospholamban, SERCA-2a and Ryanodine receptors, showing chronic improvement in septal tissue to which a field was applied chronically.

Figure 10:
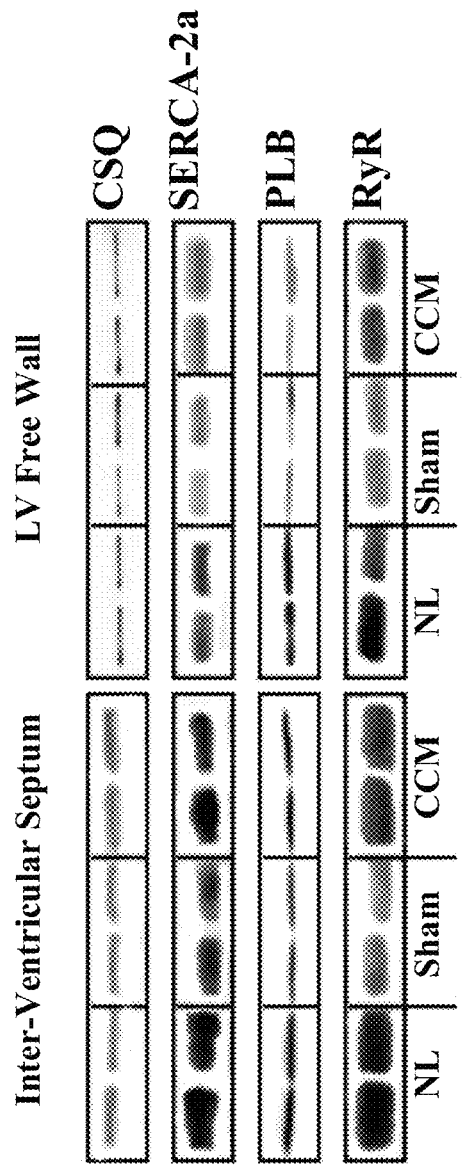
FIG. 10 presents western blot data illustrating effect of CCM according to an exemplary embodiment of the invention on protein levels of CSQ, SERCA-2a, PLB and RyR in the LV free wall and inter-ventricular septum.

Referring to the 14 dogs chronic study described above, the restoration to near normal levels of the fetal program and most SR proteins after 3 months of CCM therapy was the same in LV tissue obtained from the inter-ventricular septum, the site nearest to the CCM signal delivery leads, and the LV free wall, a site remote from the CCM leads. A typical example illustrating the changes in protein levels of CSQ, SERCA-2a, PLB and RyR between the two LV sites is shown in FIG. 10.

FIG. 8 shows phosphorylation levels in chronically treated dogs, at the application location in the septum.

In addition to examining protein expression of fetal program genes and SR proteins, protein levels of P-PLB at serine-16 and threonine-17 were also examined. Measurements were made in tissue obtained from both the inter-ventricular septum and the LV free wall. At both sites, protein levels of P-PLB at serine-16 and threonine-17 were significantly lower in sham-operated HF dogs compared to normal dogs and returned to near normal levels after 3 months of CCM therapy (FIG. 11, Table 6). In both the inter-ventricular septum and LV free wall, the ratio of P-PLB at serine-16 to total PLB and the ratio of P-PLB at threnonine-17 were also significantly lower in sham-operated HF dogs compared to normal dogs (Table 6). Long-term CCM therapy resulted in a significant increase of both ratios in both the interventricular Septum and the LV free wall (Table 6).

increases the activity/affinity of SRECA-2a for calcium and immediately improves SR calcium cycling. GATA-4 and the sodium calcium exchanger may play an additive role in the improved function. As LV function begins to improve and the LV gets smaller, many of the molecular/biochemical maladaptations begin to correct, which adds to the long-term benefits. Improved SR cardiac cycling may be a goal of some therapies in accordance with exemplary embodiments of the invention.

In open chest HF dogs, acute hemodynamic and local/remote effects were determined. Continuous delivery of CCM therapy over the course of 2 hours improved LV systolic function and associated hemodynamics. Compared to baseline before initiating CCM therapy, 2 hours of CCM therapy resulted in a significant increase of LV ejection fraction (31±2 vs. 26±1%, $p<0.05$), a reduction of $MVO_2$ that did not reach statistical significance (180±34 vs. 257±41 mols/min) and a trend toward an increase in LV mechanical efficiency that also did not reach statistical significance (33±8 vs. 19±4%).

Figure 12A:
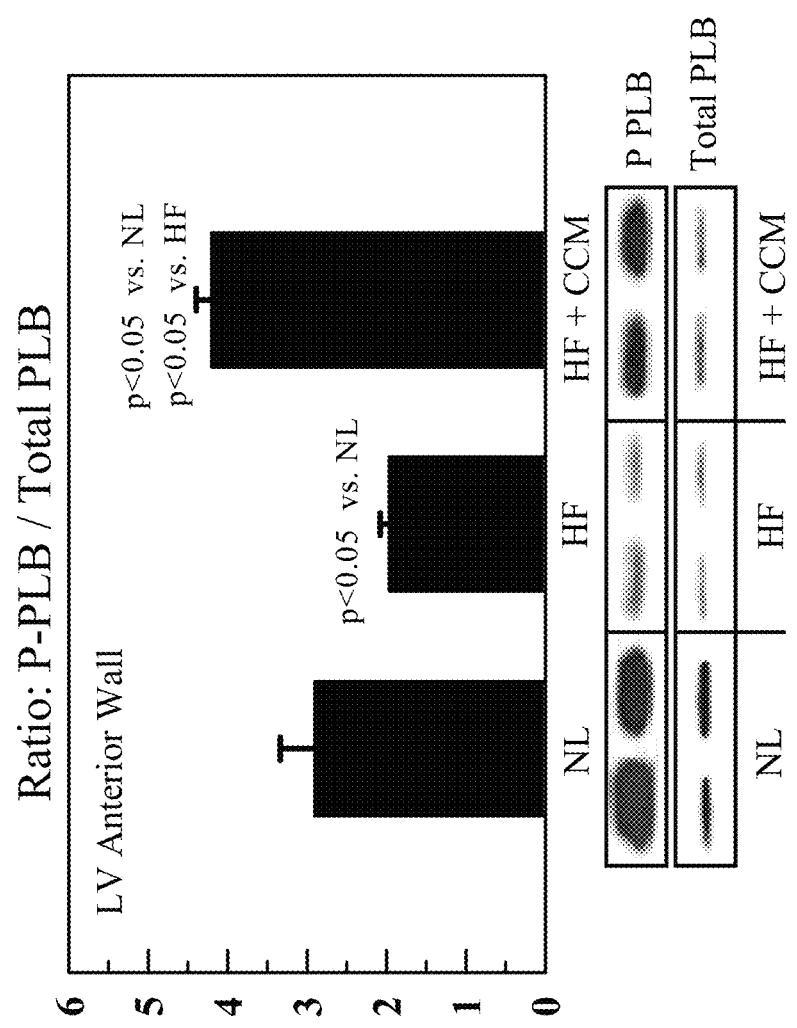
FIGS. 12A and 12B present western blot data and bar graphs illustrating effect of CCM according to an exemplary embodiment of the invention on the ratio of P-PLB to total PLB relative to untreated HF dogs in the LV anterior wall at the site of signal delivery (FIG. 12A), and in the LV posterior wall remote from the site of CCM signal delivery (FIG. 12B)
Figure 12B:
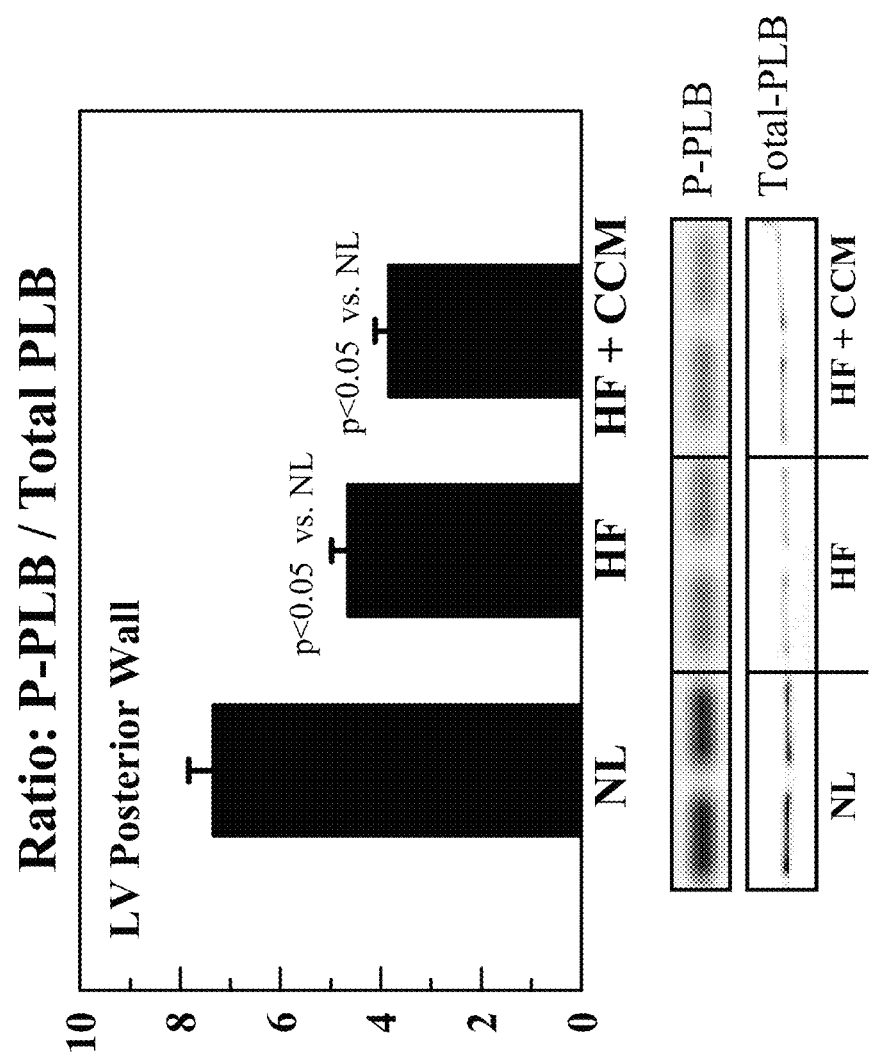

LV tissue obtained near the site of CCM lead implants, was compared to LV tissue obtained from a site remote from the CCM leads. LV tissue samples obtained from the same sites from dogs with HF that were untreated and normal dogs were used for comparisons. Compared to untreated HF dogs, the ratio of P-PLB to total PLB increased significantly in CCM-treated HF dogs compared to untreated HF dogs in the LV anterior wall at the site of signal delivery (FIG. 12A), whereas it was essentially unchanged in the LV posterior wall remote from the site of CCM signal delivery (FIG. 12B).

In an exemplary embodiment of the invention, the location to which electrification will be applied is selected based

TABLE 6

Protein Expression of Total Phospholamban and Phosphorylated Phospholamban at Serine-16 and Threonine-17 in the Inter-Ventricular Septum and Left Ventricle Free Wall of Normal Dogs (NL) (n = 6), Sham-Operated Untreated Heart Failure Dogs (Sham, n = 7) and CCM-Treated Heart Failure Dogs (CCM, n = 7))

| | Inter-Ventricular Septum | | | LV Free Wall | | |
|---|---|---|---|---|---|---|
| | NL | Sham | CCM | NL | Sham | CCM |
| Total PLB (du) | 445 ± 7 | 305 ± 23* | 299 ± 16* | 446 ± 19 | 305 ± 19* | 299 ± 9* |
| P-PLB Ser-16 (du) | 85 ± 6 | 47 ± 5* | 79 ± 6† | 128 ± 11 | 50 ± 12* | 87 ± 11*† |
| P-PLB Thr-17 (du) | 146 ± 6 | 62 ± 10* | 129 ± 12† | 137 ± 4 | 56 ± 7* | 109 ± 18† |
| P-PLB Ser-16/ Total PLB | 0.19 ± 0.01 | 0.15 ± 0.01* | 0.27 ± 0.02† | 0.29 ± 0.03 | 0.16 ± 0.03* | 0.29 ± 0.04† |
| P-PLB Thr-17/ Total PLB | 0.33 ± 0.01 | 0.21 ± 0.04* | 0.44 ± 0.05† | 0.31 ± 0.02 | 0.19 ± 0.03* | 0.36 ± 0.05† |

PLB = phopholamban;
P-PLB = phosphorylated phospholamban;
Ser-16 = serine-16;
Thr-17 = theonine-17.
*= $p < 0.05$ vs. NL;
†= $p < 0.05$ vs. Sham.

Figure 7A:
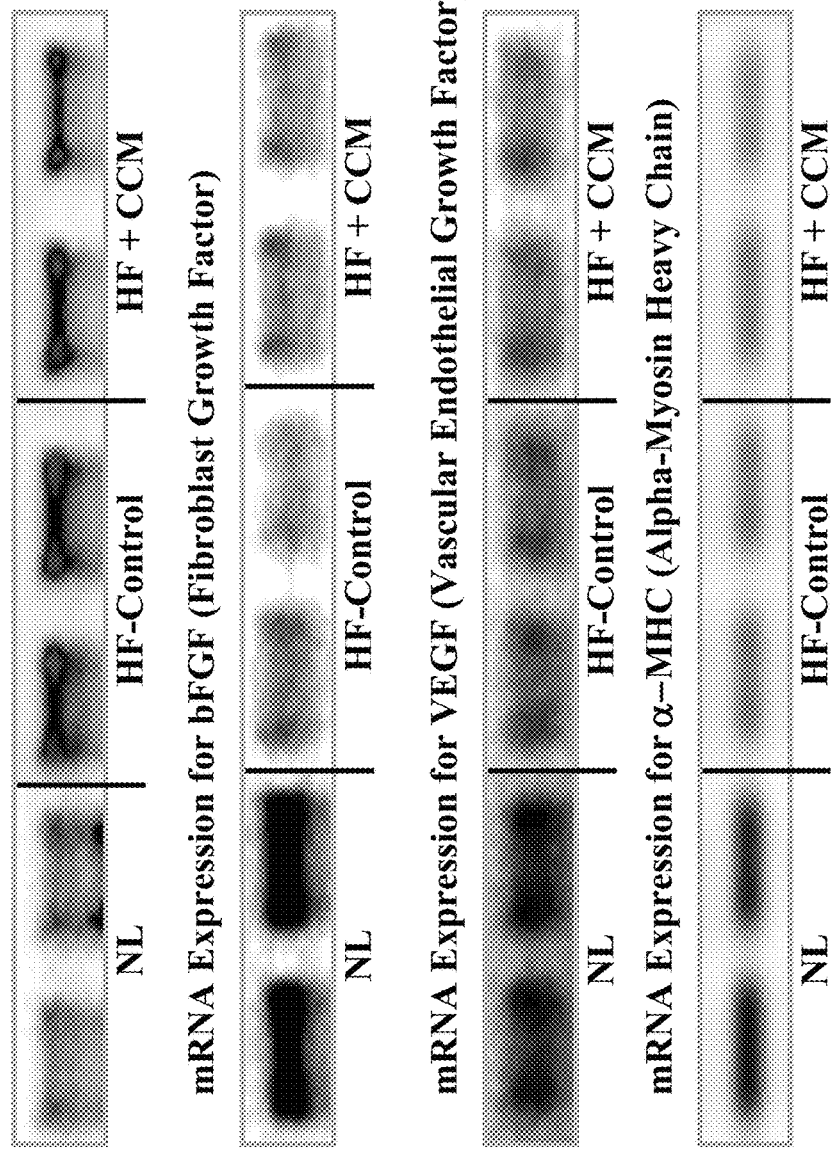
FIGS. 7A and 7B show a general lack of acute effect of CCM on tissue remote from a CCM delivery site, in accordance with an exemplary embodiment of the invention.
Figure 7B:
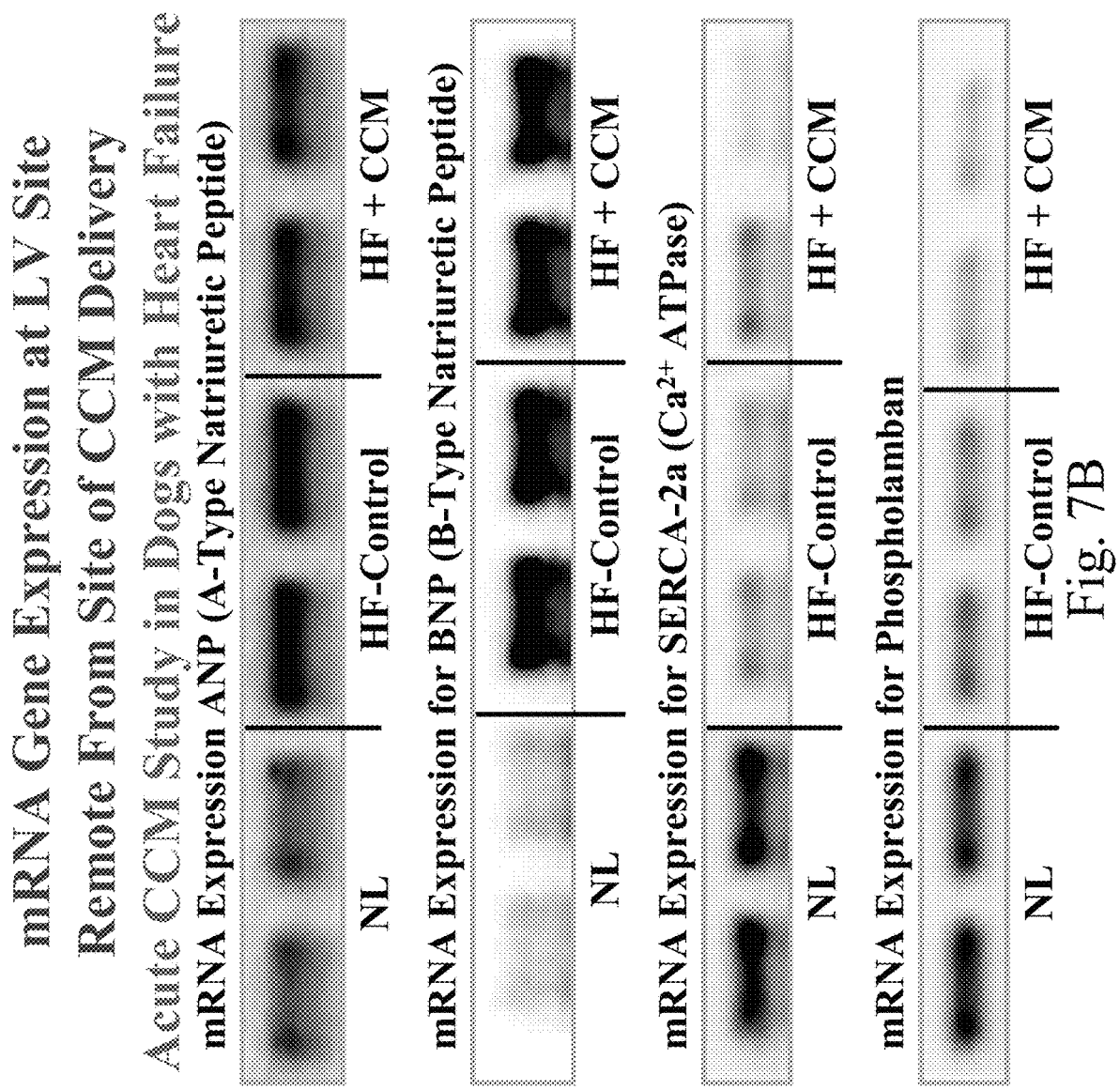

FIGS. 7A and 7B shows mRNA expression at sites remote from the application of the signal, but still within the left ventricle, at a relatively short time of four hours apparently no significant effect (mRNA, protein and/or phosphorylation) is shown. This may indicate that the effect of the CCM signal is first local, for example on a molecular level and then propagates to remote location, for example by biochemical signaling or by a mechanical signaling indicated by the change in contraction behavior of the treated tissue and/or of the chamber as a whole. The following non-limiting mechanism is suggested: the electric field causes phosphorylation of phospholamban. This in turn on a model of what areas will cause a biochemical or mechanical cascade in the heart and improve its function. Optionally, the size of areas is optimized to reduce power needs, while retain an expected time frame of treatment.

In an exemplary embodiment of the invention, an area to be treated is selected based on immediate response of tissue therein to electrical stimulation.

One example of a mechanical cascade is a desired change in stretching of tissue which will, as that tissue improve, propagate. Another example of mechanical cascade is selecting sufficient and correct tissue in the ventricle such that immediate hemodynamic effects (e.g., improvement) are seen and sensed by the rest of the chamber.

A possible mechanism of non-mechanical propagation (which may be utilized) is that healthy cells can help regulate ionic concentrations of neighboring cells via gap junctions between them. Alternatively or additionally, other communication may occur via the gap junctions.

Another possible mechanism is that low level fields reach further and take longer to have an effect. This suggests that low-level fields in general may be used, with a rapidity of effect depending on the field strength and/or mechanical or other improvement of parts of the heart.

In some embodiments of the invention, the efficacy of a treatment is measured by tracking remote effects alternatively or additionally, to tracking local effects. One or more of the following logics may be used: 1. There is more remote tissue to sample, with less danger of damage to heart. 2. The effect in remote tissue is more gradual and thus easier to track. 3. Acute effects may not occur (or be smaller) in remote tissue, thereby preventing the masking of longest term effects by acute effects. Optionally, for local or remote measurement, the measurement is made when no treatment is applied. An example of an acute effect which may mask a longer term effect is conduction velocity.

A short tabular summary of the results of FIGS. 6-8 follows:

Re FIG. 6

| Dog Numbers | |
|---|---|
| HF-Control | HF + CCM |
| 02-097 | 02-106 |
| 02-098 | 02-107 |
| 02-103 | 02-108 |
| 02-130 | 02-012 |
| 03-045 | 03-023 |
| 04-004 | 03-050 |
| 04-018 | 04-005 |

| mRNA Expression for SERCA-2a in Septum | | | |
|---|---|---|---|
| | NL | HF-Control | HF + CCM |
| | 238 | 172 | 207 |
| | 224 | 123 | 214 |
| | 203 | 167 | 178 |
| | 199 | 168 | 191 |
| | 226 | 151 | 179 |
| | 162 | 123 | 150 |
| | | 149 | 162 |
| Mean | 209 | 150 | 183 |
| STD | 27 | 21 | 23 |
| SEM | 11 | 8 | 9 |
| ANOVA = 0.001 | | | |
| p vs. NL | | <0.05 | NS |
| p vs. HF-Control | | | <0.05 |

| mRNA Expression for PLB in Septum | | | |
|---|---|---|---|
| | NL | HF-Control | HF + CCM |
| | 241 | 255 | 394 |
| | 330 | 277 | 374 |
| | 324 | 281 | 327 |
| | 344 | 276 | 364 |
| | 368 | 290 | 352 |
| | 352 | 275 | 292 |
| | | 278 | 243 |

| mRNA Expression for PLB in Septum | | | |
|---|---|---|---|
| | NL | HF-Control | HF + CCM |
| Mean | 327 | 276 | 335 |
| STD | 45 | 11 | 52 |
| SEM | 18 | 4 | 20 |
| ANOVA = 0.029 | | | |
| p vs. NL | | <0.05 | NS |
| p vs. HF-Control | | | <0.05 |

| mRNA Expression for RYR in Septum | | | |
|---|---|---|---|
| | NL | HF-Control | HF + CCM |
| | 272 | 287 | 267 |
| | 371 | 225 | 277 |
| | 289 | 229 | 300 |
| | 294 | 262 | 319 |
| | 321 | 232 | 323 |
| | 294 | 234 | 252 |
| | | 238 | 248 |
| | 307 | 244 | 284 |
| | 35 | 23 | 31 |
| | 14 | 9 | 12 |
| ANOVA = 0.005 | | | |
| p vs. NL | | <0.05 | NS |
| p vs. HF-Control | | | <0.05 |

Re FIGS. 7A and 7B:

| mRNA Expression for ANP | | | |
|---|---|---|---|
| | NL | HF-Control | HF + CCM |
| | 155 | 301 | 342 |
| | 164 | 336 | 316 |
| | 175 | 356 | 307 |
| | 170 | 325 | 303 |
| | 229 | 318 | 291 |
| | 212 | 350 | 282 |
| Mean | 184 | 331 | 307 |
| STD | 29 | 20 | 21 |
| SEM | 12 | 8 | 9 |
| ANOVA = 0.0001 | | | |
| p vs. NL | | <0.05 | <0.05 |
| p vs. HF-Control | | | NS |

| mRNA Expression for SERCA-2a | | | |
|---|---|---|---|
| | NL | HF-Control | HF + CCM |
| | 257 | 68 | 126 |
| | 266 | 50 | 57 |
| | 334 | 56 | 140 |
| | 293 | 84 | 71 |
| | 285 | 53 | 36 |
| | 263 | 47 | 38 |
| Mean | 283 | 60 | 78 |
| STD | 29 | 14 | 45 |
| SEM | 12 | 6 | 18 |
| ANOVA = 0.0001 | | | |
| p vs. NL | | <0.05 | <0.05 |
| p vs. HF-Control | | | NS |

| mRNA Expression for VEGF | | | |
|---|---|---|---|
| | NL | HF-Control | HF + CCM |
| | 14 | 4 | 8 |
| | 16 | 5 | 6 |
| | 13 | 5 | 7 |
| | 19 | 14 | 11 |
| | 24 | 8 | 13 |
| | 22 | 9 | 4 |
| Mean | 18 | 8 | 8 |
| STD | 4 | 4 | 3 |
| SEM | 2 | 2 | 1 |

ANOVA = 0.001
p vs. NL        <0.05        <0.05
p vs. HF-Control             NS

| mRNA Expression for GATA-4 | | | |
|---|---|---|---|
| | NL | HF-Control | HF + CCM |
| | 121 | 352 | 341 |
| | 129 | 367 | 349 |
| | 145 | 373 | 333 |
| | 126 | 350 | 325 |
| | 133 | 377 | 300 |
| | 136 | 394 | 262 |
| Mean | 132 | 369 | 318 |
| STD | 8 | 16 | 32 |
| SEM | 3 | 7 | 13 |

ANOVA = 0.0001
p vs. NL        <0.05        <0.05
p vs. HF-Control             <0.05

| mRNA Expression for BNP | | | |
|---|---|---|---|
| | NL | HF-Control | HF + CCM |
| | 320 | 1721 | 1862 |
| | 299 | 1629 | 2012 |
| | 331 | 1690 | 1952 |
| | 294 | 1725 | 2111 |
| | 361 | 1662 | 1991 |
| | 349 | 2016 | 1641 |
| | 326 | 1741 | 1928 |
| | 27 | 140 | 162 |
| | 11 | 57 | 66 |

ANOVA = 0.0001
p vs. NL        <0.05        <0.05
p vs. HF-Control             <0.05

| mRNA Expression for Phospholamban | | | |
|---|---|---|---|
| | NL | HF-Control | HF + CCM |
| | 18 | 9 | 14 |
| | 17 | 9 | 11 |
| | 17 | 7 | 11 |
| | 19 | 11 | 9 |
| | 20 | 7 | 6 |
| | 21 | 11 | 4 |
| | 19 | 9 | 9 |
| | 2 | 2 | 4 |
| | 1 | 1 | 1 |

ANOVA = 0.0001
p vs. NL        <0.05        <0.05
p vs. HF-Control             NS

| mRNA Expression for bFGF | | | |
|---|---|---|---|
| | NL | HF-Control | HF + CCM |
| | 186 | 90 | 110 |
| | 195 | 76 | 100 |
| | 194 | 108 | 87 |
| | 215 | 77 | 88 |
| | 189 | 104 | 83 |
| | 200 | 100 | 70 |
| | 197 | 93 | 90 |
| | 10 | 14 | 14 |
| | 4 | 6 | 6 |

ANOVA = 0.0001
p vs. NL        <0.05        <0.05
p vs. HF-Control             NS

| mRNA Expression for α-MHC | | | |
|---|---|---|---|
| | NL | HF-Control | HF + CCM |
| | 457 | 242 | 222 |
| | 609 | 228 | 218 |
| | 448 | 176 | 208 |
| | 545 | 188 | 221 |
| | 642 | 313 | 181 |
| | 557 | 220 | 156 |
| | 543 | 228 | 201 |
| | 78 | 49 | 27 |
| | 32 | 20 | 11 |

ANOVA = 0.0001
p vs. NL        <0.05        <0.05
p vs. HF-Control             NS Re FIG. 8:

| Dog Numbers | |
|---|---|
| HF-Control | HF + CCM |
| 02-097 | 02-106 |
| 02-098 | 02-107 |
| 02-103 | 02-108 |
| 02-130 | 02-012 |
| 03-045 | 03-023 |
| 04-004 | 03-050 |
| 04-018 | 04-005 |

| Phosphorylated PLB at Serine-16 | | |
|---|---|---|
| NL | HF-Control | HF + CCM |
| 143 | 86 | 99 |
| 109 | 95 | 106 |

Phosphorylated PLB at Serine-16

|                 | NL     | HF-Control | HF + CCM |
|-----------------|--------|------------|----------|
|                 | 153    | 63         | 68       |
|                 | 161    | 25         | 97       |
|                 | 102    | 15         | 105      |
|                 | 100    | 24         | 31       |
|                 |        | 43         | 106      |
| Mean            | 128    | 50         | 87       |
| STD             | 28     | 32         | 28       |
| SEM             | 11     | 12         | 11       |
| ANOVA = 0.0001  |        |            |          |
| p vs. NL        |        | <0.05      | <0.05    |
| p vs. HF-Control|        |            | <0.05    |

Phosphorylated PLB at Threonine-17

|                 | NL     | HF-Control | HF + CCM |
|-----------------|--------|------------|----------|
|                 | 135    | 90         | 80       |
|                 | 126    | 41         | 68       |
|                 | 137    | 53         | 62       |
|                 | 148    | 52         | 162      |
|                 | 146    | 32         | 168      |
|                 | 129    | 59         | 78       |
|                 |        | 67         | 147      |
|                 | 137    | 56         | 109      |
|                 | 9      | 19         | 47       |
|                 | 4      | 7          | 18       |
| ANOVA = 0.0001  |        |            |          |
| p vs. NL        |        | <0.05      | NS       |
| p vs. HF-Control|        |            | <0.05    |

Additional Proteins

Experimental results of the effect of CCM signals on other proteins is described below.

Effect of CCM on Calcium Cycling in the Sarcoplasmic Reticulum and/or S100A1 Protein.

Overexpression of the calcium-binding protein S100A1 in failing rat cardiomyocytes normalizes sarcoplasmic reticulum (SR) calcium cycling by increasing calcium-uptake and reducing SR calcium-leak from ryanodine channels. Expression of S100A1 is significantly decreased in left ventricular (LV) myocardium of explanted failed human hearts.

RNA was extracted and homogenate prepared from LV tissue obtained from 6 CCM-treated HF dogs, 6 untreated HF dogs and 6 normal (NL) dogs (these are the same dogs as above). S100A1 mRNA expression was measured using reverse transcriptase polymerase chain reaction (RT-PCR) and protein expression was measured using Western blotting. Bands obtained after gel electrophoresis were quantified in densitometric units (du).

S100A1 mRNA and protein expression decreased significantly in untreated HF dogs compared to NL dogs. Chronic CCM therapy significantly increased mRNA and protein expression of S100A1. Restoration of expression of this calcium binding protein improves calcium cycling within the SR and may account, at least in part, for the observed improvement of LV function seen following chronic CCM therapy.

mRNA and Protein Expression of S100A1

|                     | NL         | HF-Untreated | HF + CCM      |
|---------------------|------------|--------------|---------------|
| S100A1 mRNA (du)    | 13.0 ± 0.7 | 1.5 ± 0.1*   | 8.6 ± 0.5*†   |
| S100A1 Protein (du) | 215 ± 15   | 63 ± 6*      | 190 ± 8†      |

\* = p < 0.05 vs. NL;
† = p < 0.05 vs. HF-Untreated

Effect on Sorcin; Presenilin and Calstabin

RNA was extracted and homogenate prepared from LV tissue obtained from 6 CCM-treated HF dogs, 6 untreated HF dogs and 6 normal (NL) dogs. These are the same dogs as in the previous section. Sorcin, Presenilin and Calstabin mRNA expression was measured using reverse transcriptase polymerase chain reaction (RT-PCR) and protein expression was measured using Western blotting. Bands obtained after gel electrophoresis were quantified in densitometric units (du).

Sorcin mRNA and protein expression decreased significantly in untreated HF dogs compared to NL dogs. Chronic CCM therapy significantly increased mRNA and protein expression of Sorcin. Presenilin-2 increased in HF and decreased with CCM. Preseilin-1 was measured as an internal control and it did not change. This suggests that Presenilin-2 can be used as a target (e.g., treatment goal) for treating HF and as an indicator for diagnosis and modification of treatment.

Restoration of expression of Sorcin may prevent or limit the RyR2 calcium leak and in doing so improve calcium cycling within the SR. Correction of this maladaptation by CCM therapy may account, at least in part, for the observed improvement of LV function. In particular, the combined correction of Sorcin and Presenilin, which interact to regulate cardiac ryanodine calcium release channels may act as a mediator of recovery of calcium overload in cardiomyocytes due to "RyR-2 calcium leak" in heart failure.

It should be noted that Calstabin-2 decreased in heart failure but remained depressed even after 3 months of CCM therapy. This suggests that CCM does not act by merely resetting cellular function, however, as noted above, resetting may be part of the process. One possible explanation is that Castabin-2 does not rebound as it is tied to phospholamban levels. Another possible explanation is that Castabin-2 indicates a path for the progression of heart failure. Until the underlying cause is removed, it may remain depressed. Possibly, an improvement over significantly longer periods of time is to be expected. In an exemplary embodiment of the invention, this is used to estimate the ability of a patient to stop therapy. For example, if Castabin-2 levels trend to or do normalize, this can indicate that the tissue state is not diseased or becoming healthier. Optionally, this allows tracking of tissue improvement even during ongoing electrical therapy. In an exemplary embodiment of the invention, signal optimization techniques as described herein are used to find and then apply a signal specific (or more specific) to modifying Castabin-2.

Figure 13:
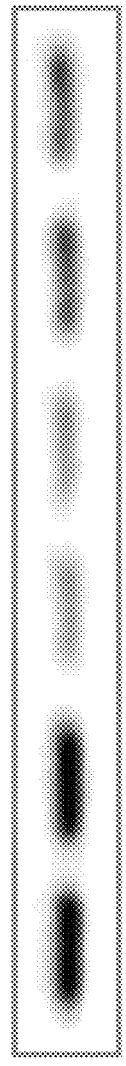
FIGS. 13A and 13B present mRNA (FIG. 13A) and protein blots (FIG. 13B) illustrating expression of Sorcin in LV tissue of HF Dogs treated with CCM for 3 months according to an exemplary embodiment of the invention.
Figure 13:
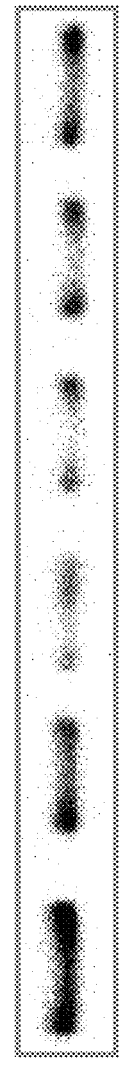
Figure 14A:
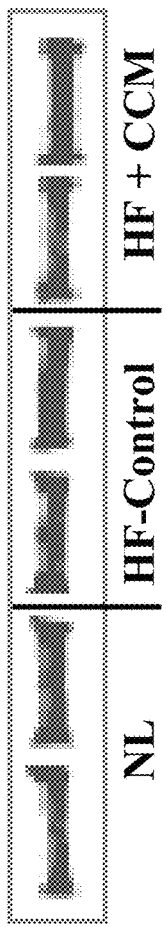
FIGS. 14A, 14B, 14C and 14D present mRNA (FIGS. 14A and 14C) and protein blots (FIGS. 14B and 14D) of the Presenilin-1 (FIGS. 14A and 14B) and Presenilin-2 (FIGS. 14C and 14D) in LV tissue of HF Dogs treated with CCM for 3 months according to an exemplary embodiment of the invention.
Figure 14B:
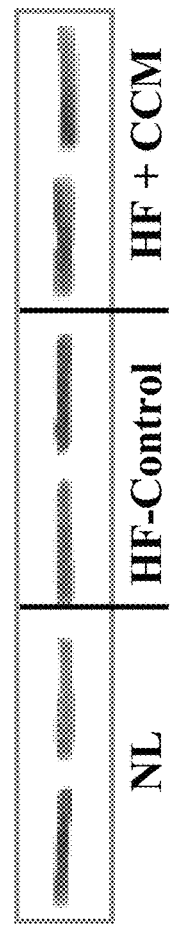
Figure 14C:
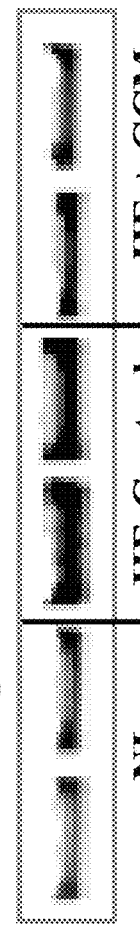
Figure 14D:

The results are shown in FIGS. 13-15 and in the tables below (in densitometric units).

FIGS. 13A and 13B present mRNA (FIG. 13A) and protein blots (FIG. 13B) illustrating expression of Sorcin in LV tissue of HF Dogs treated with CCM for 3 months according to an exemplary embodiment of the invention.

FIGS. 14A, 14B, 14C and 14D present mRNA (FIGS. 14A and 14C) and protein blots (FIGS. 14B and 14D) of the Presenilin-1 (FIGS. 14A and 14B) and Presenilin 2 (FIGS.

14C and 14D) in LV tissue of HF Dogs treated with CCM for 3 months according to an exemplary embodiment of the invention.

Figure 15A:
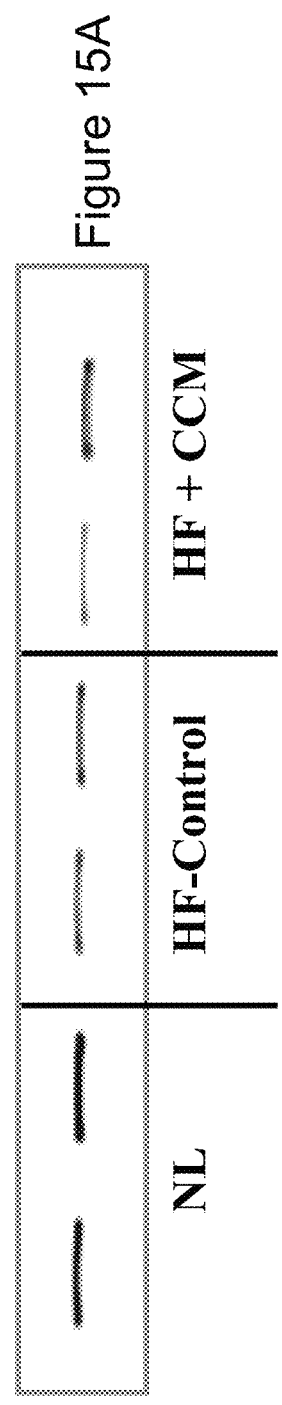
FIGS. 15A and 15B present mRNA (FIG. 15A) and protein blots (FIG. 15B) illustrating expression of Calstabin in LV tissue of HF Dogs treated with CCM for 3 months according to an exemplary embodiment of the invention.
Figure 15B:
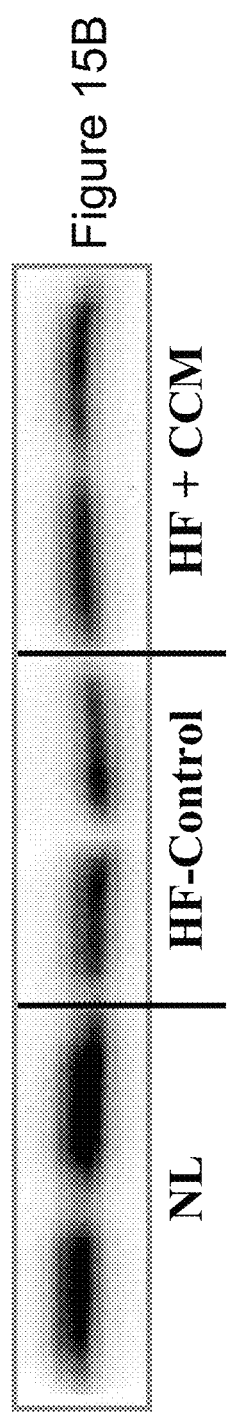

FIGS. 15A and 15B present mRNA (FIG. 15A) and protein blots (FIG. 15B) illustrating expression of Calstabin in LV tissue of HF Dogs treated with CCM for 3 months according to an exemplary embodiment of the invention.

| Dog Numbers | |
|---|---|
| HF-Control | HF + CCM |
| 02-097 | 02-106 |
| 02-098 | 02-107 |
| 02-103 | 02-108 |
| 02-130 | 02-012 |
| 03-045 | 03-023 |
| 04-018 | 03-050 |

| mRNA Expression of Sorcin | | | |
|---|---|---|---|
|  | Normal | HF-Control | HF + CCM |
|  | 0.52 | 0.19 | 0.37 |
|  | 0.41 | 0.21 | 0.37 |
|  | 0.55 | 0.25 | 0.30 |
|  | 0.53 | 0.19 | 0.29 |
|  | 0.53 | 0.18 | 0.39 |
|  | 0.59 | 0.15 | 0.37 |
| Mean | 0.52 | 0.20 | 0.35 |
| STD | 0.06 | 0.04 | 0.04 |
| SEM | 0.02 | 0.02 | 0.02 |
| ANOVA = 0.0001 | | | |
| p vs. Normal |  | <0.05 | <0.05 |
| p vs. HF-Control |  |  | <0.05 |

| Protein Expression of Sorcin | | | |
|---|---|---|---|
|  | Normal | HF-Control | HF + CCM |
|  | 0.75 | 0.30 | 0.396 |
|  | 0.65 | 0.26 | 0.456 |
|  | 0.69 | 0.28 | 0.426 |
|  | 0.75 | 0.30 | 0.412 |
|  | 0.73 | 0.25 | 0.426 |
|  | 0.68 | 0.23 | 0.486 |
| Mean | 0.71 | 0.27 | 0.43 |
| STD | 0.04 | 0.03 | 0.03 |
| SEM | 0.02 | 0.01 | 0.01 |
| ANOVA = 0.0001 | | | |
| p vs. Normal |  | <0.05 | <0.05 |
| p vs. HF-Control |  |  | <0.05 |

| mRNA Expression of Presenilin-1 | | | |
|---|---|---|---|
|  | Normal | HF-Control | HF + CCM |
|  | 0.34 | 0.4 | 0.38 |
|  | 0.36 | 0.44 | 0.4 |
|  | 0.38 | 0.39 | 0.45 |
|  | 0.39 | 0.43 | 0.39 |
|  | 0.29 | 0.38 | 0.38 |
|  | 0.32 | 0.33 | 0.35 |

| mRNA Expression of Presenilin-1 | | | |
|---|---|---|---|
|  | Normal | HF-Control | HF + CCM |
| Mean | 0.35 | 0.40 | 0.39 |
| STD | 0.04 | 0.04 | 0.03 |
| SEM | 0.02 | 0.02 | 0.01 |
| ANOVA = 0.131 | | | |
| p vs. Normal |  | NS | NS |
| p vs. HF-Control |  |  | NS |

| Protein Expression of Presenilin-1 | | | |
|---|---|---|---|
|  | Normal | HF-Control | HF + CCM |
|  | 0.12 | 0.15 | 0.14 |
|  | 0.11 | 0.19 | 0.13 |
|  | 0.09 | 0.21 | 0.14 |
|  | 0.15 | 0.11 | 0.16 |
|  | 0.16 | 0.09 | 0.18 |
|  | 0.11 | 0.13 | 0.11 |
| Mean | 0.12 | 0.15 | 0.14 |
| STD | 0.03 | 0.05 | 0.02 |
| SEM | 0.01 | 0.02 | 0.01 |
| ANOVA = 0.338 | | | |
| p vs. Normal |  | NS | NS |
| p vs. HF-Control |  |  | NS |

| mRNA Expression of Presenilin-2 | | | |
|---|---|---|---|
|  | Normal | HF-Control | HF + CCM |
|  | 0.28 | 0.63 | 0.34 |
|  | 0.32 | 0.61 | 0.31 |
|  | 0.29 | 0.59 | 0.29 |
|  | 0.35 | 0.49 | 0.42 |
|  | 0.2 | 0.56 | 0.35 |
|  | 0.31 | 0.62 | 0.38 |
| Mean | 0.29 | 0.58 | 0.35 |
| STD | 0.05 | 0.05 | 0.05 |
| SEM | 0.02 | 0.02 | 0.02 |
| ANOVA = 0.0001 | | | |
| p vs. Normal |  | <0.05 | NS |
| p vs. HF-Control |  |  | <0.05 |

| Protein Expression of Presenilin-2 | | | |
|---|---|---|---|
|  | Normal | HF-Control | HF + CCM |
|  | 0.201 | 0.52 | 0.25 |
|  | 0.159 | 0.48 | 0.29 |
|  | 0.198 | 0.55 | 0.21 |
|  | 0.285 | 0.62 | 0.19 |
|  | 0.248 | 0.49 | 0.26 |
|  | 0.196 | 0.61 | 0.11 |
|  | 0.21 | 0.55 | 0.22 |
|  | 0.04 | 0.06 | 0.06 |
|  | 0.02 | 0.02 | 0.03 |
| ANOVA = 0.0001 | | | |
| p vs. Normal |  | <0.05 | NS |
| p vs. HF-Control |  |  | <0.05 |

| mRNA Expression of Calstabin-2 | | | |
|---|---|---|---|
| | Normal | HF-Control | HF + CCM |
| | 1667 | 847 | 1477 |
| | 1488 | 1204 | 1355 |
| | 1486 | 1389 | 906 |
| | 1723 | 887 | 619 |
| | 1778 | 1120 | 1497 |
| | 1840 | 1343 | 1224 |
| Mean | 1,664 | 1,132 | 1,180 |
| STD | 148 | 227 | 350 |
| SEM | 61 | 93 | 143 |
| ANOVA = 0.004 | | | |
| p vs. Normal | | <0.05 | <0.05 |
| p vs. HF-Control | | | NS |

| Protein Expression of Calstabin-2 | | | |
|---|---|---|---|
| | Normal | HF-Control | HF + CCM |
| | 5871 | 3991 | 3679 |
| | 5602 | 3643 | 3923 |
| | 5029 | 3156 | 3560 |
| | 5579 | 4645 | 4083 |
| | 6726 | 4567 | 4600 |
| | 5190 | 4995 | 4381 |
| Mean | 5,666 | 4,166 | 4,038 |
| STD | 602 | 693 | 402 |
| SEM | 246 | 283 | 164 |
| ANOVA = 0.0001 | | | |
| p vs. Normal | | <0.05 | <0.05 |
| p vs. HF-Control | | | NS |
| Effect wash-out times | | | |

Figure 9A:
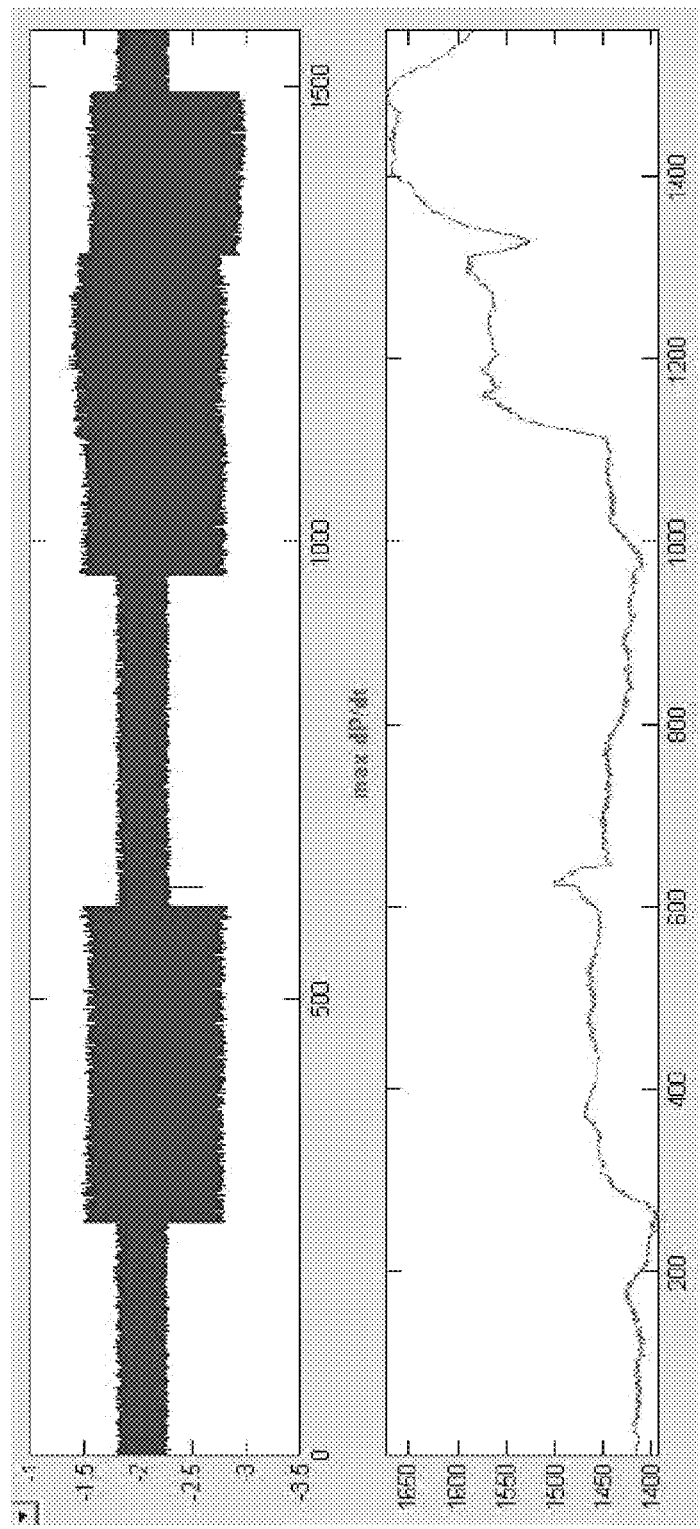
FIG. 9A and FIG. 9B show rise times and decay times for treatment using a CCM signal, in accordance with an exemplary embodiment of the invention.
Figure 9B:
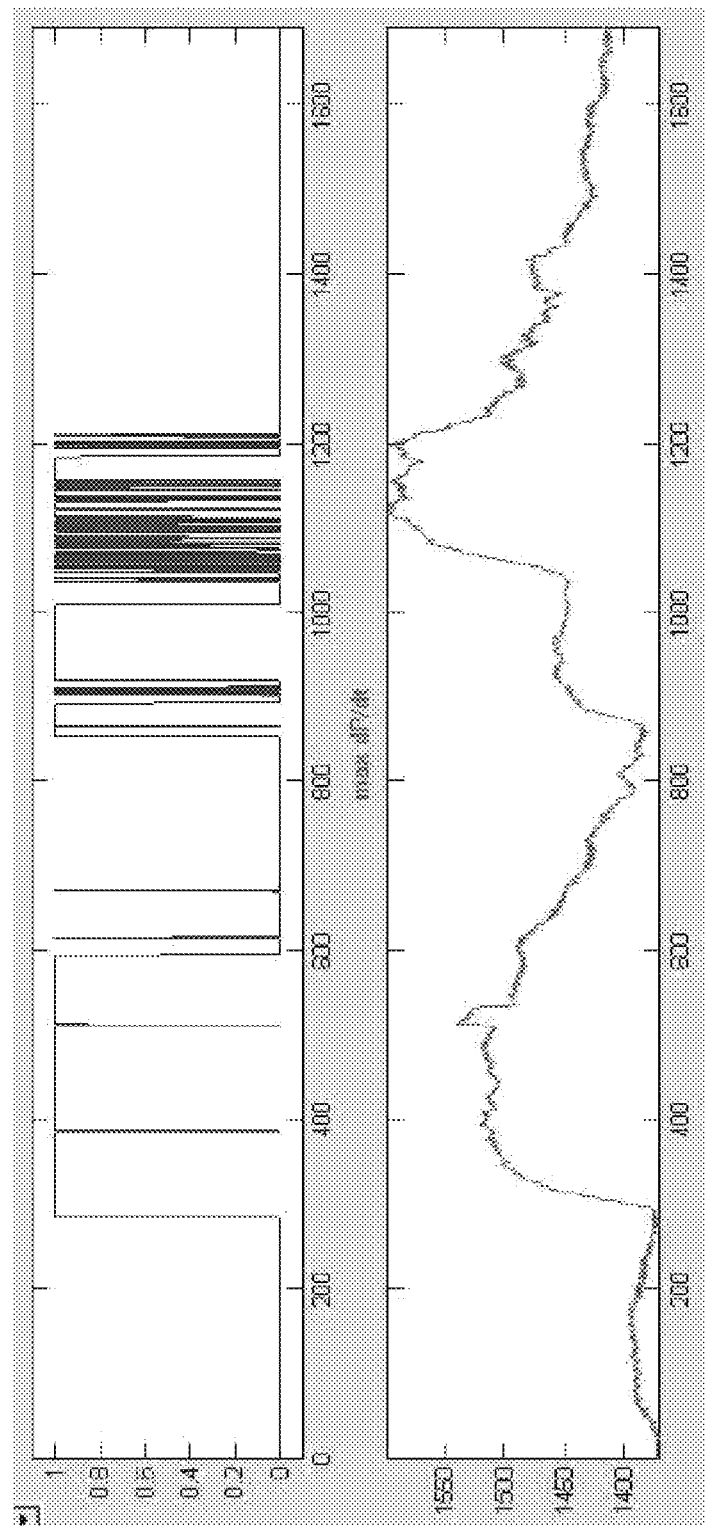

FIGS. 9A and 9B are graphs showing the relationship between rise time and decay time of a contractility increase in dogs. Similar results were observed in humans, albeit with generally slower rise times and slower decay times.

FIG. 9A, in which the scale is in seconds, shows a rise time of several tens of seconds at about time 270. Once the signal is stopped (upper graph shows the signal application times), the contractility increase decays. The blip at 600 is probably caused by an arrhythmia. The decay continues from 600 until 950. A second signal application is at about 950 with a change in signal application location at about time 1350, before the signal effect washed out. In FIG. 9B the signal is shown as an outline of a square pulse, with the signal stopped each time an arrhythmia is detected, shown as a short pause in the signal.

Again, a rise time of several tens of seconds is found. A decay time of 230 seconds is shown for the first signal. A longer decay time of over 400 seconds is shown for a second signal. The second signal caused an increase in contractility at about 1050 seconds, due to change in the applied signals.

In an exemplary embodiment of the invention, it is noted that the acute and long term effects last at least a few seconds after treatment is stopped and have different wash-out times. Thus, measuring patient parameters is possible while the treatment apparatus is off. Different waiting times may be used to selectively measure acute and longer term effects. For example, 30 minutes may be sufficient for avoiding acute effects on phosphorylation.

In an exemplary system, a controller learns the particular washout behavior of a patient and adjusts the treatment to be re-applied only after significant washout and/or be applied at a minimal length that has a washout. Optionally, the delay between application and/or length of applications are selected to optimize one or more of power consumption, danger of arrhythmia and/or discomfort to patient.

WO 2005/087310, filed as PCT/IL2005/00316 on Mar. 18, 2005, U.S. provisional application 60/719,517, filed Sep. 22, 2005 and U.S. provisional application 60/654,056, filed February 17th, the disclosures of which are incorporated herein by reference, describe methods and devices for treating metabolic diseases. In particular, 60/719,517 describes how applying a signal to a stomach has an effect on reducing blood glucose levels which lasts after the signal is stopped, for example, for more than one day. At least in combination with the results described above, this suggests that an electrical therapy may be used to change the mode of operation of tissue, on a cellular level, possibly for tissue in general or for excitable tissue at least.

It is a particular feature of some embodiments of the invention that a non-immediate effect of signal application, which lasts after the signal application is stopped, is an affirmative effect, in which the tissue exhibits a positive change in action, rather than a negative effect, for example, of preventing arrhythmia. In an exemplary embodiment of the invention, the effect is on a cellular level, rather than or in addition to an effect on an organ level, for example a cellular level as measured by protein activity and/or expression levels.

Another type of long term/wash-out effect is a long term therapeutic effect lasting days or weeks after treatment. Below are described two sets of experiments on humans. In the first set, patients were selectively treated 3 months on and 3 months off or vice versa. In the second set of experiments patients were either treated for six months or not. While the patients that were 3 months on and then 3 off fared less well (after 6 months) than those that were 3 off and then 3 on, the overall situation after 6 months was better than what would be expected from a baseline (no treatment) situation. The second set of experiments while suggesting no overall improvement after 6 months, shows a trend to lesser degradation and also suggests what the expected degradation would be. Optionally, the therapies as described herein are used to slow down degradation of a patient's situation, rather than a treatment. Optionally, each patient is selectively tested to see how long the treatment effects last and/or what minimal treatment period is required for longer term effects. Optionally, the length of treatment and/or "off" periods between treatments also vary as a function of time. Various physiological measures, for example as described above may be used to assess improvement, as well as mRNA, protein and/or phosphorylation levels.

In the first set of experiments 126 subjects with ischemic (60%) or idiopathic (40%) cardiomyopathy, EF<35%, NYHA Class II (23%) or III (73%) received a CCM pulse generator. Patients were randomly assigned to Group 1 (n=62, CCM treatment 3 months, sham treatment second 3 months) or Group 2 (n=64, sham treatment 3 months, CCM treatment second 3 months). The coprimary endpoints were differences between groups of changes in peak oxygen consumption ($VO_{2,peak}$) and Minnesota Living with Heart Failure Questionnaire (MLWHFQ).

Baseline EF (25±6% vs 26±6%), $VO_{2,peak}$ (14.4±2.5 vs 14.2±2.7 ml/kg/min) and MLWHFQ (41±20 vs 35±19) were similar in both groups. $VO_{2,peak}$ increased similarly in both groups during the first 3 months (0.64±0.36 vs 0.53±0.46 ml O2/kg/min, p=NS, possibly a placebo effect). However, during the next 3 months, $VO_{2,peak}$ decreased in the group switched to sham treatment (−0.92±0.42 ml/kg/min) and continued increasing in patients switched to active treatment (0.35±0.35 ml/kg/min, p=0.02), so that the final difference between groups was 1.2 ml/kg/min. It is hypothesized that this reduction is less than what would be expected after 3 months of an untreated patient. MLWHFQ also improved in both groups during the first 3 months (placebo effect), though the improvement trended better with treatment (−14.65±2.04 vs −9.8±2.2, p=NS). During the second 3 months, MLWHFQ increased in the group switched to sham (5.1±2.3) and continued to decrease in patients switched to active treatment (−1±2, p=0.03). However, the increase in the untreated group appeared to be less than a return to baseline values or other values that would be expected with a diseased patient with natural progression.

It should be noted that significant improvement is achieved even for patients that had an ON phase followed by an OFF phase, or at least the effects of treatment remained for a while. This suggests that the therapeutic effects are long lasting, for example, more than a week, more than a month, more than three months or longer. This is in contrast to cardiac resynchronization therapy where improvements seem to last a week or two at most. Even in this case, the heart desynchronization appears almost immediately (as is the case with electrical therapy in general which usually last a single beat).

In a second set of experiments, 49 subjects with EF<35%, normal QRS duration (105±15 ms) and NYHA Class III (n=48) or IV (n=1) despite medical therapy received a CCM pulse generator. Devices were programmed randomly to deliver CCM signals (Treatment, n=25) or to remain off (Control, n=24) for 6 months. Evaluations included NYHA, 6 minute hall walk (6MW), cardiopulmonary stress test, Minnesota Living with Heart Failure Questionnaire (MLWHFQ) and Halter.

Although most baseline features were balanced between groups, EF (31.4±7.4 vs 24.9±6.5%, p=0.003), end-diastolic dimension (52.1±21.4 vs 62.5±6.2 mm, p=0.01), peak $VO_2$ (16.0±2.9 vs 14.3±2.8 ml $O_2$/kg/min, p=0.02) and anaerobic threshold (12.3±2.5 vs 10.6±2.4 ml $O_2$/kg/min, p=0.01) were worse in Treatment than Control. Nevertheless, there was 1 death in a Control subject and more Treatment patients were free of hospitalization for any cause at 6 months (84% vs 62%). No changes in ectopy were observed. Compared to baseline, 6MW (13.4 m), peak $VO_2$ (0.2 ml $O_2$/kg/min) and anaerobic threshold (0.8 ml $O_2$/kg/min) increased more in Treatment than Controls. None of the differences were statistically significant (small sample size).

Six minute hall walk showed similar improvements in both groups at 12 weeks (~20 meters), with the curves diverging at 6 months with an approximately 15 meter greater increase in the treatment group. Peak $VO_2$ decreased over time in both groups (~−0.75 at 12 W, ~−1 at 24 weeks), but remained higher in the treatment group than in controls, by ~0.2 ml $O_2$/kg/min. In contrast, anaerobic threshold, which decreased in the control group (~−0.8 at 12 W, 24 W), decreased initially (~−0.6 at 12 W) but then returned to baseline values at 6 months in the Treatment group. At the final follow-up, the difference between the two groups averaged 0.82 ml $O_2$/kg/min. Ejection fraction increased minimally in both groups at 6 months (1.8±0.8 in the treatment group vs 1.3±1.6 in the control group).

New York Heart Association classification improved similarly in both groups. For the treatment group, the proportion of patients in Class I, II and III at 24 weeks were 19, 45 and 36, respectively. This compared to 18, 52 and 30, respectively, in the Control group. MLWHFQ also improved significantly and similarly in both groups. At the 6 month follow-up, MLWHFQ decreased from baseline values by 16.2±5.9 and 18.3±4.8 in the control and treatment groups, respectively. The significant and sustained improvements in NYHA and MLWHFQ observed in both groups speaks to the presence of a significant placebo effect.

Synergistic Interaction of Beta-Blockers and Electrical Therapy

While it might be supposed that beta blockers and electrical therapy as described here utilize similar pathways and therefore cannot be additive, the following experiment shows that this is not correct. In addition, electrical therapy may be used to increase contractility and compensate for an initial reduction in contractility caused by beta blockers. This may suggest changing the sequence amount and/or type when the medication starts having a positive effect, for example, several weeks or several months (e.g., 3) later. Alternatively or additionally, electrical therapy is used to compensate for times when medication is stopped, for example, due to adverse systemic effects. In an exemplary embodiment of the invention, the dosage of medication and the dosage of therapy are selected to minimize or reduce systemic effects and/or reduce power needs and/or side effects (if any) of electrical therapy.

In a set of experiments, dogs with intracoronary microembolization-induced chronic HF (LV EF 30%-40%) were randomized to 3 months therapy with either BB (beta-blockers) alone (extended release metoprolol succinate, 100 mg once daily), extended release metoprolol succinate (100 mg, once daily) combined with CCM therapy, or to no therapy at all (Control). LV end-diastolic volume (EDV), end-systolic volume (ESV) and EF were measured before randomization (PRE) and after 3 months of therapy (POST). To determine "treatment effect", the change Δ between PRE and POST therapy for each group was compared among the 3 study groups.

In Control dogs, LV EDV and ESV increased significantly and EF decreased significantly. Therapy with BB alone and combined therapy with BB and CCM both prevented the increase in EDV, significantly reduced ESV and significantly increased EF. Treatment effect (Δ) comparisons showed that combination therapy with BB and CCM significantly increased LV EF above that seen with BB alone (12±1% vs. 6±1%, p<0.001).

|  | Control |  | BB Alone |  | BB + CCM |  |
|---|---|---|---|---|---|---|
|  | PRE | POST | PRE | POST | PRE | POST |
| LV EDV (ml) | 60 ± 1 | 64 ± 1* | 64 ± 4 | 62 ± 5 | 70 ± 4 | 69 ± 4 |
| LV ESV (ml) | 39 ± 1 | 45 ± 1* | 41 ± 2 | 36 ± 4* | 45 ± 3 | 36 ± 3* |
| LV EF (%) | 36 ± 1 | 31 ± 1* | 36 ± 1 | 42 ± 2* | 36 ± 1 | 48 ± 1* |

*= p < 0.05 PRE vs. POST

Following are detailed results:

| CCM + Toprol-XL (n = 7) | | | | | | | |
|---|---|---|---|---|---|---|---|
| EDV (ml) | | | | ESV (ml) | | | |
| Dog# | Base | Pre | Post | Dog# | Base | Pre | Post |
| 04-112 | 61 | 78 | 77 | 04-112 | 29 | 50 | 41 |
| 04-120 | 51 | 69 | 67 | 04-120 | 25 | 44 | 35 |
| 04-124 | 56 | 72 | 74 | 04-124 | 24 | 47 | 40 |
| 04-145 | 52 | 60 | 59 | 04-145 | 22 | 37 | 29 |
| 05-025 | 51 | 56 | 55 | 05-025 | 24 | 36 | 31 |
| 05-033 | 51 | 66 | 65 | 05-033 | 23 | 41 | 33 |
| 05-034 | 56 | 64 | 62 | 05-034 | 30 | 41 | 32 |
| Mean | 54 | 66 | 66 | Mean | 25 | 42 | 34 |
| STD | 4 | 7 | 8 | STD | 3 | 5 | 5 |
| SEM | 1.4 | 2.8 | 3.0 | SEM | 1.1 | 1.9 | 1.7 |

| EF (%) | | | | |
|---|---|---|---|---|
| Dog# | Base | Pre | Post | Delta |
| 04-112 | 52 | 36 | 47 | 11 |
| 04-120 | 51 | 36 | 48 | 12 |
| 04-124 | 57 | 35 | 46 | 11 |
| 04-145 | 58 | 38 | 51 | 13 |
| 05-025 | 54 | 36 | 44 | 8 |
| 05-033 | 55 | 38 | 49 | 11 |
| 05-034 | 46 | 36 | 48 | 12 |
| Mean | 53 | 36 | 48 | 11 |
| STD | 4 | 1 | 2 | 2 |
| SEM | 1.5 | 0.4 | 0.8 | 0.6 |

Topro-XL (n = 6)

| EDV (ml) | | | | ESV (ml) | | | |
|---|---|---|---|---|---|---|---|
| Dog# | Base | Pre | Post | Dog# | Base | Pre | Post |
| 03-057 | 54 | 62 | 59 | 03-057 | 27 | 38 | 33 |
| 03-066 | 58 | 74 | 76 | 03-066 | 26 | 48 | 47 |
| 04-147 | 51 | 57 | 55 | 04-147 | 19 | 38 | 33 |
| 05-006 | 55 | 64 | 59 | 05-006 | 30 | 39 | 32 |
| 05-028 | 54 | 60 | 60 | 05-028 | 30 | 37 | 35 |
| 05-042 | 54 | 59 | 59 | 05-042 | 25 | 37 | 31 |
| Mean | 54 | 63 | 61 | Mean | 26 | 40 | 35 |
| STD | 2 | 6 | 7 | STD | 4 | 4 | 6 |
| SEM | 0.9 | 2.5 | 3.0 | SEM | 1.7 | 1.7 | 2.4 |

| EF (%) | | | | |
|---|---|---|---|---|
| Dog# | Base | Pre | Post | Delta |
| 03-057 | 50 | 38 | 44 | 6 |
| 03-066 | 55 | 35 | 38 | 3 |
| 04-147 | 62 | 33 | 40 | 7 |
| 05-006 | 46 | 39 | 46 | 7 |
| 05-028 | 44 | 38 | 42 | 4 |
| 05-042 | 54 | 37 | 47 | 10 |
| Mean | 52 | 37 | 43 | 6 |
| STD | 7 | 2 | 3 | 2 |
| SEM | 2.7 | 0.9 | 1.4 | 1.0 |

Placebo (n = 6)

| EDV (ml) | | | | ESV (ml) | | | |
|---|---|---|---|---|---|---|---|
| Dog# | Base | Pre | Post | Dog# | Base | Pre | Post |
| 03-031 | 51 | 59 | 63 | 03-031 | 24 | 39 | 46 |
| 03-065 | 54 | 61 | 68 | 03-065 | 23 | 39 | 48 |
| 04-103 | 52 | 58 | 61 | 04-103 | 21 | 37 | 43 |
| 04-122 | 48 | 63 | 64 | 04-122 | 23 | 39 | 43 |
| 05-002 | 54 | 61 | 64 | 05-002 | 28 | 39 | 43 |
| 05-027 | 59 | 60 | 64 | 05-027 | 28 | 39 | 44 |
| Mean | 53 | 60 | 64 | Mean | 25 | 39 | 45 |
| STD | 4 | 2 | 2 | STD | 3 | 1 | 2 |
| SEM | 1.5 | 0.7 | 0.9 | SEM | 1.2 | 0.3 | 0.8 |

| EF (%) | | | | |
|---|---|---|---|---|
| Dog# | Base | Pre | Post | Delta |
| 03-031 | 51 | 34 | 27 | −7 |
| 03-065 | 48 | 36 | 29 | −7 |
| 04-103 | 60 | 36 | 30 | −6 |
| 04-122 | 52 | 38 | 33 | −5 |
| 05-002 | 48 | 36 | 33 | −3 |
| 05-027 | 53 | 35 | 31 | −4 |
| Mean | 52 | 36 | 31 | −5 |
| STD | 4 | 1 | 2 | 2 |
| SEM | 1.8 | 0.5 | 1.0 | 0.7 |

EDV=LV end-diastolic volume
ESV=LV end-systolic volume
EF=LV ejection fraction

Diagnosis

In an exemplary embodiment of the invention, the above experimental results are used as a basis for diagnosis. Optionally, the diagnosis indicates one or both of a disease type and disease severity. In an exemplary embodiment of the invention, the type can be seen from the behavior of the proteins, for example comparing protein levels to calcium overload to diagnose systolic or diastolic dysfunction. In another example, the relative phosphorylation levels are used as a measure of severity.

In an exemplary embodiment of the invention, the use of multiple proteins and mRNA expression values provides a robust indicator of disease. In some embodiments, only one or two of proteins, phosphorylation and mRNA are used. Optionally, cardiac function values, such as stroke volume are used as well. Optionally, the response of tissue to a field is used as well, for example phosphorylation response.

Figure 16:
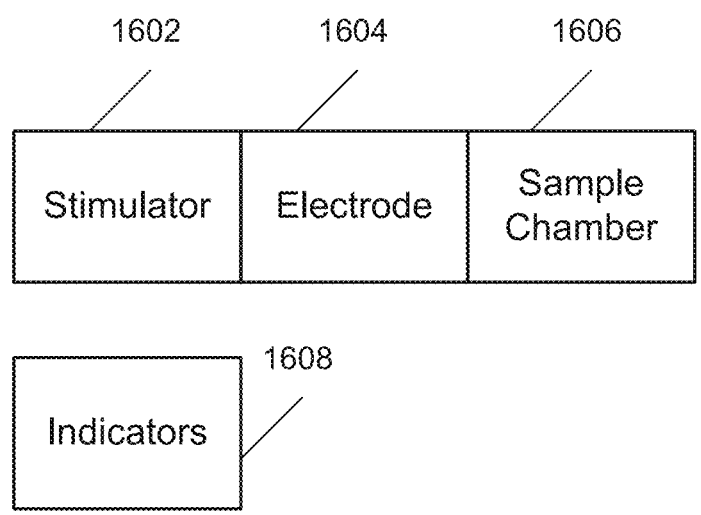
FIG. 16 is a schematic showing of a kit, in accordance with some embodiments of the invention.

FIG. 16 is a schematic showing of a kit, in accordance with some embodiments of the invention. The kit can include a stimulator 1602 for applying electric fields via one or more electrodes 1604 to a sample chamber 1606 which can contain a sample extracted from a patient. The kit can include a plurality of indicators 1608 to assay the effect of the electric fields on the extracted sample.

In an exemplary embodiment of the invention, at least 3, at least 5, at least 10, at least or more proteins levels, phosphorylation levels and/or mRNA levels are used to aid in diagnosis. Optionally, a table is maintained which includes ranges of values that match various disease types and/or conditions. Optionally, as therapy progresses, the patient is re-diagnosed. Optionally, the diagnosis is according to groups of mRNA and/or proteins that have associated functions.

In an exemplary embodiment of the invention, a DNA chip and/or protein chip and/or a biochip are used to measure the above levels.

In an exemplary embodiment of the invention, treatments are selected by applying the above pulses to tissue and measuring the effect. Optionally, a tissue sample is removed, for example by biopsy and a range of sequences are tested on the sample. Optionally, the results of the testing indicate which sequence might have a desired therapeutic effect. Such testing can include analysis and/or application of a treatment, such as an electric field. As noted above, at least some of the tests can be meaningfully applied to tissue homogenate and other unstructured tissue configurations.

In an exemplary embodiment of the invention, different parts of the tissue are tested, for example, to see which tissue part will respond better and/or avoid side effects.

Kits

In an exemplary embodiment of the invention, a kit is provided for performing such analyses as described herein.

In an exemplary embodiment of the invention, the kit comprises a set of reagents, antibodies and/or other biochemical tools as known in the art. Alternatively or additionally, the kit comprises one or more mRNA or protein detecting chips. Alternatively or additionally, the kit comprises software for analyzing gel migration.

In an exemplary embodiment of the invention, the kit comprises a source of treatment, for example electrodes and optionally a power source, for electrifying a sample for testing its responsiveness. Optionally, the kit includes a sampling means for selecting part of the sample at a predescribed time, to check temporal response of the sample. An existing kit may be modified for use, for example, a kit available from Biosite, Inc. to measure blood levels of BNP. Such a kit could include instructions for use with the methods described herein and optionally include sampling means or a timer to ensure correct timing of activities.

The kit includes or is used with a bioreactor that includes a controllable sampling element which cans electively extract a portion of the sample in the bioreactor and test it in a separate chamber. Optionally, this is embodied using lab-on-chip technology and/or fluidic control of material flow. In an exemplary embodiment of the invention, the controllable sampling element comprises a robot and a pipette that takes part of the sample and inserts it into an assaying chamber. Various automated assaying devices are known in the art of drug discovery and may be used and/or modified to be smaller and/or simpler.

In an exemplary embodiment of the invention, the kit includes a database or a link to a database (e.g., on the internet) that links biochemical markers to tissue states, treatment states and/or disease states.

Optionally, the kits are sterile and/or frozen and optionally include instructions for use as described herein. Optionally, one or more kits are packaged with a controller designed for implantation, for use in determining suitable electrode placement therefore.

Measuring Phosphorylation

In an exemplary embodiment of the invention, the kit includes one or more antibody reagents useful for detecting phosphorylated and/or dephosphorylated forms of the proteins desired.

Optionally, tracers which are anti-body based are used in-vivo, for example provided using a catheter or using the delivery electrodes or a separate needle or other injection mechanism. Optionally, the tracer is radioactive or fluorescent.

A calibration step, for example, per patient, may be carried out. Alternatively or additionally, a comparison before and after field application is used to determine change in phosphorylation.

Optionally, phosphorylation of proteins which affects ECG signals or correlated proteins which affect ECG signals is detected by detecting changes in ECG signals.

In an exemplary embodiment of the invention, changes in conduction velocity caused by increased secretion of protein are detected in an ECG measurement. Optionally, the measurement is remote from a signal application area.

Alternatively or additionally to conduction velocity, changes in contraction velocity under various conditions are assed from images of the heart or using other means.

Optionally, other physiological measures are correlated with protein effects (e.g., in a per-patient or per-population calibration process) and used to estimate effects on protein synthesis from physiological measures.

Exemplary Cardiac Applications

In an exemplary embodiment of the invention, the above sequences are used to treat tissue plugs that are removed from the body, treated and reinserted. The reinsertion may be, for example, at the location of removal, at scarred locations, at locations bordering scars or at otherwise weakened location of the heart.

In an exemplary embodiment of the invention, the above sequences are used as part of a program to re-invigorate scar or fibrotic tissue. Optionally, the effect of the sequence is to cause at least some cells to become functioning, for example in the border of the scar.

In an exemplary embodiment of the invention, the above sequence is used to selectively increase oxygen efficiency in some parts of the heart, for example, parts with a vascular blockage thereto.

In an exemplary embodiment of the invention, the above sequences are applied to tissue transplants, for example, whole heart transplants or plug transplants (from a donor), prior to and/or after transplant.

In an exemplary embodiment of the invention, the above sequences are applied after DNA or stem cell therapy to the heart, for example, to enhance effects and/or to assist in cellular functional differentiation and/or regeneration.

In an exemplary embodiment of the invention, the above sequences are used to have a desired modeling effect on the heart, for example, modifying an elasticity and/or contractility profile of a heart portion and/or directly controlling conduction velocity.

Three types of remodeling may be provided, possible to different degrees at different parts of the heart. A first type of remodeling is on the biochemical level and includes, for example, normalization of protein synthesis. A second type of remodeling is mechanical remodeling, for example, fibrosis reduction, chamber size change, vascular increase and/or wall thickening. A third type of remodeling is function remodeling which may result form a combination of biochemical and structural remodeling. This includes, for example, cardiac electrical and/or mechanical activation profile (what gets activated, to what degree and in what order), contractility enhancement and conduction velocity. As described herein, these types of remodeling may be achieved using methods described herein. Differential remodeling of different types may be achieved, for example, by selectively applying signals with a strong acute effect (which affect mechanical remodeling) and those with a long term effect. For example, tissue which is both paced and treated with non-excitatory signals may thicken, as opposed to tissue which is only treated.

In an exemplary embodiment of the invention, multiple methods of improving contractility are applied at a same time, or methods of improving contractility applied at a same time as methods that reduce contractility such as the initial effect of beta-blockers.

In an exemplary embodiment of the invention, contractility enhancement by effects on membrane proteins is carried out at least partly independently from protein effects on SR proteins. Optionally, the selectivity is using methods as described above.

In an exemplary embodiment of the invention, such enhancement is provided without adversely affecting short term activity, as pacing or inhibition might. In an exemplary embodiment of the invention, the enhancement is local and has fewer systemic effects (as would be expected with ACE-inhibitors or beta-blockers, for example). In some embodiments, short term activity is improved.

It should be noted that these proteins are also known in other body organs, such as smooth muscle cells and slow-twitch skeletal muscle cells. Thus, an electric field as described herein can be used, for example, to modify PLB phosphorylation in blood vessel cells and/or the GI tract. Optionally, elasticity compliance is restored and vasomotor tone is restored and/or responsiveness are restored to blood vessels and/or GI tract portions using the electric field as described herein. In an exemplary embodiment of the invention, a hardened aorta is made more supple (and thus relieve cardiac problems) by suitable treatment. Vascular resistance in general, may be modified. Optionally, signals as described herein are used to help increase muscle strength and/or normalize protein expression therein.

It should be noted that in smooth muscle cells the depolarization cycle is much longer and there is no danger of fatal arrhythmia, so more varied pulses may be attempted without significant danger and may provide longer term effects.

Pulse Optimization

In an exemplary embodiment of the invention, a method of optimizing treatments to the tissue is provided, taking into account effects on protein levels. For example, a CCM signal or a pacing signal, exercise or a pharmaceutical treatment may each (or in combination) have an effect on protein expression and/or behavior. In an exemplary embodiment of the invention, such a treatment is optimized so that it has a greater (desired) effect on proteins. In one example, a CCM signal is optimized by applying variations of the signals (e.g., different amplitude, frequencies pulse forms, etc.) to a set of tissue homogenate sets and selecting the signal(s) for which a better effect is achieved. It is noted that while this may be carried out in vivo, the ability to try out signals with various pulse parameters on tissue homogenate without the need for safety testing and worry about danger of damage to a patient/animal, can allow a much faster and/or cheaper search to be made. Searching methods as known in the art may be used. It is noted that such searching can also be carried out for small molecule drugs which have a direct effect on phosphorylation, for example.

It is noted that immediate protein levels may be results that are faster to achieve or have less noise, than measuring actual improvement in a patient. Thus, protein measurement may allow faster within-patient optimization and/or allow optimization based on the response to a small number of beats (e.g., 100, 50, 10, 3 or intermediate or fewer numbers), rather than waiting for a longer term effect which may damage the heart if it is negative.

In an exemplary embodiment of the invention, an existing device is optimized by changing its applied sequence with a sequence selected to have a desired protein effect.

In an exemplary embodiment of the invention, a device is programmed by a used selecting a desired pulse sequence form an existing set or by selecting parameters which are expected to have a desired protein effect.

It should be noted that the applied pulse sequence (optionally including non-treated beats) and/or desired effect may change over the course of a treatment. One type of change is when the patient state stabilizes and/or the focus of maladaptation changes. In one example, a first step of treatment is in stabilizing heart treatment and a second step is in increasing contractility and/or remodeling the heart.

Another type of change is where a different effect is desired at different times during a treatment, for example, a one series of beats being utilized to treat one protein and another series of beats to have another effect. It should be noted that not all treatments need to be synchronized the cardiac heart beat.

Both types of change may be controlled using feedback. Optionally, the change includes one or both of changing the sequence and changing the tissue to which the sequence is applied, for example by switching and/or by moving electrode(s).

In an exemplary embodiment of the invention, the applied sequence takes into account a provided pharmaceutical and/or a half-life in the body thereof. In an exemplary embodiment of the invention, a transmitter is provided to a patient to indicate to the controller that a medication was taken.

Optionally, the medication (or another treatment) is provided to specifically interact with the sequence. For example, a signal or medicine is provided which has a long effect and while that effect is going on, a signal or other treatment is provided which has an opposite effect that momentarily counteracts long-term effects. In one example, a medication which extends a refractory period is provided together with an electrical treatment that applies a phosphorylation-modifying signal. In another example, medication is provided to enforce resting of the cells, using a mechanism which does not prevent the CCM or CCM-like signal from working, possibly, a medication that blocks transmembrane channels.

It should be appreciated that some sequences that are applied therapeutically may change between applications to a same patient, for example, vary in power, shape, repetition number, duration of application and location. As noted above, such variations may be during a treatment process of a particular complaint or set of complaints.

General

The following papers, the disclosures of which are incorporated herein by reference present various results of the effect of a CCM (Cardiac Contractility Modulation) signal, on gene expression and protein phosphorylation:

a) an abstract, Control/Tracking Number: 05-A-314176-ACC "Chronic Therapy With Non-Excitatory Cardiac Contractility Modulation Electric Signals Improves Left Ventricular Function, Reduces Myocardial Oxygen Consumption and Increases Myocardial Mechanical Efficiency", by Hani N. Sabbah, Makoto Imai, Sharad Rastogi, Naveen Sharma, Margaret P. Chandler, Walid Haddad, Yuval Mika, William C. Stanley, Henry Ford Health System, Detroit, Mich., Case Western Reserve University, Cleveland, Ohio; In American College of cardiology foundation.

b) "Non-Excitatory Cardiac Contractility Modulation Electric Signals Normalize Phosphorylation and Expression of the Sodium Calcium Exchanger in Left Ventricular Myocardium of Dogs with Heart Failure", by Ramesh C. Gupta, Sudhish Mishra, Sharad Rastogi, Makato Imai, Walid Hadad, Yuval MiKa, Hani N. Sabbah, Henry Ford Health System, Detroit, Mich., Impulse Dynamics, Mount Laurel, N.J.; In Journal of the American College of Cardiology 2005; 45:151A.

c) "Short-Term Therapy with Non-Excitatory Cardiac Contractility Modulation Electric Signals Increases Phosphorylation of Phospholamban in Left Ventricular Myocardium of Dogs With Chronic Heart Failure", by Sudhish Mishra, Ramesh C. Gupta, Sharad Rastogi, Henry Ford Health System, Detroit, Mich.; Walid Haddad, Yuval Mika, Impulse Dynamics USA, Mount Laurel, N.J.; Hani N. Sabbah, Henry Ford Health System, Detroit, Mich.; In Circulation vol. 110; page 111604, 2004.

While the above described apparatus has focused on hardware and/or methods, it should be understood that the present invention includes programmable hardware, software for programmable devices, software for programming such hardware and computers including software for programming devices. For example, an external programming station may be provided, which optionally communicates with an implantable device using telemetry. Data collection using telemetry may also be practiced. In addition, computer readable media including such programs are also included. Also included are micro-code and other types of programming, as well as hardwired circuitry and ASICs. This is a list of examples and should not be considered as limiting. An exemplary device/software includes a decision making module, a timing module, a power module and/or a signal analysis modules. Section headings are provided for navigation and should not be considered as limiting their contents to that section only.

It should be understood that features and/or steps described with respect to one embodiment may be used with other embodiments and that not all embodiments of the invention have all of the features and/or steps shown in a particular figure or described with respect to one of the embodiments. Variations of embodiments described will occur to persons of the art. Furthermore, the terms "comprise," "include," "have" and their conjugates, shall mean, when used in the claims, "including but not necessarily limited to." When the term "based on" is used in the claims it is to be interpreted as meaning "at least partially based on".

It is noted that some of the above described embodiments may describe the best mode contemplated by the inventors and therefore may include structure, acts or details of structures and acts that may not be essential to the invention and which are described as examples. Structure and acts described herein are replaceable by equivalents which perform the same function, even if the structure or acts are different, as known in the art. Therefore, the scope of the invention is limited only by the elements and limitations as used in the claims, as issued.

It is the intent of the Applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of treating a cardiac disorder in a heart of a patient, comprising:
   selecting a patient with a risk of progression of heart failure;
   assessing a baseline value of one or more anatomical markers; and
   applying a non-excitatory signal to said heart of said patient during a refractory period of said heart for a duration sufficient to reverse or reduce the progression of one or more anatomical markers;
   wherein the one or more anatomical markers include one or more of interstitial fibrosis, Volume fraction of replacement fibrosis (VFRF), Volume Fraction of Interstitial Fibrosis (VFIF), cardiomyocyte cross sectional area, capillary density and oxygen diffusion distance.

2. A method according to claim 1, wherein said anatomical markers includes interstitial fibrosis.

3. A method according to claim 2, wherein said applying comprises applying said signal in a manner which inhibits one or more gelatinases.

4. A method according to claim 3, wherein said one or more gelatinases include one or both of the Matrix Metalloproteinases MMP2 and MMP9.

5. A method according to claim 1, wherein the anatomical markers include capillary density and oxygen diffusion distance and said applying normalizes one or both of capillary density and oxygen diffusion distance.

6. A method according to claim 1, wherein the anatomical markers include said VFRF and said applying improves said VFRF (Volume fraction of replacement fibrosis) by at least 23%.

7. A method according to claim 1, wherein the anatomical markers include said VFIF and said applying improves said VFIF (Volume Fraction of Interstitial Fibrosis) by at least 16%.

8. A method according to claim 1, wherein said reduces cardiomyocyte cross-sectional area by at least 19%.

9. A method according to claim 1, wherein said applying causes a reduction in myocardial oxygen consumption (MVO2) by at least 96 micromol/min.

10. A method according to claim 1, wherein said selecting comprises selecting a patient with an aim of increasing LV diastolic compliance.

11. A method according to claim 1, wherein said applying comprises applying said non-excitatory signal with every heart beat.

12. A method according to claim 11, wherein said applying comprises applying said non-excitatory signal about 80 applications per minute.

13. A method according to claim 11, wherein said applying comprises applying said non-excitatory signal between 4 and 6 phases.

14. A method according to claim 11, wherein said applying comprises applying to a right ventricular septum to treat a damaged left ventricle.

15. A method according to claim 14, wherein said applying comprises applying said non-excitatory signal using two electrodes about 1-2 cm apart.

16. A method according to claim 11, wherein said applying comprises applying for about 5 hours a day.

17. A method according to claim 1, wherein said applying of the signal lasts for a duration for at least 3 months.

* * * * *